US008858940B2

(12) United States Patent
Gonzalez Pajuelo et al.

(10) Patent No.: US 8,858,940 B2
(45) Date of Patent: Oct. 14, 2014

(54) AMINO ACID SEQUENCES DIRECTED AGAINST THE ANGIOPOIETIN/TIE SYSTEM AND POLYPEPTIDES COMPRISING THE SAME FOR THE TREATMENT OF DISEASES AND DISORDERS RELATED TO ANGIOGENESIS

(75) Inventors: Maria Gonzalez Pajuelo, Porto (PT); Michael John Scott Saunders, Brussels (BE); Johannes Joseph Wilhelmus De Haard, Oudelande (NL); Peter Vanlandschoot, Bellem (BE)

(73) Assignee: Ablynx N.V., Zwijnaarde (BE)

( * ) Notice: Subject to any disclaimer, the term of this patent is extended or adjusted under 35 U.S.C. 154(b) by 0 days.

(21) Appl. No.: 13/133,685

(22) PCT Filed: Dec. 10, 2009

(86) PCT No.: PCT/EP2009/066822
§ 371 (c)(1),
(2), (4) Date: Aug. 23, 2011

(87) PCT Pub. No.: WO2010/066836
PCT Pub. Date: Jun. 17, 2010

(65) Prior Publication Data
US 2012/0076796 A1    Mar. 29, 2012

Related U.S. Application Data

(60) Provisional application No. 61/121,228, filed on Dec. 10, 2008.

(51) Int. Cl.
*C12P 21/08*    (2006.01)
*C07K 16/28*    (2006.01)
*C07K 16/22*    (2006.01)

(52) U.S. Cl.
CPC ....... *C07K 16/2863* (2013.01); *C07K 2317/565* (2013.01); *C07K 2317/22* (2013.01); *C07K 16/22* (2013.01); *C07K 2317/569* (2013.01)
USPC .................. 424/133.1; 424/139.1; 424/141.1; 424/143.1; 530/387.3; 530/387.9; 530/388.22

(58) Field of Classification Search
None
See application file for complete search history.

(56) References Cited

U.S. PATENT DOCUMENTS

| 6,376,653 B1 * | 4/2002 | Holmes et al. ............ 530/388.22 |
| 2005/0158829 A1 * | 7/2005 | Fandl et al. .................. 435/69.1 |

FOREIGN PATENT DOCUMENTS

| EP | 0 368 684 A1 | 5/1990 |
| WO | WO 2004/068820 A2 | 8/2004 |
| WO | WO 2005/018629 A1 | 3/2005 |
| WO | WO 2005/019267 A2 | 3/2005 |
| WO | WO 2006/003388 A2 | 1/2006 |
| WO | WO 2006/030220 A1 | 3/2006 |
| WO | WO 2007/085815 A2 | 8/2007 |
| WO | WO 2008/089070 A2 | 7/2008 |
| WO | WO 2009/052830 | * 4/2009 |
| WO | WO 2009/068631 | * 6/2009 |
| WO | WO 2009/147248 A2 | 12/2009 |

OTHER PUBLICATIONS

Bach et al., Angiopoietins in malignancy. Eur J Surg Oncol. Feb. 2007;33(1):7-15. Epub Sep. 7, 2006.
Blume-Jensen et al., Oncogenic kinase signalling. Nature. May 17, 2001;411(6835):355-65.
Bouïs et al., A review on pro- and anti-angiogenic factors as targets of clinical intervention. Pharmacol Res. Feb. 2006;53(2):89-103.
Carmeliet, Angiogenesis in health and disease. Nat Med. Jun. 2003;9(6):653-60.
Debusk et al., Tie2 receptor tyrosine kinase, a major mediator of tumor necrosis factor alpha-induced angiogenesis in rheumatoid arthritis. Arthritis Rheum. Sep. 203;48(9):2461-71.
Eklund et al., Tie receptors and their angiopoietin ligands are context-dependent regulators of vascular remodeling. Exp Cell Res. Mar. 10, 2006;312(5):630-41. Epub Oct. 12, 2005.
Fiedler et al., Angiopoietins: a link between angiogenesis and inflammation. Trends Immunol. Dec. 2006;27(12):552-8. Epub Oct. 12, 2006.
Halaby et al., the immunoglobulin fold family: sequence analysis and 3D structure comparisons. Protein Eng. Jul. 1999;12(7):563-71.
Holliger et al., Engineered antibody fragments and the rise of single domains. Nat Biotechnol. Sep. 2005;23(9):1126-36.
Holt et al., Domain antibodies: proteins for therapy. Trends Biotechnol. Nov. 2003;21(11):484-90.
Kuroda et al., Altered expression of angiopoietins and Tie2 endothelium receptor in psoriasis. J Invest Dermatol. May 2001;116(5):713-20.
Le Jan et al., Angiopoietin-like 4 is a proangiogenic factor produced during ischemia and in conventional renal cell carcinoma. Am J Pathol. May 2003;162(5):1521-8.
Muyldermans, Single domain camel antibodies: current status. J Biotechnol. Jun. 2001;74(4):277-302.
Oike et al., Angiopoietin-like proteins: potential new targets for metabolic syndrome therapy. Trends Mol Med. Oct. 2005;11(10):473-9. Epub Sep. 8, 2005.
Oliner et al., Suppression of angiogenesis and tumor growth by selective inhibition of angiopoietin-2. Cancer Cell. Nov. 2004;6(5):507-16.
Pandya et al., Angiogenesis—a new target for future therapy. Vascul Pharmacol. May 2006;44(5):265-74. Epub Mar. 20, 2006.
Patel et al., Angiopoietin concentrations in diabetic retinopathy. Br J Ophthalmol. Apr. 2005;89(4):480-3.
Revets et al., Nanobodies as novel agents for cancer therapy. Expert Opin Biol Ther. Jan. 2005;5(1):111-24.
Shahrara et al., Differential expression of the angiogenic Tie receptor family in arthritic and normal synovial tissue. Arthritis Res. 2002;4(3):201-8. Epub Jan. 16, 2002.

(Continued)

*Primary Examiner* — Marianne P Allen
(74) *Attorney, Agent, or Firm* — Wolf, Greenfield & Sacks, P.C.

(57) ABSTRACT

The present invention relates to amino acid sequences that are directed against proteins from the group of the Angiopoietin/Tie family such as Tie1, Tie2, Ang1, Ang2, Ang3, Ang4, Angptl1, Angptl2, Angptl3, Angptl4, Angptl5, Angptl6, as well as to compounds or constructs, and in particular proteins and polypeptides, that comprise or essentially consist of one or more of such amino acid sequences.

11 Claims, 9 Drawing Sheets

(56) References Cited

OTHER PUBLICATIONS

Figure 1:
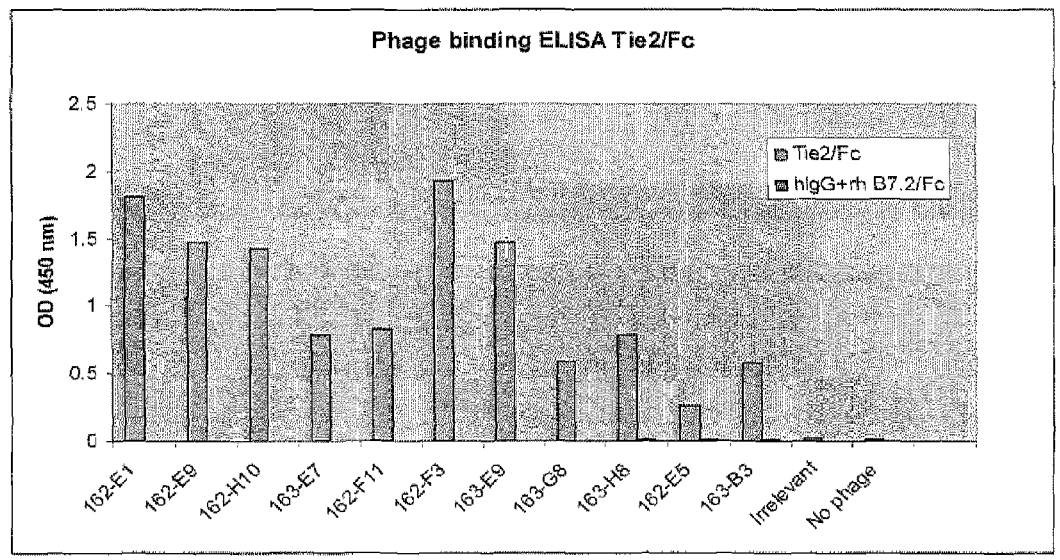

Thurston et al., Role of Angiopoietins and Tie receptor tyrosine kinases in angiogenesis and lymphangiogenesis. Cell Tissue Res. Oct. 2003;314(1):61-8. Epub Aug. 12, 2003.

Ward et al., Binding activities of a repertoire of single immunoglobulin variable domains secreted from *Escherichia coli*. Nature. Oct. 12, 1989;341(6242):544-6.

Davis et al., Isolation of angiopoietin-1, a ligand for the TIE2 receptor, by secretion-trap expression cloning. Cell. Dec. 27, 1996;87(7):1161-9.

Harfouche et al., Signaling and regulation of endothelial cell survival by angiopoietin-2. Am J Physiol Heart Circ Physiol. Oct. 2006;291(4):H1635-45. Epub May 19, 2006.

Köster et al., Transgenic angiopoietin-like (angptl)4 overexpression and targeted disruption of angptl4 and angptl3: regulation of triglyceride metabolism. Endocrinology. Nov. 2005;146(11):4943-50. Epub Aug. 4, 2005.

Mustonen et al., Endothelial receptor tyrosine kinases involved in angiogenesis. J Cell Biol. May 1995;129(4):895-8.

Yoshida et al., Angiopoietin-like protein 4 is a potent hyperlipidemia-inducing factor in mice and inhibitor of lipoprotein lipase. J Lipid Res. Nov. 2002;43(11):1770-2.

\* cited by examiner

SEQUENCE LISTING

```
<160> NUMBER OF SEQ ID NOS: 501

<210> SEQ ID NO 1
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 1

Glu Val Gln Leu Val Glu Ser Gly Gly Gly Leu Val Gln Pro Gly Gly
```

```
  1               5                  10                  15
Ser Leu Arg Leu Ser Cys Ala Ala Ser Gly Ile Pro Phe Ser Xaa Xaa
              20                  25                  30

Xaa Xaa Xaa Trp Phe Arg Gln Ala Pro Gly Lys Gln Arg Asp Ser Val
              35                  40                  45

Ala Xaa Xaa Xaa Xaa Arg Phe Thr Ile Ser Arg Asp Asn Ala Lys
    50                  55                  60

Asn Thr Val Tyr Leu Gln Met Asn Ser Leu Lys Pro Glu Asp Thr Ala
 65                  70                  75                  80

Val Tyr Arg Cys Tyr Phe Xaa Xaa Xaa Xaa Xaa Trp Gly Gln Gly Thr
              85                  90                  95

Gln Val Thr Val Ser Ser
             100

<210> SEQ ID NO 2
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 2

Gln Val Lys Leu Glu Glu Ser Gly Gly Gly Leu Val Gln Ala Gly Gly
 1               5                  10                  15

Ser Leu Arg Leu Ser Cys Val Gly Ser Gly Arg Thr Phe Ser Xaa Xaa
              20                  25                  30

Xaa Xaa Xaa Trp Phe Arg Leu Ala Pro Gly Lys Glu Arg Glu Phe Val
              35                  40                  45

Ala Xaa Xaa Xaa Xaa Xaa Arg Phe Thr Ile Ser Arg Asp Thr Ala Ser
    50                  55                  60

Asn Arg Gly Tyr Leu His Met Asn Asn Leu Thr Pro Glu Asp Thr Ala
 65                  70                  75                  80

Val Tyr Tyr Cys Ala Ala Xaa Xaa Xaa Xaa Xaa Trp Gly Gln Gly Thr
              85                  90                  95

Gln Val Thr Val Ser Ser
             100

<210> SEQ ID NO 3
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
```

```
<221> NAME/KEY: misc_feature
<222> LOCATION: (87)..(91)
<223> OTHER INFORMATION: Xaa is any amino acid

<400> SEQUENCE: 3

Ala Val Gln Leu Val Asp Ser Gly Gly Gly Leu Val Gln Ala Gly Asp
1               5                   10                  15

Ser Leu Lys Leu Ser Cys Ala Leu Thr Gly Gly Ala Phe Thr Xaa Xaa
            20                  25                  30

Xaa Xaa Xaa Trp Phe Arg Gln Thr Pro Gly Arg Glu Arg Glu Phe Val
        35                  40                  45

Ala Xaa Xaa Xaa Xaa Xaa Arg Phe Thr Ile Ser Arg Asp Asn Ala Lys
50                  55                  60

Asn Met Val Tyr Leu Arg Met Asn Ser Leu Ile Pro Glu Asp Ala Ala
65                  70                  75                  80

Val Tyr Ser Cys Ala Ala Xaa Xaa Xaa Xaa Xaa Trp Gly Gln Gly Thr
                85                  90                  95

Leu Val Thr Val Ser Ser
            100

<210> SEQ ID NO 4
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 4

Gln Val Gln Leu Val Glu Ser Gly Gly Gly Leu Val Glu Ala Gly Gly
1               5                   10                  15

Ser Leu Arg Leu Ser Cys Thr Ala Ser Glu Ser Pro Phe Arg Xaa Xaa
            20                  25                  30

Xaa Xaa Xaa Trp Phe Arg Gln Thr Ser Gly Gln Glu Arg Glu Phe Val
        35                  40                  45

Ala Xaa Xaa Xaa Xaa Xaa Arg Phe Thr Ile Ser Arg Asp Asp Ala Lys
50                  55                  60

Asn Thr Val Trp Leu His Gly Ser Thr Leu Lys Pro Glu Asp Thr Ala
65                  70                  75                  80

Val Tyr Tyr Cys Ala Ala Xaa Xaa Xaa Xaa Xaa Trp Gly Gln Gly Thr
                85                  90                  95

Gln Val Thr Val Ser Ser
            100

<210> SEQ ID NO 5
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
```

```
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 5

Ala Val Gln Leu Val Glu Ser Gly Gly Gly Leu Val Gln Gly Gly
1               5                   10                  15

Ser Leu Arg Leu Ala Cys Ala Ala Ser Glu Arg Ile Phe Asp Xaa Xaa
            20                  25                  30

Xaa Xaa Xaa Trp Tyr Arg Gln Gly Pro Gly Asn Glu Arg Glu Leu Val
        35                  40                  45

Ala Xaa Xaa Xaa Xaa Xaa Arg Phe Thr Ile Ser Met Asp Tyr Thr Lys
    50                  55                  60

Gln Thr Val Tyr Leu His Met Asn Ser Leu Arg Pro Glu Asp Thr Gly
65              70                  75                  80

Leu Tyr Tyr Cys Lys Ile Xaa Xaa Xaa Xaa Xaa Trp Gly Gln Gly Thr
            85                  90                  95

Gln Val Thr Val Ser Ser
            100

<210> SEQ ID NO 6
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 6

Asp Val Lys Phe Val Glu Ser Gly Gly Gly Leu Val Gln Ala Gly Gly
1               5                   10                  15

Ser Leu Arg Leu Ser Cys Val Ala Ser Gly Phe Asn Phe Asp Xaa Xaa
            20                  25                  30

Xaa Xaa Xaa Trp Phe Arg Gln Ala Pro Gly Lys Glu Arg Glu Val
        35                  40                  45

Ala Xaa Xaa Xaa Xaa Xaa Arg Phe Thr Ile Ser Ser Glu Lys Asp Lys
    50                  55                  60

Asn Ser Val Tyr Leu Gln Met Asn Ser Leu Lys Pro Glu Asp Thr Ala
65              70                  75                  80

Leu Tyr Ile Cys Ala Gly Xaa Xaa Xaa Xaa Xaa Trp Gly Arg Gly Thr
            85                  90                  95

Gln Val Thr Val Ser Ser
            100

<210> SEQ ID NO 7
```

-continued

```
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 7

Gln Val Arg Leu Ala Glu Ser Gly Gly Gly Leu Val Gln Ser Gly Gly
1               5                   10                  15

Ser Leu Arg Leu Ser Cys Val Ala Ser Gly Ser Thr Tyr Thr Xaa Xaa
            20                  25                  30

Xaa Xaa Xaa Trp Tyr Arg Gln Tyr Pro Gly Lys Gln Arg Ala Leu Val
        35                  40                  45

Ala Xaa Xaa Xaa Xaa Xaa Arg Phe Thr Ile Ala Arg Asp Ser Thr Lys
    50                  55                  60

Asp Thr Phe Cys Leu Gln Met Asn Asn Leu Lys Pro Glu Asp Thr Ala
65                  70                  75                  80

Val Tyr Tyr Cys Tyr Ala Xaa Xaa Xaa Xaa Xaa Trp Gly Gln Gly Thr
                85                  90                  95

Gln Val Thr Val Ser Ser
            100

<210> SEQ ID NO 8
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 8

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Ser Asp Xaa Xaa
            20                  25                  30

Xaa Xaa Xaa Trp Phe Arg Gln Ala Pro Gly Lys Pro Arg Glu Gly Val
        35                  40                  45

Ser Xaa Xaa Xaa Xaa Xaa Arg Phe Thr Ile Ser Thr Asp Asn Ala Lys
    50                  55                  60

Asn Thr Val His Leu Leu Met Asn Arg Val Asn Ala Glu Asp Thr Ala
65                  70                  75                  80

Leu Tyr Tyr Cys Ala Val Xaa Xaa Xaa Xaa Xaa Trp Gly Arg Gly Thr
```

Arg Val Thr Val Ser Ser
            100

<210> SEQ ID NO 9
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 9

Gln Val Gln Leu Val Glu Ser Gly Gly Gly Leu Val Gln Pro Gly Gly
1               5                   10                  15

Ser Leu Arg Leu Ser Cys Gln Ala Ser Gly Asp Ile Ser Thr Xaa Xaa
            20                  25                  30

Xaa Xaa Xaa Trp Tyr Arg Gln Val Pro Gly Lys Leu Arg Glu Phe Val
            35                  40                  45

Ala Xaa Xaa Xaa Xaa Xaa Arg Phe Thr Ile Ser Gly Asp Asn Ala Lys
50                  55                  60

Arg Ala Ile Tyr Leu Gln Met Asn Asn Leu Lys Pro Asp Asp Thr Ala
65                  70                  75                  80

Val Tyr Tyr Cys Asn Arg Xaa Xaa Xaa Xaa Xaa Trp Gly Gln Gly Thr
            85                  90                  95

Gln Val Thr Val Ser Pro
            100

<210> SEQ ID NO 10
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 10

Gln Val Pro Val Val Glu Ser Gly Gly Gly Leu Val Gln Ala Gly Asp
1               5                   10                  15

Ser Leu Arg Leu Phe Cys Ala Val Pro Ser Phe Thr Ser Thr Xaa Xaa
            20                  25                  30

Xaa Xaa Xaa Trp Phe Arg Gln Ala Pro Gly Lys Glu Arg Glu Phe Val
            35                  40                  45

```
Ala Xaa Xaa Xaa Xaa Arg Phe Thr Ile Ser Arg Asn Ala Thr Lys
    50              55                  60

Asn Thr Leu Thr Leu Arg Met Asp Ser Leu Lys Pro Glu Asp Thr Ala
 65              70              75                  80

Val Tyr Tyr Cys Ala Ala Xaa Xaa Xaa Xaa Xaa Trp Gly Gln Gly Thr
                85                  90              95

Gln Val Thr Val Ser Ser
            100
```

<210> SEQ ID NO 11
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 11

```
Glu Val Gln Leu Val Glu Ser Gly Gly Gly Leu Val Gln Ala Gly Asp
 1               5                  10                  15

Ser Leu Arg Leu Phe Cys Thr Val Ser Gly Gly Thr Ala Ser Xaa Xaa
            20                  25                  30

Xaa Xaa Xaa Trp Phe Arg Gln Ala Pro Gly Glu Lys Arg Glu Phe Val
        35                  40                  45

Ala Xaa Xaa Xaa Xaa Xaa Arg Phe Thr Ile Ala Arg Glu Asn Ala Gly
    50                  55                  60

Asn Met Val Tyr Leu Gln Met Asn Asn Leu Lys Pro Asp Asp Thr Ala
 65              70                  75                  80

Leu Tyr Thr Cys Ala Ala Xaa Xaa Xaa Xaa Xaa Trp Gly Arg Gly Thr
                85                  90              95

Gln Val Thr Val Ser Ser
            100
```

<210> SEQ ID NO 12
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 12

```
Ala Val Gln Leu Val Glu Ser Gly Gly Asp Ser Val Gln Pro Gly Asp
 1               5                  10                  15
```

```
Ser Gln Thr Leu Ser Cys Ala Ala Ser Gly Arg Thr Asn Ser Xaa Xaa
            20                  25                  30

Xaa Xaa Xaa Trp Phe Arg Gln Ala Pro Gly Lys Glu Arg Val Phe Leu
        35                  40                  45

Ala Xaa Xaa Xaa Xaa Xaa Arg Phe Thr Ile Ser Arg Asp Ser Ala Lys
    50                  55                  60

Asn Met Met Tyr Leu Gln Met Asn Asn Leu Lys Pro Gln Asp Thr Ala
65                  70                  75                  80

Val Tyr Tyr Cys Ala Ala Xaa Xaa Xaa Xaa Trp Gly Gln Gly Thr
                85                  90                  95

Gln Val Thr Val Ser Ser
            100

<210> SEQ ID NO 13
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 13

Ala Val Gln Leu Val Glu Ser Gly Gly Gly Leu Val Gln Ala Gly Gly
1               5                   10                  15

Ser Leu Arg Leu Ser Cys Val Val Ser Gly Leu Thr Ser Ser Xaa Xaa
            20                  25                  30

Xaa Xaa Xaa Trp Phe Arg Gln Thr Pro Trp Gln Glu Arg Asp Phe Val
        35                  40                  45

Ala Xaa Xaa Xaa Xaa Xaa Arg Phe Thr Ile Ser Arg Asp Asn Tyr Lys
    50                  55                  60

Asp Thr Val Leu Leu Glu Met Asn Phe Leu Lys Pro Glu Asp Thr Ala
65                  70                  75                  80

Ile Tyr Tyr Cys Ala Ala Xaa Xaa Xaa Xaa Xaa Trp Gly Gln Gly Thr
                85                  90                  95

Gln Val Thr Val Ser Ser
            100

<210> SEQ ID NO 14
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
```

<222> LOCATION: (87)..(91)
<223> OTHER INFORMATION: Xaa is any amino acid

<400> SEQUENCE: 14

Ala Val Gln Leu Val Glu Ser Gly Gly Gly Leu Val Gln Ala Gly Ala
1               5                   10                  15

Ser Leu Arg Leu Ser Cys Ala Thr Ser Thr Arg Thr Leu Asp Xaa Xaa
            20                  25                  30

Xaa Xaa Xaa Trp Phe Arg Gln Ala Pro Gly Arg Asp Arg Glu Phe Val
        35                  40                  45

Ala Xaa Xaa Xaa Xaa Xaa Arg Phe Thr Val Ser Arg Asp Ser Ala Glu
    50                  55                  60

Asn Thr Val Ala Leu Gln Met Asn Ser Leu Lys Pro Glu Asp Thr Ala
65                  70                  75                  80

Val Tyr Tyr Cys Ala Ala Xaa Xaa Xaa Xaa Trp Gly Gln Gly Thr
                85                  90                  95

Arg Val Thr Val Ser Ser
            100

<210> SEQ ID NO 15
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 15

Gln Val Gln Leu Val Glu Ser Gly Gly Gly Leu Val Gln Pro Gly Gly
1               5                   10                  15

Ser Leu Arg Leu Ser Cys Thr Val Ser Arg Leu Thr Ala His Xaa Xaa
            20                  25                  30

Xaa Xaa Xaa Trp Phe Arg Gln Ala Pro Gly Lys Glu Arg Glu Ala Val
        35                  40                  45

Ser Xaa Xaa Xaa Xaa Xaa Arg Phe Thr Ile Ser Arg Asp Tyr Ala Gly
    50                  55                  60

Asn Thr Ala Phe Leu Gln Met Asp Ser Leu Lys Pro Glu Asp Thr Gly
65                  70                  75                  80

Val Tyr Tyr Cys Ala Thr Xaa Xaa Xaa Xaa Xaa Trp Gly Gln Gly Thr
                85                  90                  95

Gln Val Thr Val Ser Ser
            100

<210> SEQ ID NO 16
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)

<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 16

Glu Val Gln Leu Val Glu Ser Gly Gly Glu Leu Val Gln Ala Gly Gly
1               5                   10                  15

Ser Leu Lys Leu Ser Cys Thr Ala Ser Gly Arg Asn Phe Val Xaa Xaa
            20                  25                  30

Xaa Xaa Xaa Trp Phe Arg Arg Ala Pro Gly Lys Glu Arg Glu Phe Val
        35                  40                  45

Ala Xaa Xaa Xaa Xaa Xaa Arg Phe Thr Val Ser Arg Asp Asn Gly Lys
    50                  55                  60

Asn Thr Ala Tyr Leu Arg Met Asn Ser Leu Lys Pro Glu Asp Thr Ala
65                  70                  75                  80

Asp Tyr Tyr Cys Ala Val Xaa Xaa Xaa Xaa Xaa Leu Gly Ser Gly Thr
                85                  90                  95

Gln Val Thr Val Ser Ser
            100

<210> SEQ ID NO 17
<211> LENGTH: 102
<212> TYPE: PRT
<213> ORGANISM: Artificial
<220> FEATURE:
<223> OTHER INFORMATION: GLEW-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 17

Ala Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Xaa Xaa
            20                  25                  30

Xaa Xaa Xaa Trp Val Arg Gln Ala Pro Gly Lys Val Leu Glu Trp Val
        35                  40                  45

Ser Xaa Xaa Xaa Xaa Xaa Arg Phe Thr Ile Ser Arg Asp Asn Ala Lys
    50                  55                  60

Asn Thr Leu Tyr Leu Gln Met Asn Ser Leu Lys Pro Glu Asp Thr Ala
65                  70                  75                  80

Val Tyr Tyr Cys Val Lys Xaa Xaa Xaa Xaa Xaa Gly Ser Gln Gly Thr
                85                  90                  95

Gln Val Thr Val Ser Ser
            100

<210> SEQ ID NO 18
<211> LENGTH: 102

-continued

<212> TYPE: PRT
<213> ORGANISM: Artificial
<220> FEATURE:
<223> OTHER INFORMATION: GLEW-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr Xaa Xaa
            20                  25                  30

Xaa Xaa Xaa Trp Val Arg Gln Ala Pro Gly Lys Ala Glu Glu Trp Val
        35                  40                  45

Ser Xaa Xaa Xaa Xaa Xaa Arg Phe Lys Ile Ser Arg Asp Asn Ala Lys
    50                  55                  60

Lys Thr Leu Tyr Leu Gln Met Asn Ser Leu Gly Pro Glu Asp Thr Ala
65                  70                  75                  80

Met Tyr Tyr Cys Gln Arg Xaa Xaa Xaa Xaa Xaa Arg Gly Gln Gly Thr
                85                  90                  95

Gln Val Thr Val Ser Ser
            100

<210> SEQ ID NO 19
<211> LENGTH: 102
<212> TYPE: PRT
<213> ORGANISM: Artificial
<220> FEATURE:
<223> OTHER INFORMATION: GLEW-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 19

Glu Val Gln Leu Val Glu Ser Gly Gly Gly Leu Ala Leu Pro Gly Gly
1               5                   10                  15

Ser Leu Thr Leu Ser Cys Val Phe Ser Gly Ser Thr Phe Ser Xaa Xaa
            20                  25                  30

Xaa Xaa Xaa Trp Val Arg His Thr Pro Gly Lys Ala Glu Glu Trp Val
        35                  40                  45

Ser Xaa Xaa Xaa Xaa Xaa Arg Phe Thr Ile Ser Arg Asp Asn Ala Lys
    50                  55                  60

Asn Thr Leu Tyr Leu Glu Met Asn Ser Leu Ser Pro Glu Asp Thr Ala
65                  70                  75                  80

Met Tyr Tyr Cys Gly Arg Xaa Xaa Xaa Xaa Xaa Arg Ser Lys Gly Ile
                85                  90                  95

```
Gln Val Thr Val Ser Ser
            100

<210> SEQ ID NO 20
<211> LENGTH: 102
<212> TYPE: PRT
<213> ORGANISM: Artificial
<220> FEATURE:
<223> OTHER INFORMATION: P,R,S 103-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 20

Ala Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Xaa Xaa
            20                  25                  30

Xaa Xaa Xaa Trp Phe Arg Gln Ala Pro Gly Lys Glu Arg Glu Phe Val
        35                  40                  45

Ala Xaa Xaa Xaa Xaa Xaa Arg Phe Thr Ile Ser Arg Asp Asn Ala Lys
    50                  55                  60

Asn Thr Val Tyr Leu Gln Met Asn Ser Leu Lys Pro Glu Asp Thr Ala
65                  70                  75                  80

Val Tyr Tyr Cys Ala Ala Xaa Xaa Xaa Xaa Arg Gly Gln Gly Thr
                85                  90                  95

Gln Val Thr Val Ser Ser
            100

<210> SEQ ID NO 21
<211> LENGTH: 102
<212> TYPE: PRT
<213> ORGANISM: Artificial
<220> FEATURE:
<223> OTHER INFORMATION: P,R,S 103-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 21

Asp Val Gln Leu Val Glu Ser Gly Gly Asp Leu Val Gln Pro Gly Gly
1               5                   10                  15

Ser Leu Arg Leu Ser Cys Ala Ala Ser Gly Phe Ser Phe Asp Xaa Xaa
            20                  25                  30

Xaa Xaa Xaa Trp Leu Arg Gln Thr Pro Gly Lys Gly Leu Glu Trp Val
        35                  40                  45

Gly Xaa Xaa Xaa Xaa Xaa Arg Phe Thr Ile Ser Arg Asp Asn Ala Lys
```

```
                50              55              60
Asn Met Leu Tyr Leu His Leu Asn Asn Leu Lys Ser Glu Asp Thr Ala
 65              70              75              80

Val Tyr Tyr Cys Arg Arg Xaa Xaa Xaa Xaa Leu Gly Gln Gly Thr
                 85              90              95

Gln Val Thr Val Ser Ser
            100

<210> SEQ ID NO 22
<211> LENGTH: 102
<212> TYPE: PRT
<213> ORGANISM: Artificial
<220> FEATURE:
<223> OTHER INFORMATION: P,R,S 103-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 22

Glu Val Gln Leu Val Glu Ser Gly Gly Gly Leu Val Gln Pro Gly Gly
 1               5                   10                  15

Ser Leu Arg Leu Ser Cys Val Cys Val Ser Ser Gly Cys Thr Xaa Xaa
             20                  25                  30

Xaa Xaa Xaa Trp Val Arg Gln Ala Pro Gly Lys Ala Glu Glu Trp Val
         35                  40                  45

Ser Xaa Xaa Xaa Xaa Xaa Arg Phe Lys Ile Ser Arg Asp Asn Ala Lys
     50                  55                  60

Lys Thr Leu Tyr Leu Gln Met Asn Ser Leu Gly Pro Glu Asp Thr Ala
 65              70                  75                  80

Met Tyr Tyr Cys Gln Arg Xaa Xaa Xaa Xaa Xaa Arg Gly Gln Gly Thr
                 85                  90                  95

Gln Val Thr Val Ser Ser
            100

<210> SEQ ID NO 23
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 23

Gln Val Gln Arg Val Glu Ser Gly Gly Gly Leu Val Gln Ala Gly Gly
 1               5                   10                  15

Ser Leu Arg Leu Ser Cys Ala Ala Ser Gly Arg Thr Ser Ser
             20                  25                  30

<210> SEQ ID NO 24
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 24
```

```
Gln Val Gln Leu Val Glu Ser Gly Gly Gly Leu Val Gln Thr Gly Asp
1               5                   10                  15

Ser Leu Ser Leu Ser Cys Ser Ala Ser Gly Arg Thr Phe Ser
            20                  25                  30
```

<210> SEQ ID NO 25
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 25

```
Gln Val Lys Leu Glu Glu Ser Gly Gly Gly Leu Val Gln Ala Gly Asp
1               5                   10                  15

Ser Leu Arg Leu Ser Cys Ala Ala Thr Gly Arg Ala Phe Gly
            20                  25                  30
```

<210> SEQ ID NO 26
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 26

```
Ala Val Gln Leu Val Glu Ser Gly Gly Gly Leu Val Gln Pro Gly Glu
1               5                   10                  15

Ser Leu Gly Leu Ser Cys Val Ala Ser Gly Arg Asp Phe Val
            20                  25                  30
```

<210> SEQ ID NO 27
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 27

```
Glu Val Gln Leu Val Glu Ser Gly Gly Gly Leu Val Gln Ala Gly Gly
1               5                   10                  15

Ser Leu Arg Leu Ser Cys Glu Val Leu Gly Arg Thr Ala Gly
            20                  25                  30
```

<210> SEQ ID NO 28
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 28

```
Gln Val Gln Leu Val Glu Ser Gly Gly Gly Trp Val Gln Pro Gly Gly
1               5                   10                  15

Ser Leu Arg Leu Ser Cys Ala Ala Ser Glu Thr Ile Leu Ser
            20                  25                  30
```

<210> SEQ ID NO 29
<211> LENGTH: 30
<212> TYPE: PRT
<213> ORGANISM: Artificial
<220> FEATURE:
<223> OTHER INFORMATION: KERE-class Nanobody FW1 sequence

```
<400> SEQUENCE: 29

Gln Val Gln Leu Val Glu Ser Gly Gly Gly Thr Val Gln Pro Gly Gly
1               5                   10                  15

Ser Leu Asn Leu Ser Cys Val Ala Ser Gly Asn Thr Phe Asn
            20                  25                  30

<210> SEQ ID NO 30
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 30

Glu Val Gln Leu Val Glu Ser Gly Gly Gly Leu Ala Gln Pro Gly Gly
1               5                   10                  15

Ser Leu Gln Leu Ser Cys Ser Ala Pro Gly Phe Thr Leu Asp
            20                  25                  30

<210> SEQ ID NO 31
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 31

Ala Gln Glu Leu Glu Glu Ser Gly Gly Gly Leu Val Gln Ala Gly Gly
1               5                   10                  15

Ser Leu Arg Leu Ser Cys Ala Ala Ser Gly Arg Thr Phe Asn
            20                  25                  30

<210> SEQ ID NO 32
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 32

Val Glu Ser Gly Gly Gly Leu Val Gln Pro Gly Gly Ser Leu Arg Leu
1               5                   10                  15

Ser Cys Ala Ala Ser Gly
            20

<210> SEQ ID NO 33
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 33

Val Asp Ser Gly Gly Gly Leu Val Gln Ala Gly Asp Ser Leu Lys Leu
1               5                   10                  15

Ser Cys Ala Leu Thr Gly
            20

<210> SEQ ID NO 34
<211> LENGTH: 22
<212> TYPE: PRT
<213> ORGANISM: Artificial
<220> FEATURE:
<223> OTHER INFORMATION: KERE-class Nanobody FW1 sequence
```

<400> SEQUENCE: 34

Val Asp Ser Gly Gly Gly Leu Val Gln Ala Gly Asp Ser Leu Arg Leu
1               5                   10                  15

Ser Cys Ala Ala Ser Gly
            20

<210> SEQ ID NO 35
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 35

Val Asp Ser Gly Gly Gly Leu Val Glu Ala Gly Gly Ser Leu Arg Leu
1               5                   10                  15

Ser Cys Gln Val Ser Glu
            20

<210> SEQ ID NO 36
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 36

Gln Asp Ser Gly Gly Gly Ser Val Gln Ala Gly Gly Ser Leu Lys Leu
1               5                   10                  15

Ser Cys Ala Ala Ser Gly
            20

<210> SEQ ID NO 37
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 37

Val Gln Ser Gly Gly Arg Leu Val Gln Ala Gly Asp Ser Leu Arg Leu
1               5                   10                  15

Ser Cys Ala Ala Ser Glu
            20

<210> SEQ ID NO 38
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 38

Val Glu Ser Gly Gly Thr Leu Val Gln Ser Gly Asp Ser Leu Lys Leu
1               5                   10                  15

Ser Cys Ala Ser Ser Thr
            20

<210> SEQ ID NO 39
<211> LENGTH: 22
<212> TYPE: PRT
<213> ORGANISM: Artificial
<220> FEATURE:

```
<223> OTHER INFORMATION: KERE-class Nanobody FW1 sequence

<400> SEQUENCE: 39

Met Glu Ser Gly Gly Asp Ser Val Gln Ser Gly Ser Leu Thr Leu
1               5                   10                  15

Ser Cys Val Ala Ser Gly
            20

<210> SEQ ID NO 40
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 40

Gln Ala Ser Gly Gly Gly Leu Val Gln Ala Gly Gly Ser Leu Arg Leu
1               5                   10                  15

Ser Cys Ser Ala Ser Val
            20

<210> SEQ ID NO 41
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 41

Trp Phe Arg Gln Ala Pro Gly Lys Glu Arg Glu Phe Val Ala
1               5                   10

<210> SEQ ID NO 42
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 42

Trp Phe Arg Gln Thr Pro Gly Arg Glu Arg Glu Phe Val Ala
1               5                   10

<210> SEQ ID NO 43
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 43

Trp Tyr Arg Gln Ala Pro Gly Lys Gln Arg Glu Met Val Ala
1               5                   10

<210> SEQ ID NO 44
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 44

Trp Tyr Arg Gln Gly Pro Gly Lys Gln Arg Glu Leu Val Ala
1               5                   10
```

```
<210> SEQ ID NO 45
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 45

Trp Ile Arg Gln Ala Pro Gly Lys Glu Arg Glu Gly Val Ser
1               5                   10

<210> SEQ ID NO 46
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 46

Trp Phe Arg Glu Ala Pro Gly Lys Arg Glu Gly Ile Ser
1               5                   10

<210> SEQ ID NO 47
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 47

Trp Tyr Arg Gln Ala Pro Gly Lys Glu Arg Asp Leu Val Ala
1               5                   10

<210> SEQ ID NO 48
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 48

Trp Phe Arg Gln Ala Pro Gly Lys Gln Arg Glu Glu Val Ser
1               5                   10

<210> SEQ ID NO 49
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 49

Trp Phe Arg Gln Pro Pro Gly Lys Val Arg Glu Phe Val Gly
1               5                   10

<210> SEQ ID NO 50
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 50

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Arg Cys Tyr Phe
                20                  25                  30
```

<210> SEQ ID NO 51
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 51

Arg Phe Ala Ile Ser Arg Asp Asn Asn Lys Asn Thr Gly Tyr Leu Gln
1               5                   10                  15

Met Asn Ser Leu Glu Pro Glu Asp Thr Ala Val Tyr Tyr Cys Ala Ala
            20                  25                  30

<210> SEQ ID NO 52
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 52

Arg Phe Thr Val Ala Arg Asn Asn Ala Lys Asn Thr Val Asn Leu Glu
1               5                   10                  15

Met Asn Ser Leu Lys Pro Glu Asp Thr Ala Val Tyr Tyr Cys Ala Ala
            20                  25                  30

<210> SEQ ID NO 53
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 53

Arg Phe Thr Ile Ser Arg Asp Ile Ala Lys Asn Thr Val Asp Leu Leu
1               5                   10                  15

Met Asn Asn Leu Glu Pro Glu Asp Thr Ala Val Tyr Tyr Cys Ala Ala
            20                  25                  30

<210> SEQ ID NO 54
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 54

Arg Leu Thr Ile Ser Arg Asp Asn Ala Val Asp Thr Met Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 55
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 55

Arg Phe Thr Ile Ser Arg Asp Asn Ala Lys Asn Thr Val Tyr Leu Gln
1               5                   10                  15

Met Asp Asn Val Lys Pro Glu Asp Thr Ala Ile Tyr Tyr Cys Ala Ala

<210> SEQ ID NO 56
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 56

Arg Phe Thr Ile Ser Lys Asp Ser Gly Lys Asn Thr Val Tyr Leu Gln
1               5                   10                  15

Met Thr Ser Leu Lys Pro Glu Asp Thr Ala Val Tyr Tyr Cys Ala Thr
            20                  25                  30

<210> SEQ ID NO 57
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 57

Arg Phe Thr Ile Ser Arg Asp Ser Ala Lys Asn Met Met Tyr Leu Gln
1               5                   10                  15

Met Asn Asn Leu Lys Pro Gln Asp Thr Ala Val Tyr Tyr Cys Ala Ala
            20                  25                  30

<210> SEQ ID NO 58
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 58

Arg Phe Thr Ile Ser Arg Glu Asn Asp Lys Ser Thr Val Tyr Leu Gln
1               5                   10                  15

Leu Asn Ser Leu Lys Pro Glu Asp Thr Ala Val Tyr Tyr Cys Ala Ala
            20                  25                  30

<210> SEQ ID NO 59
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 59

Arg Phe Thr Ile Ser Arg Asp Tyr Ala Gly Asn Thr Ala Tyr Leu Gln
1               5                   10                  15

Met Asn Ser Leu Lys Pro Glu Asp Thr Gly Val Tyr Tyr Cys Ala Thr
            20                  25                  30

<210> SEQ ID NO 60
<211> LENGTH: 11
<212> TYPE: PRT
<213> ORGANISM: Artificial
<220> FEATURE:
<223> OTHER INFORMATION: KERE-class Nanobody FW4 sequence

<400> SEQUENCE: 60

Trp Gly Gln Gly Thr Gln Val Thr Val Ser Ser
1               5                   10

```
<210> SEQ ID NO 61
<211> LENGTH: 11
<212> TYPE: PRT
<213> ORGANISM: Artificial
<220> FEATURE:
<223> OTHER INFORMATION: KERE-class Nanobody FW4 sequence

<400> SEQUENCE: 61

Trp Gly Lys Gly Thr Leu Val Thr Val Ser Ser
1               5                   10

<210> SEQ ID NO 62
<211> LENGTH: 11
<212> TYPE: PRT
<213> ORGANISM: Artificial
<220> FEATURE:
<223> OTHER INFORMATION: KERE-class Nanobody FW4 sequence

<400> SEQUENCE: 62

Arg Gly Gln Gly Thr Arg Val Thr Val Ser Ser
1               5                   10

<210> SEQ ID NO 63
<211> LENGTH: 11
<212> TYPE: PRT
<213> ORGANISM: Artificial
<220> FEATURE:
<223> OTHER INFORMATION: KERE-class Nanobody FW4 sequence

<400> SEQUENCE: 63

Trp Gly Leu Gly Thr Gln Val Thr Ile Ser Ser
1               5                   10

<210> SEQ ID NO 64
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 64

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 65
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 65

Glu Val His Leu Val Glu Ser Gly Gly Gly Leu Val Arg Pro Gly Gly
1               5                   10                  15

Ser Leu Arg Leu Ser Cys Ala Ala Phe Gly Phe Ile Phe Lys
            20                  25                  30

<210> SEQ ID NO 66
<211> LENGTH: 30
<212> TYPE: PRT
<213> ORGANISM: Artificial
<220> FEATURE:
<223> OTHER INFORMATION: GLEW-class Nanobody FW1 sequence
```

```
<400> SEQUENCE: 66

Gln Val Lys Leu Glu Glu Ser Gly Gly Gly Leu Ala Gln Pro Gly Gly
1               5                   10                  15

Ser Leu Arg Leu Ser Cys Val Ala Ser Gly Phe Thr Phe Ser
            20                  25                  30

<210> SEQ ID NO 67
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr
            20                  25                  30

<210> SEQ ID NO 68
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 68

Glu Val Gln Leu Val Glu Ser Gly Gly Gly Leu Ala Leu Pro Gly Gly
1               5                   10                  15

Ser Leu Thr Leu Ser Cys Val Phe Ser Gly Ser Thr Phe Ser
            20                  25                  30

<210> SEQ ID NO 69
<211> LENGTH: 22
<212> TYPE: PRT
<213> ORGANISM: Artificial
<220> FEATURE:
<223> OTHER INFORMATION: GLEW-class Nanobody FW1 sequence

<400> SEQUENCE: 69

Val Glu Ser Gly Gly Gly Leu Val Gln Pro Gly Gly Ser Leu Arg Leu
1               5                   10                  15

Ser Cys Ala Ala Ser Gly
            20

<210> SEQ ID NO 70
<211> LENGTH: 22
<212> TYPE: PRT
<213> ORGANISM: Artificial
<220> FEATURE:
<223> OTHER INFORMATION: GLEW-class Nanobody FW1 sequence

<400> SEQUENCE: 70

Glu Glu Ser Gly Gly Gly Leu Ala Gln Pro Gly Gly Ser Leu Arg Leu
1               5                   10                  15

Ser Cys Val Ala Ser Gly
            20

<210> SEQ ID NO 71
<211> LENGTH: 22
<212> TYPE: PRT
<213> ORGANISM: Artificial
<220> FEATURE:
<223> OTHER INFORMATION: GLEW-class Nanobody FW1 sequence
```

<400> SEQUENCE: 71

Val Glu Ser Gly Gly Gly Leu Ala Leu Pro Gly Gly Ser Leu Thr Leu
1               5                   10                  15

Ser Cys Val Phe Ser Gly
            20

<210> SEQ ID NO 72
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 72

Trp Val Arg Gln Ala Pro Gly Lys Val Leu Glu Trp Val Ser
1               5                   10

<210> SEQ ID NO 73
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 73

Trp Val Arg Arg Pro Pro Gly Lys Gly Leu Glu Trp Val Ser
1               5                   10

<210> SEQ ID NO 74
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 74

Trp Val Arg Gln Ala Pro Gly Met Gly Leu Glu Trp Val Ser
1               5                   10

<210> SEQ ID NO 75
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 75

Trp Val Arg Gln Ala Pro Gly Lys Glu Pro Glu Trp Val Ser
1               5                   10

<210> SEQ ID NO 76
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 76

Trp Val Arg Gln Ala Pro Gly Lys Asp Gln Glu Trp Val Ser
1               5                   10

<210> SEQ ID NO 77
<211> LENGTH: 14
<212> TYPE: PRT
<213> ORGANISM: Artificial

```
<220> FEATURE:
<223> OTHER INFORMATION: GLEW-class Nanobody FW2 sequence

<400> SEQUENCE: 77

Trp Val Arg Gln Ala Pro Gly Lys Ala Glu Glu Trp Val Ser
1               5                   10

<210> SEQ ID NO 78
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 78

Trp Val Arg Gln Ala Pro Gly Lys Gly Leu Glu Trp Val Ala
1               5                   10

<210> SEQ ID NO 79
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 79

Trp Val Arg Gln Ala Pro Gly Arg Ala Thr Glu Trp Val Ser
1               5                   10

<210> SEQ ID NO 80
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 80

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Val Lys
            20                  25                  30

<210> SEQ ID NO 81
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 81

Arg Phe Thr Ile Ser Arg Asp Asn Ala Arg Asn Thr Leu Tyr Leu Gln
1               5                   10                  15

Met Asp Ser Leu Ile Pro Glu Asp Thr Ala Leu Tyr Tyr Cys Ala Arg
            20                  25                  30

<210> SEQ ID NO 82
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 82

Arg Phe Thr Ser Ser Arg Asp Asn Ala Lys Ser Thr Leu Tyr Leu Gln
1               5                   10                  15
```

```
Met Asn Asp Leu Lys Pro Glu Asp Thr Ala Leu Tyr Tyr Cys Ala Arg
            20                  25                  30
```

<210> SEQ ID NO 83
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 83

```
Arg Phe Ile Ile Ser Arg Asp Asn Ala Lys Asn Thr Leu Tyr Leu Gln
 1               5                  10                  15
Met Asn Ser Leu Gly Pro Glu Asp Thr Ala Met Tyr Tyr Cys Gln Arg
            20                  25                  30
```

<210> SEQ ID NO 84
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 84

```
Arg Phe Thr Ala Ser Arg Asp Asn Ala Lys Asn Thr Leu Tyr Leu Gln
 1               5                  10                  15
Met Asn Ser Leu Lys Ser Glu Asp Thr Ala Arg Tyr Tyr Cys Ala Arg
            20                  25                  30
```

<210> SEQ ID NO 85
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 85

```
Arg Phe Thr Ile Ser Arg Asp Asn Ala Lys Asn Thr Leu Tyr Leu Gln
 1               5                  10                  15
Met Asp Asp Leu Gln Ser Glu Asp Thr Ala Met Tyr Tyr Cys Gly Arg
            20                  25                  30
```

<210> SEQ ID NO 86
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 86

```
Gly Ser Gln Gly Thr Gln Val Thr Val Ser Ser
 1               5                  10
```

<210> SEQ ID NO 87
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 87

```
Leu Arg Gly Gly Thr Gln Val Thr Val Ser Ser
 1               5                  10
```

<210> SEQ ID NO 88

-continued

```
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 88

Arg Gly Gln Gly Thr Leu Val Thr Val Ser Ser
1               5                   10

<210> SEQ ID NO 89
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 89

Arg Ser Arg Gly Ile Gln Val Thr Val Ser Ser
1               5                   10

<210> SEQ ID NO 90
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 90

Trp Gly Lys Gly Thr Gln Val Thr Val Ser Ser
1               5                   10

<210> SEQ ID NO 91
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 91

Trp Gly Gln Gly Thr Gln Val Thr Val Ser Ser
1               5                   10

<210> SEQ ID NO 92
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 92

Ala Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser
            20                  25                  30

<210> SEQ ID NO 93
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 93

Gln Val Gln Leu Gln Glu Ser Gly Gly Gly Met Val Gln Pro Gly Gly
1               5                   10                  15
```

```
Ser Leu Arg Leu Ser Cys Ala Ala Ser Gly Phe Asp Phe Gly
            20                  25                  30
```

<210> SEQ ID NO 94
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 94

```
Glu Val His Leu Val Glu Ser Gly Gly Gly Leu Val Arg Pro Gly Gly
1               5                   10                  15

Ser Leu Arg Leu Ser Cys Ala Ala Phe Gly Phe Ile Phe Lys
            20                  25                  30
```

<210> SEQ ID NO 95
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 95

```
Gln Val Gln Leu Ala Glu Ser Gly Gly Gly Leu Val Gln Pro Gly Gly
1               5                   10                  15

Ser Leu Lys Leu Ser Cys Ala Ala Ser Arg Thr Ile Val Ser
            20                  25                  30
```

<210> SEQ ID NO 96
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 96

```
Gln Glu His Leu Val Glu Ser Gly Gly Gly Leu Val Asp Ile Gly Gly
1               5                   10                  15

Ser Leu Arg Leu Ser Cys Ala Ala Ser Glu Arg Ile Phe Ser
            20                  25                  30
```

<210> SEQ ID NO 97
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 97

```
Gln Val Lys Leu Glu Glu Ser Gly Gly Gly Leu Ala Gln Pro Gly Gly
1               5                   10                  15

Ser Leu Arg Leu Ser Cys Val Ala Ser Gly Phe Thr Phe Ser
            20                  25                  30
```

<210> SEQ ID NO 98
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 98

```
Glu Val Gln Leu Val Glu Ser Gly Gly Gly Leu Val Gln Pro Gly Gly
1               5                   10                  15
```

```
Ser Leu Arg Leu Ser Cys Val Cys Val Ser Ser Gly Cys Thr
            20                  25                  30

<210> SEQ ID NO 99
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 99

Glu Val Gln Leu Val Glu Ser Gly Gly Gly Leu Ala Leu Pro Gly Gly
1               5                   10                  15

Ser Leu Thr Leu Ser Cys Val Phe Ser Gly Ser Thr Phe Ser
            20                  25                  30

<210> SEQ ID NO 100
<211> LENGTH: 22
<212> TYPE: PRT
<213> ORGANISM: Artificial
<220> FEATURE:
<223> OTHER INFORMATION: P,R,S 103-class Nanobody FW1 sequence

<400> SEQUENCE: 100

Val Glu Ser Gly Gly Gly Leu Val Gln Ala Gly Gly Ser Leu Arg Leu
1               5                   10                  15

Ser Cys Ala Ala Ser Gly
            20

<210> SEQ ID NO 101
<211> LENGTH: 22
<212> TYPE: PRT
<213> ORGANISM: Artificial
<220> FEATURE:
<223> OTHER INFORMATION: P,R,S 103-class Nanobody FW1 sequence

<400> SEQUENCE: 101

Ala Glu Ser Gly Gly Gly Leu Val Gln Pro Gly Gly Ser Leu Lys Leu
1               5                   10                  15

Ser Cys Ala Ala Ser Arg
            20

<210> SEQ ID NO 102
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 102

Trp Phe Arg Gln Ala Pro Gly Lys Glu Arg Glu Phe Val Ala
1               5                   10

<210> SEQ ID NO 103
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 103

Trp Val Arg Gln Ala Pro Gly Lys Val Leu Glu Trp Val Ser
1               5                   10
```

```
<210> SEQ ID NO 104
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 104

Trp Val Arg Arg Pro Pro Gly Lys Gly Leu Glu Trp Val Ser
1               5                   10

<210> SEQ ID NO 105
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 105

Trp Ile Arg Gln Ala Pro Gly Lys Glu Arg Glu Gly Val Ser
1               5                   10

<210> SEQ ID NO 106
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 106

Trp Val Arg Gln Tyr Pro Gly Lys Glu Pro Glu Trp Val Ser
1               5                   10

<210> SEQ ID NO 107
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 107

Trp Phe Arg Gln Pro Pro Gly Lys Glu His Glu Phe Val Ala
1               5                   10

<210> SEQ ID NO 108
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 108

Trp Tyr Arg Gln Ala Pro Gly Lys Arg Thr Glu Leu Val Ala
1               5                   10

<210> SEQ ID NO 109
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 109

Trp Leu Arg Gln Ala Pro Gly Gln Gly Leu Glu Trp Val Ser
1               5                   10

<210> SEQ ID NO 110
```

```
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 110

Trp Leu Arg Gln Thr Pro Gly Lys Gly Leu Glu Trp Val Gly
1               5                   10

<210> SEQ ID NO 111
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 111

Trp Val Arg Gln Ala Pro Gly Lys Ala Glu Glu Phe Val Ser
1               5                   10

<210> SEQ ID NO 112
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 112

Arg Phe Thr Ile Ser Arg Asp Asn Ala Lys Asn Thr Val Tyr Leu Gln
1               5                   10                  15
Met Asn Ser Leu Lys Pro Glu Asp Thr Ala Val Tyr Tyr Cys Ala Ala
            20                  25                  30

<210> SEQ ID NO 113
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 113

Arg Phe Thr Ile Ser Arg Asp Asn Ala Arg Asn Thr Leu Tyr Leu Gln
1               5                   10                  15
Met Asp Ser Leu Ile Pro Glu Asp Thr Ala Leu Tyr Tyr Cys Ala Arg
            20                  25                  30

<210> SEQ ID NO 114
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 114

Arg Phe Thr Ile Ser Arg Asp Asn Ala Lys Asn Glu Met Tyr Leu Gln
1               5                   10                  15
Met Asn Asn Leu Lys Thr Glu Asp Thr Gly Val Tyr Trp Cys Gly Ala
            20                  25                  30

<210> SEQ ID NO 115
<211> LENGTH: 32
<212> TYPE: PRT
<213> ORGANISM: Artificial
<220> FEATURE:
<223> OTHER INFORMATION: P,R,S 103-class Nanobody FW3 sequence
```

```
<400> SEQUENCE: 115

Arg Phe Thr Ile Ser Ser Asp Ser Asn Arg Asn Met Ile Tyr Leu Gln
1               5                   10                  15

Met Asn Asn Leu Lys Pro Glu Asp Thr Ala Val Tyr Tyr Cys Ala Ala
            20                  25                  30

<210> SEQ ID NO 116
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 116

Arg Phe Thr Ile Ser Arg Asp Asn Ala Lys Asn Met Leu Tyr Leu His
1               5                   10                  15

Leu Asn Asn Leu Lys Ser Glu Asp Thr Ala Val Tyr Tyr Cys Arg Arg
            20                  25                  30

<210> SEQ ID NO 117
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 117

Arg Phe Thr Ile Ser Arg Asp Asn Ala Lys Lys Thr Val Tyr Leu Arg
1               5                   10                  15

Leu Asn Ser Leu Asn Pro Glu Asp Thr Ala Val Tyr Ser Cys Asn Leu
            20                  25                  30

<210> SEQ ID NO 118
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 118

Arg Phe Lys Ile Ser Arg Asp Asn Ala Lys Lys Thr Leu Tyr Leu Gln
1               5                   10                  15

Met Asn Ser Leu Gly Pro Glu Asp Thr Ala Met Tyr Tyr Cys Gln Arg
            20                  25                  30

<210> SEQ ID NO 119
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 119

Arg Phe Thr Val Ser Arg Asp Asn Gly Lys Asn Thr Ala Tyr Leu Arg
1               5                   10                  15

Met Asn Ser Leu Lys Pro Glu Asp Thr Ala Asp Tyr Tyr Cys Ala Val
            20                  25                  30

<210> SEQ ID NO 120
<211> LENGTH: 11
<212> TYPE: PRT
<213> ORGANISM: Artificial
<220> FEATURE:
```

```
<223> OTHER INFORMATION: P,R,S 103-class Nanobody FW4 sequence

<400> SEQUENCE: 120

Arg Gly Gln Gly Thr Gln Val Thr Val Ser Ser
1               5                   10

<210> SEQ ID NO 121
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 121

Leu Arg Gly Gly Thr Gln Val Thr Val Ser Ser
1               5                   10

<210> SEQ ID NO 122
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 122

Gly Asn Lys Gly Thr Leu Val Thr Val Ser Ser
1               5                   10

<210> SEQ ID NO 123
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 123

Ser Ser Pro Gly Thr Gln Val Thr Val Ser Ser
1               5                   10

<210> SEQ ID NO 124
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 124

Ser Ser Gln Gly Thr Leu Val Thr Val Ser Ser
1               5                   10

<210> SEQ ID NO 125
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 125

Arg Ser Arg Gly Ile Gln Val Thr Val Ser Ser
1               5                   10

<210> SEQ ID NO 126
<211> LENGTH: 30
<212> TYPE: PRT
<213> ORGANISM: Artificial
<220> FEATURE:
<223> OTHER INFORMATION: Nanobody or Nanobody construct
```

<400> SEQUENCE: 126

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser
            20                  25                  30

<210> SEQ ID NO 127
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp
            20                  25                  30

<210> SEQ ID NO 128
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 128

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp
            20                  25                  30

<210> SEQ ID NO 129
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 129

Glu Val Gln Leu Val Glu Ser Gly Gly Gly Leu Val Gln Ala Gly Asp
1               5                   10                  15

Ser Leu Arg Leu Ser Cys Thr Thr Ser Gly Arg Thr Phe Ser
            20                  25                  30

<210> SEQ ID NO 130
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp
            20                  25                  30

<210> SEQ ID NO 131
<211> LENGTH: 30
<212> TYPE: PRT
<213> ORGANISM: Artificial
<220> FEATURE:

<223> OTHER INFORMATION: Nanobody or Nanobody construct

<400> SEQUENCE: 131

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 132
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 132

Glu Val Gln Leu Val Glu Ser Gly Gly Gly Leu Val Gln Pro Gly Asp
1               5                   10                  15

Ser Leu Arg Leu Ser Cys Ala Ala Ser Gly Phe Thr Phe Gly
            20                  25                  30

<210> SEQ ID NO 133
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly
            20                  25                  30

<210> SEQ ID NO 134
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly
            20                  25                  30

<210> SEQ ID NO 135
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 135

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Gly
            20                  25                  30

<210> SEQ ID NO 136
<211> LENGTH: 30
<212> TYPE: PRT
<213> ORGANISM: Artificial

```
<220> FEATURE:
<223> OTHER INFORMATION: Nanobody or Nanobody construct

<400> SEQUENCE: 136

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Gly
            20                  25                  30

<210> SEQ ID NO 137
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 137

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser
            20                  25                  30

<210> SEQ ID NO 138
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 138

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Gly
            20                  25                  30

<210> SEQ ID NO 139
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 139

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser
            20                  25                  30

<210> SEQ ID NO 140
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 140

Glu Val Gln Leu Val Glu Ser Gly Gly Asp Leu Val Gln Ala Gly Gly
1               5                   10                  15

Ser Leu Arg Leu Ser Cys Ala Ala Ser Gly Phe Thr Phe Gly
            20                  25                  30

<210> SEQ ID NO 141
<211> LENGTH: 30
<212> TYPE: PRT
```

```
<213> ORGANISM: Artificial
<220> FEATURE:
<223> OTHER INFORMATION: Nanobody or Nanobody construct

<400> SEQUENCE: 141

Lys Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Gly
            20                  25                  30

<210> SEQ ID NO 142
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 142

Glu Val Gln Leu Val Glu Ser Gly Gly Gly Leu Val Gln Ala Gly Gly
1               5                   10                  15

Ser Leu Arg Leu Ser Cys Val Ala Ser Gly Arg Ile Phe Thr
            20                  25                  30

<210> SEQ ID NO 143
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser
            20                  25                  30

<210> SEQ ID NO 144
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 144

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 145
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp
            20                  25                  30

<210> SEQ ID NO 146
<211> LENGTH: 30
```

```
<212> TYPE: PRT
<213> ORGANISM: Artificial
<220> FEATURE:
<223> OTHER INFORMATION: Nanobody or Nanobody construct

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser
            20                  25                  30

<210> SEQ ID NO 147
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser
            20                  25                  30

<210> SEQ ID NO 148
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 148

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Leu Asp
            20                  25                  30

<210> SEQ ID NO 149
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser
            20                  25                  30

<210> SEQ ID NO 150
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 150

Glu Val Gln Leu Val Glu Ser Gly Gly Gly Leu Val Gln Pro Gly Gly
1               5                   10                  15

Ser Leu Arg Leu Ser Cys Val Ala Ser Gly Ser Ile Arg Ser
            20                  25                  30

<210> SEQ ID NO 151
```

```
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 151

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser
            20                  25                  30

<210> SEQ ID NO 152
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 152

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Arg Ser
            20                  25                  30

<210> SEQ ID NO 153
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 153

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser
            20                  25                  30

<210> SEQ ID NO 154
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 154

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser
            20                  25                  30

<210> SEQ ID NO 155
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 155

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser
            20                  25                  30
```

```
<210> SEQ ID NO 156
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 156

Glu Val Gln Leu Val Glu Ser Gly Gly Gly Leu Val Gln Ala Gly Gly
1               5                   10                  15

Ser Leu Arg Leu Ser Cys Ala Ala Ser Glu Ser Ile Phe Ser
            20                  25                  30

<210> SEQ ID NO 157
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 157

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 158
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 158

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ser Ser
            20                  25                  30

<210> SEQ ID NO 159
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 159

Glu Val Gln Leu Val Glu Ser Gly Gly Gly Leu Val Gln Ala Gly Gly
1               5                   10                  15

Ser Leu Arg Leu Ser Cys Ala Ala Ser Gly Ile Phe Ile Ile
            20                  25                  30

<210> SEQ ID NO 160
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 160

Glu Val Gln Leu Val Glu Ser Gly Gly Gly Leu Ala Gln Ala Gly Gly
1               5                   10                  15

Ser Leu Arg Leu Ser Cys Ala Ala Ser Gly Ser Ile Ser Ser
            20                  25                  30
```

<210> SEQ ID NO 161
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 161

Glu Val Gln Leu Val Glu Ser Gly Gly Gly Gln Val Gln Ala Gly Asp
1               5                   10                  15

Ser Leu Arg Leu Ser Cys Lys Ala Ser Arg Arg Thr Ile Ser
            20                  25                  30

<210> SEQ ID NO 162
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 162

Glu Val Gln Leu Val Glu Ser Gly Gly Gly Gln Val Gln Ala Gly Asp
1               5                   10                  15

Ser Leu Arg Leu Ser Cys Lys Ala Ser Arg Arg Thr Ile Ser
            20                  25                  30

<210> SEQ ID NO 163
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 163

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser
            20                  25                  30

<210> SEQ ID NO 164
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 164

Glu Val Gln Leu Val Glu Ser Gly Gly Gly Leu Val Gln Ala Gly Gly
1               5                   10                  15

Ser Leu Arg Leu Ser Cys Ala Ala Ser Val Leu Thr Phe Gly
            20                  25                  30

<210> SEQ ID NO 165
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 165

Glu Val Gln Leu Val Glu Ser Gly Gly Gly Leu Val Gln Ala Gly Ala
1               5                   10                  15

Ser Leu Arg Leu Ser Cys Val Asp Ser Gly Asp Thr Phe Ser
            20                  25                  30

<210> SEQ ID NO 166
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 166

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser
            20                  25                  30

<210> SEQ ID NO 167
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 167

Glu Val Gln Leu Val Glu Ser Gly Gly Gly Leu Val Gln Thr Gly Gly
1               5                   10                  15

Ser Leu Arg Leu Ser Cys Ala Ala Ser Gly Arg Ser Phe Asn
            20                  25                  30

<210> SEQ ID NO 168
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 168

Glu Val Gln Leu Val Glu Ser Gly Gly Gly Leu Val Gln Ala Gly Gly
1               5                   10                  15

Ser Leu Arg Leu Ser Cys Thr Ala Ser Gly Leu Thr Phe Ser
            20                  25                  30

<210> SEQ ID NO 169
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 169

Glu Val Gln Leu Val Glu Ser Gly Gly Gly Leu Val Gln Ala Gly Gly
1               5                   10                  15

Ser Leu Arg Leu Ser Cys Val Ala Ser Gly Asp Thr Phe Asn
            20                  25                  30

<210> SEQ ID NO 170
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 170

Glu Val Gln Leu Val Glu Ser Gly Gly Gly Leu Val Gln Ala Gly Gly
1               5                   10                  15

Ser Leu Arg Leu Ser Cys Ala Ala Ser Glu Thr Ile Phe Ala

```
            20                  25                  30

<210> SEQ ID NO 171
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 171

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Pro Phe Ser
            20                  25                  30

<210> SEQ ID NO 172
<211> LENGTH: 30
<212> TYPE: PRT
<213> ORGANISM: Artificial
<220> FEATURE:
<223> OTHER INFORMATION: Nanobody or Nanobody construct

<400> SEQUENCE: 172

Glu Val Gln Leu Val Glu Ser Gly Gly Gly Gln Val Gln Ala Gly Asp
1               5                   10                  15

Ser Leu Arg Leu Ser Cys Lys Ala Ser Arg Arg Thr Ile Ser
            20                  25                  30

<210> SEQ ID NO 173
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 173

Ile Asn Ala Met Gly
1               5

<210> SEQ ID NO 174
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 174

Asp Tyr Ala Ile Gly
1               5

<210> SEQ ID NO 175
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 175

Asp Tyr Ala Ile Gly
1               5

<210> SEQ ID NO 176
<211> LENGTH: 5
<212> TYPE: PRT
<213> ORGANISM: Artificial
<220> FEATURE:
```

```
<223> OTHER INFORMATION: Nanobody or Nanobody construct

<400> SEQUENCE: 176

Asp Asp Thr Met Gly
1               5

<210> SEQ ID NO 177
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 177

Asp Tyr Ala Val Gly
1               5

<210> SEQ ID NO 178
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 178

Asp Tyr Ser Met Ser
1               5

<210> SEQ ID NO 179
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 179

Ser Asn Gly Met Arg
1               5

<210> SEQ ID NO 180
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 180

Ser Asn Gly Met Arg
1               5

<210> SEQ ID NO 181
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 181

Ser Asn Gly Met Arg
1               5

<210> SEQ ID NO 182
<211> LENGTH: 5
<212> TYPE: PRT
<213> ORGANISM: Artificial
<220> FEATURE:
<223> OTHER INFORMATION: Nanobody or Nanobody construct
```

<400> SEQUENCE: 182

Ser Thr Thr Ile Gly
1               5

<210> SEQ ID NO 183
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 183

Thr Thr Thr Ile Gly
1               5

<210> SEQ ID NO 184
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 184

Asp Thr Thr Ile Gly
1               5

<210> SEQ ID NO 185
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 185

Thr Thr Thr Ile Gly
1               5

<210> SEQ ID NO 186
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 186

Asp Thr Thr Ile Gly
1               5

<210> SEQ ID NO 187
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 187

Asp Phe Thr Ile Gly
1               5

<210> SEQ ID NO 188
<211> LENGTH: 5
<212> TYPE: PRT
<213> ORGANISM: Artificial
<220> FEATURE:
<223> OTHER INFORMATION: Nanobody or Nanobody construct

```
<400> SEQUENCE: 188

Ser Thr Thr Ile Gly
1               5

<210> SEQ ID NO 189
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 189

Asn Thr Ala Met Gly
1               5

<210> SEQ ID NO 190
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 190

Gly Asn Trp Met Tyr
1               5

<210> SEQ ID NO 191
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 191

Asn Tyr Ala Met Thr
1               5

<210> SEQ ID NO 192
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 192

Tyr Tyr Ala Ile Gly
1               5

<210> SEQ ID NO 193
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 193

Gly Asn Trp Met Tyr
1               5

<210> SEQ ID NO 194
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 194
```

```
Ser Asn Trp Met Tyr
1               5

<210> SEQ ID NO 195
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 195

Tyr Tyr Ala Ile Gly
1               5

<210> SEQ ID NO 196
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 196

Pro Ser Trp Met Tyr
1               5

<210> SEQ ID NO 197
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 197

Ile Ile His Met Gly
1               5

<210> SEQ ID NO 198
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 198

Ile Asn Ala Met Gly
1               5

<210> SEQ ID NO 199
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 199

Ile Ile His Met Gly
1               5

<210> SEQ ID NO 200
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 200
```

Thr Ser Trp Met Tyr
1               5

<210> SEQ ID NO 201
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 201

Ile Asn Thr Met Gly
1               5

<210> SEQ ID NO 202
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 202

Thr Ser Trp Met Tyr
1               5

<210> SEQ ID NO 203
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 203

Leu Tyr Val Thr Gly
1               5

<210> SEQ ID NO 204
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 204

Leu Asn Ala Met Thr
1               5

<210> SEQ ID NO 205
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 205

Ile Asn Val Met Gly
1               5

<210> SEQ ID NO 206
<211> LENGTH: 4
<212> TYPE: PRT
<213> ORGANISM: Artificial
<220> FEATURE:
<223> OTHER INFORMATION: Nanobody or Nanobody construct

<400> SEQUENCE: 206

Asp Thr Met Gly

```
<210> SEQ ID NO 207
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 207

Ile Asn Val Met Gly
1               5

<210> SEQ ID NO 208
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 208

Thr Tyr Gly Met Gly
1               5

<210> SEQ ID NO 209
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 209

Thr Tyr Gly Met Gly
1               5

<210> SEQ ID NO 210
<211> LENGTH: 8
<212> TYPE: PRT
<213> ORGANISM: Artificial
<220> FEATURE:
<223> OTHER INFORMATION: Nanobody or Nanobody construct

<400> SEQUENCE: 210

Thr Phe Asn Thr Tyr Ser Met Gly
1               5

<210> SEQ ID NO 211
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 211

Thr Tyr Thr Val Gly
1               5

<210> SEQ ID NO 212
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 212

Trp Tyr Ala Met Gly
1               5
```

```
<210> SEQ ID NO 213
<211> LENGTH: 8
<212> TYPE: PRT
<213> ORGANISM: Artificial
<220> FEATURE:
<223> OTHER INFORMATION: Nanobody or Nanobody construct

<400> SEQUENCE: 213

Thr Phe Asn Thr Tyr Ser Met Gly
1               5

<210> SEQ ID NO 214
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 214

Leu Tyr Tyr Met Gly
1               5

<210> SEQ ID NO 215
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 215

Met Tyr Ala Met Ala
1               5

<210> SEQ ID NO 216
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 216

Trp Tyr Ala Met Gly
1               5

<210> SEQ ID NO 217
<211> LENGTH: 4
<212> TYPE: PRT
<213> ORGANISM: Artificial
<220> FEATURE:
<223> OTHER INFORMATION: Nanobody or Nanobody construct

<400> SEQUENCE: 217

Ser Ala Met Gly
1

<210> SEQ ID NO 218
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 218

Met Tyr Ala Met Gly
1               5
```

<210> SEQ ID NO 219
<211> LENGTH: 5
<212> TYPE: PRT
<213> ORGANISM: Artificial
<220> FEATURE:
<223> OTHER INFORMATION: Nanobody or Nanobody construct

<400> SEQUENCE: 219

Thr Tyr Gly Met Gly
1               5

<210> SEQ ID NO 220
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 220

Trp Tyr Gln Gln Ala Pro Gly Lys Gln Arg Glu Leu Val Ala
1               5                   10

<210> SEQ ID NO 221
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 221

Trp Phe Arg Gln Ala Pro Gly Lys Glu Arg Glu Ala Val Ser
1               5                   10

<210> SEQ ID NO 222
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 222

Trp Phe Arg Gln Ala Pro Gly Lys Glu Arg Glu Gly Val Ala
1               5                   10

<210> SEQ ID NO 223
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 223

Trp Phe Arg Gln Ala Pro Arg Lys Glu Arg Glu Phe Val Ala
1               5                   10

<210> SEQ ID NO 224
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 224

Trp Phe Arg Gln Ala Pro Gly Lys Glu Arg Glu Gly Val Ser
1               5                   10

```
<210> SEQ ID NO 225
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 225

Trp Val Arg Gln Ala Pro Gly Lys Gly Leu Glu Trp Val Ser
1               5                   10

<210> SEQ ID NO 226
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 226

Trp Val Arg Gln Ala Pro Gly Lys Gly Pro Glu Trp Val Ser
1               5                   10

<210> SEQ ID NO 227
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 227

Trp Val Arg Gln Ala Pro Gly Lys Gly Pro Glu Trp Val Ser
1               5                   10

<210> SEQ ID NO 228
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 228

Trp Val Arg Gln Ala Pro Gly Lys Gly Pro Glu Trp Val Ser
1               5                   10

<210> SEQ ID NO 229
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 229

Trp Phe Arg Gln Ala Pro Gly Lys Glu Arg Glu Gly Val Ser
1               5                   10

<210> SEQ ID NO 230
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 230

Trp Phe Arg Gln Ala Pro Gly Lys Glu Arg Glu Gly Val Ser
1               5                   10

<210> SEQ ID NO 231
```

```
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 231

Trp Phe Arg Gln Ala Pro Gly Lys Glu Arg Glu Gly Ile Ser
1               5                   10

<210> SEQ ID NO 232
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 232

Trp Phe Arg Gln Ala Pro Gly Lys Glu Arg Glu Val Val Ser
1               5                   10

<210> SEQ ID NO 233
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 233

Trp Phe Arg Gln Ala Pro Gly Lys Glu Arg Glu Gly Ile Ser
1               5                   10

<210> SEQ ID NO 234
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 234

Trp Phe Arg Gln Ala Pro Gly Lys Glu Arg Glu Gly Val Ser
1               5                   10

<210> SEQ ID NO 235
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 235

Trp Phe Arg Gln Ala Pro Gly Lys Glu Arg Glu Gly Val Ser
1               5                   10

<210> SEQ ID NO 236
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 236

Trp Tyr Arg Gln Ala Pro Gly Lys Trp Arg Glu Leu Val Ala
1               5                   10

<210> SEQ ID NO 237
<211> LENGTH: 14
```

<212> TYPE: PRT
<213> ORGANISM: Artificial
<220> FEATURE:
<223> OTHER INFORMATION: Nanobody or Nanobody construct

<400> SEQUENCE: 237

Trp Leu Arg Gln Ala Pro Gly Lys Gly Leu Glu Trp Ile Ser
1               5                   10

<210> SEQ ID NO 238
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 238

Trp Val Arg Gln Ala Pro Gly Lys Gly Leu Glu Trp Val Ser
1               5                   10

<210> SEQ ID NO 239
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 239

Trp Phe Arg Gln Ala Pro Gly Lys Glu Arg Glu Gly Val Ser
1               5                   10

<210> SEQ ID NO 240
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 240

Trp Leu Arg Gln Ala Pro Gly Lys Gly Leu Glu Trp Ile Ser
1               5                   10

<210> SEQ ID NO 241
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 241

Trp Leu Arg Gln Ala Pro Gly Lys Gly Leu Glu Trp Ile Ser
1               5                   10

<210> SEQ ID NO 242
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 242

Trp Tyr Arg Gln Ala Pro Gly Lys Glu Arg Glu Trp Val Ser
1               5                   10

<210> SEQ ID NO 243
<211> LENGTH: 14
<212> TYPE: PRT

<213> ORGANISM: Artificial
<220> FEATURE:
<223> OTHER INFORMATION: Nanobody or Nanobody construct

<400> SEQUENCE: 243

Trp Leu Arg Gln Ala Pro Gly Lys Gly Leu Glu Trp Val Ser
1               5                   10

<210> SEQ ID NO 244
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 244

Trp Tyr Arg Gln Ala Pro Gly Asn Glu Arg Asp Leu Val Ala
1               5                   10

<210> SEQ ID NO 245
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 245

Trp Tyr Arg Gln Ala Pro Gly Asn Gln Arg Asp Leu Val Ala
1               5                   10

<210> SEQ ID NO 246
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 246

Trp Tyr Arg Gln Thr Pro Gly Asn Glu Arg Asp Met Val Ala
1               5                   10

<210> SEQ ID NO 247
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 247

Trp Leu Arg Gln Ala Pro Gly Lys Gly Leu Glu Trp Val Ser
1               5                   10

<210> SEQ ID NO 248
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 248

Trp Tyr Arg Gln Ala Pro Gly Asn Gln Arg Asp Leu Val Ala
1               5                   10

<210> SEQ ID NO 249
<211> LENGTH: 14
<212> TYPE: PRT
<213> ORGANISM: Artificial

<220> FEATURE:
<223> OTHER INFORMATION: Nanobody or Nanobody construct

<400> SEQUENCE: 249

Trp Leu Arg Gln Ala Pro Gly Lys Gly Leu Glu Trp Val Ser
1               5                   10

<210> SEQ ID NO 250
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 250

Trp Tyr Arg Gln Ala Pro Gly Lys Gln Arg Glu Leu Val Ala
1               5                   10

<210> SEQ ID NO 251
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 251

Trp Val Arg Gln Ala Pro Gly Lys Gly Leu Glu Trp Val Ser
1               5                   10

<210> SEQ ID NO 252
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 252

Trp Tyr Arg Gln Ala Pro Gly Lys Gln Arg Asp Leu Val Ala
1               5                   10

<210> SEQ ID NO 253
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 253

Trp Tyr Arg Gln Ala Pro Gly Lys Gln Arg Glu Leu Val Ala
1               5                   10

<210> SEQ ID NO 254
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 254

Trp Tyr Arg Gln Ala Pro Gly Lys Gln Arg Asp Leu Val Ala
1               5                   10

<210> SEQ ID NO 255
<211> LENGTH: 14
<212> TYPE: PRT
<213> ORGANISM: Artificial
<220> FEATURE:

<223> OTHER INFORMATION: Nanobody or Nanobody construct

<400> SEQUENCE: 255

Trp Phe Arg Gln Ala Pro Gly Asp Lys Arg Asp Leu Val Ser
1               5                   10

<210> SEQ ID NO 256
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 256

Trp Phe Arg Gln Ala Pro Gly Asp Lys Arg Asp Leu Val Ser
1               5                   10

<210> SEQ ID NO 257
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 257

Trp Phe Arg Gln Ala Pro Gly Lys Glu Arg Glu Phe Val Ala
1               5                   10

<210> SEQ ID NO 258
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 258

Trp Phe Arg Gln Ala Pro Gly Lys Glu Arg Glu Phe Val Ser
1               5                   10

<210> SEQ ID NO 259
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 259

Trp Phe Arg Gln Gln Ala Pro Gly Lys Glu Arg Glu Phe Val
1               5                   10

<210> SEQ ID NO 260
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 260

Trp Phe Arg Gln Ala Pro Gly Lys Glu Arg Glu Phe Val Ala
1               5                   10

<210> SEQ ID NO 261
<211> LENGTH: 14
<212> TYPE: PRT
<213> ORGANISM: Artificial
<220> FEATURE:
<223> OTHER INFORMATION: Nanobody or Nanobody construct

```
<400> SEQUENCE: 261

Trp Phe Arg Gln Ala Pro Gly Arg Glu Arg Glu Phe Val Ala
1               5                   10

<210> SEQ ID NO 262
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 262

Trp Ile Arg Leu Ala Pro Gly Lys Glu Arg Glu Val Ile Ala
1               5                   10

<210> SEQ ID NO 263
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 263

Trp Phe Arg Gln Gln Ala Pro Gly Lys Glu Arg Glu Phe Val
1               5                   10

<210> SEQ ID NO 264
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 264

Trp Tyr Arg Gln Pro Pro Gly Lys Gln Arg Glu Leu Val Ala
1               5                   10

<210> SEQ ID NO 265
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 265

Trp Phe Arg Gln Ala Pro Gly Lys Glu Arg Glu Phe Val Thr
1               5                   10

<210> SEQ ID NO 266
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 266

Trp Phe Arg Gln Ala Pro Gly Asp Lys Arg Asp Leu Val Ser
1               5                   10

<210> SEQ ID NO 267
<211> LENGTH: 16
<212> TYPE: PRT
<213> ORGANISM: Artificial
<220> FEATURE:
<223> OTHER INFORMATION: Nanobody or Nanobody construct
```

```
<400> SEQUENCE: 267

Phe Ile Thr Ser Val Gly Thr Thr Asn Tyr Ala Asp Ser Val Lys Gly
1               5                   10                  15

<210> SEQ ID NO 268
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 268

Cys Ile Ser Ser Val Asp Gly Ser Thr His Tyr Ala Asp Ser Val Lys
1               5                   10                  15

Gly

<210> SEQ ID NO 269
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 269

Cys Ile Ser Ser Ser Asp Gly Ser Thr Tyr Tyr Ala Asp Ser Val Lys
1               5                   10                  15

Gly

<210> SEQ ID NO 270
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 270

Ala Ile Leu Trp Asp Ser Ile Lys Thr Tyr Tyr Ala Asp Ser Val Lys
1               5                   10                  15

Gly

<210> SEQ ID NO 271
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 271

Cys Ile Gly Ser Ser Tyr Gly Ser Thr Tyr Tyr Ala Asp Ser Val Lys
1               5                   10                  15

Gly

<210> SEQ ID NO 272
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 272

Ala Ile Ser Gly Gly Gly Glu Val Thr Thr Tyr Ala Asp Ser Val Lys
1               5                   10                  15

Gly
```

```
<210> SEQ ID NO 273
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 273

Ser Ile Asn Ser Asp Gly Thr Ser Thr Tyr Tyr Ala Asp Ser Val Lys
1               5                   10                  15

Gly

<210> SEQ ID NO 274
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 274

Ser Ile Asn Ser Asp Gly Thr Ser Ala Phe Tyr Ala Glu Ser Val Lys
1               5                   10                  15

Gly

<210> SEQ ID NO 275
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 275

Ser Ile Asn Ser Asp Gly Thr Ser Thr Tyr Tyr Ala Glu Ser Val Lys
1               5                   10                  15

Gly

<210> SEQ ID NO 276
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 276

Cys Ile Ser Thr Gly Asp Gly Ser Thr Tyr Tyr Ala Glu Ser Val Lys
1               5                   10                  15

Gly

<210> SEQ ID NO 277
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 277

Cys Ile Ser Thr Gly Asp Gly Ser Thr Asn Tyr Ala Glu Ser Val Lys
1               5                   10                  15

Gly

<210> SEQ ID NO 278
<211> LENGTH: 17
```

```
<212> TYPE: PRT
<213> ORGANISM: Artificial
<220> FEATURE:
<223> OTHER INFORMATION: Nanobody or Nanobody construct

<400> SEQUENCE: 278

Cys Ile Ser Thr Gly Asp Gly Ser Thr Tyr Tyr Ala Glu Ser Val Lys
1               5                   10                  15

Gly

<210> SEQ ID NO 279
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 279

Cys Ile Ser Thr Gly Gly Gly Ser Thr Tyr Tyr Thr Glu Ser Val Lys
1               5                   10                  15

Gly

<210> SEQ ID NO 280
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 280

Cys Ile Ser Thr Gly Asp Gly Ser Thr Tyr Tyr Ala Glu Ser Val Lys
1               5                   10                  15

Gly

<210> SEQ ID NO 281
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 281

Cys Ile Asn Thr Gly Asp Gly Ser Thr Asn Tyr Ala Glu Ser Val Lys
1               5                   10                  15

Gly

<210> SEQ ID NO 282
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 282

Cys Ile Ser Thr Gly Asp Gly Ser Thr Tyr Tyr Ala Glu Ser Val Lys
1               5                   10                  15

Gly

<210> SEQ ID NO 283
<211> LENGTH: 16
<212> TYPE: PRT
<213> ORGANISM: Artificial
<220> FEATURE:
<223> OTHER INFORMATION: Nanobody or Nanobody construct
```

```
<400> SEQUENCE: 283

Thr Ile Tyr Ser Gly Gly Ser Thr Lys Tyr Ile Asp Ser Val Lys Gly
1               5                   10                  15

<210> SEQ ID NO 284
<211> LENGTH: 16
<212> TYPE: PRT
<213> ORGANISM: Artificial
<220> FEATURE:
<223> OTHER INFORMATION: Nanobody or Nanobody construct

<400> SEQUENCE: 284

Thr Ile Thr Pro Arg Gly Leu Thr Ala Tyr Ala Asp Ser Val Lys Gly
1               5                   10                  15

<210> SEQ ID NO 285
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 285

Asp Ile Ser Trp Asp Gly Asp Ile Thr Thr Tyr Ala Ala Ser Val Lys
1               5                   10                  15
Gly

<210> SEQ ID NO 286
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 286

Tyr Ile Ser Ser Ser Asp Gly Arg Thr Tyr Tyr Ala Asp Ser Val Lys
1               5                   10                  15
Gly

<210> SEQ ID NO 287
<211> LENGTH: 16
<212> TYPE: PRT
<213> ORGANISM: Artificial
<220> FEATURE:
<223> OTHER INFORMATION: Nanobody or Nanobody construct

<400> SEQUENCE: 287

Thr Ile Thr Pro Arg Gly Leu Thr Ala Tyr Ala Asp Ser Val Lys Gly
1               5                   10                  15

<210> SEQ ID NO 288
<211> LENGTH: 16
<212> TYPE: PRT
<213> ORGANISM: Artificial
<220> FEATURE:
<223> OTHER INFORMATION: Nanobody or Nanobody construct

<400> SEQUENCE: 288

Thr Ile Thr Pro Arg Asp Leu Thr Ala Tyr Ala Asp Ser Val Lys Gly
1               5                   10                  15

<210> SEQ ID NO 289
<211> LENGTH: 18
<212> TYPE: PRT
```

```
<213> ORGANISM: Artificial
<220> FEATURE:
<223> OTHER INFORMATION: Nanobody or Nanobody construct

<400> SEQUENCE: 289

Cys Ile Ser Ser Ser Asn Tyr Gly Ile Thr Thr Tyr Ala Asp Ser Val
1               5                   10                  15

Lys Gly

<210> SEQ ID NO 290
<211> LENGTH: 16
<212> TYPE: PRT
<213> ORGANISM: Artificial
<220> FEATURE:
<223> OTHER INFORMATION: Nanobody or Nanobody construct

<400> SEQUENCE: 290

Thr Ile Thr Pro Arg Gly Leu Thr Glu Tyr Ala Asn Ser Val Lys Gly
1               5                   10                  15

<210> SEQ ID NO 291
<211> LENGTH: 16
<212> TYPE: PRT
<213> ORGANISM: Artificial
<220> FEATURE:
<223> OTHER INFORMATION: Nanobody or Nanobody construct

<400> SEQUENCE: 291

Val Ile Ile Asp Ser Arg Thr Thr Lys Tyr Ser Glu Ser Val Lys Gly
1               5                   10                  15

<210> SEQ ID NO 292
<211> LENGTH: 16
<212> TYPE: PRT
<213> ORGANISM: Artificial
<220> FEATURE:
<223> OTHER INFORMATION: Nanobody or Nanobody construct

<400> SEQUENCE: 292

Ala Ile Thr Ser Gly Asp Ser Thr Lys Tyr Ala Asp Phe Val Lys Gly
1               5                   10                  15

<210> SEQ ID NO 293
<211> LENGTH: 16
<212> TYPE: PRT
<213> ORGANISM: Artificial
<220> FEATURE:
<223> OTHER INFORMATION: Nanobody or Nanobody construct

<400> SEQUENCE: 293

Val Ile Ile Asp Ser Arg Thr Thr Lys Tyr Ala Glu Ser Val Lys Gly
1               5                   10                  15

<210> SEQ ID NO 294
<211> LENGTH: 16
<212> TYPE: PRT
<213> ORGANISM: Artificial
<220> FEATURE:
<223> OTHER INFORMATION: Nanobody or Nanobody construct

<400> SEQUENCE: 294

Thr Ile Thr Pro Arg Gly Leu Thr Asp Tyr Thr Asp Ser Val Lys Gly
1               5                   10                  15

<210> SEQ ID NO 295
<211> LENGTH: 16
```

```
<212> TYPE: PRT
<213> ORGANISM: Artificial
<220> FEATURE:
<223> OTHER INFORMATION: Nanobody or Nanobody construct

<400> SEQUENCE: 295

Ala Ile Thr Asn Gly Gly Ser Thr Lys Tyr Val Asp Ser Val Lys Gly
1               5                   10                  15

<210> SEQ ID NO 296
<211> LENGTH: 16
<212> TYPE: PRT
<213> ORGANISM: Artificial
<220> FEATURE:
<223> OTHER INFORMATION: Nanobody or Nanobody construct

<400> SEQUENCE: 296

Thr Ile Thr Pro Arg Gly Leu Thr Asp Tyr Thr Asn Ser Val Lys Gly
1               5                   10                  15

<210> SEQ ID NO 297
<211> LENGTH: 16
<212> TYPE: PRT
<213> ORGANISM: Artificial
<220> FEATURE:
<223> OTHER INFORMATION: Nanobody or Nanobody construct

<400> SEQUENCE: 297

Ser Ile Thr Ser Gly Gly Ser Leu Thr Tyr Ala Asp Ser Val Lys Gly
1               5                   10                  15

<210> SEQ ID NO 298
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 298

Thr Ile Ser Ser Gly Gly Trp Thr Ser Tyr Ala Asp Ser Val Lys
1               5                   10                  15

Gly

<210> SEQ ID NO 299
<211> LENGTH: 16
<212> TYPE: PRT
<213> ORGANISM: Artificial
<220> FEATURE:
<223> OTHER INFORMATION: Nanobody or Nanobody construct

<400> SEQUENCE: 299

Thr Ile Thr Arg Ala Leu Asn Thr Ala Tyr Ala Thr Ser Val Lys Gly
1               5                   10                  15

<210> SEQ ID NO 300
<211> LENGTH: 16
<212> TYPE: PRT
<213> ORGANISM: Artificial
<220> FEATURE:
<223> OTHER INFORMATION: Nanobody or Nanobody construct

<400> SEQUENCE: 300

Ser Ile Thr Pro Thr Gly Asn Thr Asn Tyr Val Asp Ser Val Lys Gly
1               5                   10                  15

<210> SEQ ID NO 301
```

```
<211> LENGTH: 16
<212> TYPE: PRT
<213> ORGANISM: Artificial
<220> FEATURE:
<223> OTHER INFORMATION: Nanobody or Nanobody construct

<400> SEQUENCE: 301

Val Ile Thr Arg Ala Leu Asn Thr Asn Tyr Ala Thr Ser Val Lys Gly
1               5                   10                  15

<210> SEQ ID NO 302
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 302

Ser Ile Ser Ala Ser Gly Ala Ser Thr Tyr Tyr Val Asp Ser Val Lys
1               5                   10                  15

Gly

<210> SEQ ID NO 303
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 303

Ser Ile Ser Ala Ser Gly Ala Ser Thr Tyr Tyr Val Asp Ser Val Lys
1               5                   10                  15

Gly

<210> SEQ ID NO 304
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 304

Ala Ile Ser Arg Gly Gly Asn Val Thr Pro Tyr Ala Asp Ser Val Lys
1               5                   10                  15

Gly

<210> SEQ ID NO 305
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 305

Ile Ile Thr Gly Ser Gly Thr Tyr Asn Asp Tyr Ala Asp Ser Val Lys
1               5                   10                  15

Gly

<210> SEQ ID NO 306
<211> LENGTH: 18
<212> TYPE: PRT
<213> ORGANISM: Artificial
<220> FEATURE:
<223> OTHER INFORMATION: Nanobody or Nanobody construct
```

```
<400> SEQUENCE: 306

Ser Ser Ile Ser Gly Gly Gly Ser Asn Thr Val Tyr Ala Asp Ser Val
1               5                   10                  15

Lys Gly

<210> SEQ ID NO 307
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 307

Ala Ile Ser Arg Ser Gly Asn Val Thr Pro Tyr Ala Asp Ser Val Lys
1               5                   10                  15

Gly

<210> SEQ ID NO 308
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 308

Gly Ile Ser Gly Ser Gly Gly Ser Thr Phe Tyr Gly Asp Ser Val Lys
1               5                   10                  15

Gly

<210> SEQ ID NO 309
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 309

Ala Ile Asp Trp Ser Gly Gly Ser Thr Phe Tyr Gly Asp Ser Val Lys
1               5                   10                  15

Gly

<210> SEQ ID NO 310
<211> LENGTH: 18
<212> TYPE: PRT
<213> ORGANISM: Artificial
<220> FEATURE:
<223> OTHER INFORMATION: Nanobody or Nanobody construct

<400> SEQUENCE: 310

Ser Ala Ile Ser Gly Gly Gly Ser Asn Ile Val Tyr Val Asp Ser Val
1               5                   10                  15

Lys Gly

<210> SEQ ID NO 311
<211> LENGTH: 16
<212> TYPE: PRT
<213> ORGANISM: Artificial
<220> FEATURE:
<223> OTHER INFORMATION: Nanobody or Nanobody construct

<400> SEQUENCE: 311

Arg Ile Thr Arg Gly Gly Ser Thr Asn Tyr Ala Glu Ser Val Lys Gly
1               5                   10                  15
```

```
<210> SEQ ID NO 312
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 312

Val Ile Thr Trp Ser Gly Gly Ser Thr Tyr Tyr Ala Asp Ser Val Lys
1               5                   10                  15

Gly

<210> SEQ ID NO 313
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 313

Ser Ile Ser Ala Ser Gly Ala Ser Thr Tyr Tyr Val Asp Ser Val Lys
1               5                   10                  15

Gly

<210> SEQ ID NO 314
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 314

Arg Phe Ile Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 315
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 315

Arg Phe Thr Ile Ser Arg Asp Asn Ala Lys Asp Thr Val Tyr Leu Gln
1               5                   10                  15

Met Asn Ser Leu Lys Pro Glu Asp Thr Ala Ala Tyr Tyr Cys Ala Val
            20                  25                  30

<210> SEQ ID NO 316
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 316

Arg Phe Thr Ile Ser Ser Asp Asn Ala Lys Asn Thr Val Tyr Leu Gln
1               5                   10                  15

Met Asn Ser Leu Lys Pro Glu Asp Thr Ala Val Tyr Ser Cys Ser Ala
            20                  25                  30
```

<210> SEQ ID NO 317
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 317

Arg Phe Thr Ile Ser Arg Asp Asn Ala Lys Asn Thr Val Tyr Leu Gln
1               5                   10                  15

Met Asp Ser Leu Lys Pro Glu Asp Thr Ala Val Tyr Tyr Cys Ala Ala
            20                  25                  30

<210> SEQ ID NO 318
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 318

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Val
            20                  25                  30

<210> SEQ ID NO 319
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 319

Arg Phe Thr Ile Ser Arg Asp Asn Ala Lys Asn Thr Leu Tyr Leu Gln
1               5                   10                  15

Met Ser Ser Leu Lys Pro Glu Asp Thr Ala Leu Tyr Tyr Cys Ala Glu
            20                  25                  30

<210> SEQ ID NO 320
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 320

Arg Phe Thr Ile Ser Arg Asp Asn Ala Lys Asn Thr Leu Cys Leu Gln
1               5                   10                  15

Met Asn Ser Leu Lys Pro Glu Asp Thr Ala Val Tyr Tyr Cys Thr Thr
            20                  25                  30

<210> SEQ ID NO 321
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 321

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Thr Thr
            20                  25                  30

<210> SEQ ID NO 322
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 322

Arg Phe Thr Ile Ser Arg Asp Asn Ala Lys Asn Thr Leu Tyr Leu Gln
1               5                   10                  15

Met His Ser Leu Lys Pro Glu Asp Thr Ala Val Tyr Tyr Cys Thr Thr
            20                  25                  30

<210> SEQ ID NO 323
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 323

Arg Phe Thr Ile Ser Ser Asp Asn Ala Lys Asn Thr Val Tyr Leu Gln
1               5                   10                  15

Met Asn Ser Leu Lys Pro Glu Asp Thr Ala Val Tyr Tyr Cys Ala Leu
            20                  25                  30

<210> SEQ ID NO 324
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 324

Arg Phe Thr Ile Ser Ser Asp Asn Ala Lys Asn Thr Val Tyr Leu Gln
1               5                   10                  15

Met Asn Ser Leu Lys Pro Glu Asp Thr Ala Val Tyr Tyr Cys Ala Leu
            20                  25                  30

<210> SEQ ID NO 325
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 325

Arg Phe Thr Ile Ser Ser Asp Asn Ala Lys Asn Thr Val Tyr Leu Gln
1               5                   10                  15

Met Asn Ser Leu Asn Pro Glu Asp Thr Ala Val Tyr Tyr Cys Ala Leu
            20                  25                  30

<210> SEQ ID NO 326
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 326

Arg Phe Thr Ile Ser Ser Asp Asn Ala Lys Asn Thr Val Tyr Leu Gln
1               5                   10                  15

Met Asn Ser Leu Lys Pro Glu Asp Thr Ala Val Tyr Tyr Cys Ala Leu

```
                    20                  25                  30

<210> SEQ ID NO 327
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 327

Arg Phe Thr Ile Ser Ser Asp Asn Ala Lys Asn Thr Val Tyr Leu Gln
1               5                   10                  15

Met Asn Ser Leu Asn Pro Glu Asp Thr Ala Val Tyr Tyr Cys Ala Leu
                20                  25                  30

<210> SEQ ID NO 328
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 328

Arg Phe Thr Ile Ser Ser Asp Asn Ala Lys Asn Thr Val Tyr Leu Gln
1               5                   10                  15

Met Asn Ser Leu Lys Pro Glu Asp Thr Ala Val Tyr Tyr Cys Ala Leu
                20                  25                  30

<210> SEQ ID NO 329
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 329

Arg Phe Thr Ile Ser Ser Asp Asn Ala Lys Asn Thr Val Tyr Leu Gln
1               5                   10                  15

Met Asn Ser Leu Lys Pro Glu Asp Thr Ala Val Tyr Tyr Cys Ala Leu
                20                  25                  30

<210> SEQ ID NO 330
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 330

Arg Phe Ile Ile Ser Arg Asp Asn Thr Arg Asn Thr Val His Leu Gln
1               5                   10                  15

Met Asn Ser Leu Lys Pro Glu Asp Thr Ala Val Tyr Tyr Cys Asn Thr
                20                  25                  30

<210> SEQ ID NO 331
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 331

Arg Phe Thr Ile Ser Arg Asp Ile Ala Glu Asn Thr Leu Tyr Leu Gln
1               5                   10                  15
```

Met Asn Ser Leu Lys Ser Gly Asp Thr Ala Val Tyr Tyr Cys Ala Arg
            20                  25                  30

<210> SEQ ID NO 332
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 332

Arg Phe Thr Ile Ser Arg Asp Asn Ala Lys Lys Thr Leu Tyr Leu Gln
1               5                   10                  15

Met Asn Ser Leu Lys Pro Glu Asp Ser Ala Val Tyr Tyr Cys Asn Thr
            20                  25                  30

<210> SEQ ID NO 333
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 333

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Thr
            20                  25                  30

<210> SEQ ID NO 334
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 334

Arg Phe Thr Ile Ser Arg Asp Ile Ala Glu Asn Thr Leu Tyr Leu Gln
1               5                   10                  15

Met Asn Ser Leu Lys Ser Gly Asp Thr Ala Val Tyr Tyr Cys Ala Arg
            20                  25                  30

<210> SEQ ID NO 335
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 335

Arg Phe Thr Ile Ser Arg Asp Asn Ala Glu Asn Thr Leu Tyr Leu Gln
1               5                   10                  15

Met Asn Ser Leu Lys Ser Glu Asp Thr Ala Val Tyr Tyr Cys Ala Lys
            20                  25                  30

<210> SEQ ID NO 336
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 336

Arg Phe Thr Ile Ser Arg Asp Asn Ala Lys Asn Thr Val Tyr Leu Gln
1               5                   10                  15

```
Met Asn Ser Leu Lys Pro Glu Asp Thr Ala Ile Tyr Tyr Cys Ala Thr
            20                  25                  30
```

<210> SEQ ID NO 337
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 337

```
Arg Phe Thr Ile Ser Lys Asp Asn Ala Lys Asn Thr Leu Tyr Leu Gln
1               5                   10                  15

Met Asn Ser Leu Lys Ser Glu Asp Thr Ala Val Tyr Tyr Cys Thr Arg
            20                  25                  30
```

<210> SEQ ID NO 338
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 338

```
Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Asn Ala
            20                  25                  30
```

<210> SEQ ID NO 339
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 339

```
Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30
```

<210> SEQ ID NO 340
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 340

```
Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Asn Ala
            20                  25                  30
```

<210> SEQ ID NO 341
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 341

```
Arg Phe Thr Ile Ser Arg Asp Ser Ala Lys Asn Thr Leu Tyr Leu Gln
```

```
            1               5                  10                 15
Met Asn Ser Leu Lys Ser Glu Asp Thr Ala Asp Tyr Tyr Cys Thr Arg
            20                 25                 30
```

<210> SEQ ID NO 342
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 342

```
Arg Phe Thr Ile Ser Arg Asp Asn Ala Lys Asn Thr Val Tyr Leu Gln
1               5                  10                 15
Met Asn Ser Leu Lys Pro Glu Asp Thr Ala Val Tyr Tyr Cys Ala Ala
            20                 25                 30
```

<210> SEQ ID NO 343
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 343

```
Arg Phe Thr Val Ser Arg Asp Asn Ala Lys Asn Thr Leu Tyr Leu Gln
1               5                  10                 15
Met Asn Ser Leu Lys Ser Glu Asp Thr Ala Val Tyr Tyr Cys Thr Lys
            20                 25                 30
```

<210> SEQ ID NO 344
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 344

```
Arg Phe Thr Ile Ser Arg Asp Asn Ala Lys Asn Thr Val His Leu Gln
1               5                  10                 15
Met His Ser Leu Lys Pro Glu Asp Thr Ala Val Tyr Phe Cys Asn Gly
            20                 25                 30
```

<210> SEQ ID NO 345
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 345

```
Arg Phe Thr Ile Ser Arg Asp Asn Ala Lys Asn Thr Leu Tyr Leu Gln
1               5                  10                 15
Met Asn Ser Leu Lys Pro Glu Asp Met Ala Val Tyr Tyr Cys Ala Lys
            20                 25                 30
```

<210> SEQ ID NO 346
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 346

Arg Phe Thr Ile Ser Arg Asp Asn Phe Thr Asn Val Tyr Leu Gln
1               5                   10                  15

Met Asn Ser Leu Glu Pro Glu Asp Thr Ala Val Tyr Tyr Cys Asn Ala
            20                  25                  30

<210> SEQ ID NO 347
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 347

Arg Phe Ala Ile Ser Arg Asp Asn Asn Lys Asn Thr Met His Leu Gln
1               5                   10                  15

Met Asn Ser Leu Lys Pro Glu Asp Thr Ala Val Tyr Tyr Cys Asn Ala
            20                  25                  30

<210> SEQ ID NO 348
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 348

Arg Phe Thr Ile Ser Arg Asp Asp Phe Lys Asp Thr Val Tyr Leu Gln
1               5                   10                  15

Met Asn Ser Leu Glu Pro Glu Asp Thr Ala Val Tyr Tyr Cys Asn Ala
            20                  25                  30

<210> SEQ ID NO 349
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 349

Arg Phe Thr Ile Ser Arg Asp Asn Ile Lys Asn Thr Val Tyr Leu Gln
1               5                   10                  15

Met Asn Ser Leu Lys Pro Glu Asp Ala Ala Val Tyr Tyr Cys Ala Ala
            20                  25                  30

<210> SEQ ID NO 350
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 350

Arg Phe Thr Ile Ser Arg Asp Asn Ile Lys Asn Thr Val Tyr Leu Gln
1               5                   10                  15

Met Asn Ser Leu Lys Pro Glu Asp Ala Ala Val Tyr Tyr Cys Ala Ala
            20                  25                  30

<210> SEQ ID NO 351
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 351

```
Arg Phe Ala Ile Ser Arg Asp Asn Ala Lys Asn Thr Val Ala Leu Gln
1               5                   10                  15

Met Asn Ser Leu Lys Pro Glu Asp Thr Ala Val Tyr Tyr Cys Ala Ala
            20                  25                  30
```

<210> SEQ ID NO 352
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 352

```
Arg Phe Thr Val Ser Arg Asp Asn Ala Lys Asn Thr Val Tyr Leu Gln
1               5                   10                  15

Met Asn Ser Leu Lys Ser Glu Asp Thr Ala Val Tyr Tyr Cys Ala Ala
            20                  25                  30
```

<210> SEQ ID NO 353
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 353

```
Arg Phe Thr Val Ser Arg Asp Arg Ala Lys Asn Thr Val Tyr Leu Gln
1               5                   10                  15

Met Asn Ser Leu Lys Pro Glu Asp Ser Gly Val Tyr Tyr Cys Ala Ala
            20                  25                  30
```

<210> SEQ ID NO 354
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 354

```
Arg Phe Ala Ile Ser Arg Asp Asn Ala Lys Asn Thr Leu Thr Leu Gln
1               5                   10                  15

Met Asn Ser Leu Lys Pro Glu Asp Thr Ala Val Tyr Tyr Cys Ala Ala
            20                  25                  30
```

<210> SEQ ID NO 355
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 355

```
Arg Phe Thr Ile Ser Arg Asp Asn Leu Lys Asn Thr Met Tyr Leu Gln
1               5                   10                  15

Met Asn Ser Leu Lys Pro Glu Asp Thr Ala Val Tyr Tyr Cys Gln Ser
            20                  25                  30
```

<210> SEQ ID NO 356
<211> LENGTH: 32
<212> TYPE: PRT
<213> ORGANISM: Artificial
<220> FEATURE:
<223> OTHER INFORMATION: Nanobody or Nanobody construct

```
<400> SEQUENCE: 356

Arg Phe Thr Ile Ser Arg Asp Asn Ala Lys Asn Thr Val Tyr Leu Glu
1               5                   10                  15

Met Asn Ser Leu Lys Pro Glu Asp Thr Ala Val Tyr Tyr Cys Ala Ala
            20                  25                  30

<210> SEQ ID NO 357
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 357

Arg Phe Thr Val Ser Arg Asp Arg Ile Lys Asn Thr Val Tyr Leu Gln
1               5                   10                  15

Met Asn Ser Leu Lys Pro Glu Asp Ser Gly Val Tyr Tyr Cys Ala Val
            20                  25                  30

<210> SEQ ID NO 358
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 358

Arg Phe Ala Ile Ser Arg Asp Asn Ala Asp Ser Thr Leu Tyr Leu Arg
1               5                   10                  15

Met Asn Asn Leu Lys Pro Glu Asp Thr Ala Val Tyr Tyr Cys Asn Ala
            20                  25                  30

<210> SEQ ID NO 359
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 359

Arg Phe Thr Ile Ser Lys Asp Ile Ala Lys Asn Thr Val Tyr Leu Gln
1               5                   10                  15

Met Asn Ser Leu Lys Pro Asp Asp Met Ala Val Tyr Tyr Cys Ala Ala
            20                  25                  30

<210> SEQ ID NO 360
<211> LENGTH: 32
<212> TYPE: PRT
<213> ORGANISM: Artificial
<220> FEATURE:
<223> OTHER INFORMATION: Nanobody or Nanobody construct

<400> SEQUENCE: 360

Arg Phe Thr Ile Ser Arg Asp Asn Ile Lys Asn Thr Val Tyr Leu Gln
1               5                   10                  15

Met Asn Ser Leu Lys Pro Glu Asp Ala Ala Val Tyr Tyr Cys Ala Ala
            20                  25                  30

<210> SEQ ID NO 361
<211> LENGTH: 9
<212> TYPE: PRT
<213> ORGANISM: Artificial
<220> FEATURE:
<223> OTHER INFORMATION: Nanobody or Nanobody construct
```

```
<400> SEQUENCE: 361

Asp Leu His Tyr Ser Gly Pro Asn Tyr
1               5

<210> SEQ ID NO 362
<211> LENGTH: 19
<212> TYPE: PRT
<213> ORGANISM: Artificial
<220> FEATURE:
<223> OTHER INFORMATION: Nanobody or Nanobody construct

<400> SEQUENCE: 362

Gln Gly Tyr Ser Gly Gly Tyr Tyr Tyr Thr Cys Glu Asp Ser Ala Asp
1               5                   10                  15

Phe Gly Phe

<210> SEQ ID NO 363
<211> LENGTH: 10
<212> TYPE: PRT
<213> ORGANISM: Artificial
<220> FEATURE:
<223> OTHER INFORMATION: Nanobody or Nanobody construct

<400> SEQUENCE: 363

Gly Ser Val Ala Gly Cys Ile Pro Tyr Tyr
1               5                   10

<210> SEQ ID NO 364
<211> LENGTH: 16
<212> TYPE: PRT
<213> ORGANISM: Artificial
<220> FEATURE:
<223> OTHER INFORMATION: Nanobody or Nanobody construct

<400> SEQUENCE: 364

Thr Pro Thr Ala Tyr Gly Thr Asp Trp Tyr Arg Asn Asn Tyr His Tyr
1               5                   10                  15

<210> SEQ ID NO 365
<211> LENGTH: 19
<212> TYPE: PRT
<213> ORGANISM: Artificial
<220> FEATURE:
<223> OTHER INFORMATION: Nanobody or Nanobody construct

<400> SEQUENCE: 365

Gln Gly Tyr Ser Gly Gly Tyr Tyr Tyr Thr Cys Glu Asp Ser Ala Asp
1               5                   10                  15

Phe Gly Phe

<210> SEQ ID NO 366
<211> LENGTH: 13
<212> TYPE: PRT
<213> ORGANISM: Artificial
<220> FEATURE:
<223> OTHER INFORMATION: Nanobody or Nanobody construct

<400> SEQUENCE: 366

His Leu Asn Phe Tyr Ser Val Ser Val Arg Ser Ser Pro
1               5                   10

<210> SEQ ID NO 367
<211> LENGTH: 6
<212> TYPE: PRT
```

```
<213> ORGANISM: Artificial
<220> FEATURE:
<223> OTHER INFORMATION: Nanobody or Nanobody construct

<400> SEQUENCE: 367

Thr Glu Asp Pro Tyr Pro
1               5

<210> SEQ ID NO 368
<211> LENGTH: 6
<212> TYPE: PRT
<213> ORGANISM: Artificial
<220> FEATURE:
<223> OTHER INFORMATION: Nanobody or Nanobody construct

<400> SEQUENCE: 368

Thr Met Asn Pro Asn Pro
1               5

<210> SEQ ID NO 369
<211> LENGTH: 6
<212> TYPE: PRT
<213> ORGANISM: Artificial
<220> FEATURE:
<223> OTHER INFORMATION: Nanobody or Nanobody construct

<400> SEQUENCE: 369

Thr Glu Asn Pro Asn Pro
1               5

<210> SEQ ID NO 370
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 370

Asp Gln Ala Pro Met Trp Ser Ser Trp Ser Ala Pro Tyr Glu Tyr Asp
1               5                   10                  15

Tyr

<210> SEQ ID NO 371
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 371

Asp Gln Ala Pro Met Trp Ser Ser Trp Ser Ala Pro Tyr Glu Tyr Asp
1               5                   10                  15

Tyr

<210> SEQ ID NO 372
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 372

Asp Gln Ala Pro Leu Trp Ser Thr Trp Ser Ala Pro Tyr Glu Tyr Asp
1               5                   10                  15

Tyr
```

<210> SEQ ID NO 373
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 373

Asp Gln Ala Pro Met Trp Ser Asn Trp Ser Ala Pro Tyr Glu Tyr Asp
1               5                   10                  15

Tyr

<210> SEQ ID NO 374
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 374

Asp Gln Ala Pro Leu Trp Ser Thr Trp Ser Ala Pro Tyr Glu Tyr Asp
1               5                   10                  15

Tyr

<210> SEQ ID NO 375
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 375

Asp Gln Ala Pro Met Trp Ser Ser Trp Ser Ala Pro Tyr Glu Tyr Asp
1               5                   10                  15

Tyr

<210> SEQ ID NO 376
<211> LENGTH: 17
<212> TYPE: PRT
<213> ORGANISM: Artificial
<220> FEATURE:
<223> OTHER INFORMATION: Nanobody or Nanobody construct

<400> SEQUENCE: 376

Asp Gln Ala Pro Met Trp Ser Ser Trp Ser Ala Pro Tyr Glu Tyr Asp
1               5                   10                  15

Tyr

<210> SEQ ID NO 377
<211> LENGTH: 6
<212> TYPE: PRT
<213> ORGANISM: Artificial
<220> FEATURE:
<223> OTHER INFORMATION: Nanobody or Nanobody construct

<400> SEQUENCE: 377

Val Gly Ala Gly Ser Tyr
1               5

<210> SEQ ID NO 378
<211> LENGTH: 6
<212> TYPE: PRT
<213> ORGANISM: Artificial

```
<220> FEATURE:
<223> OTHER INFORMATION: Nanobody or Nanobody construct

<400> SEQUENCE: 378

Asp Lys Thr Gly Glu Arg
1               5

<210> SEQ ID NO 379
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 379

Tyr Gly Tyr Asp Ser Gly Arg Tyr Tyr Ser Tyr
1               5                   10

<210> SEQ ID NO 380
<211> LENGTH: 15
<212> TYPE: PRT
<213> ORGANISM: Artificial
<220> FEATURE:
<223> OTHER INFORMATION: Nanobody or Nanobody construct

<400> SEQUENCE: 380

Asp Leu Ser Gly Arg Gly Asp Val Ser Glu Tyr Glu Tyr Asp Tyr
1               5                   10                  15

<210> SEQ ID NO 381
<211> LENGTH: 6
<212> TYPE: PRT
<213> ORGANISM: Artificial
<220> FEATURE:
<223> OTHER INFORMATION: Nanobody or Nanobody construct

<400> SEQUENCE: 381

Asp Lys Thr Gly Glu Arg
1               5

<210> SEQ ID NO 382
<211> LENGTH: 6
<212> TYPE: PRT
<213> ORGANISM: Artificial
<220> FEATURE:
<223> OTHER INFORMATION: Nanobody or Nanobody construct

<400> SEQUENCE: 382

Asp Lys Ala Gly Glu Arg
1               5

<210> SEQ ID NO 383
<211> LENGTH: 16
<212> TYPE: PRT
<213> ORGANISM: Artificial
<220> FEATURE:
<223> OTHER INFORMATION: Nanobody or Nanobody construct

<400> SEQUENCE: 383

Asn Thr Arg Arg Lys Tyr Gly Arg Leu Cys Asp Leu Asn Ala Asp Tyr
1               5                   10                  15

<210> SEQ ID NO 384
<211> LENGTH: 6
<212> TYPE: PRT
<213> ORGANISM: Artificial
<220> FEATURE:
```

<223> OTHER INFORMATION: Nanobody or Nanobody construct

<400> SEQUENCE: 384

Asp Lys Asn Gly Pro Pro
1               5

<210> SEQ ID NO 385
<211> LENGTH: 13
<212> TYPE: PRT
<213> ORGANISM: Artificial
<220> FEATURE:
<223> OTHER INFORMATION: Nanobody or Nanobody construct

<400> SEQUENCE: 385

Leu Ala Leu Gly Thr Asp Gln Ser Ser Thr Phe Asp Ser
1               5                   10

<210> SEQ ID NO 386
<211> LENGTH: 7
<212> TYPE: PRT
<213> ORGANISM: Artificial
<220> FEATURE:
<223> OTHER INFORMATION: Nanobody or Nanobody construct

<400> SEQUENCE: 386

Glu Leu Leu Gly Lys Trp Tyr
1               5

<210> SEQ ID NO 387
<211> LENGTH: 13
<212> TYPE: PRT
<213> ORGANISM: Artificial
<220> FEATURE:
<223> OTHER INFORMATION: Nanobody or Nanobody construct

<400> SEQUENCE: 387

Leu Ala Leu Gly Thr Asp Gln Ser Ser Thr Phe Asp Ser
1               5                   10

<210> SEQ ID NO 388
<211> LENGTH: 6
<212> TYPE: PRT
<213> ORGANISM: Artificial
<220> FEATURE:
<223> OTHER INFORMATION: Nanobody or Nanobody construct

<400> SEQUENCE: 388

Asp Lys Asn Gly Pro Pro
1               5

<210> SEQ ID NO 389
<211> LENGTH: 7
<212> TYPE: PRT
<213> ORGANISM: Artificial
<220> FEATURE:
<223> OTHER INFORMATION: Nanobody or Nanobody construct

<400> SEQUENCE: 389

Glu Ser Leu Gly Arg Trp Gly
1               5

<210> SEQ ID NO 390
<211> LENGTH: 6
<212> TYPE: PRT
<213> ORGANISM: Artificial
<220> FEATURE:
<223> OTHER INFORMATION: Nanobody or Nanobody construct

```
<400> SEQUENCE: 390

Asp Lys Asn Gly Pro Pro
1               5

<210> SEQ ID NO 391
<211> LENGTH: 12
<212> TYPE: PRT
<213> ORGANISM: Artificial
<220> FEATURE:
<223> OTHER INFORMATION: Nanobody or Nanobody construct

<400> SEQUENCE: 391

Arg Ser Ile Gly Val Asp Asp Met Pro Tyr Val Tyr
1               5                   10

<210> SEQ ID NO 392
<211> LENGTH: 9
<212> TYPE: PRT
<213> ORGANISM: Artificial
<220> FEATURE:
<223> OTHER INFORMATION: Nanobody or Nanobody construct

<400> SEQUENCE: 392

Gly Ser Glu Phe Asn Gly Tyr Glu Val
1               5

<210> SEQ ID NO 393
<211> LENGTH: 13
<212> TYPE: PRT
<213> ORGANISM: Artificial
<220> FEATURE:
<223> OTHER INFORMATION: Nanobody or Nanobody construct

<400> SEQUENCE: 393

Gly Gly Tyr Tyr Thr Asn Leu Arg Thr Gly Gly Asn Tyr
1               5                   10

<210> SEQ ID NO 394
<211> LENGTH: 16
<212> TYPE: PRT
<213> ORGANISM: Artificial
<220> FEATURE:
<223> OTHER INFORMATION: Nanobody or Nanobody construct

<400> SEQUENCE: 394

Val Tyr Pro Arg Tyr Tyr Gly Asp Asp Arg Pro Pro Val Asp Ser
1               5                   10                  15

<210> SEQ ID NO 395
<211> LENGTH: 13
<212> TYPE: PRT
<213> ORGANISM: Artificial
<220> FEATURE:
<223> OTHER INFORMATION: Nanobody or Nanobody construct

<400> SEQUENCE: 395

Gly Gly Tyr Tyr Thr Asn Leu Arg Thr Gly Gly Asn Tyr
1               5                   10

<210> SEQ ID NO 396
<211> LENGTH: 15
<212> TYPE: PRT
<213> ORGANISM: Artificial
<220> FEATURE:
<223> OTHER INFORMATION: Nanobody or Nanobody construct
```

```
<400> SEQUENCE: 396

Ala Pro Asn Gly Arg Phe Ile Thr Met Ser Ala His Val Asp Ser
1               5                   10                  15

<210> SEQ ID NO 397
<211> LENGTH: 15
<212> TYPE: PRT
<213> ORGANISM: Artificial
<220> FEATURE:
<223> OTHER INFORMATION: Nanobody or Nanobody construct

<400> SEQUENCE: 397

Ala Pro Asn Gly Arg Phe Ile Thr Met Ser Thr His Val Asp Tyr
1               5                   10                  15

<210> SEQ ID NO 398
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 398

Ser Lys Ile Gly Ile Ala Ser Thr Ile Arg Tyr Tyr Asp Tyr
1               5                   10

<210> SEQ ID NO 399
<211> LENGTH: 15
<212> TYPE: PRT
<213> ORGANISM: Artificial
<220> FEATURE:
<223> OTHER INFORMATION: Nanobody or Nanobody construct

<400> SEQUENCE: 399

Arg His Trp Gly Met Phe Ser Arg Ser Glu Asn Asp Tyr Asn Tyr
1               5                   10                  15

<210> SEQ ID NO 400
<211> LENGTH: 18
<212> TYPE: PRT
<213> ORGANISM: Artificial
<220> FEATURE:
<223> OTHER INFORMATION: Nanobody or Nanobody construct

<400> SEQUENCE: 400

Asp Lys Arg Trp Gly Ser Pro Ala Thr Ser Arg Ser Thr His Asp Tyr
1               5                   10                  15

Asp Phe

<210> SEQ ID NO 401
<211> LENGTH: 14
<212> TYPE: PRT
<213> ORGANISM: Artificial
<220> FEATURE:
<223> OTHER INFORMATION: Nanobody or Nanobody construct

<400> SEQUENCE: 401

Ser Lys Ile Gly Ile Ala Ser Thr Ile Arg Tyr Tyr Asp Tyr
1               5                   10

<210> SEQ ID NO 402
<211> LENGTH: 13
<212> TYPE: PRT
<213> ORGANISM: Artificial
<220> FEATURE:
<223> OTHER INFORMATION: Nanobody or Nanobody construct
```

<400> SEQUENCE: 402

Ser Arg Arg Ile Ile Thr Asn Pro Arg Glu Tyr Gly Tyr
1               5                   10

<210> SEQ ID NO 403
<211> LENGTH: 19
<212> TYPE: PRT
<213> ORGANISM: Artificial
<220> FEATURE:
<223> OTHER INFORMATION: Nanobody or Nanobody construct

<400> SEQUENCE: 403

Asn Arg Arg Ile Tyr Ser Ser Gly Ser Ser Leu Ser Asp Asn Ser Leu
1               5                   10                  15

Tyr Asn Phe

<210> SEQ ID NO 404
<211> LENGTH: 18
<212> TYPE: PRT
<213> ORGANISM: Artificial
<220> FEATURE:
<223> OTHER INFORMATION: Nanobody or Nanobody construct

<400> SEQUENCE: 404

Asp Lys Arg Trp Gly Ser Pro Ala Thr Ser Arg Ser Thr His Asp Tyr
1               5                   10                  15

Asp Phe

<210> SEQ ID NO 405
<211> LENGTH: 12
<212> TYPE: PRT
<213> ORGANISM: Artificial
<220> FEATURE:
<223> OTHER INFORMATION: Nanobody or Nanobody construct

<400> SEQUENCE: 405

Asp Thr Ile Gly His Ser Ser Ser Tyr Ile Thr Tyr
1               5                   10

<210> SEQ ID NO 406
<211> LENGTH: 15
<212> TYPE: PRT
<213> ORGANISM: Artificial
<220> FEATURE:
<223> OTHER INFORMATION: Nanobody or Nanobody construct

<400> SEQUENCE: 406

Ala Arg Arg Tyr Gly Asn Leu Tyr Asn Thr Asn Asn Tyr Asp Tyr
1               5                   10                  15

<210> SEQ ID NO 407
<211> LENGTH: 15
<212> TYPE: PRT
<213> ORGANISM: Artificial
<220> FEATURE:
<223> OTHER INFORMATION: Nanobody or Nanobody construct

<400> SEQUENCE: 407

Ala Pro Asn Gly Arg Phe Ile Thr Met Ser Thr His Val Asp Ser
1               5                   10                  15

<210> SEQ ID NO 408
<211> LENGTH: 11
<212> TYPE: PRT

<213> ORGANISM: Artificial
<220> FEATURE:
<223> OTHER INFORMATION: Nanobody or Nanobody construct

<400> SEQUENCE: 408

Trp Gly Gln Gly Thr Gln Val Thr Val Ser Ser
1               5                   10

<210> SEQ ID NO 409
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 409

Trp Gly Gln Gly Thr Gln Val Thr Val Ser Ser
1               5                   10

<210> SEQ ID NO 410
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 410

Trp Gly Gln Gly Thr Gln Val Thr Val Ser Ser
1               5                   10

<210> SEQ ID NO 411
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 411

Trp Gly Gln Gly Thr Gln Val Thr Val Ser Ser
1               5                   10

<210> SEQ ID NO 412
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 412

Trp Gly Gln Gly Thr Gln Val Thr Val Ser Ser
1               5                   10

<210> SEQ ID NO 413
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 413

Thr Ser Gln Gly Thr Gln Val Thr Val Ser Ser
1               5                   10

<210> SEQ ID NO 414
<211> LENGTH: 11
<212> TYPE: PRT
<213> ORGANISM: Artificial

```
<220> FEATURE:
<223> OTHER INFORMATION: Nanobody or Nanobody construct

<400> SEQUENCE: 414

Arg Gly Gln Gly Thr Gln Val Thr Val Ser Ser
1               5                   10

<210> SEQ ID NO 415
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 415

Arg Gly Gln Gly Thr Gln Val Thr Val Ser Ser
1               5                   10

<210> SEQ ID NO 416
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 416

Arg Gly Pro Gly Thr Gln Val Thr Val Ser Ser
1               5                   10

<210> SEQ ID NO 417
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 417

Trp Gly Gln Gly Thr Gln Val Thr Val Ser Ser
1               5                   10

<210> SEQ ID NO 418
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 418

Trp Gly Gln Gly Thr Gln Val Thr Val Ser Ser
1               5                   10

<210> SEQ ID NO 419
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 419

Trp Gly Gln Gly Thr Gln Val Thr Val Ser Ser
1               5                   10

<210> SEQ ID NO 420
<211> LENGTH: 11
<212> TYPE: PRT
<213> ORGANISM: Artificial
<220> FEATURE:
```

-continued

<223> OTHER INFORMATION: Nanobody or Nanobody construct

<400> SEQUENCE: 420

Trp Gly Gln Gly Thr Gln Val Thr Val Ser Ser
1               5                   10

<210> SEQ ID NO 421
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 421

Trp Gly Gln Gly Thr Gln Val Thr Val Ser Ser
1               5                   10

<210> SEQ ID NO 422
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 422

Trp Gly Gln Gly Thr Gln Val Thr Val Ser Ser
1               5                   10

<210> SEQ ID NO 423
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 423

Trp Gly Gln Gly Thr Gln Val Thr Val Ser Ser
1               5                   10

<210> SEQ ID NO 424
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 424

Trp Gly Gln Gly Ala Gln Val Thr Val Ser Ser
1               5                   10

<210> SEQ ID NO 425
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 425

Arg Gly Gln Gly Thr Gln Val Thr Val Ser Ser
1               5                   10

<210> SEQ ID NO 426
<211> LENGTH: 11
<212> TYPE: PRT
<213> ORGANISM: Artificial
<220> FEATURE:
<223> OTHER INFORMATION: Nanobody or Nanobody construct

```
<400> SEQUENCE: 426

Trp Gly Gln Gly Thr Gln Val Thr Val Ser Ser
1               5                   10

<210> SEQ ID NO 427
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 427

Trp Gly Gln Gly Thr Gln Val Thr Val Ser Ser
1               5                   10

<210> SEQ ID NO 428
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 428

Arg Gly Gln Gly Thr Gln Val Thr Val Ser Ser
1               5                   10

<210> SEQ ID NO 429
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 429

Arg Gly Gln Gly Thr Gln Val Thr Val Ser Ser
1               5                   10

<210> SEQ ID NO 430
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 430

Trp Gly Gln Gly Thr Gln Val Thr Val Ser Ser
1               5                   10

<210> SEQ ID NO 431
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 431

Met Gly Gln Gly Thr Gln Val Thr Val Ser Ser
1               5                   10

<210> SEQ ID NO 432
<211> LENGTH: 11
<212> TYPE: PRT
<213> ORGANISM: Artificial
<220> FEATURE:
<223> OTHER INFORMATION: Nanobody or Nanobody construct
```

```
<400> SEQUENCE: 432

Trp Gly Gln Gly Thr Gln Val Thr Val Ser Ser
1               5                   10

<210> SEQ ID NO 433
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 433

Trp Gly Gln Gly Thr Gln Val Thr Val Ser Ser
1               5                   10

<210> SEQ ID NO 434
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 434

Trp Gly Gln Gly Thr Gln Val Thr Val Ser Ser
1               5                   10

<210> SEQ ID NO 435
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 435

Met Gly Gln Gly Thr Gln Val Thr Val Ser Ser
1               5                   10

<210> SEQ ID NO 436
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 436

Trp Gly Gln Gly Thr Gln Val Thr Val Ser Ser
1               5                   10

<210> SEQ ID NO 437
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 437

Met Gly Gln Gly Thr Gln Val Thr Val Ser Ser
1               5                   10

<210> SEQ ID NO 438
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 438
```

Trp Gly Gln Gly Thr Gln Val Thr Val Ser Ser
1               5                   10

<210> SEQ ID NO 439
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 439

Arg Gly Gln Gly Thr Gln Val Thr Val Ser Ser
1               5                   10

<210> SEQ ID NO 440
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 440

Trp Gly Gln Gly Thr Gln Val Thr Val Ser Ser
1               5                   10

<210> SEQ ID NO 441
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 441

Trp Gly Gln Gly Thr Arg Val Thr Val Ser Ser
1               5                   10

<210> SEQ ID NO 442
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 442

Trp Gly Gln Gly Thr Gln Val Thr Val Ser Ser
1               5                   10

<210> SEQ ID NO 443
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 443

Trp Gly Gln Gly Thr Gln Val Thr Val Ser Ser
1               5                   10

<210> SEQ ID NO 444
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 444

Trp Gly Gln Gly Thr Gln Val Thr Val Ser Ser
1               5                   10

<210> SEQ ID NO 445
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 445

Trp Gly Gln Gly Thr Gln Val Thr Val Ser Ser
1               5                   10

<210> SEQ ID NO 446
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 446

Trp Gly Gln Gly Thr Gln Val Thr Val Ser Ser
1               5                   10

<210> SEQ ID NO 447
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 447

Trp Gly Gln Gly Thr Gln Val Thr Val Ser Ser
1               5                   10

<210> SEQ ID NO 448
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 448

Trp Gly Gln Gly Thr Gln Val Thr Val Ser Ser
1               5                   10

<210> SEQ ID NO 449
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 449

Trp Gly Gln Gly Thr Gln Val Thr Val Ser Ser
1               5                   10

<210> SEQ ID NO 450
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 450

Trp Gly Gln Gly Thr Gln Val Thr Val Ser Ser

-continued

```
<210> SEQ ID NO 451
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 451

Trp Gly Gln Gly Thr Gln Val Thr Val Ser Ser
1               5                   10

<210> SEQ ID NO 452
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 452

Trp Gly Gln Gly Thr Gln Val Thr Val Ser Ser
1               5                   10

<210> SEQ ID NO 453
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 453

Trp Gly Gln Gly Thr Gln Val Thr Val Ser Ser
1               5                   10

<210> SEQ ID NO 454
<211> LENGTH: 11
<212> TYPE: PRT
<213> ORGANISM: Artificial
<220> FEATURE:
<223> OTHER INFORMATION: Nanobody or Nanobody construct

<400> SEQUENCE: 454

Trp Gly Gln Gly Thr Gln Val Thr Val Ser Ser
1               5                   10

<210> SEQ ID NO 455
<211> LENGTH: 117
<212> TYPE: PRT
<213> ORGANISM: Artificial
<220> FEATURE:
<223> OTHER INFORMATION: Nanobody or Nanobody construct

<400> SEQUENCE: 455

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Gln Gln Ala Pro Gly Lys Gln Arg Glu Leu Val
        35                  40                  45

Ala Phe Ile Thr Ser Val Gly Thr Thr Asn Tyr Ala Asp Ser Val Lys
    50                  55                  60

Gly Arg Phe Ile Ile Ser Arg Asp Asn Ala Lys Asn Thr Val Tyr Leu
65                  70                  75                  80
```

-continued

Gln Met Asn Ser Leu Lys Pro Glu Asp Thr Ala Val Tyr Tyr Cys Ala
                85                  90                  95

Ala Asp Leu His Tyr Ser Gly Pro Asn Tyr Trp Gly Gln Gly Thr Gln
            100                 105                 110

Val Thr Val Ser Ser
        115

<210> SEQ ID NO 456
<211> LENGTH: 128
<212> TYPE: PRT
<213> ORGANISM: Artificial
<220> FEATURE:
<223> OTHER INFORMATION: Nanobody or Nanobody construct

<400> SEQUENCE: 456

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Asp Tyr
            20                  25                  30

Ala Ile Gly Trp Phe Arg Gln Ala Pro Gly Lys Glu Arg Glu Ala Val
        35                  40                  45

Ser Cys Ile Ser Ser Val Asp Gly Ser Thr His Tyr Ala Asp Ser Val
    50                  55                  60

Lys Gly Arg Phe Thr Ile Ser Arg Asp Asn Ala Lys Asp Thr Val Tyr
65                  70                  75                  80

Leu Gln Met Asn Ser Leu Lys Pro Glu Asp Thr Ala Ala Tyr Tyr Cys
                85                  90                  95

Ala Val Gln Gly Tyr Ser Gly Gly Tyr Tyr Tyr Thr Cys Glu Asp Ser
            100                 105                 110

Ala Asp Phe Gly Phe Trp Gly Gln Gly Thr Gln Val Thr Val Ser Ser
        115                 120                 125

<210> SEQ ID NO 457
<211> LENGTH: 119
<212> TYPE: PRT
<213> ORGANISM: Artificial
<220> FEATURE:
<223> OTHER INFORMATION: Nanobody or Nanobody construct

<400> SEQUENCE: 457

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ala Cys Ile Ser Ser Ser Asp Gly Ser Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Ser Cys
                85                  90                  95

Ser Ala Gly Ser Val Ala Gly Cys Ile Pro Tyr Tyr Trp Gly Gln Gly
            100                 105                 110

Thr Gln Val Thr Val Ser Ser
        115

<210> SEQ ID NO 458

```
<211> LENGTH: 125
<212> TYPE: PRT
<213> ORGANISM: Artificial
<220> FEATURE:
<223> OTHER INFORMATION: Nanobody or Nanobody construct

<400> SEQUENCE: 458

Glu Val Gln Leu Val Glu Ser Gly Gly Gly Leu Val Gln Ala Gly Asp
1               5                   10                  15

Ser Leu Arg Leu Ser Cys Thr Thr Ser Gly Arg Thr Phe Ser Asp Asp
            20                  25                  30

Thr Met Gly Trp Phe Arg Gln Ala Pro Arg Lys Glu Arg Glu Phe Val
        35                  40                  45

Ala Ala Ile Leu Trp Asp Ser Ile Lys Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asp Ser Leu Lys Pro Glu Asp Thr Ala Val Tyr Tyr Cys
                85                  90                  95

Ala Ala Thr Pro Thr Ala Tyr Gly Tyr Asp Trp Tyr Arg Asn Asn Tyr
            100                 105                 110

His Tyr Trp Gly Gln Gly Thr Gln Val Thr Val Ser Ser
        115                 120                 125

<210> SEQ ID NO 459
<211> LENGTH: 128
<212> TYPE: PRT
<213> ORGANISM: Artificial
<220> FEATURE:
<223> OTHER INFORMATION: Nanobody or Nanobody construct

<400> SEQUENCE: 459

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Asp Tyr
            20                  25                  30

Ala Val Gly Trp Phe Arg Gln Ala Pro Gly Lys Glu Arg Glu Gly Val
        35                  40                  45

Ser Cys Ile Gly Ser Ser Tyr Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Val Gln Gly Tyr Ser Gly Tyr Tyr Tyr Thr Cys Glu Asp Ser
            100                 105                 110

Ala Asp Phe Gly Phe Trp Gly Gln Gly Thr Gln Val Thr Val Ser Ser
        115                 120                 125

<210> SEQ ID NO 460
<211> LENGTH: 122
<212> TYPE: PRT
<213> ORGANISM: Artificial
<220> FEATURE:
<223> OTHER INFORMATION: Nanobody or Nanobody construct

<400> SEQUENCE: 460

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asp Tyr
            20                  25                  30

Ser Met Ser Trp Val Arg Gln Ala Pro Gly Lys Gly Leu Glu Trp Val
            35                  40                  45

Ser Ala Ile Ser Gly Gly Gly Glu Val Thr Thr Tyr Ala Asp Ser Val
 50                      55                  60

Lys Gly Arg Phe Thr Ile Ser Arg Asp Asn Ala Lys Asn Thr Leu Tyr
 65                  70                  75                  80

Leu Gln Met Ser Ser Leu Lys Pro Glu Asp Thr Ala Leu Tyr Tyr Cys
                 85                  90                  95

Ala Glu His Leu Asn Phe Tyr Ser Val Ser Val Arg Ser Ser Pro Thr
                100                 105                 110

Ser Gln Gly Thr Gln Val Thr Val Ser Ser
            115                 120
```

<210> SEQ ID NO 461
<211> LENGTH: 115
<212> TYPE: PRT
<213> ORGANISM: Artificial
<220> FEATURE:
<223> OTHER INFORMATION: Nanobody or Nanobody construct

<400> SEQUENCE: 461

```
Glu Val Gln Leu Val Glu Ser Gly Gly Gly Leu Val Gln Pro Gly Asp
 1               5                  10                  15

Ser Leu Arg Leu Ser Cys Ala Ala Ser Gly Phe Thr Phe Gly Ser Asn
            20                  25                  30

Gly Met Arg Trp Val Arg Gln Ala Pro Gly Lys Gly Pro Glu Trp Val
            35                  40                  45

Ser Ser Ile Asn Ser Asp Gly Thr Ser Thr Tyr Tyr Ala Asp Ser Val
 50                      55                  60

Lys Gly Arg Phe Thr Ile Ser Arg Asp Asn Ala Lys Asn Thr Leu Cys
 65                  70                  75                  80

Leu Gln Met Asn Ser Leu Lys Pro Glu Asp Thr Ala Val Tyr Tyr Cys
                 85                  90                  95

Thr Thr Thr Glu Asp Pro Tyr Pro Arg Gly Gln Gly Thr Gln Val Thr
                100                 105                 110

Val Ser Ser
        115
```

<210> SEQ ID NO 462
<211> LENGTH: 115
<212> TYPE: PRT
<213> ORGANISM: Artificial
<220> FEATURE:
<223> OTHER INFORMATION: Nanobody or Nanobody construct

<400> SEQUENCE: 462

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Gly Ser Asn
            20                  25                  30

Gly Met Arg Trp Val Arg Gln Ala Pro Gly Lys Gly Pro Glu Trp Val
            35                  40                  45

Ser Ser Ile Asn Ser Asp Gly Thr Ser Ala Phe Tyr Ala Glu Ser Val
 50                      55                  60

Lys Gly Arg Phe Thr Ile Ser Arg Asp Asn Ala Lys Asn Thr Leu Tyr
 65                  70                  75                  80
```

-continued

Leu Gln Met Asn Ser Leu Lys Pro Glu Asp Thr Ala Val Tyr Tyr Cys
                85                  90                  95

Thr Thr Thr Met Asn Pro Asn Pro Arg Gly Gln Gly Thr Gln Val Thr
            100                 105                 110

Val Ser Ser
        115

<210> SEQ ID NO 463
<211> LENGTH: 115
<212> TYPE: PRT
<213> ORGANISM: Artificial
<220> FEATURE:
<223> OTHER INFORMATION: Nanobody or Nanobody construct

<400> SEQUENCE: 463

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Asn
            20                  25                  30

Gly Met Arg Trp Val Arg Gln Ala Pro Gly Lys Gly Pro Glu Trp Val
        35                  40                  45

Ser Ser Ile Asn Ser Asp Gly Thr Ser Thr Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met His Ser Leu Lys Pro Glu Asp Thr Ala Val Tyr Tyr Cys
                85                  90                  95

Thr Thr Thr Glu Asn Pro Asn Pro Arg Gly Pro Gly Thr Gln Val Thr
            100                 105                 110

Val Ser Ser
        115

<210> SEQ ID NO 464
<211> LENGTH: 126
<212> TYPE: PRT
<213> ORGANISM: Artificial
<220> FEATURE:
<223> OTHER INFORMATION: Nanobody or Nanobody construct

<400> SEQUENCE: 464

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Gly Ser Thr
            20                  25                  30

Thr Ile Gly Trp Phe Arg Gln Ala Pro Gly Lys Glu Arg Glu Gly Val
        35                  40                  45

Ser Cys Ile Ser Thr Gly Asp Gly Ser Thr Tyr Tyr Ala Glu Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Leu Asp Gln Ala Pro Met Trp Ser Ser Trp Ser Ala Pro Tyr Glu
            100                 105                 110

Tyr Asp Tyr Trp Gly Gln Gly Thr Gln Val Thr Val Ser Ser
        115                 120                 125

-continued

<210> SEQ ID NO 465
<211> LENGTH: 126
<212> TYPE: PRT
<213> ORGANISM: Artificial
<220> FEATURE:
<223> OTHER INFORMATION: Nanobody or Nanobody construct

<400> SEQUENCE: 465

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Gly Thr Thr
            20                  25                  30

Thr Ile Gly Trp Phe Arg Gln Ala Pro Gly Lys Glu Arg Glu Gly Val
        35                  40                  45

Ser Cys Ile Ser Thr Gly Asp Gly Ser Thr Asn Tyr Ala Glu Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Leu Asp Gln Ala Pro Met Trp Ser Ser Trp Ser Ala Pro Tyr Glu
            100                 105                 110

Tyr Asp Tyr Trp Gly Gln Gly Thr Gln Val Thr Val Ser Ser
        115                 120                 125

<210> SEQ ID NO 466
<211> LENGTH: 126
<212> TYPE: PRT
<213> ORGANISM: Artificial
<220> FEATURE:
<223> OTHER INFORMATION: Nanobody or Nanobody construct

<400> SEQUENCE: 466

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Asp Thr
            20                  25                  30

Thr Ile Gly Trp Phe Arg Gln Ala Pro Gly Lys Glu Arg Glu Gly Ile
        35                  40                  45

Ser Cys Ile Ser Thr Gly Asp Gly Ser Thr Tyr Tyr Ala Glu Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Asn Pro Glu Asp Thr Ala Val Tyr Tyr Cys
                85                  90                  95

Ala Leu Asp Gln Ala Pro Leu Trp Ser Thr Trp Ser Ala Pro Tyr Glu
            100                 105                 110

Tyr Asp Tyr Trp Gly Gln Gly Thr Gln Val Thr Val Ser Ser
        115                 120                 125

<210> SEQ ID NO 467
<211> LENGTH: 126
<212> TYPE: PRT
<213> ORGANISM: Artificial
<220> FEATURE:
<223> OTHER INFORMATION: Nanobody or Nanobody construct

<400> SEQUENCE: 467

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Gly Thr Thr
            20                  25                  30

Thr Ile Gly Trp Phe Arg Gln Ala Pro Gly Lys Glu Arg Glu Val Val
        35                  40                  45

Ser Cys Ile Ser Thr Gly Gly Ser Thr Tyr Tyr Thr Glu Ser Val
50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
            85                  90                  95

Ala Leu Asp Gln Ala Pro Met Trp Ser Asn Trp Ser Ala Pro Tyr Glu
            100                 105                 110

Tyr Asp Tyr Trp Gly Gln Gly Thr Gln Val Thr Val Ser Ser
            115                 120                 125

<210> SEQ ID NO 468
<211> LENGTH: 126
<212> TYPE: PRT
<213> ORGANISM: Artificial
<220> FEATURE:
<223> OTHER INFORMATION: Nanobody or Nanobody construct

<400> SEQUENCE: 468

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Ser Asp Thr
            20                  25                  30

Thr Ile Gly Trp Phe Arg Gln Ala Pro Gly Lys Glu Arg Glu Gly Ile
        35                  40                  45

Ser Cys Ile Ser Thr Gly Asp Gly Ser Thr Tyr Tyr Ala Glu Ser Val
50                  55                  60

Lys Gly Arg Phe Thr Ile Ser Ser Asp Asn Ala Lys Asn Thr Val Tyr
65                  70                  75                  80

Leu Gln Met Asn Ser Leu Asn Pro Glu Asp Thr Ala Val Tyr Tyr Cys
            85                  90                  95

Ala Leu Asp Gln Ala Pro Leu Trp Ser Thr Trp Ser Ala Pro Tyr Glu
            100                 105                 110

Tyr Asp Tyr Trp Gly Gln Gly Thr Gln Val Thr Val Ser Ser
            115                 120                 125

<210> SEQ ID NO 469
<211> LENGTH: 126
<212> TYPE: PRT
<213> ORGANISM: Artificial
<220> FEATURE:
<223> OTHER INFORMATION: Nanobody or Nanobody construct

<400> SEQUENCE: 469

Glu Val Gln Leu Val Glu Ser Gly Gly Asp Leu Val Gln Ala Gly Gly
1               5                   10                  15

Ser Leu Arg Leu Ser Cys Ala Ala Ser Gly Phe Thr Phe Gly Asp Phe
            20                  25                  30

Thr Ile Gly Trp Phe Arg Gln Ala Pro Gly Lys Glu Arg Glu Gly Val
        35                  40                  45

Ser Cys Ile Asn Thr Gly Asp Gly Ser Thr Asn Tyr Ala Glu Ser Val
50                  55                  60

Lys Gly Arg Phe Thr Ile Ser Ser Asp Asn Ala Lys Asn Thr Val Tyr

```
                65                  70                  75                  80
Leu Gln Met Asn Ser Leu Lys Pro Glu Asp Thr Ala Val Tyr Tyr Cys
                    85                  90                  95

Ala Leu Asp Gln Ala Pro Met Trp Ser Ser Trp Ser Ala Pro Tyr Glu
                100                 105                 110

Tyr Asp Tyr Trp Gly Gln Gly Thr Gln Val Thr Val Ser Ser
                115                 120                 125

<210> SEQ ID NO 470
<211> LENGTH: 126
<212> TYPE: PRT
<213> ORGANISM: Artificial
<220> FEATURE:
<223> OTHER INFORMATION: Nanobody or Nanobody construct

<400> SEQUENCE: 470

Lys Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Gly Ser Thr
                20                  25                  30

Thr Ile Gly Trp Phe Arg Gln Ala Pro Gly Lys Glu Arg Glu Gly Val
                35                  40                  45

Ser Cys Ile Ser Thr Gly Asp Gly Ser Thr Tyr Tyr Ala Glu Ser Val
                50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Leu Asp Gln Ala Pro Met Trp Ser Ser Trp Ser Ala Pro Tyr Glu
                100                 105                 110

Tyr Asp Tyr Trp Gly Gln Gly Thr Gln Val Thr Val Ser Ser
                115                 120                 125

<210> SEQ ID NO 471
<211> LENGTH: 114
<212> TYPE: PRT
<213> ORGANISM: Artificial
<220> FEATURE:
<223> OTHER INFORMATION: Nanobody or Nanobody construct

<400> SEQUENCE: 471

Glu Val Gln Leu Val Glu Ser Gly Gly Gly Leu Val Gln Ala Gly Gly
1               5                   10                  15

Ser Leu Arg Leu Ser Cys Val Ala Ser Gly Arg Ile Phe Thr Asn Thr
                20                  25                  30

Ala Met Gly Trp Tyr Arg Gln Ala Pro Gly Lys Trp Arg Glu Leu Val
                35                  40                  45

Ala Thr Ile Tyr Ser Gly Gly Ser Thr Lys Tyr Ile Asp Ser Val Lys
                50                  55                  60

Gly Arg Phe Ile Ile Ser Arg Asp Asn Thr Asn Thr Val His Leu
65                  70                  75                  80

Gln Met Asn Ser Leu Lys Pro Glu Asp Thr Ala Val Tyr Tyr Cys Asn
                85                  90                  95

Thr Val Gly Ala Gly Ser Tyr Trp Gly Gln Gly Ala Gln Val Thr Val
                100                 105                 110

Ser Ser
```

```
<210> SEQ ID NO 472
<211> LENGTH: 114
<212> TYPE: PRT
<213> ORGANISM: Artificial
<220> FEATURE:
<223> OTHER INFORMATION: Nanobody or Nanobody construct

<400> SEQUENCE: 472

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Gly Asn
            20                  25                  30

Trp Met Tyr Trp Leu Arg Gln Ala Pro Gly Lys Gly Leu Glu Trp Ile
        35                  40                  45

Ser Thr Ile Thr Pro Arg Gly Leu Thr Ala Tyr Ala Asp Ser Val Lys
    50                  55                  60

Gly Arg Phe Thr Ile Ser Arg Asp Ile Ala Glu Asn Thr Leu Tyr Leu
65                  70                  75                  80

Gln Met Asn Ser Leu Lys Ser Gly Asp Thr Ala Val Tyr Tyr Cys Ala
                85                  90                  95

Arg Asp Lys Thr Gly Glu Arg Gly Gln Gly Thr Gln Val Thr Val
            100                 105                 110

Ser Ser

<210> SEQ ID NO 473
<211> LENGTH: 120
<212> TYPE: PRT
<213> ORGANISM: Artificial
<220> FEATURE:
<223> OTHER INFORMATION: Nanobody or Nanobody construct

<400> SEQUENCE: 473

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Asp Ile Ser Trp Asp Gly Asp Ile Thr Thr Tyr Ala Ala Ser Val
    50                  55                  60

Lys Gly Arg Phe Thr Ile Ser Arg Asp Asn Ala Lys Lys Thr Leu Tyr
65                  70                  75                  80

Leu Gln Met Asn Ser Leu Lys Pro Glu Asp Ser Ala Val Tyr Tyr Cys
                85                  90                  95

Asn Thr Tyr Gly Tyr Asp Ser Gly Arg Tyr Tyr Ser Tyr Trp Gly Gln
            100                 105                 110

Gly Thr Gln Val Thr Val Ser Ser
        115                 120

<210> SEQ ID NO 474
<211> LENGTH: 124
<212> TYPE: PRT
<213> ORGANISM: Artificial
<220> FEATURE:
<223> OTHER INFORMATION: Nanobody or Nanobody construct

<400> SEQUENCE: 474

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ser Tyr Ile Ser Ser Ser Asp Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Thr Asp Leu Ser Gly Arg Gly Asp Val Ser Glu Tyr Glu Tyr Asp
            100                 105                 110

Tyr Trp Gly Gln Gly Thr Gln Val Thr Val Ser Ser
            115                 120

<210> SEQ ID NO 475
<211> LENGTH: 114
<212> TYPE: PRT
<213> ORGANISM: Artificial
<220> FEATURE:
<223> OTHER INFORMATION: Nanobody or Nanobody construct

<400> SEQUENCE: 475

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Gly Asn
            20                  25                  30

Trp Met Tyr Trp Leu Arg Gln Ala Pro Gly Lys Gly Leu Glu Trp Ile
        35                  40                  45

Ser Thr Ile Thr Pro Arg Gly Leu Thr Ala Tyr Ala Asp Ser Val Lys
    50                  55                  60

Gly Arg Phe Thr Ile Ser Arg Asp Ile Ala Glu Asn Thr Leu Tyr Leu
65                  70                  75                  80

Gln Met Asn Ser Leu Lys Ser Gly Asp Thr Ala Val Tyr Tyr Cys Ala
                85                  90                  95

Arg Asp Lys Thr Gly Glu Arg Gly Gln Gly Thr Gln Val Thr Val
            100                 105                 110

Ser Ser

<210> SEQ ID NO 476
<211> LENGTH: 114
<212> TYPE: PRT
<213> ORGANISM: Artificial
<220> FEATURE:
<223> OTHER INFORMATION: Nanobody or Nanobody construct

<400> SEQUENCE: 476

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Asn
            20                  25                  30

Trp Met Tyr Trp Leu Arg Gln Ala Pro Gly Lys Gly Leu Glu Trp Ile
        35                  40                  45

Ser Thr Ile Thr Pro Arg Asp Leu Thr Ala Tyr Ala Asp Ser Val Lys
    50                  55                  60

Gly Arg Phe Thr Ile Ser Arg Asp Asn Ala Glu Asn Thr Leu Tyr Leu
65                  70                  75                  80
```

Gln Met Asn Ser Leu Lys Ser Glu Asp Thr Ala Val Tyr Tyr Cys Ala
            85                  90                  95

Lys Asp Lys Ala Gly Glu Arg Arg Gly Gln Gly Thr Gln Val Thr Val
            100                 105                 110

Ser Ser

<210> SEQ ID NO 477
<211> LENGTH: 126
<212> TYPE: PRT
<213> ORGANISM: Artificial
<220> FEATURE:
<223> OTHER INFORMATION: Nanobody or Nanobody construct

<400> SEQUENCE: 477

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Leu Asp Tyr Tyr
            20                  25                  30

Ala Ile Gly Trp Tyr Arg Gln Ala Pro Gly Lys Glu Arg Glu Trp Val
            35                  40                  45

Ser Cys Ile Ser Ser Ser Asn Tyr Gly Ile Thr Thr Tyr Ala Asp Ser
        50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Ile Tyr Tyr
            85                  90                  95

Cys Ala Thr Asn Thr Arg Arg Lys Tyr Gly Arg Leu Cys Asp Leu Asn
            100                 105                 110

Ala Asp Tyr Trp Gly Gln Gly Thr Gln Val Thr Val Ser Ser
            115                 120                 125

<210> SEQ ID NO 478
<211> LENGTH: 114
<212> TYPE: PRT
<213> ORGANISM: Artificial
<220> FEATURE:
<223> OTHER INFORMATION: Nanobody or Nanobody construct

<400> SEQUENCE: 478

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Pro Ser
            20                  25                  30

Trp Met Tyr Trp Leu Arg Gln Ala Pro Gly Lys Gly Leu Glu Trp Val
            35                  40                  45

Ser Thr Ile Thr Pro Arg Gly Leu Thr Glu Tyr Ala Asn Ser Val Lys
        50                  55                  60

Gly Arg Phe Thr Ile Ser Lys Asp Asn Ala Lys Asn Thr Leu Tyr Leu
65                  70                  75                  80

Gln Met Asn Ser Leu Lys Ser Glu Asp Thr Ala Val Tyr Tyr Cys Thr
            85                  90                  95

Arg Asp Lys Asn Gly Pro Pro Met Gly Gln Gly Thr Gln Val Thr Val
            100                 105                 110

Ser Ser

<210> SEQ ID NO 479
<211> LENGTH: 121
<212> TYPE: PRT

<213> ORGANISM: Artificial
<220> FEATURE:
<223> OTHER INFORMATION: Nanobody or Nanobody construct

<400> SEQUENCE: 479

Glu Val Gln Leu Val Glu Ser Gly Gly Gly Leu Val Gln Pro Gly Gly
1               5                   10                  15

Ser Leu Arg Leu Ser Cys Val Ala Ser Gly Ser Ile Arg Ser Ile Ile
            20                  25                  30

His Met Gly Trp Tyr Arg Gln Ala Pro Gly Asn Glu Arg Asp Leu Val
        35                  40                  45

Ala Val Ile Ile Asp Ser Arg Thr Thr Lys Tyr Ser Glu Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Leu Ala Leu Gly Thr Asp Ser Ser Thr Phe Ser Trp Gly
            100                 105                 110

Gln Gly Thr Gln Val Thr Val Ser Ser
        115                 120

<210> SEQ ID NO 480
<211> LENGTH: 115
<212> TYPE: PRT
<213> ORGANISM: Artificial
<220> FEATURE:
<223> OTHER INFORMATION: Nanobody or Nanobody construct

<400> SEQUENCE: 480

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Asn Gln Arg Asp Leu Val
        35                  40                  45

Ala Ala Ile Thr Ser Gly Asp Ser Thr Lys Tyr Ala Asp Phe Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Glu Leu Leu Gly Lys Trp Tyr Trp Gly Gln Gly Thr Gln Val Thr
            100                 105                 110

Val Ser Ser
    115

<210> SEQ ID NO 481
<211> LENGTH: 121
<212> TYPE: PRT
<213> ORGANISM: Artificial
<220> FEATURE:
<223> OTHER INFORMATION: Nanobody or Nanobody construct

<400> SEQUENCE: 481

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Arg Ser Ile Ile
            20                  25                  30

-continued

```
His Met Gly Trp Tyr Arg Gln Thr Pro Gly Asn Glu Arg Asp Met Val
            35                  40                  45

Ala Val Ile Ile Asp Ser Arg Thr Thr Lys Tyr Ala Glu Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
            85                  90                  95

Ala Leu Ala Leu Gly Thr Asp Gln Ser Ser Thr Phe Asp Ser Trp Gly
            100                 105                 110

Gln Gly Thr Gln Val Thr Val Ser Ser
            115                 120

<210> SEQ ID NO 482
<211> LENGTH: 114
<212> TYPE: PRT
<213> ORGANISM: Artificial
<220> FEATURE:
<223> OTHER INFORMATION: Nanobody or Nanobody construct

<400> SEQUENCE: 482

Glu Val Gln Leu Val Glu Ser Gly Gly Gly Leu Val Gln Pro Gly Gly
 1               5                  10                  15

Ser Leu Arg Leu Ser Cys Ala Thr Ser Gly Phe Thr Phe Ser Thr Ser
            20                  25                  30

Trp Met Tyr Trp Leu Arg Gln Ala Pro Gly Lys Gly Leu Glu Trp Val
            35                  40                  45

Ser Thr Ile Thr Pro Arg Gly Leu Thr Asp Tyr Thr Asp Ser Val Lys
 50                  55                  60

Gly Arg Phe Thr Ile Ser Arg Asp Ser Ala Lys Asn Thr Leu Tyr Leu
 65                  70                  75                  80

Gln Met Asn Ser Leu Lys Ser Glu Asp Thr Ala Asp Tyr Tyr Cys Thr
            85                  90                  95

Arg Asp Lys Asn Gly Pro Pro Met Gly Gln Gly Thr Gln Val Thr Val
            100                 105                 110

Ser Ser

<210> SEQ ID NO 483
<211> LENGTH: 115
<212> TYPE: PRT
<213> ORGANISM: Artificial
<220> FEATURE:
<223> OTHER INFORMATION: Nanobody or Nanobody construct

<400> SEQUENCE: 483

Glu Val Gln Leu Val Glu Ser Gly Gly Gly Leu Val Gln Ala Gly Gly
 1               5                  10                  15

Ser Leu Arg Leu Ser Cys Ala Ala Ser Gly Ser Ile Phe Ser Ile Asn
            20                  25                  30

Thr Met Gly Trp Tyr Arg Gln Ala Pro Gly Asn Gln Arg Asp Leu Val
            35                  40                  45

Ala Ala Ile Thr Asn Gly Gly Ser Thr Lys Tyr Val Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Ala
            85                  90                  95
```

Ala Glu Ser Leu Gly Arg Trp Gly Trp Gly Gln Gly Thr Gln Val Thr
            100                 105                 110

Val Ser Ser
        115

<210> SEQ ID NO 484
<211> LENGTH: 114
<212> TYPE: PRT
<213> ORGANISM: Artificial
<220> FEATURE:
<223> OTHER INFORMATION: Nanobody or Nanobody construct

<400> SEQUENCE: 484

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Thr Ser
            20                  25                  30

Trp Met Tyr Trp Leu Arg Gln Ala Pro Gly Lys Gly Leu Glu Trp Val
        35                  40                  45

Ser Thr Ile Thr Pro Arg Gly Leu Thr Asp Tyr Thr Asn Ser Val Lys
    50                  55                  60

Gly Arg Phe Thr Val Ser Arg Asp Asn Ala Lys Asn Thr Leu Tyr Leu
65                  70                  75                  80

Gln Met Asn Ser Leu Lys Ser Glu Asp Thr Ala Val Tyr Tyr Cys Thr
            85                  90                  95

Lys Asp Lys Asn Gly Pro Pro Met Gly Gln Gly Thr Gln Val Thr Val
            100                 105                 110

Ser Ser

<210> SEQ ID NO 485
<211> LENGTH: 120
<212> TYPE: PRT
<213> ORGANISM: Artificial
<220> FEATURE:
<223> OTHER INFORMATION: Nanobody or Nanobody construct

<400> SEQUENCE: 485

Glu Val Gln Leu Val Glu Ser Gly Gly Gly Leu Val Gln Ala Gly Gly
1               5                   10                  15

Ser Leu Arg Leu Ser Cys Ala Ala Ser Glu Ser Ile Phe Ser Leu Tyr
            20                  25                  30

Val Thr Gly Trp Tyr Arg Gln Ala Pro Gly Lys Gln Arg Glu Leu Val
        35                  40                  45

Ala Ser Ile Thr Ser Gly Gly Ser Leu Thr Tyr Ala Asp Ser Val Lys
    50                  55                  60

Gly Arg Phe Thr Ile Ser Arg Asp Asn Ala Lys Asn Thr Val His Leu
65                  70                  75                  80

Gln Met His Ser Leu Lys Pro Glu Asp Thr Ala Val Tyr Phe Cys Asn
            85                  90                  95

Gly Arg Ser Ile Gly Val Asp Asp Met Pro Tyr Val Tyr Trp Gly Gln
            100                 105                 110

Gly Thr Gln Val Thr Val Ser Ser
        115                 120

<210> SEQ ID NO 486
<211> LENGTH: 118
<212> TYPE: PRT
<213> ORGANISM: Artificial -continued
<220> FEATURE:
<223> OTHER INFORMATION: Nanobody or Nanobody construct

<400> SEQUENCE: 486

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Leu Asn
            20                  25                  30

Ala Met Thr Trp Val Arg Gln Ala Pro Gly Lys Gly Leu Glu Trp Val
        35                  40                  45

Ser Thr Ile Ser Ser Gly Gly Trp Thr Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Met Ala Val Tyr Tyr Cys
                85                  90                  95

Ala Lys Gly Ser Glu Phe Asn Gly Tyr Glu Val Arg Gly Gln Gly Thr
            100                 105                 110

Gln Val Thr Val Ser Ser
        115

<210> SEQ ID NO 487
<211> LENGTH: 121
<212> TYPE: PRT
<213> ORGANISM: Artificial
<220> FEATURE:
<223> OTHER INFORMATION: Nanobody or Nanobody construct

<400> SEQUENCE: 487

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ser Ser Ile Asn
            20                  25                  30

Val Met Gly Trp Tyr Arg Gln Ala Pro Gly Lys Gln Arg Asp Leu Val
        35                  40                  45

Ala Thr Ile Thr Arg Ala Leu Asn Thr Ala Tyr Ala Thr Ser Val Lys
    50                  55                  60

Gly Arg Phe Thr Ile Ser Arg Asp Asn Phe Asn Thr Val Tyr Leu
65                  70                  75                  80

Gln Met Asn Ser Leu Glu Pro Glu Asp Thr Ala Val Tyr Tyr Cys Asn
                85                  90                  95

Ala Gly Gly Tyr Tyr Thr Asn Leu Arg Thr Gly Gly Asn Tyr Trp Gly
            100                 105                 110

Gln Gly Thr Gln Val Thr Val Ser Ser
        115                 120

<210> SEQ ID NO 488
<211> LENGTH: 123
<212> TYPE: PRT
<213> ORGANISM: Artificial
<220> FEATURE:
<223> OTHER INFORMATION: Nanobody or Nanobody construct

<400> SEQUENCE: 488

Glu Val Gln Leu Val Glu Ser Gly Gly Gly Leu Val Gln Ala Gly Gly
1               5                   10                  15

Ser Leu Arg Leu Ser Cys Ala Ser Gly Ile Phe Ile Ile Asp Thr
            20                  25                  30

Met Gly Trp Tyr Arg Gln Ala Pro Gly Lys Gln Arg Glu Leu Val Ala
            35                  40                  45

Ser Ile Thr Pro Thr Gly Asn Thr Asn Tyr Val Asp Ser Val Lys Gly
 50                  55                  60

Arg Phe Ala Ile Ser Arg Asp Asn Asn Lys Asn Thr Met His Leu Gln
 65                  70                  75                  80

Met Asn Ser Leu Lys Pro Glu Asp Thr Ala Val Tyr Tyr Cys Asn Ala
                85                  90                  95

Val Tyr Pro Arg Tyr Tyr Gly Asp Asp Arg Pro Val Asp Ser
                100                 105                 110

Trp Gly Gln Gly Thr Arg Val Thr Val Ser Ser
            115                 120

<210> SEQ ID NO 489
<211> LENGTH: 121
<212> TYPE: PRT
<213> ORGANISM: Artificial
<220> FEATURE:
<223> OTHER INFORMATION: Nanobody or Nanobody construct

<400> SEQUENCE: 489

Glu Val Gln Leu Val Glu Ser Gly Gly Gly Leu Ala Gln Ala Gly Gly
 1               5                  10                  15

Ser Leu Arg Leu Ser Cys Ala Ala Ser Gly Ser Ile Ser Ser Ile Asn
                20                  25                  30

Val Met Gly Trp Tyr Arg Gln Ala Pro Gly Lys Gln Arg Asp Leu Val
            35                  40                  45

Ala Val Ile Thr Arg Ala Leu Asn Thr Asn Tyr Ala Thr Ser Val Lys
 50                  55                  60

Gly Arg Phe Thr Ile Ser Arg Asp Asp Phe Lys Asp Thr Val Tyr Leu
 65                  70                  75                  80

Gln Met Asn Ser Leu Glu Pro Glu Asp Thr Ala Val Tyr Tyr Cys Asn
                85                  90                  95

Ala Gly Gly Tyr Tyr Thr Asn Leu Arg Thr Gly Gly Asn Tyr Trp Gly
                100                 105                 110

Gln Gly Thr Gln Val Thr Val Ser Ser
            115                 120

<210> SEQ ID NO 490
<211> LENGTH: 124
<212> TYPE: PRT
<213> ORGANISM: Artificial
<220> FEATURE:
<223> OTHER INFORMATION: Nanobody or Nanobody construct

<400> SEQUENCE: 490

Glu Val Gln Leu Val Glu Ser Gly Gly Gly Val Gln Ala Gly Asp
 1               5                  10                  15

Ser Leu Arg Leu Ser Cys Lys Ala Ser Arg Arg Thr Ile Ser Thr Tyr
                20                  25                  30

Gly Met Gly Trp Phe Arg Gln Ala Pro Gly Asp Lys Arg Asp Leu Val
            35                  40                  45

Ser Ser Ile Ser Ala Ser Gly Ala Ser Thr Tyr Tyr Val Asp Ser Val
 50                  55                  60

Lys Gly Arg Phe Thr Ile Ser Arg Asp Asn Ile Lys Asn Thr Val Tyr
 65                  70                  75                  80

Leu Gln Met Asn Ser Leu Lys Pro Glu Asp Ala Ala Val Tyr Tyr Cys
                85                  90                  95

-continued

```
Ala Ala Ala Pro Asn Gly Arg Phe Ile Thr Met Ser Ala His Val Asp
            100                 105                 110

Ser Trp Gly Gln Gly Thr Gln Val Thr Val Ser Ser
        115                 120

<210> SEQ ID NO 491
<211> LENGTH: 124
<212> TYPE: PRT
<213> ORGANISM: Artificial
<220> FEATURE:
<223> OTHER INFORMATION: Nanobody or Nanobody construct

<400> SEQUENCE: 491

Glu Val Gln Leu Val Glu Ser Gly Gly Gly Val Gln Ala Gly Asp
1               5                   10                  15

Ser Leu Arg Leu Ser Cys Lys Ala Ser Arg Thr Ile Ser Thr Tyr
            20                  25                  30

Gly Met Gly Trp Phe Arg Gln Ala Pro Gly Asp Lys Arg Asp Leu Val
        35                  40                  45

Ser Ser Ile Ser Ala Ser Gly Ala Ser Thr Tyr Tyr Val Asp Ser Val
    50                  55                  60

Lys Gly Arg Phe Thr Ile Ser Arg Asp Asn Ile Lys Asn Thr Val Tyr
65                  70                  75                  80

Leu Gln Met Asn Ser Leu Lys Pro Glu Asp Ala Val Tyr Tyr Cys
                85                  90                  95

Ala Ala Ala Pro Asn Gly Arg Phe Ile Thr Met Ser Thr His Val Asp
            100                 105                 110

Tyr Trp Gly Gln Gly Thr Gln Val Thr Val Ser Ser
        115                 120

<210> SEQ ID NO 492
<211> LENGTH: 126
<212> TYPE: PRT
<213> ORGANISM: Artificial
<220> FEATURE:
<223> OTHER INFORMATION: Nanobody or Nanobody construct

<400> SEQUENCE: 492

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Thr Phe
            20                  25                  30

Asn Thr Tyr Ser Met Gly Trp Phe Arg Gln Ala Pro Gly Lys Glu Arg
        35                  40                  45

Glu Phe Val Ala Ala Ile Ser Arg Gly Gly Asn Val Thr Pro Tyr Ala
    50                  55                  60

Asp Ser Val Lys Gly Arg Phe Ala Ile Ser Arg Asp Asn Ala Lys Asn
65                  70                  75                  80

Thr Val Ala Leu Gln Met Asn Ser Leu Lys Pro Glu Asp Thr Ala Val
                85                  90                  95

Tyr Tyr Cys Ala Ala Ser Lys Ile Gly Ile Ala Ser Thr Ile Arg Tyr
            100                 105                 110

Tyr Asp Tyr Trp Gly Gln Gly Thr Gln Val Thr Val Ser Ser
        115                 120                 125

<210> SEQ ID NO 493
<211> LENGTH: 124
<212> TYPE: PRT
```

```
<213> ORGANISM: Artificial
<220> FEATURE:
<223> OTHER INFORMATION: Nanobody or Nanobody construct

<400> SEQUENCE: 493

Glu Val Gln Leu Val Glu Ser Gly Gly Gly Leu Val Gln Ala Gly Gly
1               5                   10                  15

Ser Leu Arg Leu Ser Cys Ala Ala Ser Val Leu Thr Phe Gly Thr Tyr
            20                  25                  30

Thr Val Gly Trp Phe Arg Gln Ala Pro Gly Lys Glu Arg Glu Phe Val
        35                  40                  45

Ser Ile Ile Thr Gly Ser Gly Thr Tyr Asn Asp Tyr Ala Asp Ser Val
50                  55                  60

Lys Gly Arg Phe Thr Val Ser Arg Asp Asn Ala Lys Asn Thr Val Tyr
65                  70                  75                  80

Leu Gln Met Asn Ser Leu Lys Ser Glu Asp Thr Ala Val Tyr Tyr Cys
                85                  90                  95

Ala Ala Arg His Trp Gly Met Phe Ser Arg Ser Glu Asn Asp Tyr Asn
            100                 105                 110

Tyr Trp Gly Gln Gly Thr Gln Val Thr Val Ser Ser
        115                 120

<210> SEQ ID NO 494
<211> LENGTH: 128
<212> TYPE: PRT
<213> ORGANISM: Artificial
<220> FEATURE:
<223> OTHER INFORMATION: Nanobody or Nanobody construct

<400> SEQUENCE: 494

Glu Val Gln Leu Val Glu Ser Gly Gly Gly Leu Val Gln Ala Gly Ala
1               5                   10                  15

Ser Leu Arg Leu Ser Cys Val Asp Ser Gly Asp Thr Phe Ser Trp Tyr
            20                  25                  30

Ala Met Gly Trp Phe Arg Gln Gln Ala Pro Gly Lys Glu Arg Glu Phe
        35                  40                  45

Val Ser Ser Ile Ser Gly Gly Gly Ser Asn Thr Val Tyr Ala Asp Ser
50                  55                  60

Val Lys Gly Arg Phe Thr Val Ser Arg Asp Arg Ala Lys Asn Thr Val
65                  70                  75                  80

Tyr Leu Gln Met Asn Ser Leu Lys Pro Glu Asp Ser Gly Val Tyr Tyr
                85                  90                  95

Cys Ala Ala Asp Lys Arg Trp Gly Ser Pro Ala Thr Ser Arg Ser Thr
            100                 105                 110

His Asp Tyr Asp Phe Trp Gly Gln Gly Thr Gln Val Thr Val Ser Ser
        115                 120                 125

<210> SEQ ID NO 495
<211> LENGTH: 126
<212> TYPE: PRT
<213> ORGANISM: Artificial
<220> FEATURE:
<223> OTHER INFORMATION: Nanobody or Nanobody construct

<400> SEQUENCE: 495

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Thr Phe
            20                  25                  30
```

```
Asn Thr Tyr Ser Met Gly Trp Phe Arg Gln Ala Pro Gly Lys Glu Arg
            35                  40                  45

Glu Phe Val Ala Ala Ile Ser Arg Ser Gly Asn Val Thr Pro Tyr Ala
 50                  55                  60

Asp Ser Val Lys Gly Arg Phe Ala Ile Ser Arg Asp Asn Ala Lys Asn
 65                  70                  75                  80

Thr Leu Thr Leu Gln Met Asn Ser Leu Lys Pro Glu Asp Thr Ala Val
                 85                  90                  95

Tyr Tyr Cys Ala Ala Ser Lys Ile Gly Ile Ala Ser Thr Ile Arg Tyr
            100                 105                 110

Tyr Asp Tyr Trp Gly Gln Gly Thr Gln Val Thr Val Ser Ser
            115                 120                 125

<210> SEQ ID NO 496
<211> LENGTH: 122
<212> TYPE: PRT
<213> ORGANISM: Artificial
<220> FEATURE:
<223> OTHER INFORMATION: Nanobody or Nanobody construct

<400> SEQUENCE: 496

Glu Val Gln Leu Val Glu Ser Gly Gly Gly Leu Val Gln Thr Gly Gly
 1               5                  10                  15

Ser Leu Arg Leu Ser Cys Ala Ala Ser Gly Arg Ser Phe Asn Leu Tyr
            20                  25                  30

Tyr Met Gly Trp Phe Arg Gln Ala Pro Gly Arg Glu Arg Glu Phe Val
            35                  40                  45

Ala Gly Ile Ser Gly Ser Gly Gly Ser Thr Phe Tyr Gly Asp Ser Val
 50                  55                  60

Lys Gly Arg Phe Thr Ile Ser Arg Asp Asn Leu Lys Asn Thr Met Tyr
 65                  70                  75                  80

Leu Gln Met Asn Ser Leu Lys Pro Glu Asp Thr Ala Val Tyr Tyr Cys
                 85                  90                  95

Gln Ser Ser Arg Arg Ile Ile Thr Asn Pro Arg Glu Tyr Gly Tyr Trp
            100                 105                 110

Gly Gln Gly Thr Gln Val Thr Val Ser Ser
            115                 120

<210> SEQ ID NO 497
<211> LENGTH: 128
<212> TYPE: PRT
<213> ORGANISM: Artificial
<220> FEATURE:
<223> OTHER INFORMATION: Nanobody or Nanobody construct

<400> SEQUENCE: 497

Glu Val Gln Leu Val Glu Ser Gly Gly Gly Leu Val Gln Ala Gly Gly
 1               5                  10                  15

Ser Leu Arg Leu Ser Cys Thr Ala Ser Gly Leu Thr Phe Ser Met Tyr
            20                  25                  30

Ala Met Ala Trp Ile Arg Leu Ala Pro Gly Lys Glu Arg Glu Val Ile
            35                  40                  45

Ala Ala Ile Asp Trp Ser Gly Ser Thr Phe Tyr Gly Asp Ser Val
 50                  55                  60

Lys Gly Arg Phe Thr Ile Ser Arg Asp Asn Ala Lys Asn Thr Val Tyr
 65                  70                  75                  80

Leu Glu Met Asn Ser Leu Lys Pro Glu Asp Thr Ala Val Tyr Tyr Cys
```

-continued

```
                85                  90                  95
Ala Ala Asn Arg Arg Ile Tyr Ser Ser Gly Ser Ser Leu Ser Asp Asn
            100                 105                 110

Ser Leu Tyr Asn Phe Trp Gly Gln Gly Thr Gln Val Thr Val Ser Ser
            115                 120                 125

<210> SEQ ID NO 498
<211> LENGTH: 128
<212> TYPE: PRT
<213> ORGANISM: Artificial
<220> FEATURE:
<223> OTHER INFORMATION: Nanobody or Nanobody construct

<400> SEQUENCE: 498

Glu Val Gln Leu Val Glu Ser Gly Gly Gly Leu Val Gln Ala Gly Gly
1               5                   10                  15

Ser Leu Arg Leu Ser Cys Val Ala Ser Gly Asp Thr Phe Asn Trp Tyr
            20                  25                  30

Ala Met Gly Trp Phe Arg Gln Gln Ala Pro Gly Lys Glu Arg Glu Phe
        35                  40                  45

Val Ser Ala Ile Ser Gly Gly Gly Ser Asn Ile Val Tyr Val Asp Ser
50                  55                  60

Val Lys Gly Arg Phe Thr Val Ser Arg Asp Arg Ile Lys Asn Thr Val
65                  70                  75                  80

Tyr Leu Gln Met Asn Ser Leu Lys Pro Glu Asp Ser Gly Val Tyr Tyr
                85                  90                  95

Cys Ala Val Asp Lys Arg Trp Gly Ser Pro Ala Thr Ser Arg Ser Thr
            100                 105                 110

His Asp Tyr Asp Phe Trp Gly Gln Gly Thr Gln Val Thr Val Ser Ser
            115                 120                 125

<210> SEQ ID NO 499
<211> LENGTH: 119
<212> TYPE: PRT
<213> ORGANISM: Artificial
<220> FEATURE:
<223> OTHER INFORMATION: Nanobody or Nanobody construct

<400> SEQUENCE: 499

Glu Val Gln Leu Val Glu Ser Gly Gly Gly Leu Val Gln Ala Gly Gly
1               5                   10                  15

Ser Leu Arg Leu Ser Cys Ala Ala Ser Glu Thr Ile Phe Ala Ser Ala
            20                  25                  30

Met Gly Trp Tyr Arg Gln Pro Pro Gly Lys Gln Arg Glu Leu Val Ala
        35                  40                  45

Arg Ile Thr Arg Gly Gly Ser Thr Asn Tyr Ala Glu Ser Val Lys Gly
    50                  55                  60

Arg Phe Ala Ile Ser Arg Asp Asn Ala Asp Ser Thr Leu Tyr Leu Arg
65                  70                  75                  80

Met Asn Asn Leu Lys Pro Glu Asp Thr Ala Val Tyr Tyr Cys Asn Ala
                85                  90                  95

Asp Thr Ile Gly His Ser Ser Ser Tyr Ile Thr Tyr Trp Gly Gln Gly
            100                 105                 110

Thr Gln Val Thr Val Ser Ser
            115

<210> SEQ ID NO 500
<211> LENGTH: 124
```

```
<212> TYPE: PRT
<213> ORGANISM: Artificial
<220> FEATURE:
<223> OTHER INFORMATION: Nanobody or Nanobody construct

<400> SEQUENCE: 500

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Pro Phe Ser Met Tyr
            20                  25                  30

Ala Met Gly Trp Phe Arg Gln Ala Pro Gly Lys Glu Arg Glu Phe Val
        35                  40                  45

Thr Val Ile Thr Trp Ser Gly Ser Thr Tyr Tyr Ala Asp Ser Val
    50                  55                  60

Lys Gly Arg Phe Thr Ile Ser Lys Asp Ile Ala Lys Asn Thr Val Tyr
65                  70                  75                  80

Leu Gln Met Asn Ser Leu Lys Pro Asp Asp Met Ala Val Tyr Tyr Cys
                85                  90                  95

Ala Ala Ala Arg Arg Tyr Gly Asn Leu Tyr Asn Thr Asn Asn Tyr Asp
                100                 105                 110

Tyr Trp Gly Gln Gly Thr Gln Val Thr Val Ser Ser
                115                 120

<210> SEQ ID NO 501
<211> LENGTH: 124
<212> TYPE: PRT
<213> ORGANISM: Artificial
<220> FEATURE:
<223> OTHER INFORMATION: Nanobody or Nanobody construct

<400> SEQUENCE: 501

Glu Val Gln Leu Val Glu Ser Gly Gly Gly Val Gln Ala Gly Asp
1               5                   10                  15

Ser Leu Arg Leu Ser Cys Lys Ala Ser Arg Arg Thr Ile Ser Thr Tyr
            20                  25                  30

Gly Met Gly Trp Phe Arg Gln Ala Pro Gly Asp Lys Arg Asp Leu Val
        35                  40                  45

Ser Ser Ile Ser Ala Ser Gly Ala Ser Thr Tyr Tyr Val Asp Ser Val
    50                  55                  60

Lys Gly Arg Phe Thr Ile Ser Arg Asp Asn Ile Lys Asn Thr Val Tyr
65                  70                  75                  80

Leu Gln Met Asn Ser Leu Lys Pro Glu Asp Ala Ala Val Tyr Tyr Cys
                85                  90                  95

Ala Ala Ala Pro Asn Gly Arg Phe Ile Thr Met Ser Thr His Val Asp
                100                 105                 110

Ser Trp Gly Gln Gly Thr Gln Val Thr Val Ser Ser
                115                 120
```

AMINO ACID SEQUENCES DIRECTED AGAINST THE ANGIOPOIETIN/TIE SYSTEM AND POLYPEPTIDES COMPRISING THE SAME FOR THE TREATMENT OF DISEASES AND DISORDERS RELATED TO ANGIOGENESIS

RELATED APPLICATIONS

This application is a national stage filing under 35 U.S.C. §371 of international application PCT/EP2009/066822, filed Dec. 10, 2009, which was published under PCT Article 21(2) in English, and claims the benefit under 35 U.S.C. §119(e) of U.S. provisional application serial number 61/121,228, filed Dec. 10, 2008, the disclosures of which are incorporated by reference herein in their entireties.

The present invention relates to amino acid sequences that are directed against proteins from the group of the Angiopoietin/Tie family such as Tie1, Tie2, Ang1, Ang2, Ang3, Ang4, Angptl1, Angptl2, Angptl3, Angptl4, Angptl5, Angptl6, as well as to compounds or constructs, and in particular proteins and polypeptides, that comprise or essentially consist of one or more of such amino acid sequences.

The invention also relates to nucleic acids encoding such amino acid sequences and polypeptides (also referred to herein as "nucleic acids of the invention" or "nucleotide sequences of the invention"); to methods for preparing such amino acid sequences and polypeptides; to host cells expressing or capable of expressing such amino acid sequences or polypeptides; to compositions, and in particular to pharmaceutical compositions, that comprise such amino acid sequences, polypeptides, nucleic acids and/or host cells; and to uses of such amino acid sequences or polypeptides, nucleic acids, host cells and/or compositions, in particular for prophylactic, therapeutic or diagnostic purposes, such as the prophylactic, therapeutic or diagnostic purposes mentioned herein.

Other aspects, embodiments, advantages and applications of the invention will become clear from the further description herein.

Angiopoietins 1-4 (Ang1-Ang4) constitute a family of growth factors that function as ligands of Tie2, a Receptor Tyrosine Kinase (RTK) expressed mainly in endothelial cells. Angs/Tie2 signaling is involved in multiple steps of angiogenesis such as the destabilization of existing vessels and endothelial cell migration (Bouis et al 2006). Ang1 and 4 have been shown to act as obligatory agonists promoting structural integrity of blood vessels, whereas Ang2 and Ang3 function as a context-dependent antagonist or agonist. In spite of the structural homology with Tie2, none of the known Angs bind to another RTK named Tie1, although some studies indicate an essential role for Tie1 in vascular development (Eklund L., Olsen B. R. Tie receptors and their angiopoietin ligands are context-dependent regulators of vascular remodeling. Experimental. Cell Research (2006) 312: 630-641). Based in their similarity in structure with Angs six angiopoietin-like proteins (Angptls) have being identified. Interestingly, Angptls also function in angiogenesis through regulating survival and migration of endothelial cells, although these proteins do not bind the angiopoietin receptor Tie2 (Oike Y, Akao M., Kubota E, Suda T. Angiopoietin-like proteins: potential new targets for metabolic syndrome therapy. TRENDS in Molecular Medicine (2005). 11: 473-479; Bouis D, Kusumanto Y, Meijer C, Mulder N H, Hospers G A P. A review on pro- and anti-angiogenic factors as targets of clinical intervention. Pharmacological Research 53 (2006) 89-103, Review). Deregulated angiogenesis leads to numerous malignant, ischemic, inflammatory, infectious and immune disorders (Carmeliet P. Angiogenesis in health and disease. Nature Medicine 9 (2003) 653-660) and therefore, the modulation of Tie receptors, Angs and Angptls may have many interesting potential therapeutic applications.

Tie receptors are endothelial-specific RTKs that share a high degree of homology. The extracellular regions of both receptors Tie1 and Tie2, with 33% similarity, contain an immunoglobulin-like loop, three EGF-like domains, a second Ig-like loop, and three fibronectin type III repeats. The cytoplasmic regions of both receptors, presenting 76% of similarity, contain tyrosine kinase domains including a number of phosphorylation and protein interaction sites (Thurston G. Role of Angiopoietins and Tie receptor tyrosine kinases in angiogenesis and lymphangiogenesis. Cell Tissue Res (2003) 314:61-68; Fiedler U., Augustin H. G. Angiopoietins: a link between angiogenesis and inflammation. TRENDS in Immunology. (2006) 27:552-558). Signaling through dimerisation and autophosphorylation of Tie2 upon binding of agonist Angs has been studied and results suggest that the major signalling pathway involves activation of phosphatidylinositol 3' kinase (Eklund and Olsen, 2006, supra). Also, as will be clear from the further disclosure herein, and depending on the Tie against which they are directed and their desired (therapeutic) effect, the amino acid sequences, Nanobodies and polypeptides of the invention may act as (full or partial) agonists, (full or partial, and competitive or non-competitive) antagonists or as inverse agonists of Tie, e.g. Tie2 and/or of the biological function, pathway, mechanism, effect, signalling or response associated therewith. They may do so in an irreversible but preferably reversible manner.

Angs contain an amino-terminal angiopoietin-specific domain followed by a coiled-coil domain, a linker peptide and a carboxy-terminal fibrinogen homology domain. The fibrinogen homology domain is responsible for receptor binding, the coiled-coil domain is required for dimerization of angiopoietin monomers and the short amino-terminal region forms ring-like structures that cluster dimers into variable sized multimers necessary for Tie2 activation (Eklund and Olsen, 2006, supra). Human Ang1 shares approximately 97% amino acid sequence identity with mouse Ang-1, while human and mouse Ang2 share only 85% amino acid sequence identity. Mouse and human Ang2 are 60% identical to their Ang1 homologs. In the case of human Ang4 it shares 45%. 47% and 54% amino acid sequence identity with human Ang1, human Ang2 and mouse Ang3 respectively. Structurally very similar to Angs, Angptls contain a coiled-coiled domain and a fibrinogen-like domain similar to those found in Angs.

List of Tie, Angs and Angptls: (Bouis et al., 2006; Eklund and Olsen, 2006; Oike et al., 2005, supra)

Tie-family
Tie1
Tie2
Angs-family
Ang1
Ang2
Ang3
Ang4
Angptls-family
Angptl1
Angptl2
Angptl3
Angptl4
Angptl5
Angptl6

Angiogenesis plays a major role in several pathologic processes as tumour vascularisation, diabetic retinopathy, psoriasis and reumathoid arthritis, where pro- and anti-angiogenic angiopoietins and Tie receptors are widely expressed (Bach F., Uddin Burke D. Angiopoietins in malignancy. EJSO (2007). 33:7-15; Pandya N. M., Dhalla N. S., Santani D. D. Angiogenesis—a new target for future therapy. Vascular Pharmacology (2006) 44: 265-274; Carmeliet, 2003, supra). Many anti-angiogenic factors targeting Tie and angiopoietins are in development. It has been reported that modulation of the expression and inhibition of these angiogenesis-related proteins caused a reduction on tumour growth and metastasis by inhibiting tumour angiogenesis (Bach et al., 2007, supra; Onliner J. et al., Suppression of angiogenesis and tumor growth by selective inhibition of angiopoietin-2. Cancer Cell (2004), 6: 507-516; Bouis et al. 2006, supra). The role of Ang2 is not that clear since it is context dependent. It seems that in a non-pathological situation function Ang2 works as an antagonist and the ratio Ang1:Ang2 is 1:1 but in malignancy with tumor angiogenesis the expression of Ang2 increases.

Furthermore, a pro-angiogenic therapy could be beneficial in treatment of ischemic diseases.

The polypeptides and/or compositions of the present invention can generally be used to modulate, and in particular inhibit and/or prevent of the angiopoietin-Tie interactions and in particular the binding of angiopoietin ligands (Ang 1 to 4) to receptor Tie1 and/or Tie2, and thus to modulate, and in particular inhibit or prevent, the signalling that is mediated by said interactions, to modulate the biological pathways in which ligands and/or targets are involved, and/or to modulate the biological mechanisms, responses and effects associated with such signalling or these pathways. Similarly, angiopoietin-like ligands (Angptl to Angptl6) interactions may be disrupted by polypeptides and/or compositions of the present invention.

As such, the polypeptides and compositions of the present invention can be used for the prevention and treatment of diseases and disorders related to angiogenesis. Generally, "said diseases and disorders related to angiogensis" can be defined as diseases and disorders that can be prevented and/or treated, respectively, by suitably administering to a subject in need thereof (i.e. having the disease or disorder or at least one symptom thereof and/or at risk of attracting or developing the disease or disorder) of either a polypeptide or composition of the invention (and in particular, of a pharmaceutically active amount thereof) and/or of a known active principle active against the angiopoietin/Tie system or a biological pathway or mechanism in which said system is involved (and in particular, of a pharmaceutically active amount thereof). Examples of such diseases and disorders will be clear to the skilled person based on the disclosure herein, and for example include the following diseases and disorders:

Cancer and Angiopoietins:
  Bach F, Uddin F J., Burke D. Angiopoietins in malignancy. EJSO (2007). 33:7-15.
Cancer and Tie Receptors:
  Blume-Jensen P and Hunter T. Oncogenic kinase signaling. Nature (2001). 44: 355-365.
Diabetic Retinopathy and Angiopoietins:
  Patel J. I., Hykin P. G., Gregor Z. J., Boulton M. and Cree I. A. Angiopoietin concentrations in diabetic retinopathy. Br. J. Ophthalmol (2005). 89: 480-483.
Rheumatoid Arthritis and Tie2 and Angiopoietins:
  DeBusk L. M., Chen Y., Nishishita T., Chen J., Thomas J. W., Lin P. C. Tie2 receptor tyrosine kinase, a major mediator of tumor necrosis factor a-induced angiogenesis in rheumatoid arthritis. ARTHRITIS& RHEUMATISM (2003). 48: 2461-2471.
  Shahrara S., Volin M. V., Connors M. A., Haines G. K., Koch A. E. Differential expression of the angiogenic Tie receptor family in arthritic and normal synovial tissue. Arthritis Res (2002) 4: 201-208.
Psoriasis and Tie2 and Angiopoietins:
Kuroda K., Sapadin A., Shoji T., Fleischmajer R., Lebwohl M. Altered expression of angiopoietins and Tie2 endothelium receptor in psoriasis. The journal of investigate dermatology. (2001). 116: 713-720.
Ischemia, Renal Carcinoma and Angptl4:
LeJan S., Amy C., Cazes A., Monnot C., Lamande N., Favier J., Philippe J., Sibony M., Gasc 1-M, Corvol P., Germain S. Angiopoietin-like 4 is a proangiogenic factor produced during Ischemia and conventional renal cell carcinoma. American Journal of Pathology (2003) 162: 1521-1528.

In particular, the polypeptides and compositions of the present invention can be used for the prevention and/or treatment of diseases and disorders related to angiogenesis which are characterized by excessive and/or unwanted creation of blood vessels or lack of creation of blood vessels. Examples of such disorders are cardiovascular disorders, cancers, diabetic retinopathy, wound healing, rheumatoid arthritis, obesity, alveolarization and psoriasis.

Thus, without being limited thereto, the amino acid sequences and polypeptides of the invention can for example be used to prevent and/or to treat all diseases and disorders that are currently being prevented or treated with active principles that can modulate angiogenesis, such as those mentioned in the prior art cited above and others. It is also envisaged that the polypeptides of the invention can be used to prevent and/or to treat all diseases and disorders for which treatment with such active principles is currently being developed, has been proposed, or will be proposed or developed in future. In addition, it is envisaged that, because of their favourable properties as further described herein, the polypeptides of the present invention may be used for the prevention and treatment of other diseases and disorders than those for which these known active principles are being used or will be proposed or developed; and/or that the polypeptides of the present invention may provide new methods and regimens for treating the diseases and disorders described herein.

Other applications and uses of the amino acid sequences and polypeptides of the invention will become clear to the skilled person from the further disclosure herein.

Generally, it is an object of the invention to provide pharmacologically active agents, as well as compositions comprising the same, that can be used in the diagnosis, prevention and/or treatment of cancers, diabetic retinopathy, wound healing, rheumatoid arthritis, obesity, alveolarization and psoriasis and of the further diseases and disorders mentioned herein; and to provide methods for the diagnosis, prevention and/or treatment of such diseases and disorders that involve the administration and/or use of such agents and compositions.

In particular, it is an object of the invention to provide such pharmacologically active agents, compositions and/or methods that have certain advantages compared to the agents, compositions and/or methods that are currently used and/or known in the art. These advantages will become clear from the further description below.

More in particular, it is an object of the invention to provide therapeutic proteins that can be used as pharmacologically active agents, as well as compositions comprising the same, for the diagnosis, prevention and/or treatment cancers, diabetic retinopathy, wound healing, rheumatoid arthritis, obesity, alveolarization and psoriasis and of the further diseases and disorders mentioned herein; and to provide methods for the diagnosis, prevention and/or treatment of such diseases and disorders that involve the administration and/or the use of such therapeutic proteins and compositions.

Accordingly, it is a specific object of the present invention to provide amino acid sequences that are directed against Tie1, Tie2, Ang1, Ang2, Ang3, Ang4, Angptl1, Angptl2, Angptl3, Angptl4, Angptl5, or Angptl6 (as defined herein), in particular against Tie2, Ang1, Ang2, Ang4 or Angptl4 from a warm-blooded animal, more in particular Tie2, Ang1, Ang2, Ang4 or Angptl4 from a mammal, and especially against human Tie2, Ang1, Ang2, Ang4 or Angptl4; and to provide proteins and polypeptides comprising or essentially consisting of at least one such amino acid sequence.

In particular, it is a specific object of the present invention to provide such amino acid sequences and such proteins and/or polypeptides that are suitable for prophylactic, therapeutic and/or diagnostic use in a warm-blooded animal, and in particular in a mammal, and more in particular in a human being.

More in particular, it is a specific object of the present invention to provide such amino acid sequences and such proteins and/or polypeptides that can be used for the prevention, treatment, alleviation and/or diagnosis of one or more diseases, disorders or conditions associated with Tie1, Tie2, Ang1, Ang2, Ang3, Ang4, Angptl1, Angptl2, Angptl3, Angptl4, Angptl5, Angptl6 and/or mediated by Tie1, Tie2, Ang1, Ang2, Ang3, Ang4, Angptl1, Angptl2, Angptl3, Angptl4, Angptl5, or Angptl6 (such as the diseases, disorders and conditions mentioned herein) in a warm-blooded animal, in particular in a mammal, and more in particular in a human being.

It is also a specific object of the invention to provide such amino acid sequences and such proteins and/or polypeptides that can be used in the preparation of pharmaceutical or veterinary compositions for the prevention and/or treatment of one or more diseases, disorders or conditions associated with and/or mediated by Tie1, Tie2, Ang1, Ang2, Ang3, Ang4, Angptl1, Angptl2, Angptl3, Angptl4, Angptl5, or Angptl6 (such as the diseases, disorders and conditions mentioned herein) in a warm-blooded animal, in particular in a mammal, and more in particular in a human being.

In the invention, generally, these objects are achieved by the use of the amino acid sequences, proteins, polypeptides and compositions that are described herein.

In general, the invention provides amino acid sequences that are directed against (as defined herein) and/or can specifically bind (as defined herein) to Tie1, Tie2, Ang1, Ang2, Ang3, Ang4, Angptl1, Angptl2, Angptl3, Angptl4, Angptl5, or Angptl6; as well as compounds and constructs, and in particular proteins and polypeptides, that comprise at least one such amino acid sequence.

More in particular, the invention provides amino acid sequences that can bind to Tie1, Tie2, Ang1, Ang2, Ang3, Ang4, Angptl1, Angptl2, Angptl3, Angptl4, Angptl5, or Angptl6 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein; as well as compounds and constructs, and in particular proteins and polypeptides, that comprise at least one such amino acid sequence.

In particular, amino acid sequences and polypeptides of the invention are preferably such that they:

bind to Tie1, Tie2, Ang1, Ang2, Ang3, Ang4, Angptl1, Angptl2, Angptl3, Angptl4, Angptl5, or Angptl6 with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that they:

bind to Tie1, Tie2, Ang1, Ang2, Ang3, Ang4, Angptl1, Angptl2, Angptl3, Angptl4, Angptl5, or Angptl6 with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$;

and/or such that they:

bind to Tie1, Tie2, Ang1, Ang2, Ang3, Ang4, Angptl1, Angptl2, Angptl3, Angptl4, Angptl5, or Angptl6 with a $k_{off}$-rate between 1 $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Preferably, a monovalent amino acid sequence of the invention (or a polypeptide that contains only one amino acid sequence of the invention) is preferably such that it will bind to Tie1, Tie2, Ang1, Ang2, Ang3, Ang4, Angptl1, Angptl2, Angptl3, Angptl4, Angptl5, or Angptl6 with an affinity less than 500 nM, preferably less than 200 nM, more preferably less than 10 nM, such as less than 500 μM.

Some preferred IC50 values for binding of the amino acid sequences or polypeptides of the invention to Tie1, Tie2, Ang1, Ang2, Ang3, Ang4, Angptl1, Angptl2, Angptl3, Angptl4, Angptl5, or Angptl6 will become clear from the further description and examples herein.

For binding to Tie1, Tie2, Ang1, Ang2, Ang3, Ang4, Angptl1, Angptl2, Angptl3, Angptl4, Angptl5, or Angptl6, an amino acid sequence of the invention will usually contain within its amino acid sequence one or more amino acid residues or one or more stretches of amino acid residues (i.e. with each "stretch" comprising two or amino acid residues that are adjacent to each other or in close proximity to each other, i.e. in the primary or tertiary structure of the amino acid sequence) via which the amino acid sequence of the invention can bind to Tie1, Tie2, Ang1, Ang2, Ang3, Ang4, Angptl1, Angptl2, Angptl3, Angptl4, Angptl5, or Angptl6, which amino acid residues or stretches of amino acid residues thus form the "site" for binding to Tie1, Tie2, Ang1, Ang2, Ang3, Ang4, Angptl1, Angptl2, Angptl3, Angptl4, Angptl5, or Angptl6 (also referred to herein as the "antigen binding site").

The amino acid sequences provided by the invention are preferably in essentially isolated form (as defined herein), or form part of a protein or polypeptide of the invention (as defined herein), which may comprise or essentially consist of one or more amino acid sequences of the invention and which may optionally further comprise one or more further amino acid sequences (all optionally linked via one or more suitable linkers). For example, and without limitation, the one or more amino acid sequences of the invention may be used as a binding unit in such a protein or polypeptide, which may optionally contain one or more further amino acid sequences that can serve as a binding unit (i.e. against one or more other targets than Tie1, Tie2, Ang1, Ang2, Ang3, Ang4, Angptl1, Angptl2, Angptl3, Angptl4, Angptl5, or Angptl6, so as to provide a monovalent, multivalent or multispecific polypeptide of the invention, respectively, all as described herein. Such a protein or polypeptide may also be in essentially isolated form (as defined herein).

The amino acid sequences and polypeptides of the invention as such preferably essentially consist of a single amino acid chain that is not linked via disulphide bridges to any other amino acid sequence or chain (but that may or may not contain one or more intramolecular disulphide bridges. For example, it is known that Nanobodies—as described herein—may sometimes contain a disulphide bridge between CDR3 and CDR1 or FR2). However, it should be noted that one or more amino acid sequences of the invention may be linked to each other and/or to other amino acid sequences (e.g. via disulphide bridges) to provide peptide constructs that may also be useful in the invention (for example Fab' fragments, F(ab')$_2$ fragments, ScFv constructs, "diabodies" and other multispecific constructs. Reference is for example made to the review by Holliger and Hudson, Nat. Biotechnol. 2005 September; 23(9):1126-36).

Generally, when an amino acid sequence of the invention (or a compound, construct or polypeptide comprising the same) is intended for administration to a subject (for example for therapeutic and/or diagnostic purposes as described herein), it is preferably either an amino acid sequence that does not occur naturally in said subject; or, when it does occur naturally in said subject, in essentially isolated form (as defined herein).

It will also be clear to the skilled person that for pharmaceutical use, the amino acid sequences of the invention (as well as compounds, constructs and polypeptides comprising the same) are preferably directed against human Tie2, Ang1, Ang2, or Ang4; whereas for veterinary purposes, the amino acid sequences and polypeptides of the invention are preferably directed against Tie2, Ang1, Ang2, Ang4 or Angptl4 from the species to be treated, or at least cross-reactive with Tie2, Ang1, Ang2, Ang4 or Angptl4 from the species to be treated.

Furthermore, an amino acid sequence of the invention may optionally, and in addition to the at least one binding site for binding against Tie1, Tie2, Ang1, Ang2, Ang3, Ang4, Angptl1, Angptl2, Angptl3, Angptl4, Angptl5, or Angptl6, contain one or more further binding sites for binding against other antigens, proteins or targets.

The efficacy of the amino acid sequences and polypeptides of the invention, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person, and for example include Solid-phase receptor binding and blocking assays, Receptor activation/inactivation assays, In vivo angiogenesis assay, In vivo direct anti angiogenic effect, Lipoprotein lipase (LPL) assay, In vivo .CAM (chick chorioallantoric membrane) assay, In vivo animal model studies as well as the assays and animal models used in the experimental part below and in the prior art cited herein.

Also, according to the invention, amino acid sequences and polypeptides that are directed against Tie1, Tie2, Ang1, Ang2, Ang3, Ang4, Angptl1, Angptl2, Angptl3, Angptl4, Angptl5, or Angptl6 from a first species of warm-blooded animal may or may not show cross-reactivity with Tie1, Tie2, Ang1, Ang2, Ang3, Ang4, Angptl1, Angptl2, Angptl3, Angptl4, Angptl5, or Angptl6 from one or more other species of warm-blooded animal. For example, amino acid sequences and polypeptides directed against human Tie1, Tie2, Ang1, Ang2, Ang3, Ang4, Angptl1, Angptl2, Angptl3, Angptl4, Angptl5, or Angptl6 may or may not show cross reactivity with Tie1, Tie2, Ang1, Ang2, Ang3, Ang4, Angptl1, Angptl2, Angptl3, Angptl4, Angptl5, or Angptl6 from one or more other species of primates (such as, without limitation, monkeys from the genus *Macaca* (such as, and in particular, cynomologus monkeys (*Macaca fascicularis*) and/or rhesus monkeys (*Macaca mulatta*)) and baboon (*Papio ursinus*)) and/or with Tie1, Tie2, Ang1, Ang2, Ang3, Ang4, Angptl1, Angptl2, Angptl3, Angptl4, Angptl5, or Angptl6 from one or more species of animals that are often used in animal models for diseases (for example mouse, rat, rabbit, pig or dog), and in particular in animal models for diseases and disorders associated with Tie1, Tie2, Ang1, Ang2, Ang3, Ang4, Angptl1, Angptl2, Angptl3, Angptl4, Angptl5, or Angptl6 (such as the species and animal models mentioned herein). In this respect, it will be clear to the skilled person that such cross-reactivity, when present, may have advantages from a drug development point of view, since it allows the amino acid sequences and polypeptides against human Tie1, Tie2, Ang1, Ang2, Ang3, Ang4, Angptl1, Angptl1, Angptl3, Angptl4, Angptl5, or Angptl6 to be tested in such disease models.

More generally, amino acid sequences and polypeptides of the invention that are cross-reactive with Tie1, Tie2, Ang1, Ang2, Ang3, Ang4, Angptl1, Angptl2, Angptl3, Angptl4, Angptl5, or Angptl6 from multiple species of mammal will usually be advantageous for use in veterinary applications, since it will allow the same amino acid sequence or polypeptide to be used across multiple species. Thus, it is also encompassed within the scope of the invention that amino acid sequences and polypeptides directed against Tie1, Tie2, Ang1, Ang2, Ang3, Ang4, Angptl1, Angptl2, Angptl3, Angptl4, Angptl5, or Angptl6 from one species of animal (such as amino acid sequences and polypeptides against human Tie1, Tie2, Ang1, Ang2, Ang3, Ang4, Angptl1, Angptl2, Angptl3, Angptl4, Angptl5, or Angptl6 can be used in the treatment of another species of animal, as long as the use of the amino acid sequences and/or polypeptides provide the desired effects in the species to be treated.

The present invention is in its broadest sense also not particularly limited to or defined by a specific antigenic determinant, epitope, part, domain, subunit or confirmation (where applicable) of Tie1, Tie2, Ang1, Ang2, Ang3, Ang4, Angptl1, Angptl2, Angptl3, Angptl4, Angptl5, or Angptl6 against which the amino acid sequences and polypeptides of the invention are directed. However, it is generally assumed and preferred that the amino acid sequences and polypeptides of the invention are preferably directed against the Ang1 binding site on Tie2, or the Tie2 binding site on Ang2—see experimental part. Thus, in one preferred, but non-limiting aspect, the amino acid sequences and polypeptides of the invention are directed against Ang1 binding site of Tie2 or the Tie2 binding site of Ang2, and are as further defined herein.

It is also within the scope of the invention that, where applicable, an amino acid sequence of the invention can bind to two or more antigenic determinants, epitopes, parts, domains, subunits or confirmations of Tie1, Tie2, Ang1, Ang2, Ang3, Ang4, Angptl1, Angptl2, Angptl3, Angptl4, Angptl5, or Angptl6. In such a case, the antigenic determinants, epitopes, parts, domains or subunits of Tie1, Tie2, Ang1, Ang2, Ang3, Ang4, Angptl1, Angptl2, Angptl3, Angptl4, Angptl5, or Angptl6 to which the amino acid sequences and/or polypeptides of the invention bind may be essentially the same (for example, if Tie1, Tie2, Ang1, Ang2, Ang3, Ang4, Angptl1, Angptl2, Angptl3, Angptl4, Angptl5, or Angptl6 contains repeated structural motifs or occurs in a multimeric form) or may be different (and in the latter case, the amino acid sequences and polypeptides of the invention may bind to such different antigenic determinants, epitopes, parts, domains, subunits of Tie1, Tie2, Ang1, Ang2, Ang3, Ang4, Angptl1, Angptl2, Angptl3, Angptl4, Angptl5, or Angptl6 with an affinity and/or specificity which may be the same or different). Also, far example, when Tie1, Tie2, Ang1, Ang2, Ang3, Ang4, Angptl1, Angptl2, Angptl3, Angptl4, Angptl5, or Angptl6 exists in an activated conformation and in an inactive conformation, the amino acid sequences and polypeptides of the invention may bind to either one of these confirmation, or may bind to both these confirmations (i.e. with an affinity and/or specificity which may be the same or different). Also, for example, the amino acid sequences and polypeptides of the invention may bind to a conformation of Tie1, Tie2, Ang1, Ang2, Ang3, Ang4, Angptl1, Angptl2, Angptl3, Angptl4, Angptl5, or Angptl6 in which it is bound to a pertinent ligand, may bind to a conformation of Tie1, Tie2, Ang1, Ang2, Ang3, Ang4, Angptl1, Angptl2, Angptl3, Angptl4, Angptl5, or Angptl6 in which it not bound to a pertinent ligand, or may bind to both such conformations (again with an affinity and/or specificity which may be the same or different).

It is also expected that the amino acid sequences and polypeptides of the invention will generally bind to all naturally occurring or synthetic analogs, variants, mutants, alleles, parts and fragments of Tie1, Tie2, Ang1, Ang2, Ang3, Ang4, Angptl1, Angptl2, Angptl3, Angptl4, Angptl5, or Angptl6; or at least to those analogs, variants, mutants, alleles, parts and fragments of Tie1, Tie2, Ang1, Ang2, Ang3, Ang4, Angptl1, Angptl2, Angptl3, Angptl4, Angptl5, or Angptl6 that contain one or more antigenic determinants or epitopes that are essentially the same as the antigenic determinant(s) or epitope(s) to which the amino acid sequences and polypeptides of the invention bind in Tie1, Tie2, Ang1, Ang2, Ang3, Ang4, Angptl1, Angptl2, Angptl3, Angptl4, Angptl5, or Angptl6 (e.g. in wild-type Tie1, Tie2, Ang1, Ang2, Ang3, Ang4, Angptl1, Angptl2, Angptl3, Angptl4, Angptl5, or Angptl6). Again, in such a case, the amino acid sequences and polypeptides of the invention may bind to such analogs, variants, mutants, alleles, parts and fragments with an affinity and/or specificity that are the same as, or that are different from (i.e. higher than or lower than), the affinity and specificity with which the amino acid sequences of the invention bind to (wild-type) Tie1, Tie2, Ang1, Ang2, Ang3, Ang4, Angptl1, Angptl2, Angptl3, Angptl4, Angptl5, or Angptl6. It is also included within the scope of the invention that the amino acid sequences and polypeptides of the invention bind to some analogs, variants, mutants, alleles, parts and fragments of Tie1, Tie2, Ang1, Ang2, Ang3, Ang4, Angptl1, Angptl2, Angptl3, Angptl4, Angptl5, or Angptl6, but not to others.

When Tie1, Tie2, Ang1, Ang2, Ang3, Ang4, Angptl1, Angptl2, Angptl3, Angptl4, Angptl5, or Angptl6 exists in a monomeric form and in one or more multimeric forms, it is within the scope of the invention that the amino acid sequences and polypeptides of the invention only bind to Tie1, Tie2, Ang1, Ang2, Ang3, Ang4, Angptl1, Angptl2, Angptl3, Angptl4, Angptl5, or Angptl6 in monomeric form, only bind to Tie1, Tie2, Ang1, Ang2, Ang3, Ang4, Angptl1, Angptl2, Angptl3, Angptl4, Angptl5, or Angptl6 in multimeric form, or bind to both the monomeric and the multimeric form. Again, in such a case, the amino acid sequences and polypeptides of the invention may bind to the monomeric form with an affinity and/or specificity that are the same as, or that are different from (i.e. higher than or lower than), the affinity and specificity with which the amino acid sequences of the invention bind to the multimeric form.

Also, when Tie1, Tie2, Ang1, Ang2, Ang3, Ang4, Angptl1, Angptl2, Angptl3, Angptl4, Angptl5, or Angptl6 can associate with other proteins or polypeptides to form protein complexes (e.g. with multiple subunits), it is within the scope of the invention that the amino acid sequences and polypeptides of the invention bind to Tie1, Tie2, Ang1, Ang2, Ang3, Ang4, Angptl1, Angptl2, Angptl3, Angptl4, Angptl5, or Angptl6 in its non-associated state, bind to Tie1, Tie2, Ang1, Ang2, Ang3, Ang4, Angptl1, Angptl2, Angptl3, Angptl4, Angptl5, or Angptl6 in its associated state, or bind to both. In all these cases, the amino acid sequences and polypeptides of the invention may bind to such multimers or associated protein complexes with an affinity and/or specificity that may be the same as or different from (i.e. higher than or lower than) the affinity and/or specificity with which the amino acid sequences and polypeptides of the invention bind to Tie1, Tie2, Ang1, Ang2, Ang3, Ang4, Angptl1, Angptl2, Angptl3, Angptl4, Angptl5, or Angptl6 in its monomeric and non-associated state.

Also, as will be clear to the skilled person, proteins or polypeptides that contain two or more amino acid sequences directed against Tie1, Tie2, Ang1, Ang2, Ang3, Ang4, Angptl1, Angptl2, Angptl3, Angptl4, Angptl5, or Angptl6 may bind with higher avidity to Tie1, Tie2, Ang1, Ang2, Ang3, Ang4, Angptl1, Angptl2, Angptl3, Angptl4, Angptl5, or Angptl6 than the corresponding monomeric amino acid sequence(s). For example, and without limitation, proteins or polypeptides that contain two or more amino acid sequences directed against different epitopes of Tie1, Tie2, Ang1, Ang2, Ang3, Ang4, Angptl1, Angptl2, Angptl3, Angptl4, Angptl5, or Angptl6 may (and usually will) bind with higher avidity than each of the different monomers, and proteins or polypeptides that contain two or more amino acid sequences directed against Tie1, Tie2, Ang1, Ang2, Ang3, Ang4, Angptl1, Angptl2, Angptl3, Angptl4, Angptl5, or Angptl6 may (and usually will) bind also with higher avidity to a multimer of Tie1, Tie2, Ang1, Ang2, Ang3, Ang4, Angptl1, Angptl2, Angptl3, Angptl4, Angptl5, or Angptl6.

Generally, amino acid sequences and polypeptides of the invention will at least bind to those forms of Tie1, Tie2, Ang1, Ang2, Ang3, Ang4, Angptl1, Angptl2, Angptl3, Angptl4, Angptl5, or Angptl6 (including monomeric, multimeric and associated forms) that are the most relevant from a biological and/or therapeutic point of view, as will be clear to the skilled person.

It is also within the scope of the invention to use parts, fragments, analogs, mutants, variants, alleles and/or derivatives of the amino acid sequences and polypeptides of the invention, and/or to use proteins or polypeptides comprising or essentially consisting of one or more of such parts, fragments, analogs, mutants, variants, alleles and/or derivatives, as long as these are suitable for the uses envisaged herein. Such parts, fragments, analogs, mutants, variants, alleles and/or derivatives will usually contain (at least part of) a functional antigen-binding site for binding against Tie1, Tie2, Ang1, Ang2, Ang3, Ang4, Angptl1, Angptl2, Angptl3, Angptl4, Angptl5, or Angptl6; and more preferably will be capable of specific binding to Tie1, Tie2, Ang1, Ang2, Ang3, Ang4, Angptl1, Angptl2, Angptl3, Angptl4, Angptl5, or Angptl6, and even more preferably capable of binding to Tie1, Tie2, Ang1, Ang2, Ang3, Ang4, Angptl1, Angptl2, Angptl3, Angptl4, Angptl5, or Angptl6 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. Some non-limiting examples of such parts, fragments, analogs, mutants, variants, alleles, derivatives, proteins and/or polypeptides will become clear from the further description herein. Additional fragments or polypeptides of the invention may also be provided by suitably combining (i.e. by linking or genetic fusion) one or more (smaller) parts or fragments as described herein.

In one specific, but non-limiting aspect of the invention, which will be further described herein, such analogs, mutants, variants, alleles, derivatives have an increased half-life in serum (as further described herein) compared to the amino acid sequence from which they have been derived. For example, an amino acid sequence of the invention may be linked (chemically or otherwise) to one or more groups or moieties that extend the half-life (such as PEG), so as to provide a derivative of an amino acid sequence of the invention with increased half-life.

In one specific, but non-limiting aspect, the amino acid sequence of the invention may be an amino acid sequence that comprises an immunoglobulin fold or may be an amino acid sequence that, under suitable conditions (such as physiological conditions) is capable of forming an immunoglobulin fold (i.e. by folding). Reference is inter alia made to the review by Halaby et al., J. (1999) Protein Eng. 12, 563-71. Preferably, when properly folded so as to form an immunoglobulin fold, such an amino acid sequence is capable of specific binding (as defined herein) to Tie1, Tie2, Ang1, Ang2, Ang3, Ang4, Angptl1, Angptl2, Angptl3, Angptl4, Angptl5, or Angptl6; and more preferably capable of binding to Tie1, Tie2, Ang1, Ang2, Ang3, Ang4, Angptl1, Angptl2, Angptl3, Angptl4, Angptl5, or Angptl6 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. Also, parts, fragments, analogs, mutants, variants, alleles and/or derivatives of such amino acid sequences are preferably such that they comprise an immunoglobulin fold or are capable for forming, under suitable conditions, an immunoglobulin fold.

In particular, but without limitation, the amino acid sequences of the invention may be amino acid sequences that essentially consist of 4 framework regions (FR1 to FR4 respectively) and 3 complementarity determining regions (CDR1 to CDR3 respectively); or any suitable fragment of such an amino acid sequence (which will then usually contain at least some of the amino acid residues that form at least one of the CDR's, as further described herein).

The amino acid sequences of the invention may in particular be an immunoglobulin sequence or a suitable fragment thereof, and more in particular be an immunoglobulin variable domain sequence or a suitable fragment thereof, such as light chain variable domain sequence (e.g. a $V_L$-sequence) or a suitable fragment thereof; or a heavy chain variable domain sequence (e.g. a $V_H$-sequence) or a suitable fragment thereof. When the amino acid sequence of the invention is a heavy chain variable domain sequence, it may be a heavy chain variable domain sequence that is derived from a conventional four-chain antibody (such as, without limitation, a $V_H$ sequence that is derived from a human antibody) or be a so-called $V_{HH}$-sequence (as defined herein) that is derived from a so-called "heavy chain antibody" (as defined herein).

However, it should be noted that the invention is not limited as to the origin of the amino acid sequence of the invention (or of the nucleotide sequence of the invention used to express it), nor as to the way that the amino acid sequence or nucleotide sequence of the invention is (or has been) generated or obtained. Thus, the amino acid sequences of the invention may be naturally occurring amino acid sequences (from any suitable species) or synthetic or semi-synthetic amino acid sequences. In a specific but non-limiting aspect of the invention, the amino acid sequence is a naturally occurring immunoglobulin sequence (from any suitable species) or a synthetic or semi-synthetic immunoglobulin sequence, including but not limited to "humanized" (as defined herein) immunoglobulin sequences (such as partially or fully humanized mouse or rabbit immunoglobulin sequences, and in particular partially or fully humanized. $V_{HH}$ sequences or Nanobodies), "camelized" (as defined herein) immunoglobulin sequences, as well as immunoglobulin sequences that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing. Reference is for example made to the standard handbooks, as well as to the further description and prior art mentioned herein.

Similarly, the nucleotide sequences of the invention may be naturally occurring nucleotide sequences or synthetic or semi-synthetic sequences, and may for example be sequences that are isolated by PCR from a suitable naturally occurring template (e.g. DNA or RNA isolated from a cell), nucleotide sequences that have been isolated from a library (and in particular, an expression library), nucleotide sequences that have been prepared by introducing mutations into a naturally occurring nucleotide sequence (using any suitable technique known per se, such as mismatch PCR), nucleotide sequence that have been prepared by PCR using overlapping primers, or nucleotide sequences that have been prepared using techniques for DNA synthesis known per se.

The amino acid sequence of the invention may in particular a "single variable domain" or "single variable domains" (hereinafter "single variable domains"). The single variable domains of the invention are any variable domain that forms a single antigen binding unit. Generally, such single variable domains will be amino acid sequences that essentially consist of 4 framework regions (FR1 to FR4 respectively) and 3 complementarity determining regions (CDR1 to CDR3 respectively); or any suitable fragment of such an amino acid sequence (which will then usually contain at least some of the amino acid residues that form at least one of the CDR's, as further described herein). Such single variable domains and fragments are most preferably such that they comprise an immunoglobulin fold or are capable for forming, under suitable conditions, an immunoglobulin fold. As such, the single variable domain may for example comprise a light chain variable domain sequence (e.g. a $V_L$-sequence) or a suitable fragment thereof; or a heavy chain variable domain sequence (e.g. a $V_H$-sequence or $V_{HH}$ sequence) or a suitable fragment thereof; as long as it is capable of forming a single antigen binding unit (i.e. a functional antigen binding unit that essentially consists of the single variable domain, such that the single antigen binding domain does not need to interact with another variable domain to form a functional antigen binding unit, as is for example the case for the variable domains that are present in for example conventional antibodies and ScFv fragments that need to interact with another variable domain—e.g. through a $V_H/V_L$ interaction—to form a functional antigen binding domain).

For example, the single variable domain may be a domain antibody (or an amino acid sequence that is suitable for use as a domain antibody), a single domain antibody (or an amino acid sequence that is suitable for use as a single domain antibody), a "dAb" (or an amino acid sequence that is suitable for use as a dAb) or a Nanobody™ (as defined herein, and including but not limited to a $V_{HH}$ sequence); other single variable domains, or any suitable fragment of any one thereof. For a general description of (single) domain antibodies, reference is also made to the prior art cited above, as well as to EP 0 368 684. For the term "dAb's", reference is for example made to Ward et al. (Nature 1989 Oct. 12; 341 (6242): 544-6), to Holt et al., Trends Biotechnol., 2003, 21(10:484-490; as well as to for example WO 04/068820, WO 06/030220, WO 06/003388 and other published patent applications of Domantis Ltd. It should also be noted that, although less preferred in the context of the present invention because they are not of mammalian origin, single domain antibodies or single variable domains can be derived from certain species of shark (for example, the so-called "IgNAR domains", see for example WO 05/18629).

In particular, the amino acid sequence of the invention may be a Nanobody™ or a suitable fragment thereof. [Note: Nanobody™ Nanohodies™ and Nanoclone™ are trademarks of Ablynx N.V.] For a further description of $V_{HH}$'s and Nanobodies, reference is made to the review article by Muyldermans in Reviews in Molecular Biotechnology 74 (2001), 277-302; as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Generally, Nanobodies (in particular $V_{HH}$ sequences and partially humanized Nanobodies) can in particular be characterized by the presence of one or more "Hallmark residues" in one or more of the framework sequences.

The amino acid sequence of the invention may in particular be a domain antibody (or an amino acid sequence that is suitable for use as a domain antibody), a single domain antibody (or an amino acid sequence that is suitable for use as a single domain antibody), a "dAb" (or an amino acid sequence that is suitable for use as a dAb) or a Nanobody™ (as defined herein, and including but not limited to a $V_{HH}$ sequence); other single variable domains, or any suitable fragment of any one thereof. For a general description of (single) domain antibodies, reference is also made to the prior art cited above, as well as to EP 0 368 684. For the term "dAb's", reference is for example made to Ward et al. (Nature 1989 Oct. 12; 341 (6242): 544-6), to Holt et al., Trends Biotechnol., 2003, 21(11):484-490; as well as to for example WO 06/030220, WO 06/003388 and other published patent applications of Domantis Ltd. It should also be noted that, although less preferred in the context of the present invention because they are not of mammalian origin, single domain antibodies or single variable domains can be derived from certain species of shark (for example, the so-called "IgNAR domains", see for example WO 05/18629).

In particular, the amino acid sequence of the invention may be a Nanobody® (as defined herein) or a suitable fragment thereof [Note: Nanobody®; Nanobodies® and Nanoclone® are trademarks of Ablynx N.V.] Such Nanobodies directed against Tie1, Tie2, Ang1, Ang2, Ang3, Ang4, Angptl1, Angptl2, Angptl3, Angptl4, Angptl5, or Angptl6 will also be referred to herein as "Nanobodies of the invention".

For a general description of Nanobodies, reference is made to the further description below, as well as to the prior art cited herein. In this respect, it should however be noted that this description and the prior art mainly described Nanobodies of the so-called "$V_H3$ class" (i.e. Nanobodies with a high degree of sequence homology to human germline sequences of the $V_H3$ class such as DP-47, DP-51 or DP-29), which Nanobodies form a preferred aspect of this invention. It should however be noted that the invention in its broadest sense generally covers any type of Nanobody directed against Tie1, Tie2, Ang1, Ang2, Ang3, Ang4, Angptl1, Angptl2, Angptl3, Angptl4, Angptl5, or Angptl6, and for example also covers the Nanobodies belonging to the so-called "$V_H4$ class" (i.e. Nanobodies with a high degree of sequence homology to human germline sequences of the $V_H4$ class such as DP-78), as for example described in the U.S. provisional application 60/792,279 by Ablynx N.V. entitled "DP-78-like Nanobodies" filed on Apr. 14, 2006.

Generally, Nanobodies (in particular $V_{HH}$ sequences and partially humanized Nanobodies) can in particular be characterized by the presence of one or more "Hallmark residues" (as described herein) in one or more of the framework sequences (again as further described herein).

Thus, generally, a Nanobody can be defined as an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which one or more of the Hallmark residues are as further defined herein.

In particular, a Nanobody can be an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which the framework sequences are as further defined herein.

More in particular, a Nanobody can be an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
i) preferably one or more of the amino acid residues at positions 11, 37, 44, 45, 47, 83, 84, 103, 104 and 108 according to the Kabat numbering are chosen from the Hallmark residues mentioned in Table A-3 below;
and in which:
ii) said amino acid sequence has at least 80% amino acid identity with at least one of the amino acid sequences of SEQ ID NO's: 1 to 22, in which for the purposes of determining the degree of amino acid identity, the amino acid residues that form the CDR sequences (indicated with X in the sequences of SEQ ID NO's: 1 to 22) are disregarded.

In these Nanobodies, the CDR sequences are generally as further defined herein.

Thus, the invention also relates to such Nanobodies that can bind to (as defined herein) and/or are directed against Tie1, Tie2, Ang1, Ang2, Ang3, Ang4, Angptl1, Angptl2, Angptl3, Angptl4, Angptl5, or Angptl6, to suitable fragments thereof, as well as to polypeptides that comprise or essentially consist of one or more of such Nanobodies and/or suitable fragments.

SEQ ID NO's 455 to 501 give the amino acid sequences of a number of $V_{HH}$ sequences that have been raised against Tie2, Ang1, Ang2, and Ang4.

Accordingly, some particularly preferred Nanobodies of the invention are Nanobodies which can bind (as further defined herein) to and/or are directed against to Tie2, Ang1, Ang2, Ang4 or Angptl4 and which:

i) have 80% amino acid identity with at least one of the amino acid sequences of SEQ ID NO's: 455 to 501, in which for the purposes of determining the degree of amino acid identity, the amino acid residues that form the CDR sequences are disregarded. In this respect, reference is also made to Table A-1, which lists the framework 1 sequences (SEQ ID NO's: 126 to 172), framework 2 sequences (SEQ ID NO's: 220 to 266), framework 3 sequences (SEQ ID NO's: 314 to 360) and framework 4 sequences (SEQ ID NO's: 408 to 454) of the Nanobodies of SEQ ID NO's: 455 to 501 (with respect to the amino acid residues at positions 1 to 4 and 27 to 30 of the framework 1 sequences, reference is also made to the comments made below. Thus, for determining the degree of amino acid identity, these residues are preferably disregarded);

and in which:

ii) preferably one or more of the amino acid residues at positions 11, 37, 44, 45, 47, 83, 84, 103, 104 and 108 according to the Kabat numbering are chosen from the Hallmark residues mentioned in Table A-3 below.

In these Nanobodies, the CDR sequences are generally as further defined herein.

Again, such Nanobodies may be derived in any suitable manner and from any suitable source, and may for example be naturally occurring $V_{HH}$ sequences (i.e. from a suitable species of *Camelid*) or synthetic or semi-synthetic amino acid sequences, including but not limited to "humanized" (as defined herein) Nanobodies, "camelized" (as defined herein) immunoglobulin sequences (and in particular camelized heavy chain variable domain sequences), as well as Nanobodies that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. Also, when a Nanobody comprises a $V_{HH}$ sequence, said Nanobody may be suitably humanized, as further described herein, so as to provide one or more further (partially or fully) humanized Nanobodies of the invention. Similarly, when a Nanobody comprises a synthetic or semi-synthetic sequence (such as a partially humanized sequence), said Nanobody may optionally be further suitably humanized, again as described herein, again so as to provide one or more further (partially or fully) humanized Nanobodies of the invention.

In particular, humanized Nanobodies may be amino acid sequences that are as generally defined for Nanobodies in the previous paragraphs, but in which at least one amino acid residue is present (and in particular, in at least one of the framework residues) that is and/or that corresponds to a humanizing substitution (as defined herein). Some preferred, but non-limiting humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$-sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) a Nanobody may be partially humanized or fully humanized.

Some particularly preferred humanized Nanobodies of the invention are humanized variants of the Nanobodies of SEQ ID NO's: 455 to 501, of which the amino acid sequences of SEQ ID NO's: 455 to 457, 459, 460, 464 to 469 are some especially preferred examples.

Thus, some other preferred Nanobodies of the invention are Nanobodies which can block (as further defined herein) the Ang1/Tie2 or Ang2/Tie2 interaction and which:

i) preferably one or more of the amino acid residues at positions 11, 37, 44, 45, 47, 83, 84, 103, 104 and 108 according to the Kabat numbering are chosen from the Hallmark residues mentioned in Table A-3 below.

According to another specific aspect of the invention, the invention provides a number of stretches of amino acid residues (i.e. small peptides) that are particularly suited for binding to Tie1, Tie2, Ang1, Ang2, Ang3, Ang4, Angptl1, Angptl2, Angptl3, Angptl4, Angptl5, or Angptl6. These stretches of amino acid residues may be present in, and/or may be incorporated into an amino acid sequence of the invention, in particular in such a way that they form (part of) the antigen binding site of an amino acid sequence of the invention. As these stretches of amino acid residues were first generated as CDR sequences of heavy chain antibodies or $V_{HH}$ sequences that were raised against Tie1, Tie2, Ang1, Ang2, Ang3, Ang4, Angptl1, Angptl2, Angptl3, Angptl4, Angptl5, or Angptl6 (or may be based on and/or derived from such CDR sequences, as further described herein), they will also generally be referred to herein as "CDR sequences" (i.e. as CDR1 sequences, CDR2 sequences and CDR3 sequences, respectively). It should however be noted that the invention in its broadest sense is not limited to a specific structural role or function that these stretches of amino acid residues may have in an amino acid sequence of the invention, as long as these stretches of amino acid residues allow the amino acid sequence of the invention to bind to Tie1, Tie2, Ang1, Ang2, Ang3, Ang4, Angptl 1, Angptl2, Angptl3, Angptl4, Angptl5, or Angptl6. Thus, generally, the invention in its broadest sense comprises any amino acid sequence that is capable of binding to Tie1, Tie2, Ang1, Ang2, Ang3, Ang4, Angptl1, Angptl2, Angptl3, Angptl4, Angptl5, or Angptl6 and that comprises one or more CDR sequences as described herein, and in particular a suitable combination of two or more such CDR sequences, that are suitably linked to each other via one or more further amino acid sequences, such that the entire amino acid sequence forms a binding domain and/or binding unit that is capable of binding to Tie1, Tie2, Ang1, Ang2, Ang3, Ang4, Angptl1, Angptl2, Angptl3, Angptl4. Angptl5, or Angptl6. It should however also be noted that the presence of only one such CDR sequence in an amino acid sequence of the invention may by itself already be sufficient to provide an amino acid sequence of the invention that is capable of binding to Tie1, Tie2, Ang1, Ang2, Ang3, Ang4, Angptl1, Angptl2, Angptl3, Angptl4, Angptl5, or Angptl6; reference is for example again made to the so-called "Expedite fragments" described in WO 03/050531.

Thus, in another specific, but non-limiting aspect, the amino acid sequence of the invention may be an amino acid sequence that comprises at least one amino acid sequence that is chosen from the group consisting of the CDR1 sequences, CDR2 sequences and CDR3 sequences that are described herein (or any suitable combination thereof). In particular, an amino acid sequence of the invention may be an amino acid sequence that comprises at least one antigen binding site, wherein said antigen binding site comprises at least one amino acid sequence that is chosen from the group consisting of the CDR1 sequences, CDR2 sequences and CDR3 sequences that are described herein (or any suitable combination thereof).

Generally, in this aspect of the invention, the amino acid sequence of the invention may be any amino acid sequence that comprises at least one stretch of amino acid residues, in which said stretch of amino acid residues has an amino acid sequence that corresponds to the sequence of at least one of the CDR sequences described herein. Such an amino acid sequence may or may not comprise an immunoglobulin fold. For example, and without limitation, such an amino acid sequence may be a suitable fragment of an immunoglobulin sequence that comprises at least one such CDR sequence, but that is not large enough to form a (complete) immunoglobulin fold (reference is for example again made to the "Expedite fragments" described in WO 03/050531). Alternatively, such an amino acid sequence may be a suitable "protein scaffold" that comprises least one stretch of amino acid residues that corresponds to such a CDR sequence (i.e. as part of its antigen binding site). Suitable scaffolds for presenting amino acid sequences will be clear to the skilled person, and for example comprise, without limitation, to binding scaffolds based on or derived from immunoglobulins (i.e. other than the immunoglobulin sequences already described herein), protein scaffolds derived from protein A domains (such as Affibodies™), tendamistat, fibronectin, lipocalin, CTLA-4, T-cell receptors, designed ankyrin repeats, avimers and PDZ domains (Binz et al., Nat. Biotech 2005. Vol 23:1257), and binding moieties based on DNA or RNA including but not limited to DNA or RNA aptamers (Ulrich et al., Comb Chem High Throughput Screen 2006 9(8):619-32).

Again, any amino acid sequence of the invention that comprises one or more of these CDR sequences is preferably such that it can specifically bind (as defined herein) to Tie1, Tie2, Ang1, Ang2, Ang3, Ang4, Angptl1, Angptl2, Angptl3, Angptl4, Angptl5, or Angptl6, and more in particular such that it can bind to Tie1, Tie2, Ang1, Ang2, Ang3, Ang4, Angptl1, Angptl2, Angptl3, Angptl4, Angptl5, or Angptl6 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein), that is as defined herein.

More in particular, the amino acid sequences according to this aspect of the invention may be any amino acid sequence that comprises at least one antigen binding site, wherein said antigen binding site comprises at least two amino acid sequences that are chosen from the group consisting of the CDR1 sequences described herein, the CDR2 sequences described herein and the CDR3 sequences described herein, such that (i) when the first amino acid sequence is chosen from the CDR1 sequences described herein, the second amino acid sequence is chosen from the CDR2 sequences described herein or the CDR3 sequences described herein; (ii) when the first amino acid sequence is chosen from the CDR2 sequences described herein, the second amino acid sequence is chosen from the CDR1 sequences described herein or the CDR3 sequences described herein; or (iii) when the first amino acid sequence is chosen from the CDR3 sequences described herein, the second amino acid sequence is chosen from the CDR1 sequences described herein or the CDR3 sequences described herein.

Even more in particular, the amino acid sequences of the invention may be amino acid sequences that comprise at least one antigen binding site, wherein said antigen binding site comprises at least three amino acid sequences that are chosen from the group consisting of the CDR1 sequences described herein, the CDR2 sequences described herein and the CDR3 sequences described herein, such that the first amino acid sequence is chosen from the CDR1 sequences described herein, the second amino acid sequence is chosen from the CDR2 sequences described herein, and the third amino acid sequence is chosen from the CDR3 sequences described herein. Preferred combinations of CDR1, CDR2 and CDR3 sequences will become clear from the further description herein. As will be clear to the skilled person, such an amino acid sequence is preferably an immunoglobulin sequence (as further described herein), but it may for example also be any other amino acid sequence that comprises a suitable scaffold for presenting said CDR sequences.

Thus, in one specific, but non-limiting aspect, the invention relates to an amino acid sequence directed against Tie1, Tie2, Ang1, Ang2, Ang3, Ang4, Angptl1, Angptl2, Angptl3, Angptl4, Angptl5, or Angptl6, that comprises one or more stretches of amino acid residues chosen from the group consisting of:

a) the amino acid sequences of SEQ ID NO's: 173 to 219;
b) amino acid sequences that have at least 80% amino acid identity with at least one of the amino acid sequences of SEQ ID NO's: 173 to 219;
c) amino acid sequences that have 3, 2, or 1 amino acid difference with at least one of the amino acid sequences of SEQ ID NO's: 173 to 219;
d) the amino acid sequences of SEQ ID NO's: 267 to 313;
e) amino acid sequences that have at least 80% amino acid identity with at least one of the amino acid sequences of SEQ ID NO's: 267 to 313;
f) amino acid sequences that have 3, 2, or 1 amino acid difference with at least one of the amino acid sequences of SEQ ID NO's: 267 to 313;
g) the amino acid sequences of SEQ ID NO's: 361 to 454;
h) amino acid sequences that have at least 80% amino acid identity with at least one of the amino acid sequences of SEQ ID NO's: 361 to 454;
i) amino acid sequences that have 3, 2, or 1 amino acid difference with at least one of the amino acid sequences of SEQ ID NO's: 361 to 454;
or any suitable combination thereof.

When an amino acid sequence of the invention contains one or more amino acid sequences according to b) and/or c):

i) any amino acid substitution in such an amino acid sequence according to b) and/or c) is preferably, and compared to the corresponding amino acid sequence according to a), a conservative amino acid substitution, (as defined herein); and/or ii) the amino acid sequence according to b) and/or c) preferably only contains amino acid substitutions, and no amino acid deletions or insertions, compared to the corresponding amino acid sequence according to a); and/or iii) the amino acid sequence according to b) and/or c) may be an amino acid sequence that is derived from an amino acid sequence according to a) by means of affinity maturation using one or more techniques of affinity maturation known per se.

Similarly, when an amino acid sequence of the invention contains one or more amino acid sequences according to e) and/or f):

i) any amino acid substitution in such an amino acid sequence according to e) and/or f) is preferably, and compared to the corresponding amino acid sequence according to d), a conservative amino acid substitution, (as defined herein); and/or ii) the amino acid sequence according to e) and/or f) preferably only contains amino acid substitutions, and no amino acid deletions or insertions, compared to the corresponding amino acid sequence according to d); and/or iii) the amino acid sequence according to e) and/or f) may be an amino acid sequence that is derived from an amino acid sequence according to d) by means of affinity maturation using one or more techniques of affinity maturation known per se.

Also, similarly, when an amino acid sequence of the invention contains one or more amino acid sequences according to h) and/or i):

i) any amino acid substitution in such an amino acid sequence according to h) and/or i) is preferably, and compared to the corresponding amino acid sequence according to g), a conservative amino acid substitution, (as defined herein); and/or ii) the amino acid sequence according to h) and/or i) preferably only contains amino acid substitutions, and no amino acid deletions or insertions, compared to the corresponding amino acid sequence according to g); and/or iii) the amino acid sequence according to h) and/or i) may be an amino acid sequence that is derived from an amino acid sequence according to g) by means of affinity maturation using one or more techniques of affinity maturation known per se.

It should be understood that the last preceding paragraphs also generally apply to any amino acid sequences of the invention that comprise one or more amino acid sequences according to b), c), e), f), h) or i), respectively.

In this specific aspect, the amino acid sequence preferably comprises one or more stretches of amino acid residues chosen from the group consisting of:
i) the amino acid sequences of SEQ ID NO's: 173 to 219;
ii) the amino acid sequences of SEQ ID NO's: 267 to 313; and
iii) the amino acid sequences of SEQ ID NO's: 361 to 454;
or any suitable combination thereof.

Also, preferably, in such an amino acid sequence, at least one of said stretches of amino acid residues forms part of the antigen binding site for binding against Tie1, Tie2, Ang1, Ang2, Ang3, Ang4, Angptl1, Angptl2, Angptl3, Angptl4, Angptl5, or Angptl6.

In a more specific, but again non-limiting aspect, the invention relates to an amino acid sequence directed against Tie1, Tie2, Ang1, Ang2, Ang3, Ang4, Angptl1, Angptl2, Angptl3, Angptl4, Angptl5, or Angptl6, that comprises two or more stretches of amino acid residues chosen from the group consisting of:
a) the amino acid sequences of SEQ ID NO's: 173 to 219;
b) amino acid sequences that have at least 80% amino acid identity with at least one of the amino acid sequences of SEQ ID NO's: 173 to 219;
c) amino acid sequences that have 3, 2, or 1 amino acid difference with at least one of the amino acid sequences of SEQ ID NO's: 173 to 219;
d) the amino acid sequences of SEQ ID NO's: 267 to 313;
e) amino acid sequences that have at least 80% amino acid identity with at least one of the amino acid sequences of SEQ ID NO's: 267 to 313;
f) amino acid sequences that have 3, 2, or 1 amino acid difference with at least one of the amino acid sequences of SEQ ID NO's: 267 to 313;
g) the amino acid sequences of SEQ ID NO's: 361 to 454;
h) amino acid sequences that have at least 80% amino acid identity with at least one of the amino acid sequences of SEQ ID NO's: 361 to 454;
i) amino acid sequences that have 3, 2, or 1 amino acid difference with at least one of the amino acid sequences of SEQ ID NO's: 361 to 454;
such that (i) when the first stretch of amino acid residues corresponds to one of the amino acid sequences according to a), b) or c), the second stretch of amino acid residues corresponds to one of the amino acid sequences according to d), e), f), g), h) or i); (ii) when the first stretch of amino acid residues corresponds to one of the amino acid sequences according to d), e) or f), the second stretch of amino acid residues corresponds to one of the amino acid sequences according to a), b), c), g), h) or i); or (iii) when the first stretch of amino acid residues corresponds to one of the amino acid sequences according to g), h) or i), the second stretch of amino acid residues corresponds to one of the amino acid sequences according to a), b), c), d), e) or f).

In this specific aspect, the amino acid sequence preferably comprises two or more stretches of amino acid residues chosen from the group consisting of:
i) the amino acid sequences of SEQ ID NO's: 173 to 219;
ii) the amino acid sequences of SEQ ID NO's: 267 to 313; and
iii) the amino acid sequences of SEQ ID NO's: 361 to 454;
such that, (i) when the first stretch of amino acid residues corresponds to one of the amino acid sequences of SEQ ID NO's: 173 to 219, the second stretch of amino acid residues corresponds to one of the amino acid sequences of SEQ ID NO's: 267 to 313 or of SEQ ID NO's: 361 to 454; (ii) when the first stretch of amino acid residues corresponds to one of the amino acid sequences of SEQ ID NO's: 267 to 313, the second stretch of amino acid residues corresponds to one of the amino acid sequences of SEQ ID NO's: 173 to 219 or of SEQ ID NO's: 361 to 454; or (iii) when the first stretch of amino acid residues corresponds to one of the amino acid sequences of SEQ ID NO's: 361 to 454, the second stretch of amino acid residues corresponds to one of the amino acid sequences of SEQ ID NO's: 173 to 219 or of SEQ ID NO's: 267 to 313.

Also, in such an amino acid sequence, the at least two stretches of amino acid residues again preferably form part of the antigen binding site for binding against Tie1, Tie2, Ang1, Ang2, Ang3, Ang4, Angptl1, Angptl2, Angptl3, Angptl4, Angptl5, or Angptl6.

In an even more specific, but non-limiting aspect, the invention relates to an amino acid sequence directed against Tie1, Tie2, Ang1, Ang2, Ang3, Ang4, Angptl1, Angptl2, Angptl3, Angptl4, Angptl5, or Angptl6, that comprises three or more stretches of amino acid residues, in which the first stretch of amino acid residues is chosen from the group consisting of:
a) the amino acid sequences of SEQ ID NO's: 173 to 219;
b) amino acid sequences that have at least 80% amino acid identity with at least one of the amino acid sequences of SEQ ID NO's: 173 to 219;
c) amino acid sequences that have 3, 2, or 1 amino acid difference with at least one of the amino acid sequences of SEQ ID NO's: 173 to 219;
the second stretch of amino acid residues is chosen from the group consisting of:
d) the amino acid sequences of SEQ ID NO's: 267 to 313;
e) amino acid sequences that have at least 80% amino acid identity with at least one of the amino acid sequences of SEQ ID NO's: 267 to 313;
f) amino acid sequences that have 3, 2, or 1 amino acid difference with at least one of the amino acid sequences of SEQ ID NO's: 267 to 313;
and the third stretch of amino acid residues is chosen from the group consisting of:
g) the amino acid sequences of SEQ ID NO's: 361 to 454;
h) amino acid sequences that have at least 80% amino acid identity with at least one of the amino acid sequences of SEQ ID NO's: 361 to 454;
i) amino acid sequences that have 3, 2, or 1 amino acid difference with at least one of the amino acid sequences of SEQ ID NO's: 361 to 454.

Preferably, in this specific aspect, the first stretch of amino acid residues is chosen from the group consisting of the amino acid sequences of SEQ ID NO's: 173 to 219; the second stretch of amino acid residues is chosen from the group consisting of the amino acid sequences of SEQ ID NO's: 267 to 313; and the third stretch of amino acid residues is chosen from the group consisting of the amino acid sequences of SEQ ID NO's: 361 to 454.

Again, preferably, in such an amino acid sequence, the at least three stretches of amino acid residues forms part of the antigen binding site for binding against Tie1, Tie2, Ang1, Ang2, Ang3, Ang4, Angptl1, Angptl2, Angptl3, Angptl4, Angptl5, or Angptl6.

Preferred combinations of such stretches of amino acid sequences will become clear from the further disclosure herein.

Preferably, in such amino acid sequences the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 455 to 501. This degree of amino acid identity can for example be determined by determining the degree of amino acid identity (in a manner described herein) between said amino acid sequence and one or more of the sequences of SEQ ID NO's: 455 to 501, in which the amino acid residues that form the framework regions are disregarded. Also, such amino acid sequences of the invention can be as further described herein.

Also, such amino acid sequences are preferably such that they can specifically bind (as defined herein) to Tie1, Tie2, Ang1, Ang2, Ang3, Ang4, Angptl1, Angptl2, Angptl3, Angptl4, Angptl5, or Angptl6; and more in particular bind to Tie1, Tie2, Ang1, Ang2, Ang3, Ang4, Angptl1, Angptl2, Angptl3, Angptl4, Angptl5, or Angptl6 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein.

When the amino acid sequence of the invention essentially consists of 4 framework regions (FR1 to FR4, respectively) and 3 complementarity determining regions (CDR1 to CDR3, respectively), the amino acid sequence of the invention is preferably such that:
CDR1 is chosen from the group consisting of:
a) the amino acid sequences of SEQ ID NO's: 173 to 219;
b) amino acid sequences that have at least 80% amino acid identity with at least one of the amino acid sequences of SEQ ID NO's: 173 to 219;
c) amino acid sequences that have 3, 2, or 1 amino acid difference with at least one of the amino acid sequences of SEQ ID NO's: 173 to 219;
and/or
CDR2 is chosen from the group consisting of:
d) the amino acid sequences of SEQ ID NO's: 267 to 313;
e) amino acid sequences that have at least 80% amino acid identity with at least one of the amino acid sequences of SEQ ID NO's: 267 to 313;
f) amino acid sequences that have 3, 2, or 1 amino acid difference with at least one of the amino acid sequences of SEQ ID NO's: 267 to 313;
and/or
CDR3 is chosen from the group consisting of:
g) the amino acid sequences of SEQ ID NO's: 361 to 454;
h) amino acid sequences that have at least 80% amino acid identity with at least one of the amino acid sequences of SEQ ID NO's: 361 to 454;
i) amino acid sequences that have 3, 2, or 1 amino acid difference with at least one of the amino acid sequences of SEQ ID NO's: 361 to 454.

In particular, such an amino acid sequence of the invention may be such that CDR1 is chosen from the group consisting of the amino acid sequences of SEQ ID NO's: 173 to 219; and/or CDR2 is chosen from the group consisting of the amino acid sequences of SEQ ID NO's: 267 to 313, and/or CDR3 is chosen from the group consisting of the amino acid sequences of SEQ ID NO's: 361 to 454.

In particular, when the amino acid sequence of the invention essentially consists of 4 framework regions (FR1 to FR4, respectively) and 3 complementarity determining regions (CDR1 to CDR3, respectively), the amino acid sequence of the invention is preferably such that:
CDR1 is chosen from the group consisting of:
a) the amino acid sequences of SEQ ID NO's: 173 to 219;
b) amino acid sequences that have at least 80% amino acid identity with at least one of the amino acid sequences of SEQ ID NO's: 173 to 219;
c) amino acid sequences that have 3, 2, or 1 amino acid difference with at least one of the amino acid sequences of SEQ ID NO's: 173 to 219;
and
CDR2 is chosen from the group consisting of:
d) the amino acid sequences of SEQ ID NO's: 267 to 313;
e) amino acid sequences that have at least 80% amino acid identity with at least one of the amino acid sequences of SEQ ID NO's: 267 to 313;

f) amino acid sequences that have 3, 2, or 1 amino acid difference with at least one of the amino acid sequences of SEQ ID NO's: 267 to 313;
and
CDR3 is chosen from the group consisting of:
g) the amino acid sequences of SEQ ID NO's: 267 to 313;
h) amino acid sequences that have at least 80% amino acid identity with at least one of the amino acid sequences of SEQ ID NO's: 267 to 313;
i) amino acid sequences that have 3, 2, or 1 amino acid difference with at least one of the amino acid sequences of SEQ ID NO's: 267 to 313; or any suitable fragment of such an amino acid sequence In particular, such an amino acid sequence of the invention may be such that CDR1 is chosen from the group consisting of the amino acid sequences of SEQ ID NO's: 173 to 219; and CDR2 is chosen from the group consisting of the amino acid sequences of SEQ ID NO's: 267 to 313; and CDR3 is chosen from the group consisting of the amino acid sequences of SEQ ID NO's: 361 to 454.

Again, preferred combinations of CDR sequences will become clear from the further description herein.

Also, such amino acid sequences are preferably such that they can specifically bind (as defined herein) to Tie1, Tie2, Ang1, Ang2, Ang3, Ang4, Angptl1, Angptl2, Angptl3, Angptl4, Angptl5, or Angptl6; and more in particular bind to Tie1, Tie2, Ang1, Ang2, Ang3, Ang4, Angptl1, Angptl2, Angptl3, Angptl4, Angptl5, or Angptl6 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein.

In one preferred, but non-limiting aspect, the invention relates to an amino acid sequence that essentially consists of 4 framework regions (FR1 to FR4, respectively) and 3 complementarity determining regions (CDR1 to CDR3, respectively), in which the CDR sequences of said amino acid sequence have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 455 to 501. This degree of amino acid identity can for example be determined by determining the degree of amino acid identity (in a manner described herein) between said amino acid sequence and one or more of the sequences of SEQ ID NO's: 455 to 501, in which the amino acid residues that form the framework regions are disregarded. Such amino acid sequences of the invention can be as further described herein.

In one preferred, but non-limiting aspect, the invention relates to an amino acid sequence that binds to Tie2, blocks interaction with Ang1 and essentially consists of 4 framework regions (FR1 to FR4, as described above, e.g. humanized framework regions FR1, FR2, FR3 or FR4 of any FR1, FR2, FR3 or FR4 as shown in Table A-1 (or preferably any corresponding FR for Tie2 binders with SEQ ID NO's: 455 to 457, 459, or 460) or any FR1, FR2, FR3 or FR4 as shown in Table A-1 (or preferably any corresponding FR for Tie2 binders with SEQ ID NO's: 455 to 457, 459, or 460)) and 3 complementarity determining regions (CDR1 to CDR3, respectively), in which the CDR sequences of said amino acid sequence have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 455 to 457, 459, or 460. This degree of amino acid identity can for example be determined by determining the degree of amino acid identity (in a manner described herein) between said amino acid sequence and one or more of the sequences of SEQ ID NO's: 455 to 457, 459, or 460, in which the amino acid residues that form the framework regions are disregarded. Such amino acid sequences of the invention can be as further described herein.

In one preferred, but non-limiting aspect, the invention relates to an amino acid sequence that binds to Ang2, blocks interaction with Tie2 and essentially consists of 4 framework regions (FR1 to FR4, as described above, e.g. humanized framework regions FR1, FR2, FR3 or FR4 of any FR1, FR2, FR3 or FR4 as shown in Table A-1 (or preferably any corresponding FR for Ang2 binders with SEQ ID NO's: 464 to 469) or any FR1, FR2, FR3 or FR4 as shown in Table A-1 (or preferably any corresponding FR for Ang2 binders with SEQ ID NO's: 464 to 469)) and 3 complementarity determining regions (CDR1 to CDR3, respectively), in which the CDR sequences of said amino acid sequence have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 464 to 469. This degree of amino acid identity can for example be determined by determining the degree of amino acid identity (in a manner described herein) between said amino acid sequence and one or more of the sequences of SEQ ID NO's: 464 to 469, in which the amino acid residues that form the framework regions are disregarded. Such amino acid sequences of the invention can be as further described herein.

In one preferred, but non-limiting aspect, the invention relates to an amino acid sequence that binds to Tie2, blocks interaction with Ang1 and essentially consists of 4 framework regions (FR1 to FR4 as described in SEQ ID NO: 455, or a humanized framework thereof) and 3 complementarity determining regions (CDR1 to CDR3, respectively), in which the CDR sequences of said amino acid sequence have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 455. This degree of amino acid identity can for example be determined by determining the degree of amino acid identity (in a manner described herein) between said amino acid sequence and the sequence of SEQ ID NO's: 455, in which the amino acid residues that form the framework regions are disregarded. Such amino acid sequences of the invention can be as further described herein.

In one preferred, but non-limiting aspect, the invention relates to an amino acid sequence that binds to Tie2, blocks interaction with Ang1 and essentially consists of 4 framework regions (FR1 to FR4 as described in SEQ ID NO: 456, or a humanized framework thereof) and 3 complementarity determining regions (CDR1 to CDR3, respectively), in which the CDR sequences of said amino acid sequence have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 456. This degree of amino acid identity can for example be determined by determining the degree of amino acid identity (in a manner described herein) between said amino acid sequence and the sequence of SEQ ID NO's: 456, in which the amino acid residues that form the framework regions are disregarded.

Such amino acid sequences of the invention can be as further described herein.

In one preferred, but non-limiting aspect, the invention relates to an amino acid sequence that binds to Tie2, blocks interaction with Ang1 and essentially consists of 4 framework regions (FR1 to FR4 as described in SEQ ID NO: 457, or a humanized framework thereof) and 3 complementarity determining regions (CDR1 to CDR3, respectively), in which the CDR sequences of said amino acid sequence have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 457. This degree of amino acid identity can for example be determined by determining the degree of amino acid identity (in a manner described herein) between said amino acid sequence and the sequence of SEQ ID NO's: 457, in which the amino acid residues that form the framework regions are disregarded. Such amino acid sequences of the invention can be as further described herein.

In one preferred, but non-limiting aspect, the invention relates to an amino acid sequence that binds to Tie2, blocks interaction with Ang1 and essentially consists of 4 framework regions (FR1 to FR4 as described in SEQ ID NO: 459, or a humanized framework thereof) and 3 complementarity determining regions (CDR1 to CDR3, respectively), in which the CDR sequences of said amino acid sequence have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 459. This degree of amino acid identity can for example be determined by determining the degree of amino acid identity (in a manner described herein) between said amino acid sequence and the sequence of SEQ ID NO's: 459, in which the amino acid residues that form the framework regions are disregarded. Such amino acid sequences of the invention can be as further described herein.

In one preferred, but non-limiting aspect, the invention relates to an amino acid sequence that binds to Tie2, blocks interaction with Ang1 and essentially consists of 4 framework regions (FR1 to FR4 as described in SEQ ID NO: 460, or a humanized framework thereof) and 3 complementarity determining regions (CDR1 to CDR3, respectively), in which the CDR sequences of said amino acid sequence have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 460. This degree of amino acid identity can for example be determined by determining the degree of amino acid identity (in a manner described herein) between said amino acid sequence and the sequence of SEQ ID NO's: 460, in which the amino acid residues that form the framework regions are disregarded. Such amino acid sequences of the invention can be as further described herein.

In one preferred, but non-limiting aspect, the invention relates to an amino acid sequence that binds to Ang2, blocks interaction with Tie2 and essentially consists of 4 framework regions (FR1 to FR4 as described in SEQ ID NO: 464, or a humanized framework thereof) and 3 complementarity determining regions (CDR1 to CDR3, respectively), in which the CDR sequences of said amino acid sequence have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 464. This degree of amino acid identity can for example be determined by determining the degree of amino acid identity (in a manner described herein) between said amino acid sequence and the sequence of SEQ ID NO's: 464, in which the amino acid residues that form the framework regions are disregarded. Such amino acid sequences of the invention can be as further described herein.

In one preferred, but non-limiting aspect, the invention relates to an amino acid sequence that binds to Ang2, blocks interaction with Tie2 and essentially consists of 4 framework regions (FR1 to FR4 as described in SEQ ID NO: 465, or a humanized framework thereof) and 3 complementarity determining regions (CDR1 to CDR3, respectively), in which the CDR sequences of said amino acid sequence have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 465. This degree of amino acid identity can for example be determined by determining the degree of amino acid identity (in a manner described herein) between said amino acid sequence and the sequence of SEQ ID NO's: 465, in which the amino acid residues that form the framework regions are disregarded. Such amino acid sequences of the invention can be as further described herein.

In one preferred, but non-limiting aspect, the invention relates to an amino acid sequence that binds to Ang2, blocks interaction with Tie2 and essentially consists of 4 framework regions (FR1 to FR4 as described in SEQ ID NO: 466, or a humanized framework thereof) and 3 complementarity determining regions (CDR1 to CDR3, respectively), in which the CDR sequences of said amino acid sequence have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 466. This degree of amino acid identity can for example be determined by determining the degree of amino acid identity (in a manner described herein) between said amino acid sequence and the sequence of SEQ ID NO's: 466, in which the amino acid residues that form the framework regions are disregarded. Such amino acid sequences of the invention can be as further described herein.

In one preferred, but non-limiting aspect, the invention relates to an amino acid sequence that binds to Ang2, blocks interaction with Tie2 and essentially consists of 4 framework regions (FR1 to FR4 as described in SEQ ID NO: 467, or a humanized framework thereof) and 3 complementarity determining regions (CDR1 to CDR3, respectively), in which the CDR sequences of said amino acid sequence have at least 70%/amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 467. This degree of amino acid identity can for example be determined by determining the degree of amino acid identity (in a manner described herein) between said amino acid sequence and the sequence of SEQ ID NO's: 467, in which the amino acid residues that form the framework regions are disregarded.

Such amino acid sequences of the invention can be as further described herein.

In one preferred, but non-limiting aspect, the invention relates to an amino acid sequence that binds to Ang2, blocks interaction with Tie2 and essentially consists of 4 framework regions (FR1 to FR4 as described in SEQ ID NO: 468, or a humanized framework thereof) and 3 complementarity determining regions (CDR1 to CDR3, respectively), in which the CDR sequences of said amino acid sequence have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 468. This degree of amino acid identity can for example be determined by determining the degree of amino acid identity (in a manner described herein) between said amino acid sequence and the sequence of SEQ ID NO's: 468, in which the amino acid residues that form the framework regions are disregarded. Such amino acid sequences of the invention can be as further described herein.

In one preferred, but non-limiting aspect, the invention relates to an amino acid sequence that binds to Ang2, blocks interaction with Tie2 and essentially consists of 4 framework regions (FR1 to FR4 as described in SEQ ID NO: 469, or a humanized framework thereof) and 3 complementarity determining regions (CDR1 to CDR3, respectively), in which the CDR sequences of said amino acid sequence have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 469. This degree of amino acid identity can for example be determined by determining the degree of amino acid identity (in a manner described herein) between said amino acid sequence and the sequence of SEQ ID NO's: 469, in which the amino acid residues that form the framework regions are disregarded. Such amino acid sequences of the invention can be as further described herein.

In such an amino acid sequence of the invention, the framework sequences may be any suitable framework sequences, and examples of suitable framework sequences will be clear to the skilled person, for example on the basis the standard handbooks and the further disclosure and prior art mentioned herein.

The framework sequences are preferably (a suitable combination of) immunoglobulin framework sequences or framework sequences that have been derived from immunoglobulin framework sequences (for example, by humanization or camelization). For example, the framework sequences may be framework sequences derived from a light chain variable domain (e.g. a $V_L$-sequence) and/or from a heavy chain variable domain (e.g. a $V_H$-sequence). In one particularly preferred aspect, the framework sequences are either framework sequences that have been derived from a $V_{HH}$-sequence (in which said framework sequences may optionally have been partially or fully humanized) or are conventional $V_H$ sequences that have been camelized (as defined herein).

The framework sequences are preferably such that the amino acid sequence of the invention is a domain antibody (or an amino acid sequence that is suitable for use as a domain antibody); is a single domain antibody (or an amino acid sequence that is suitable for use as a single domain antibody); is a "dAb" (or an amino acid sequence that is suitable for use as a dAb); or is a Nanobody™ (including but not limited to $V_{HH}$ sequence). Again, suitable framework sequences will be clear to the skilled person, for example on the basis the standard handbooks and the further disclosure and prior art mentioned herein.

In particular, the framework sequences present in the amino acid sequences of the invention may contain one or more of Hallmark residues (as defined herein), such that the amino acid sequence of the invention is a Nanobody™. Some preferred, but non-limiting examples of (suitable combinations of) such framework sequences will become clear from the further disclosure herein.

Again, as generally described herein for the amino acid sequences of the invention, it is also possible to use suitable fragments (or combinations of fragments) of any of the foregoing, such as fragments that contain one or more CDR sequences, suitably flanked by and/or linked via one or more framework sequences (for example, in the same order as these CDR's and framework sequences may occur in the full-sized immunoglobulin sequence from which the fragment has been derived). Such fragments may also again be such that they comprise or can form an immunoglobulin fold, or alternatively be such that they do not comprise or cannot form an immunoglobulin fold.

In one specific aspect, such a fragment comprises a single CDR sequence as described herein (and in particular a CDR3 sequence), that is flanked on each side by (part of) a framework sequence (and in particular, part of the framework sequence(s) that, in the immunoglobulin sequence from which the fragment is derived, are adjacent to said CDR sequence. For example, a CDR3 sequence may be preceded by (part of) a FR3 sequence and followed by (part of) a FR4 sequence). Such a fragment may also contain a disulphide bridge, and in particular a disulphide bridge that links the two framework regions that precede and follow the CDR sequence, respectively (for the purpose of forming such a disulphide bridge, cysteine residues that naturally occur in said framework regions may be used, or alternatively cysteine residues may be synthetically added to or introduced into said framework regions).

For a further description of these "Expedite fragments", reference is again made to WO 03/050531, as well as to the US provisional application of Ablynx N.V. entitled "Peptides capable of binding to serum proteins" of Ablynx N.V. (inventors: Revets, Hilde Adi Pierrette; Kolkman, Joost Alexander; and Hoogenboom, Hendricus Renerus Jacobus Mattheus) filed on Dec. 5, 2006.

In one preferred, but non-limiting aspect, the invention relates to an amino acid sequence that binds to Tie2, blocks interaction with Ang1 and essentially consists of 4 framework regions and 3 complementarity determining regions, in which said amino acid sequence has at least 70% amino acid identity, preferably at least 80% amino acid identity, more preferably at least 90% amino acid identity, such as 95% amino acid identity or more or less essentially 99 or 100% amino acid identity with the sequence of at least one of the amino acid sequences of SEQ ID NO's: 455 to 457, 459, or 460. This degree of amino acid identity can for example be determined by determining the degree of amino acid identity (in a manner described herein) between said amino acid sequence and the sequences of SEQ ID NO's: 455 to 457, 459, or 460. Such amino acid sequences of the invention can be as further described herein, e.g. humanized and/or formatted into a multivalent and/or multispecific embodiment.

In a further preferred, but non-limiting aspect, the invention relates to an amino acid sequence that binds to Ang2, blocks interaction with Tie2 and essentially consists of 4 framework regions and 3 complementarity determining regions, in which said amino acid sequence has at least 70% amino acid identity, preferably at least 80% amino acid identity, more preferably at least 90% amino acid identity, such as 95% amino acid identity or more or less essentially 99 or 100% amino acid identity with the sequence of at least one of the amino acid sequences of SEQ ID NO's: 464 to 469. This degree of amino acid identity can for example be determined by determining the degree of amino acid identity (in a manner described herein) between said amino acid sequence and the sequences of SEQ ID NO's: 464 to 469. Such amino acid sequences of the invention can be as further described herein, e.g. humanized and/or formatted into a multivalent and/or multispecific embodiment.

In another aspect, the invention relates to a compound or construct, and in particular a protein or polypeptide (also referred to herein as a "compound of the invention" or "polypeptide of the invention", respectively) that comprises or essentially consists of one or more amino acid sequences of the invention (or suitable fragments thereof), and optionally further comprises one or more other groups, residues, moieties or binding units. As will become clear to the skilled person from the further disclosure herein, such further groups, residues, moieties, binding units or amino acid sequences may or may not provide further functionality to the amino acid sequence of the invention (and/or to the compound or construct in which it is present) and may or may not modify the properties of the amino acid sequence of the invention.

For example, such further groups, residues, moieties or binding units may be one or more additional amino acid sequences, such that the compound or construct is a (fusion) protein or (fusion) polypeptide. In a preferred but non-limiting aspect, said one or more other groups, residues, moieties or binding units are immunoglobulin sequences. Even more preferably, said one or more other groups, residues, moieties or binding units are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

Alternatively, such groups, residues, moieties or binding units may for example be chemical groups, residues, moieties, which may or may not by themselves be biologically and/or pharmacologically active. For example, and without limitation, such groups may be linked to the one or more amino acid sequences of the invention so as to provide a "derivative" of an amino acid sequence or polypeptide of the invention, as further described herein.

Also within the scope of the present invention are compounds or constructs, that comprises or essentially consists of one or more derivatives as described herein, and optionally further comprises one or more other groups, residues, moieties or binding units, optionally linked via one or more linkers. Preferably, said one or more other groups, residues, moieties or binding units are amino acid sequences.

In the compounds or constructs described above, the one or more amino acid sequences of the invention and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting compound or construct is a fusion (protein) or fusion (polypeptide).

The compounds or polypeptides of the invention can generally be prepared by a method which comprises at least one step of suitably linking the one or more amino acid sequences of the invention to the one or more further groups, residues, moieties or binding units, optionally via the one or more suitable linkers, so as to provide the compound or polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

The process of designing/selecting and/or preparing a compound or polypeptide of the invention, starting from an amino acid sequence of the invention, is also referred to herein as "formatting" said amino acid sequence of the invention; and an amino acid of the invention that is made part of a compound or polypeptide of the invention is said to be "formatted" or to be in the format of said compound or polypeptide of the invention. Examples of ways in which an amino acid sequence of the invention can be formatted and examples of such formats will be clear to the skilled person based on the disclosure herein; and such formatted amino acid sequences form a further aspect of the invention.

In one specific aspect of the invention, a compound of the invention or a polypeptide of the invention may have an increased half-life, compared to the corresponding amino acid sequence of the invention. Some preferred, but non-limiting examples of such compounds and polypeptides will become clear to the skilled person based on the further disclosure herein, and for example comprise amino acid sequences or polypeptides of the invention that have been chemically modified to increase the half-life thereof (for example, by means of pegylation); amino acid sequences of the invention that comprise at least one additional binding site for binding to a serum protein (such as serum albumin); or polypeptides of the invention that comprise at least one amino acid sequence of the invention that is linked to at least one moiety (and in particular at least one amino acid sequence) that increases the half-life of the amino acid sequence of the invention. Examples of polypeptides of the invention that comprise such half-life extending moieties or amino acid sequences will become clear to the skilled person based on the further disclosure herein; and for example include, without limitation, polypeptides in which the one or more amino acid sequences of the invention are suitable linked to one or more serum proteins or fragments thereof (such as (human) serum albumin or suitable fragments thereof) or to one or more binding units that can bind to serum proteins (such as, for example, domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies that can bind to serum proteins such as serum albumin (such as human serum albumin), serum immunoglobulins such as IgG, or transferrine; reference is made to the further description and references mentioned herein); polypeptides in which an amino acid sequence of the invention is linked to an Fc portion (such as a human Fc) or a suitable part or fragment thereof; or polypeptides in which the one or more amino acid sequences of the invention are suitable linked to one or more small proteins or peptides that can bind to serum proteins (such as, without limitation, the proteins and peptides described in WO 91/01743, WO 01/45746, WO 02/076489 and to the US provisional application of Ablynx N.V. entitled "Peptides capable of binding to serum proteins" of Ablynx N.V. filed on Dec. 5, 2006.

Generally, the compounds or polypeptides of the invention with increased half-life preferably have a half-life that is at least 1.5 times, preferably at least 2 times, such as at least 5 times, for example at least 10 times or more than 20 times, greater than the half-life of the corresponding amino acid sequence of the invention per se. For example, the compounds or polypeptides of the invention with increased half-life may have a half-life that is increased with more than 1 hours, preferably more than 2 hours, more preferably more than 6 hours, such as more than 12 hours, or even more than 24, 48 or 72 hours, compared to the corresponding amino acid sequence of the invention per se.

In a preferred, but non-limiting aspect of the invention, such compounds or polypeptides of the invention have a serum half-life that is increased with more than 1 hours, preferably more than 2 hours, more preferably more than 6 hours, such as more than 12 hours, or even more than 24.48 or 72 hours, compared to the corresponding amino acid sequence of the invention per se.

In another preferred, but non-limiting aspect of the invention, such compounds or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In another aspect, the invention relates to a nucleic acid that encodes an amino acid sequence of the invention or a polypeptide of the invention (or a suitable fragment thereof). Such a nucleic acid will also be referred to herein as a "nucleic acid of the invention" and may for example be in the form of a genetic construct, as further described herein.

In another aspect, the invention relates to a host or host cell that expresses (or that under suitable circumstances is capable of expressing) an amino acid sequence of the invention and/or a polypeptide of the invention; and/or that contains a nucleic acid of the invention. Some preferred but non-limiting examples of such hosts or host cells will become clear from the further description herein.

The invention further relates to a product or composition containing or comprising at least one amino acid sequence of the invention, at least one polypeptide of the invention (or a suitable fragment thereof) and/or at least one nucleic acid of the invention, and optionally one or more further components of such compositions known per se, i.e. depending on the intended use of the composition. Such a product or composition may for example be a pharmaceutical composition (as described herein), a veterinary composition or a product or composition for diagnostic use (as also described herein). Some preferred but non-limiting examples of such products or compositions will become clear from the further description herein.

The invention also relates to the use of an amino acid sequence, Nanobody or polypeptide of the invention, or of a composition comprising the same, in (methods or compositions for) modulating Tie1, Tie2, Ang1, Ang2, Ang3, Ang4, Angptl1, Angptl2, Angptl3, Angptl4, Angptl5, or Angptl6, either in vitro (e.g. in an in vitro or cellular assay) or in vivo (e.g. in an a single cell or in a multicellular organism, and in particular in a mammal, and more in particular in a human being, such as in a human being that is at risk of or suffers from a malignant, ischemic, inflammatory, infectious and immune disorder.

The invention also relates to methods for modulating Tie1, Tie2, Ang1 Ang2, Ang3, Ang4, Angptl1, Angptl2, Angptl3, Angptl4, Angptl5, or Angptl6, either in vitro (e.g. in an in vitro or cellular assay) or in vivo (e.g. in an a single cell or multicellular organism, and in particular in a mammal, and more in particular in a human being, such as in a human being that is at risk of or suffers from a malignant, ischemic, inflammatory, infectious and immune disorder, which method comprises at least the step of contacting Tie1, Tie2, Ang1, Ang2, Ang3, Ang4, Angptl1, Angptl2, Angptl3, Angptl4, Angptl5, or Angptl6 with at least one amino acid sequence, Nanobody or polypeptide of the invention, or with a composition comprising the same, in a manner and in an amount suitable to modulate Tie1, Tie2, Ang1, Ang2, Ang3, Ang4, Angptl1, Angptl2, Angptl3, Angptl4, Angptl5, or Angptl6, with at least one amino acid sequence, Nanobody or polypeptide of the invention.

The invention also relates to the use of an one amino acid sequence, Nanobody or polypeptide of the invention in the preparation of a composition (such as, without limitation, a pharmaceutical composition or preparation as further described herein) for modulating Tie1, Tie2, Ang1, Ang2, Ang3, Ang4, Angptl1, Angptl2, Angptl3, Angptl4, Angptl5, or Angptl6, either in vitro (e.g. in an in vitro or cellular assay) or in vivo (e.g. in an a single cell or multicellular organism, and in particular in a mammal, and more in particular in a human being, such as in a human being that is at risk of or suffers from a malignant, ischemic, inflammatory, infectious and immune disorder.

In the context of the present invention, "modulating" or "to modulate" generally means either reducing or inhibiting the activity of, or alternatively increasing the activity of, Tie1, Tie2, Ang1, Ang2, Ang3, Ang4, Angptl1, Angptl2, Angptl3, Angptl4, Angptl5, or Angptl6, as measured using a suitable in vitro, cellular or in vivo assay (such as those mentioned herein). In particular, "modulating" or "to modulate" may mean either reducing or inhibiting the activity of, or alternatively increasing the activity of Tie1, Tie2, Ang1, Ang2, Ang3, Ang4, Angptl1, Angptl2, Angptl3, Angptl4, Angptl5, or Angptl6, as measured using a suitable in vitro, cellular or in vivo assay (such as those mentioned herein), by at least 1%, preferably at least 5%, such as at least 10% or at least 25%, for example by at least 50%, at least 60%, at least 70%, at least 80%, or 90% or more, compared to activity of Tie1, Tie2, Ang1, Ang2, Ang3, Ang4, Angptl1, Angptl2, Angptl3, Angptl4, Angptl5, or Angptl6 in the same assay under the same conditions but without the presence of the amino acid sequence, Nanobody or polypeptide of the invention.

As will be clear to the skilled person, "modulating" may also involve effecting a change (which may either be an increase or a decrease) in affinity, avidity, specificity and/or selectivity of Tie1, Tie2, Ang1, Ang2, Ang3, Ang4, Angptl1, Angptl2, Angptl3, Angptl4, Angptl5, or Angptl6 for one or more of its targets, ligands or substrates; and/or effecting a change (which may either be an increase or a decrease) in the sensitivity of Tie1, Tie2, Ang1, Ang2, Ang3, Ang4, Angptl1, Angptl2, Angptl3, Angptl4, Angptl5, or Angptl6 for one or more conditions in the medium or surroundings in which Tie1, Tie2, Ang1, Ang2, Ang3, Ang4, Angptl1, Angptl2, Angptl3, Angptl4, Angptl5, or Angptl6 is present (such as pH, ion strength, the presence of co-factors, etc.), compared to the same conditions but without the presence of the amino acid sequence, Nanobody or polypeptide of the invention. As will be clear to the skilled person, this may again be determined in any suitable manner and/or using any suitable assay known per se, such as the assays described herein or in the prior art cited herein.

"Modulating" may also mean effecting a change (i.e. an activity as an agonist or as an antagonist, respectively) with respect to one or more biological or physiological mechanisms, effects, responses, functions, pathways or activities in which Tie1, Tie2, Ang1, Ang2, Ang3, Ang4, Angptl1, Angptl2, Angptl3, Angptl4, Angptl5, or Angptl6 is involved. Again, as will be clear to the skilled person, such an action as an agonist or an antagonist may be determined in any suitable manner and/or using any suitable (in vitro and usually cellular or in assay) assay known per se, such as the assays described herein or in the prior art cited herein. In particular, an action as an agonist or antagonist may be such that an intended biological or physiological activity is increased or decreased, respectively, by at least 1%, preferably at least 5%, such as at least 10% or at least 25%, for example by at least 50%, at least 60%, at least 70%, at least 80%, or 90% or more, compared to the biological or physiological activity in the same assay under the same conditions but without the presence of the amino acid sequence, Nanobody or polypeptide of the invention.

Modulating may for example involve reducing or inhibiting the binding of Tie1 or Tie2 to one of its substrates or ligands such as e.g. Ang1, Ang2, Ang3, Ang4. Angptl1, Angptl2, Angptl3, Angptl4, Angptl5, or Angptl6 and/or competing with a natural ligand, substrate for binding. Modulating may also involve activating Tie1, Tie2, Ang1, Ang2, Ang3, Ang4, Angptl1, Angptl2, Angptl3, Angptl4, Angptl5, or Angptl6 or the mechanism or pathway in which it is involved. Modulating may be reversible or irreversible, but for pharmaceutical and pharmacological purposes will usually be in a reversible manner.

The invention further relates to methods for preparing or generating the amino acid sequences, polypeptides, nucleic acids, host cells, products and compositions described herein. Some preferred but non-limiting examples of such methods will become clear from the further description herein.

Generally, these methods may comprise the steps of:
a) providing a set, collection or library of amino acid sequences; and
b) screening said set, collection or library of amino acid sequences for amino acid sequences that can bind to and/or have affinity for Tie1, Tie2, Ang1, Ang2, Ang3, Ang4, Angptl1, Angptl2, Angptl3, Angptl4, Angptl5, or Angptl6; and
c) isolating the amino acid sequence(s) that can bind to and/or have affinity for Tie1, Tie2, Ang1, Ang2, Ang3, Ang4, Angptl1, Angptl2, Angptl3, Angptl4, Angptl5, or Angptl6.

In such a method, the set, collection or library of amino acid sequences may be any suitable set, collection or library of amino acid sequences. For example, the set, collection or library of amino acid sequences may be a set, collection or library of immunoglobulin sequences (as described herein), such as a naïve set, collection or library of immunoglobulin sequences; a synthetic or semi-synthetic set, collection or library of immunoglobulin sequences; and/or a set, collection or library of immunoglobulin sequences that have been subjected to affinity maturation.

Also, in such a method, the set, collection or library of amino acid sequences may be a set, collection or library of heavy chain variable domains (such as $V_H$ domains or $V_{HH}$ domains) or of light chain variable domains. For example, the set, collection or library of amino acid sequences may be a set, collection or library of domain antibodies or single domain antibodies, or may be a set, collection or library of amino acid sequences that are capable of functioning as a domain antibody or single domain antibody.

In a preferred aspect of this method, the set, collection or library of amino acid sequences may be an immune set, collection or library of immunoglobulin sequences, for example derived from a mammal that has been suitably immunized with Tie1, Tie2, Ang1, Ang2, Ang3, Ang4, Angptl1, Angptl2, Angptl3, Angptl4, Angptl5, or Angptl6 or with a suitable antigenic determinant based thereon or derived there from, such as an antigenic part, fragment, region, domain, loop or other epitope thereof. In one particular aspect, said antigenic determinant may be an extracellular part, region, domain, loop or other extracellular epitope(s).

In the above methods, the set, collection or library of amino acid sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art, for example on the basis of the further disclosure herein. Reference is also made to the review by Hoogenboom in Nature Biotechnology, 23, 9, 1105-1116 (2005).

In another aspect, the method for generating amino acid sequences comprises at least the steps of:
a) providing a collection or sample of cells expressing amino acid sequences;
b) screening said collection or sample of cells for cells that express an amino acid sequence that can bind to and/or have affinity for Tie1, Tie2, Ang1, Ang2, Ang3, Ang4, Angptl1, Angptl2, Angptl3, Angptl4, Angptl5, or Angptl6; and
c) either (i) isolating said amino acid sequence; or (ii) isolating from said cell a nucleic acid sequence that encodes said amino acid sequence, followed by expressing said amino acid sequence.

For example, when the desired amino acid sequence is an immunoglobulin sequence, the collection or sample of cells may for example be a collection or sample of B-cells. Also, in this method, the sample of cells may be derived from a mammal that has been suitably immunized with Tie1, Tie2, Ang1, Ang2, Ang3, Ang4, Angptl1, Angptl2, Angptl3, Angptl4, Angptl5, or Angptl6 or with a suitable antigenic determinant based thereon or derived there from, such as an antigenic part, fragment, region, domain, loop or other epitope thereof. In one particular aspect, said antigenic determinant may be an extracellular part, region, domain, loop or other extracellular epitope(s).

The above method may be performed in any suitable manner, as will be clear to the skilled person. Reference is for example made to EP 0 542 810, WO 05/19824, WO 04/051268 and WO 04/106377. The screening of step b) is preferably performed using a flow cytometry technique such as FACS. For this, reference is for example made to Lieby et al., Blood, Vol. 97, No. 12, 3820 (2001).

In another aspect, the method for generating an amino acid sequence directed against Tie1, Tie2, Ang1, Ang2, Ang3, Ang4, Angptl1, Angptl2, Angptl3, Angptl4, Angptl5, or Angptl6 may comprise at least the steps of:
a) providing a set, collection or library of nucleic acid sequences encoding amino acid sequences;
b) screening said set, collection or library of nucleic acid sequences for nucleic acid sequences that encode an amino acid sequence that can bind to and/or has affinity for Tie1, Tie2, Ang1, Ang2, Ang3, Ang4, Angptl1, Angptl2, Angptl3, Angptl4, Angptl5, or Angptl6; and c) isolating said nucleic acid sequence, followed by expressing said amino acid sequence.

In such a method, the set, collection or library of nucleic acid sequences encoding amino acid sequences may for example be a set, collection or library of nucleic acid sequences encoding a naïve set, collection or library of immunoglobulin sequences; a set, collection or library of nucleic acid sequences encoding a synthetic or semi-synthetic set, collection or library of immunoglobulin sequences; and/or a set, collection or library of nucleic acid sequences encoding a set, collection or library of immunoglobulin sequences that have been subjected to affinity maturation.

Also, in such a method, the set, collection or library of nucleic acid sequences may encode a set, collection or library of heavy chain variable domains (such as $V_H$ domains or $V_{HH}$ domains) or of light chain variable domains. For example, the set, collection or library of nucleic acid sequences may encode a set, collection or library of domain antibodies or single domain antibodies, or a set, collection or library of amino acid sequences that are capable of functioning as a domain antibody or single domain antibody.

In a preferred aspect of this method, the set, collection or library of amino acid sequences may be an immune set, collection or library of nucleic acid sequences, for example derived from a mammal that has been suitably immunized with Tie1, Tie2, Ang1, Ang2, Ang3, Ang4, Angptl1, Angptl2, Angptl3, Angptl4, Angptl5, or Angptl6 or with a suitable antigenic determinant based thereon or derived there from, such as an antigenic part, fragment, region, domain, loop or other epitope thereof. In one particular aspect, said antigenic determinant may be an extracellular part, region, domain, loop or other extracellular epitope(s).

The set, collection or library of nucleic acid sequences may for example encode an immune set, collection or library of heavy chain variable domains or of light chain variable domains. In one specific aspect, the set, collection or library of nucleotide sequences may encode a set, collection or library of $V_{HH}$ sequences.

In the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding amino acid sequences will be clear to the person skilled in the art, for example on the basis of the further disclosure herein. Reference is also made to the review by Hoogenboom in Nature Biotechnology, 23, 9, 1105-1116 (2005).

The invention also relates to amino acid sequences that are obtained by the above methods, or alternatively by a method that comprises the one of the above methods and in addition at least the steps of determining the nucleotide sequence or amino acid sequence of said immunoglobulin sequence; and of expressing or synthesizing said amino acid sequence in a manner known per se, such as by expression in a suitable host cell or host organism or by chemical synthesis.

Also, following the steps above, one or more amino acid sequences of the invention may be suitably humanized (or alternatively camelized); and/or the amino acid sequence(s) thus obtained may be linked to each other or to one or more other suitable amino acid sequences (optionally via one or more suitable linkers) so as to provide a polypeptide of the invention.

Also, a nucleic acid sequence encoding an amino acid sequence of the invention may be suitably humanized (or alternatively camelized) and suitably expressed; and/or one or more nucleic acid sequences encoding an amino acid sequence of the invention may be linked to each other or to one or more nucleic acid sequences that encode other suitable amino acid sequences (optionally via nucleotide sequences that encode one or more suitable linkers), after which the nucleotide sequence thus obtained may be suitably expressed so as to provide a polypeptide of the invention.

The invention further relates to applications and uses of the amino acid sequences, compounds, constructs, polypeptides, nucleic acids, host cells, products and compositions described herein, as well as to methods for the prevention and/or treatment for diseases and disorders associated with Tie1, Tie2, Ang1, Ang2, Ang3, Ang4, Angptl1, Angptl2, Angptl3, Angptl4, Angptl5, or Angptl6. Some preferred but non-limiting applications and uses will become clear from the further description herein.

The invention also relates to the amino acid sequences, compounds, constructs, polypeptides, nucleic acids, host cells, products and compositions described herein for use in therapy.

In particular, the invention also relates to the amino acid sequences, compounds, constructs, polypeptides, nucleic acids, host cells, products and compositions described herein for use in therapy of a disease or disorder that can be prevented or treated by administering, to a subject in need thereof, of (a pharmaceutically effective amount of) an amino acid sequence, compound, construct or polypeptide as described herein.

More in particular, the invention relates to the amino acid sequences, compounds, constructs, polypeptides, nucleic acids, host cells, products and compositions described herein for use in therapy of diseases and disorders related to angiogenesis.

Other aspects, embodiments, advantages and applications of the invention will also become clear from the further description herein, in which the invention will be described and discussed in more detail with reference to the Nanobodies of the invention and polypeptides of the invention comprising the same, which form some of the preferred aspects of the invention.

As will become clear from the further description herein, Nanobodies generally offer certain advantages (outlined herein) compared to "dAb's" or similar (single) domain antibodies or immunoglobulin sequences, which advantages are also provided by the Nanobodies of the invention. However, it will be clear to the skilled person that the more general aspects of the teaching below can also be applied (either directly or analogously) to other amino acid sequences of the invention.

DETAILED DESCRIPTION OF THE INVENTION

In the present description, examples and claims:
a) Unless indicated or defined otherwise, all terms used have their usual meaning in the art, which will be clear to the skilled person. Reference is for example made to the standard handbooks, such as Sambrook et al, "Molecular Cloning: A Laboratory Manual" (2".Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", $2^{nd}$ edition, University of California Press, Berkeley, Calif. (1981); Roitt et al., "Immunology" ($6^{th}$. Ed.), Mosby/Elsevier, Edinburgh (2001); Roitt et al., Roitt's Essential Immunology, $10^{th}$ Ed.

Blackwell Publishing, UK (2001); and Janeway et al., "Immunobiology" (6$^{th}$ Ed.), Garland Science Publishing/Churchill Livingstone, New York (2005), as well as to the general background art cited herein;

b) Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}^{-1}$ domains or $V_H/V_L$, domains, respectively). In addition, the term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation. Also, the term "nucleotide sequence" as used herein also encompasses a nucleic acid molecule with said nucleotide sequence, so that the terms "nucleotide sequence" and "nucleic acid" should be considered equivalent and are used interchangeably herein;

c) Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, Adv. Drug Deliv. Rev. 2006, 58 (5-6): 640-56; Levin and Weiss, Mol. Biosyst. 2006, 2(1): 49-57; Irving et al., J. Immunol. Methods, 2001, 248(1-2), 31-45; Schmitz et al., Placenta, 2000, 21 Suppl. A, S106-12, Gonzales et al., Tumour Biol., 2005, 26(1), 31-43, which describe techniques for protein engineering, such as affinity maturation and other techniques for improving the specificity and other desired properties of proteins such as immunoglobulins.

d) Amino acid residues will be indicated according to the standard three-letter or one-letter amino acid code, as mentioned in Table A-2;

TABLE A-2

| one-letter and three-letter amino acid code | | | |
|---|---|---|---|
| Nonpolar, uncharged (at pH 6.0-7.0)[3] | Alanine | Ala | A |
| | Valine | Val | V |
| | Leucine | Leu | L |
| | Isoleucine | Ile | I |
| | Phenylalanine | Phe | F |
| | Methionine[1] | Met | M |
| | Tryptophan | Trp | W |
| | Proline | Pro | P |
| Polar, uncharged (at pH 6.0-7.0) | Glycine[2] | Gly | G |
| | Serine | Ser | S |
| | Threonine | Thr | T |
| | Cysteine | Cys | C |
| | Asparagine | Asn | N |
| | Glutamine | Gln | Q |
| | Tyrosine | Tyr | Y |
| Polar, charged | Lysine | Lys | K |
| | Arginine | Arg | R |
| (at pH 6.0-7.0) | Histidine[4] | His | H |
| | Aspartate | Asp | D |
| | Glutamate | Glu | E |

Notes:
[1]Sometimes also considered to be a polar uncharged amino acid.
[2]Sometimes also considered to be a nonpolar uncharged amino acid.
[3]As will be clear to the skilled person, the fact that an amino acid residue is referred to in this Table as being either charged or uncharged at pH 6.0 to 7.0 does not reflect in any way on the charge said amino acid residue may have at a pH lower than 6.0 and/or at a pH higher than 7.0; the amino acid residues mentioned in the Table can be either charged and/or uncharged at such a higher or lower pH, as will be clear to the skilled person.
[4]As is known in the art, the charge of a His residue is greatly dependant upon even small shifts in pH, but a His residu can generally be considered essentially uncharged at a pH of about 6.5.

e) For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position).

Alternatively, the degree of sequence identity between two or more nucleotide sequences may be calculated using a known computer algorithm for sequence alignment such as NCBI Blast v2.0, using standard settings.

Some other techniques, computer algorithms and settings for determining the degree of sequence identity are for example described in WO 04/037999, EP 0 967 284, EP 1 085 089, WO 00/55318, WO 00/78972, WO 98/49185 and GB 2 357 768-A.

Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence;

f) For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e. as an "amino acid difference" as defined herein.

Alternatively, the degree of sequence identity between two amino acid sequences may be calculated using a known computer algorithm, such as those mentioned above for determining the degree of sequence identity for nucleotide sequences, again using standard settings.

Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB-A-3 357 768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp.

Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Len or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Nad. Acad. Sci. USA 81: 140-144, 1984; Kyte & Doolittle; J. Molec. Biol. 157: 105-132, 198 I, and Goldman et al., Aim. Rev. Biophys. Chem. 15: 321-353, 1986, all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the prior art cited above.

g) Amino acid sequences and nucleic acid sequences are said to be "exactly the same" if they have 100% sequence identity (as defined herein) over their entire length;
h) When comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences;
i) When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the first mentioned nucleotide sequence or amino acid sequence, respectively, but more usually this generally means that the first mentioned nucleotide sequence or amino acid sequence comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when a Nanobody of the invention is said to comprise a CDR sequence, this may mean that said CDR sequence has been incorporated into the Nanobody of the invention, but more usually this generally means that the Nanobody of the invention contains within its sequence a stretch of amino acid residues with the same amino acid sequence as said CDR sequence, irrespective of how said Nanobody of the invention has been generated or obtained. It should also be noted that when the latter amino acid sequence has a specific biological or structural function, it preferably has essentially the same, a similar or an equivalent biological or structural function in the first mentioned amino acid sequence (in other words, the first mentioned amino acid sequence is preferably such that the latter sequence is capable of performing essentially the same, a similar or an equivalent biological or structural function). For example, when a Nanobody of the invention is said to comprise a CDR sequence or framework sequence, respectively, the CDR sequence and framework are preferably capable, in said Nanobody, of functioning as a CDR sequence or framework sequence, respectively. Also, when a nucleotide sequence is said to comprise another nucleotide sequence, the first mentioned nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleotide sequence).
j) A nucleic acid sequence or amino acid sequence is considered to be "(in) essentially isolated (form)"—for example, compared to its native biological source and/or the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid sequence or amino acid sequence is considered "essentially isolated" when it has been purified at least 2-fold, in particular at least 10-fold, more in particular at least 100-fold, and up to 1000-fold or more. A nucleic acid sequence or amino acid sequence that is "in essentially isolated form" is preferably essentially homogeneous, as determined using a suitable technique, such as a suitable chromatographical technique, such as polyacrylamide-gel electrophoresis;
k) The term "domain" as used herein generally refers to a globular region of an amino acid sequence (such as an antibody chain, and in particular to a globular region of a heavy chain antibody), or to a polypeptide that essentially consists of such a globular region. Usually, such a domain will comprise peptide loops (for example 3 or 4 peptide loops) stabilized, for example, as a sheet or by disulfide bonds. The term "binding domain" refers to such a domain that is directed against an antigenic determinant (as defined herein);

l) The term "antigenic determinant" refers to the epitope on the antigen recognized by the antigen-binding molecule (such as a Nanobody or a polypeptide of the invention) and more in particular by the antigen-binding site of said molecule. The terms "antigenic determinant" and "epitope" may also be used interchangeably herein.

m) An amino acid sequence (such as a Nanobody, an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

n) The term "specificity" refers to the number of different types of antigens or antigenic determinants to which a particular antigen-binding molecule or antigen-binding protein (such as a Nanobody or a polypeptide of the invention) molecule can bind. The specificity of an antigen-binding protein can be determined based on affinity and/or avidity. The affinity, represented by the equilibrium constant for the dissociation of an antigen with an antigen-binding protein ($K_D$), is a measure for the binding strength between an antigenic determinant and an antigen-binding site on the antigen-binding protein: the lesser the value of the $K_D$, the stronger the binding strength between an antigenic determinant and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest. Avidity is the measure of the strength of binding between an antigen-binding molecule (such as a Nanobody or polypeptide of the invention) and the pertinent antigen. Avidity is related to both the affinity between an antigenic determinant and its antigen binding site on the antigen-binding molecule and the number of pertinent binding sites present on the antigen-binding molecule. Typically, antigen-binding proteins (such as the amino acid sequences, Nanobodies and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^4$ mol/liter (or any $K_A$ value lower than $10^4$ M$^{-1}$) liters/mol is generally considered to indicate non-specific binding. Preferably, a monovalent immunoglobulin sequence of the invention will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radio immunoassay (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person. Methods for determining the dissociation constant will be clear to the skilled person, and for example include the techniques mentioned herein. In this respect, it will also be clear that it may not be possible to measure dissociation constants of more then $10^{-1}$ moles/liter or $10^{-3}$ moles/liter (e.g., of $10^{-2}$ moles/liter). Optionally, as will also be clear to the skilled person, the (actual or apparent) dissociation constant may be calculated on the basis of the (actual or apparent) association constant ($K_A$), by means of the relationship [$K_D=1/K_A$].

The affinity denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of (mol/liter)$^{-1}$ (or M$^{-1}$). In the present specification, the stability of the interaction between two molecules (such as an amino acid sequence, Nanobody or polypeptide of the invention and its intended target) will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the free energy (DG) of binding by the well known relation. DG=RT. ln($K_D$) (equivalently DG=–RT. ln($K_A$)), where R equals the gas constant, T equals the absolute temperature and ln denotes the natural logarithm.

The $K_D$ for biological interactions which are considered meaningful (e.g. specific) are typically in the range of $10^{-10}$ M (0.1 nM) to $10^{-5}$ M (10000 nM). The stronger an interaction is the lower is its $K_D$.

The $K_D$ can also be expressed as the ratio of the dissociation rate constant of a complex, denoted as $k_{off}$ to the rate of its association, denoted $k_{on}$ (so that $K_D=k_{off}/k_{on}$ and $K_A=k_{on}/k_{off}$). The off-rate $k_{off}$ has unit's s$^{-1}$ (where s is the SI unit notation of second). The on-rate $k_{on}$ has units M$^{-1}$s$^{-1}$. The on-rate may vary between $10^2$ M$^{-1}$s$^{-1}$ to about $10^7$ M$^{-1}$s$^{-1}$, approaching the diffusion-limited association rate constant for bimolecular interactions. The off-rate is related to the half-life of a given molecular interaction by the relation $t_{1/2}=\ln(2)/k_{off}$. The off-rate may vary between $10^{-6}$ s$^{-1}$ (near irreversible complex with a $t_{1/2}$ of multiple days) to 1 s$^{-1}$ ($t_{1/2}$-0.69 s).

The affinity of a molecular interaction between two molecules can be measured via different techniques known per se, such as the well known surface plasmon resonance (SPR) biosensor technique (see for example Ober et al., Intern. Immunology, 13, 1551-1559, 2001) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIACORE instruments.

It will also be clear to the skilled person that the measured $K_D$ may correspond to the apparent $K_D$ if the measuring process somehow influences the intrinsic binding affinity of the implied molecules for example by artefacts related to the coating on the biosensor of one molecule. Also, an apparent $K_D$ may be measured if one molecule contains more than one recognition sites for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. (J. Immunol. Methods, 77, 305-19, 1985). This method establishes a solution phase binding equilibrium measurement and avoids possible artefacts relating to adsorption of one of the molecules on a support such as plastic.

However, the accurate measurement of $K_D$ may be quite labour-intensive and as consequence, often apparent $K_D$ values are determined to assess the binding strength of two molecules. It should be noted that as long all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance. Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection.). Typically, the reference molecule C is kept at a fixed concentration and the concentration of A is varied for a given concentration or amount of B. As a result an $IC_{50}$ value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D=IC_{50}/(1+c_{ref}/K_{D\ ref})$. Note that if $c_{ref} \ll K_{D\ ref}$, $K_D \approx IC_{50}$. Provided the measurement of the $IC_{50}$ is performed in a consistent way (e.g. keeping $c_{ref}$ fixed) for the binders that are compared, the strength or stability of a molecular interaction can be assessed by the $IC_{50}$ and this measurement is judged as equivalent to $K_D$ or to apparent $K_D$ throughout this text.

o) The half-life of an amino acid sequence, compound or polypeptide of the invention can generally be defined as the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally involve the steps of suitably administering to a warm-blooded animal (i.e. to a human or to another suitable mammal, such as a mouse, rabbit, rat, pig, dog or a primate, for example monkeys from the genus *Macaca* (such as, and in particular, cynomologus monkeys (*Macaca fascicularis*) and/or rhesus monkeys (*Macaca mulatta*)) and baboon (*Papio ursinus*)) a suitable dose of the amino acid sequence, compound or polypeptide of the invention; collecting blood samples or other samples from said animal; determining the level or concentration of the amino acid sequence, compound or polypeptide of the invention in said blood sample; and calculating, from (a plot of) the data thus obtained, the time until the level or concentration of the amino acid sequence, compound or polypeptide of the invention has been reduced by 50% compared to the initial level upon dosing. Reference is for example made to the Experimental Part below, as well as to Dennis et al., J. Biol. Chem. 277:35035-42 (2002), and to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982).

As will also be clear to the skilled person (see for example pages 6 and 7 of WO 04/003019 and in the further references cited therein), the half-life can be expressed using parameters such as the t1/2-alpha, t1/2-beta and the area under the curve (AUC). In the present specification, an "increase in half-life" refers to an increase in any one of these parameters, such as any two of these parameters, or essentially all three these parameters. As used herein "increase in half-life" or "increased half-life" in particular refers to an increase in the t1/2-beta, either with or without an increase in the t1/2-alpha and/or the AUC or both.

For example, the half-life of an amino acid sequence or polypeptide of the invention may be determined by means of a pharmacokinetic study, performed in a rodent or non-human primate model, as follows. Groups of animals (n=2-10) are given an intravenous bolus injection of 1 mg/kg or 10 mg/kg 2D3-17D12 fusion protein. Plasma samples are obtained via a vein at different timepoints after dosing (eg. 1, 2, 4, 6, 8, 12, 24, 48, 144, 192, 240, 288 and 336 h after dosing) and analyzed for the presence of the 2D3-17D12 fusion protein by ELISA. Plasma concentration versus time are fitted to a two-compartment elimination model. The pharmacokinetic parameters of clearance, V1, steady state volume (Vss), T½, AUC, and AUC corrected for actual dose administered (AUC/dose) are averaged for each treatment group. Differences between groups are determined by analysis of variance.

p) In the context of the present invention, "modulating" or "to modulate" generally means either reducing or inhibiting the activity of, or alternatively increasing the activity of, a target or antigen, as measured using a suitable in vitro, cellular or in vivo assay. In particular, "modulating" or "to modulate" may mean either reducing or inhibiting the activity of, or alternatively increasing a (relevant or intended) biological activity of, a target or antigen, as measured using a suitable in vitro, cellular or in vivo assay (which will usually depend on the target or antigen involved), by at least 1%, preferably at least 5%, such as at least 10% or at least 25%, for example by at least 50%, at least 60%, at least 70%, at least 80%, or 90% or more, compared to activity of the target or antigen in the same assay under the same conditions but without the presence of the construct of the invention.

As will be clear to the skilled person, "modulating" may also involve effecting a change (which may either be an increase or a decrease) in affinity, avidity, specificity and/or selectivity of a target or antigen for one or more of its ligands, binding partners, partners for association into a homomultimeric or heteromultimeric form, or substrates; and/or effecting a change (which may either be an increase or a decrease) in the sensitivity of the target or antigen for one or more conditions in the medium or surroundings in which the target or antigen is present (such as pH, ion strength, the presence of co-factors, etc.), compared to the same conditions but without the presence of the construct of the invention. As will be clear to the skilled person, this may again be determined in any suitable manner and/or using any suitable assay known per se, depending on the target or antigen involved.

"Modulating" may also mean effecting a change (i.e. an activity as an agonist, as an antagonist or as a reverse agonist, respectively, depending on the target or antigen and the desired biological or physiological effect) with respect to one or more biological or physiological mechanisms, effects, responses, functions, pathways or activities in which the target or antigen (or in which its substrate(s), ligand(s) or pathway(s) are involved, such as its signalling pathway or metabolic pathway and their associated biological or physiological effects) is involved. Again, as will be clear to the skilled person, such an action as an agonist or an antagonist may be determined in any suitable manner and/or using any suitable (in vitro and usually cellular or in assay) assay known per se, depending on the target or antigen involved. In particular, an action as an agonist or antagonist may be such that an intended biological or physiological activity is increased or decreased, respectively, by at least 1%, preferably at least 5%, such as at least 10% or at least 25%, for example by at least 50%, at least 60%, at least 70%, at least 80%, or 90% or more, compared to the biological or physiological activity in the same assay under the same conditions but without the presence of the construct of the invention.

Modulating may for example also involve allosteric modulation of the target or antigen; and/or reducing or inhibiting the binding of the target or antigen to one of its substrates or ligands and/or competing with a natural ligand, substrate for binding to the target or antigen. Modulating may also involve activating the target or antigen or the mechanism or pathway in which it is involved. Modulating may for example also involve effecting a change in respect of the folding or confirmation of the target or antigen, or in respect of the ability of the target or antigen to fold, to change its confirmation (for example, upon binding of a ligand), to associate with other (sub)units, or to disassociate. Modulating may for example also involve effecting a change in the ability of the target or antigen to transport other compounds or to serve as a channel for other compounds (such as ions).

Modulating may be reversible or irreversible, but for pharmaceutical and pharmacological purposes will usually be in a reversible manner, o) The invention also provides amino acid sequences that cross-block the binding of one of the amino acid sequences described in this application and/or are cross-blocked from binding Ang, Angptl, or Tie by one of the amino acid sequences described in this application. The terms "cross-block", "cross-blocked" and "cross-blocking" are used interchangeably herein to mean the ability of an amino acid sequence or other binding agents to interfere with the binding of other amino acid sequences or binding agents of the invention to Ang, Angptl, or Tie. The extend to which an amino acid sequence or other binding agents of the invention is able to interfere with the binding of another to Ang, Angptl, or Tie, and therefore whether it can be said to cross-block according to the invention, can be determined using competition binding assays. One particularly suitable quantitative assay uses a Biacore machine which can measure the extent of interactions using surface plasmon resonance technology. Another suitable quantitative cross-blocking assay uses an ELISA-based approach to measure competition between amino acid sequence or another binding agents in terms of their binding to Ang, Angptl, or Tie. Other preferred amino acid sequences of the invention are amino acid sequences comprising at least one single variable domain that cross-block at least one amino acid sequence with SEQ ID NOs 455 to 501 or are cross-blocked by the at least one amino acid sequence with SEQ ID NOs 455 to 501. The following generally describes a suitable Biacore assay for determining whether an amino acid sequence or other binding agent cross-blocks or is capable of cross-blocking according to the invention. It will be appreciated that the assay can be used with any of the Ang, Angptl, or Tie binding agents described herein. The Biacore machine (for example the Biacore 3000) is operated in line with the manufacturer's recommendations. Thus in one cross-blocking assay, the Ang, Angptl, or Tie protein is coupled to a CM5 Biacore chip using standard amine coupling chemistry to generate a Ang, Angptl, or Tie-coated surface. Typically 200-800 resonance units of Ang, Angptl, or Tie would be coupled to the chip (an amount that gives easily measurable levels of binding but that is readily saturable by the concentrations of test reagent being used). Two test amino acid sequences (termed A* and B*) to be assessed for their ability to cross-block each other are mixed at a one to one molar ratio of binding sites in a suitable buffer to create the test mixture. When calculating the concentrations on a binding site basis the molecular weight of an amino acid sequence is assumed to be the total molecular weight of the amino acid sequence divided by the number of Ang, Angptl, or Tie binding sites on that amino acid sequence. The concentration of each amino acid sequence in the test mix should be high enough to readily saturate the binding sites for that amino acid sequence on the Ang, Angptl, or Tie molecules captured on the Biacore chip. The amino acid sequences in the mixture are at the same molar concentration (on a binding basis) and that concentration would typically be between 1.00 and 1.5 micromolar (on a binding site basis). Separate solutions containing A* alone and B* alone are also prepared. A* and B* in these solutions should be in the same buffer and at the same concentration as in the test mix. The test mixture is passed over the Ang, Angptl, or Tie-coated Biacore chip and the total amount of binding recorded. The chip is then treated in such a way as to remove the bound amino acid sequences without damaging the chip-bound Ang, Angptl, or Tie. Typically this is done by treating the chip with 30 mM HCl for 60 seconds. The solution of A* alone is then passed over the Ang, Angptl, or Tie-coated surface and the amount of binding recorded. The chip is again treated to remove all of the bound amino acid sequences without damaging the chip-bound Ang, Angptl, or Tie. The solution of B* alone is then passed over the Ang, Angptl, or Tie-coated surface and the amount of binding recorded. The maximum theoretical binding of the mixture of A* and B* is next calculated, and is the sum of the binding of each amino acid sequence when passed over the Ang, Angptl, or Tie surface alone. If the actual recorded binding of the mixture is less than this theoretical maximum then the two amino acid sequences are cross-blocking each other. Thus, in general, a cross-blocking amino acid sequence or other binding agent according to the invention is one which will bind to Ang, Angptl, or Tie in the above Biacore cross-blocking assay such that during the assay and in the presence of a second amino acid sequence or other binding agent of the invention the recorded binding is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%) of maximum theoretical binding (as just defined above) of the two amino acid sequences or binding agents in combination. The Biacore assay described above is a primary assay used to determine if amino acid sequences or other binding agents cross-block each other according to the invention. On rare occasions particular amino acid sequences or other binding agents may not bind to Ang, Angptl, or Tie coupled via amine chemistry to a CM5 Biacore chip (this usually occurs when the relevant binding site on Ang, Angptl, or Tie is masked or destroyed by the coupling to the chip). In such cases cross-blocking can be determined using a tagged version of Ang, Angptl, or Tie, for example N-terminal His-tagged Ang, Angptl, or Tie (R & D Systems, Minneapolis, Minn., USA; 2005 cat#1406-ST-025). In this particular format, an anti-His amino acid sequence would be coupled to the Biacore chip and then the His-tagged Ang, Angptl, or Tie would be passed over the surface of the chip and captured by the anti-His amino acid sequence. The cross blocking analysis would be carried out essentially as described above, except that after each chip regeneration cycle, new His-tagged Ang, Angptl, or Tie would be loaded back onto the anti-His amino acid sequence coated surface. In addition to the example given using N-terminal His-tagged Ang, Angptl, or Tie, C-terminal His-tagged Ang, Angptl, or Tie could alternatively be used. Furthermore, various other tags and tag binding protein combinations that are known in the art could be used for such a cross-blocking analysis (e.g. HA tag with anti-HA antibodies; FLAG tag with anti-FLAG antibodies; biotin tag with streptavidin). The following generally describes an ELISA assay for determining whether an anti-Ang. Angptl, or Tie amino acid sequence or other Ang, Angptl, or Tie binding agent cross-blocks or is capable of cross-blocking according to the invention. It will be appreciated that the assay can be used with any of the Ang, Angptl, or Tie binding agents described herein. The general principal of the assay is to have an anti-Ang, Angptl, or Tie amino acid sequence coated onto the wells of an ELISA plate. An excess amount of a second, potentially cross-blocking, anti-Ang, Angptl, or Tie amino acid sequence is added in solution (i.e. not bound to the ELISA plate). A limited amount of Ang, Angptl, or Tie is then added to the wells. The coated amino acid sequence and the amino acid sequence in solution compete for binding of the limited number of Ang, Angptl, or Tie molecules. The plate is washed to remove Ang, Angptl, or Tie that has not been bound by the coated [amino acid sequence] and to also remove the second, solution phase amino acid sequence as well as any complexes formed between the second, solution phase amino acid sequence and Ang, Angptl, or Tie. The amount of bound Ang, Angptl, or Tie is then measured using an appropriate Ang, Angptl, or Tie detection reagent. An amino acid sequence in solution that is able to cross-block the coated amino acid sequence will be able to cause a decrease in the number of Ang, Angptl, or Tie molecules that the coated amino acid sequence can bind relative to the number of Ang, Angptl, or Tie molecules that the coated amino acid sequence can bind in the absence of the second, solution phase, amino acid sequence. In the instance where the first amino acid sequence, e.g. an Nanobody-X, is chosen to be the immobilized amino acid sequence, it is coated onto the wells of the ELISA plate, after which the plates are blocked with a suitable blocking solution to minimize non-specific binding of reagents that are subsequently added. An excess amount of the second amino acid sequence, i.e. Nanobody-Y, is then added to the ELISA plate such that the moles of Nanobody-Y Ang, Angptl, or Tie binding sites per well are at least 10 fold higher than the moles of Nanobody-X Ang, Angptl, or Tie binding sites that were used, per well, during the coating of the ELISA plate. Ang. Angptl, or Tie is then added such that the moles of Ang, Angptl, or Tie added per well are at least 25-fold lower than the moles of Nanobody-X Ang, Angptl, or Tie binding sites that were used for coating each well. Following a suitable incubation period the ELISA plate is washed and a Ang, Angptl, or Tie detection reagent is added to measure the amount of Ang, Angptl, or Tie specifically bound by the coated anti-Mg, Angptl, or Tie amino acid sequence (in this case Nanobody-X). The background signal for the assay is defined as the signal obtained in wells with the coated amino acid sequence (in this case Nanobody-X), second solution phase amino acid sequence (in this case Nanobody-Y), Ang, Angptl, or Tie buffer only (i.e. no Ang, Angptl, or Tie) and Ang, Angptl, or Tie detection reagents. The positive control signal for the assay is defined as the signal obtained in wells with the coated amino acid sequence (in this case Nanobody-X), second solution phase amino acid sequence buffer only (i.e. no second solution phase amino acid sequence), Ang, Angptl, or Tie and Ang, Angptl, or Tie detection reagents. The ELISA assay may be run in such a manner so as to have the positive control signal be at least 6 times the background signal. To avoid any artefacts (e.g. significantly different affinities between Nanobody-X and Nanobody-Y for Ang, Angptl, or Tie) resulting from the choice of which amino acid sequence to use as the coating amino acid sequence and which to use as the second (competitor) amino acid sequence, the cross-blocking assay may to be run in two formats: 1) format 1 is where Nanobody-X is the amino acid sequence that is coated onto the ELISA plate and Nanobody-Y is the competitor amino acid sequence that is in solution and 2) format 2 is where Nanobody-Y is the amino acid sequence that is coated onto the ELISA plate and Nanobody-X is the competitor amino acid sequence that is in solution. Nanobody-X and Nanobody-Y are defined as cross-blocking if, either in format 1 or in format 2, the solution phase anti-Ang, Angptl, or Tie amino acid sequence is able to cause a reduction of between 60% and 100%, specifically between 70% and 100%, and more specifically between 80% and 100%, of the Ang, Angptl, or Tie detection signal {i.e. the amount of Ang, Angptl, or Tie bound by the coated amino acid sequence) as compared to the Ang, Angptl, or Tie detection signal obtained in the absence of the solution phase anti-Ang, Angptl, or Tie amino acid sequence (i.e. the positive control wells). An example of such an ELISA-based cross blocking assay can be found in Example [xxx] ("ELISA-based cross-blocking assay").

p) As further described herein, the total number of amino acid residues in a Nanobody can be in the region of 110-120, is preferably 112-115, and is most preferably 113. It should however be noted that parts, fragments, analogs or derivatives (as further described herein) of a Nanobody are not particularly limited as to their length and/or size, as long as such parts, fragments, analogs or derivatives meet the further requirements outlined herein and are also preferably suitable for the purposes described herein;

q) The amino acid residues of a Nanobody are numbered according to the general numbering for $V_H$ domains given by Kabat et al. ("Sequence of proteins of immunological interest", US Public Health Services, NIH Bethesda, Md., Publication No. 91), as applied to $V_{HH}$ domains from Camelids in the article of Riechmann and Muyldermans, J. Immunol. Methods 2000 Jun. 23; 240 (1-2): 185-195 (see for example FIG. 2 of this publication); or referred to herein. According to this numbering, FR1 of a Nanobody comprises the amino acid residues at positions 1-30, CDR1 of a Nanobody comprises the amino acid residues at positions 31-35, FR2 of a Nanobody comprises the amino acids at positions 36-49, CDR2 of a Nanobody comprises the amino acid residues at positions 50-65. FR3 of a Nanobody comprises the amino acid residues at positions 66-94, CDR3 of a Nanobody comprises the amino acid residues at positions 95-102, and FR4 of a Nanobody comprises the amino acid residues at positions 103-113. [In this respect, it should be noted that—as is well known in the art for $V_H$ domains and for $V_{HH}$ domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.].

Alternative methods for numbering the amino acid residues of $V_H$ domains, which methods can also be applied in an analogous manner to $V_{HH}$ domains from Camelids and to Nanobodies, are the method described by Chothia et al. (Nature 342, 877-883 (1989)), the so-called "AbM definition" and the so-called "contact definition". However, in the present description, claims and figures, the numbering according to Kabat as applied to $V_{HH}$ domains by Riechmann and Muyldermans will be followed, unless indicated otherwise;

r) In respect of a target or antigen, the term "interaction site" on the target or antigen means a site, epitope, antigenic determinant, part, domain or stretch of amino acid residues on the target or antigen that is a site for binding to a ligand, receptor or other binding partner, a catalytic site, a cleavage site, a site for allosteric interaction, a site involved in multimerisation (such as homomerization or heterodimerization) of the target or antigen; or any other site, epitope, antigenic determinant, part, domain or stretch of amino acid residues on the target or antigen that is involved in a biological action or mechanism of the target or antigen. More generally, an "interaction site" can be any site, epitope, antigenic determinant, part, domain or stretch of amino acid residues on the target or antigen to which an amino acid sequence or polypeptide of the invention can bind such that the target or antigen (and/or any pathway, interaction, signalling, biological mechanism or biological effect in which the target or antigen is involved) is modulated (as defined herein); and s) The Figures, Sequence Listing and the Experimental Part/Examples are only given to further illustrate the invention and should not be interpreted or construed as limiting the scope of the invention and/or of the appended claims in any way, unless explicitly indicated otherwise herein.

For a general description of heavy chain antibodies and the variable domains thereof, reference is inter alia made to the prior art cited herein, to the review article by Muyldermans in Reviews in Molecular Biotechnology 74 (2001), 277-302; as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 EP 1 433 793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference.

In accordance with the terminology used in the art (see the above references), the variable domains present in naturally occurring heavy chain antibodies will also be referred to as "$V_{HH}$ domains", in order to distinguish them from the heavy chain variable domains that are present in conventional 4-chain antibodies (which will be referred to herein below as "$V_H$ domains") and from the light chain variable domains that are present in conventional 4-chain antibodies (which will be referred to herein below as "$V_L$ domains").

As mentioned in the prior art referred to above, $V_{HH}$ domains have a number of unique structural characteristics and functional properties which make isolated $V_{HH}$ domains (as well as Nanobodies based thereon, which share these structural characteristics and functional properties with the naturally occurring $V_{HH}$ domains) and proteins containing the same highly advantageous for use as functional antigen-binding domains or proteins. In particular, and without being limited thereto, $V_{HH}$ domains (which have been "designed" by nature to functionally bind to an antigen without the presence of, and without any interaction with, a light chain variable domain) and Nanobodies can function as a single, relatively small, functional antigen-binding structural unit, domain or protein. This distinguishes the $V_{HH}$ domains from the $V_H$ and $V_L$ domains of conventional 4-chain antibodies, which by themselves are generally not suited for practical application as single antigen-binding proteins or domains, but need to be combined in some form or another to provide a functional antigen-binding unit (as in for example conventional antibody fragments such as Fab fragments; in ScFv's fragments, which consist of a $V_H$ domain covalently linked to a $V_L$ domain).

Because of these unique properties, the use of $V_{HH}$ domains and Nanobodies as single antigen-binding proteins or as antigen-binding domains (i.e. as part of a larger protein or polypeptide) offers a number of significant advantages over the use of conventional $V_H$ and $V_L$ domains, scFv's or conventional antibody fragments (such as Fab- or F(ab')$_2$-fragments):

only a single domain is required to bind an antigen with high affinity and with high selectivity, so that there is no need to have two separate domains present, nor to assure that these two domains are present in the right special conformation and configuration (i.e. through the use of especially designed linkers, as with scFv's);

$V_{HH}$ domains and Nanobodies can be expressed from a single gene and require no post-translational folding or modifications;

$V_{HH}$ domains and Nanobodies can easily be engineered into multivalent and multispecific formats (as further discussed herein);

$V_{HH}$ domains and Nanobodies are highly soluble and do not have a tendency to aggregate (as with the mouse-derived "dAb's" described by Ward et al., Nature, Vol. 341, 1989, p. 544);

$V_{HH}$ domains and Nanobodies are highly stable to heat, pH, proteases and other denaturing agents or conditions (see for example Ewert et al, supra);

$V_{HH}$ domains and Nanobodies are easy and relatively cheap to prepare, even on a scale required for production. For example, $V_{HH}$ domains, Nanobodies and proteins/polypeptides containing the same can be produced using microbial fermentation (e.g. as further described below) and do not require the use of mammalian expression systems, as with for example conventional antibody fragments;

$V_{HH}$ domains and Nanobodies are relatively small (approximately 1.5 kDa, or 10 times smaller than a conventional IgG) compared to conventional 4-chain antibodies and antigen-binding fragments thereof, and therefore show high(er) penetration into tissues (including but not limited to solid tumours and other dense tissues) than such conventional 4-chain antibodies and antigen-binding fragments thereof;

$V_{HH}$ domains and Nanobodies can show so-called cavity-binding properties (inter alia due to their extended CDR3 loop, compared to conventional $V_H$ domains) and can therefore also access targets and epitopes not accessible to conventional 4-chain antibodies and antigen-binding fragments thereof. For example, it has been shown that $V_{HH}$ domains and Nanobodies can inhibit enzymes (see for example WO 97/49805; Transue et al., Proteins 1998 Sep. 1; 32(4): 515-22; Lauwereys et al., EMBO J. 1998 Jul. 1; 17(13): 3512-20).

In a specific and preferred aspect, the invention provides Nanobodies against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2; and in particular Nanobodies against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 from a warm-blooded animal, and more in particular Nanobodies against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 from a mammal, and especially Nanobodies against human Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2; as well as proteins and/or polypeptides comprising at least one such Nanobody.

In particular, the invention provides Nanobodies against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, and proteins and/or polypeptides comprising the same, that have improved therapeutic and/or pharmacological properties and/or other advantageous properties (such as, for example, improved ease of preparation and/or reduced costs of goods), compared to conventional antibodies against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 or fragments thereof, compared to constructs that could be based on such conventional antibodies or antibody fragments (such as Fab' fragments, F(ab')$_2$ fragments, ScFv constructs, "diabodies" and other multispecific constructs (see for example the review by Holliger and Hudson, Nat Biotechnol. 2005 September; 23(9):1126-36)), and also compared to the so-called "dAb's" or similar (single) domain antibodies that may be derived from variable domains of conventional antibodies. These improved and advantageous properties will become clear from the further description herein, and for example include, without limitation, one or more of:

increased affinity and/or avidity for Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, either in a monovalent format, in a multivalent format (for example in a bivalent format) and/or in a multispecific format (for example one of the multispecific formats described herein below);

better suitability for formatting in a multivalent format (for example in a bivalent format);

better suitability for formatting in a multispecific format (for example one of the multispecific formats described herein below); improved suitability or susceptibility for "humanizing" substitutions (as defined herein);

less immunogenicity, either in a monovalent format, in a multivalent format (for example in a bivalent format) and/or in a multispecific format (for example one of the multispecific formats described herein below);

increased stability, either in a monovalent format, in a multivalent format (for example in a bivalent format) and/or in a multispecific format (for example one of the multispecific formats described herein below);

increased specificity towards any of Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, either in a monovalent format, in a multivalent format (for example in a bivalent format) and/or in a multispecific format (for example one of the multispecific formats described herein below);

decreased or where desired increased cross-reactivity with any of Tie1, Tie2, Ang1, Ang2, Ang3, Ang4, Angptl1, Angptl2, Angptl3, Angptl4, Angptl5, or Angptl6, more preferably Tie2, Ang2, Ang1 Ang4, or Angptl4, more preferably Tie2 or Ang2 from different species;

and/or one or more other improved properties desirable for pharmaceutical use (including prophylactic use and/or therapeutic use) and/or for diagnostic use (including but not limited to use for imaging purposes), either in a monovalent format, in a multivalent format (for example in a bivalent format) and/or in a multispecific format (for example one of the multispecific formats described herein below).

As generally described herein for the amino acid sequences of the invention, the Nanobodies of the invention are preferably in essentially isolated form (as defined herein), or form part of a protein or polypeptide of the invention (as defined herein), which may comprise or essentially consist of one or more Nanobodies of the invention and which may optionally further comprise one or more further amino acid sequences (all optionally linked via one or more suitable linkers). For example, and without limitation, the one or more amino acid sequences of the invention may be used as a binding unit in such a protein or polypeptide, which may optionally contain one or more further amino acid sequences that can serve as a binding unit (i.e. against one or more other targets than Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2), so as to provide a monovalent, multivalent or multispecific polypeptide of the invention, respectively, all as described herein. In particular, such a protein or polypeptide may comprise or essentially consist of one or more Nanobodies of the invention and optionally one or more (other) Nanobodies (i.e. directed against other targets than Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2), all optionally linked via one or more suitable linkers, so as to provide a monovalent, multivalent or multispecific Nanobody construct, respectively, as further described herein. Such proteins or polypeptides may also be in essentially isolated form (as defined herein).

In a Nanobody of the invention, the binding site for binding against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 is preferably formed by the CDR sequences. Optionally, a Nanobody of the invention may also, and in addition to the at least one binding site for binding against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, contain one or more further binding sites for binding against other antigens, proteins or targets. For methods and positions for introducing such second binding sites, reference is for example made to Keck and Huston, Biophysical. Journal, 71, October 1996, 2002-2011; EP 0 640 130; WO 06/07260 and the US provisional application by Ablynx N.V, entitled "Immunoglobulin domains with multiple binding sites" filed on Nov. 27, 2006.

As generally described herein for the amino acid sequences of the invention, when a Nanobody of the invention (or a polypeptide of the invention comprising the same) is intended for administration to a subject (for example for therapeutic and/or diagnostic purposes as described herein), it is preferably directed against human Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2; whereas for veterinary purposes, it is preferably directed against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 from the species to be treated. Also, as with the amino acid sequences of the invention, a Nanobody of the invention may or may not be cross-reactive (i.e. directed against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 from two or more species of mammal, such as against human Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 and Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 from at least one of the species of mammal mentioned herein).

Also, again as generally described herein for the amino acid sequences of the invention, the Nanobodies of the invention may generally be directed against any antigenic determinant, epitope, part, domain, subunit or confirmation (where applicable) of Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2. However, it is generally assumed and preferred that the Nanobodies of the invention (and polypeptides comprising the same) are directed against the binding site of Ang1 on Tie2 or the binding site of Tie2 on Ang2.

As already described herein, the amino acid sequence and structure of a Nanobody can be considered—without however being limited thereto—to be comprised of four framework regions or "FR's" (or sometimes also referred to as "FW's"), which are referred to in the art and herein as "Framework region 1" or "FR1."; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively. Some preferred framework sequences and CDR's (and combinations thereof) that are present in the Nanobodies of the invention are as described herein. Other suitable CDR sequences can be obtained by the methods described herein.

According to a non-limiting but preferred aspect of the invention, (the CDR sequences present in) the Nanobodies of the invention are such that:

the Nanobodies can bind to Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that:

the Nanobodies can bind to Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$;

and/or such that they:

the Nanobodies can bind to Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 with a $k_{off}$ rate between $1s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Preferably, (the CDR sequences present in) the Nanobodies of the invention are such that: a monovalent Nanobody of the invention (or a polypeptide that contains only one Nanobody of the invention) is preferably such that it will bind to Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 with an affinity less than 500 nM, preferably less than 200 nM, more preferably less than 10 nM, such as less than 500 pM.

The affinity of the Nanobody of the invention against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 can be determined in a manner known per se, for example using the general techniques for measuring $K_D$, $K_A$, $k_{off}$ or $k_{on}$ mentioned herein, as well as some of the specific assays described herein.

Some preferred IC50 values for binding of the Nanobodies of the invention (and of polypeptides comprising the same) to Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 will become clear from the further description and examples herein.

In a preferred but non-limiting aspect, the invention relates to a Nanobody (as defined herein) against Tie1, Tie2, Ang1, Ang2, Ang3, Ang4, Angptl1, Angptl2, Angptl3, Angptl4, Angptl5, or Angptl6, more preferably Tie2, Ang2, Ang1 Ang4, or Angptl4, more preferably Tie2 or Ang2, which consists of 4 framework regions (FR1 to FR4 respectively) and 3 complementarity determining regions (CDR1 to CDR3 respectively), in which:

CDR1 is chosen from the group consisting of:
a) the amino acid sequences of SEQ ID NO's: 173 to 219;
b) amino acid sequences that have at least 80% amino acid identity with at least one of the amino acid sequences of SEQ ID NO's: 173 to 219;
c) amino acid sequences that have 3, 2, or 1 amino acid difference with at least one of the amino acid sequences of SEQ ID NO's: 173 to 219;
and/or
CDR2 is chosen from the group consisting of:
d) the amino acid sequences of SEQ ID NO's: 267 to 313;
e) amino acid sequences that have at least 80% amino acid identity with at least one of the amino acid sequences of SEQ ID NO's: 267 to 313;
f) amino acid sequences that have 3, 2, or 1 amino acid difference with at least one of the amino acid sequences of SEQ ID NO's: 267 to 313;
and/or
CDR3 is chosen from the group consisting of:
g) the amino acid sequences of SEQ ID NO's: 361 to 454;
h) amino acid sequences that have at least 80% amino acid identity with at least one of the amino acid sequences of SEQ ID NO's: 361 to 454;
i) amino acid sequences that have 3, 2, or 1 amino acid difference with at least one of the amino acid sequences of SEQ ID NO's: 361 to 454;
or any suitable fragment of such an amino acid sequence.

In particular, according to this preferred but non-limiting aspect, the invention relates to a Nanobody (as defined herein) against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, which consists of 4 framework regions (FR1 to FR4 respectively) and 3 complementarity determining regions (CDR1 to CDR3 respectively), in which:

CDR1 is chosen from the group consisting of:
a) the amino acid sequences of SEQ ID NO's: 173 to 219;
b) amino acid sequences that have at least 80% amino acid identity with at least one of the amino acid sequences of SEQ ID NO's: 173 to 219;
c) amino acid sequences that have 3, 2, or 1 amino acid difference with at least one of the amino acid sequences of SEQ ID NO's: 173 to 219;
and
CDR2 is chosen from the group consisting of:
d) the amino acid sequences of SEQ ID NO's: 267 to 313;
e) amino acid sequences that have at least 80% amino acid identity with at least one of the amino acid sequences of SEQ ID NO's: 267 to 313;
f) amino acid sequences that have 3, 2, or 1 amino acid difference with at least one of the amino acid sequences of SEQ ID NO's: 267 to 313;
and
CDR3 is chosen from the group consisting of:
g) the amino acid sequences of SEQ ID NO's: 361 to 454;
h) amino acid sequences that have at least 80% amino acid identity with at least one of the amino acid sequences of SEQ ID NO's: 361 to 454;
i) amino acid sequences that have 3, 2, or 1 amino acid difference with at least one of the amino acid sequences of SEQ ID NO's: 361 to 454;
or any suitable fragment of such an amino acid sequences.

As generally mentioned herein for the amino acid sequences of the invention, when a Nanobody of the invention contains one or more CDR1 sequences according to b) and/or c):
i) any amino acid substitution in such a CDR according to b) and/or c) is preferably, and compared to the corresponding CDR according to a), a conservative amino acid substitution (as defined herein);
and/or
ii) the CDR according to b) and/or c) preferably only contains amino acid substitutions, and no amino acid deletions or insertions, compared to the corresponding CDR according to a);
and/or
iii) the CDR according to b) and/or c) may be a CDR that is derived from a CDR according to a) by means of affinity maturation using one or more techniques of affinity maturation known per se.

Similarly, when a Nanobody of the invention contains one or more CDR2 sequences according to e) and/or f):
i) any amino acid substitution in such a CDR according to e) and/or f) is preferably, and compared to the corresponding CDR according to d), a conservative amino acid substitution (as defined herein);
and/or
ii) the CDR according to e) and/or f) preferably only contains amino acid substitutions, and no amino acid deletions or insertions, compared to the corresponding CDR according to d);
and/or
iii) the CDR according to e) and/or f) may be a CDR that is derived from a CDR according to d) by means of affinity maturation using one or more techniques of affinity maturation known per se.

Also, similarly, when a Nanobody of the invention contains one or more CDR3 sequences according to h) and/or i):
i) any amino acid substitution in such a CDR according to h) and/or i) is preferably, and compared to the corresponding CDR according to g), a conservative amino acid substitution (as defined herein);
and/or
ii) the CDR according to h) and/or 1) preferably only contains amino acid substitutions, and no amino acid deletions or insertions, compared to the corresponding CDR according to g);
and/or
iii) the CDR according to h) and/or i) may be a CDR that is derived from a CDR according to g) by means of affinity maturation using one or more techniques of affinity maturation known per se.

It should be understood that the last three paragraphs generally apply to any Nanobody of the invention that comprises one or more CDR1 sequences, CDR2 sequences and/or CDR3 sequences according to b), c), e), h) or i), respectively.

Of the Nanobodies of the invention, Nanobodies comprising one or more of the CDR's explicitly listed above are particularly preferred; Nanobodies comprising two or more of the CDR's explicitly listed above are more particularly preferred; and Nanobodies comprising three of the CDR's explicitly listed above are most particularly preferred.

Some particularly preferred, but non-limiting combinations of CDR sequences, as well as preferred combinations of CDR sequences and framework sequences, are mentioned in Table A-1 below, which lists the CDR sequences and framework sequences that are present in a number of preferred (but non-limiting) Nanobodies of the invention. As will be clear to the skilled person, a combination of CDR1, CDR2 and CDR3 sequences that occur in the same clone (i.e. CDR1, CDR2 and CDR3 sequences that are mentioned on the same line in Table A-1) will usually be preferred (although the invention in its broadest sense is not limited thereto, and also comprises other suitable combinations of the CDR sequences mentioned in Table A-1). Also, a combination of CDR sequences and framework sequences that occur in the same clone (i.e. CDR sequences and framework sequences that are mentioned on the same line in Table A-1) will usually be preferred (although the invention in its broadest sense is not limited thereto, and also comprises other suitable combinations of the CDR sequences and framework sequences mentioned in Table A-1, as well as combinations of such CDR sequences and other suitable framework sequences, e.g. as further described herein).

Also, in the Nanobodies of the invention that comprise the combinations of CDR's mentioned in Table A-1, each CDR can be replaced by a CDR chosen from the group consisting of amino acid sequences that have at least 80%, preferably at least 90%, more preferably at least 95%, even more preferably at least 99% sequence identity (as defined herein) with the mentioned CDR's; in which:
i) any amino acid substitution in such a CDR is preferably, and compared to the corresponding CDR sequence mentioned in Table A-1, a conservative amino acid substitution (as defined herein);
and/or
ii) any such CDR sequence preferably only contains amino acid substitutions, and no amino acid deletions or insertions, compared to the corresponding CDR sequence mentioned in Table A-1;
and/or
iii) any such CDR sequence is a CDR that is derived by means of a technique for affinity maturation known per se, and in particular starting from the corresponding CDR sequence mentioned in Table A-1.

However, as will be clear to the skilled person, the (combinations of) CDR sequences, as well as (the combinations of) CDR sequences and framework sequences mentioned in Table A-1 will generally be preferred.

TABLE A-1

Preferred combinations of CDR sequences, preferred combinations of framework sequences, and preferred combinations of framework and CDR sequences.

| Clone | ID | FR1 | ID | CDR1 | ID | FR2 | ID | CDR2 | ID | FR3 | ID | CDR3 | ID | FR4 | ID |
|---|---|---|---|---|---|---|---|---|---|---|---|---|---|---|---|
| 162-E1 | 455 | EVQLVESGGGL VQAGGSLRLSC AASGSIFS | 126 | INAMG | 173 | WYQQAPGKQ RELVA | 226 | FITSVG TTNYAD SVKG | 267 | RFIISRDNAKNTVYLQ MNSLKPEDTAVYYCA | 314 | DLHYSGPN Y | 361 | WGQGTQVTV SS | 408 |
| 162-E9 | 456 | EVQLVESGGGL VQPGGSLRLSC AASGFTLD | 127 | DYAIG | 174 | WFRQAPGKE REAVS | 221 | CISSVD GSTHYA DSVKG | 268 | RFTISRDNAKDTVYL QMNSLKPEDTAAYYC AV | 315 | QGYSGGYY YTCEDSAD FGF | 362 | WGQGTQVTV SS | 409 |
| 162-F11 | 457 | EVQLVESGGGL VQAGGSLRLSC AASGFTLD | 128 | DYAIG | 175 | WFRQAPGKE REGVA | 222 | CISSSD GSTYYA DSVKG | 269 | RFTISSDNAKNTVYLQ SS MNSLKPEDTAVYSCS A | 316 | GSVAGCIP YY | 363 | WGQGTQVTV SS | 410 |
| 162-F3 | 458 | EVQLVESGGGL VQAGDSL-RLSCT TSGRTFS | 129 | DDTMG | 176 | WFRQAPRKE REFVA | 223 | AILWDS IKTYYA DSVKG | 270 | RFTISRDNAKNTVYL QMDSLKPEDTAVYC AA | 317 | TPTAYGTD WYRNNYHY | 364 | WGQGTQVTV SS | 411 |
| 162-H10 | 459 | EVQLVESGGGL VQPGGSLRLSC AASGFTLD | 130 | DYAVG | 177 | WFRQAPGKE REGVS | 224 | CIGSSY GSTYYA DSVKG | 271 | RFTISRDNAKNTVYL QMNSLKPEDTAVYYC AV | 318 | QGYSGGYY YTCEDSAD FGF | 365 | WGQGTQVTV SS | 412 |
| 163-E7 | 460 | EVQLVESGGGL VQPGGSLRLSC AASGFTFS | 131 | DYSMS | 178 | WVRQAPGKG LEWVS | 225 | AISGGGE VTTYADS VKG | 272 | RFTISRDNAKNTLYLQ MSSLKPEDTALYYCA E | 319 | HLNFYSVS VRSSP | 366 | TSQGTQVTVS | 413 |
| 163-E9 | 461 | EVQLVESGGGL VQPGDSLRLSC AASGFTFG | 132 | SNGMR | 179 | WVRQAPGKG PEWVS | 226 | SINSDGT STYYADS VKG | 273 | RFTISRDNAKNTLCLQ MNSLKPEDTAVYYC T | 320 | TEDPYP | 367 | RGQGTQVTV SS | 414 |
| 163-GB | 462 | VQLVESGGGL VQPGGSLRLSC AASGFTFG | 133 | SNGMR | 180 | WVRQAPGKG PEWVS | 227 | SINSDGT SAFYAES VKG | 274 | RFTISRDNAKNTLYLQ MNSLKPEDTAVYYCT T | 321 | TMNPNP | 368 | RGQGTQVTV SS | 415 |

TABLE A-1-continued

Preferred combinations of CDR sequences, preferred combinations of framework sequences, and preferred combinations of framework and CDR sequences.

| Clone | ID | FR1 | ID | CDR1 | ID | FR2 | ID | CDR2 | ID | FR3 | ID | CDR3 | ID | FR4 | ID |
|---|---|---|---|---|---|---|---|---|---|---|---|---|---|---|---|
| 163-H8 | 463 | EVQLVESGGGLVQPGGSLRLSCAASGFTFG | 134 | SNGMR | 181 | WVRQAPGKGPEWVS | 228 | SINSDGTSTYYAESVKG | 275 | RFTISRDNAKNTLYLQMHSLKPEDTAVYYCT | 322 | TENPNP | 369 | RGPGTQVTVSS | 416 |
| 166-C1 | 464 | EVQLVESGGGLVQAGGSLRLSCAASGFTFG | 135 | STTIG | 182 | WFRQAPGKEREGVS | 229 | CISTGDGSTYYAESVKG | 276 | RFTISSDNAKNTVYLQMNSLKPEDTAVYYCAL | 323 | DQAPMWSSWSAPYEYDY | 370 | WGQGTQVTVSS | 417 |
| 166-C10 | 465 | EVQLVESGGGLVQAGGSLRLSCAASGFTFG | 136 | TTTLG | 183 | WFRQAPGKEREGVS | 230 | CISTGDGSTNYAESVKG | 277 | RFTISSDNAKNTVYLQMNSLKPEDTAVYYCAL | 324 | DQAPMWSSWSAPYEYDY | 371 | WGQGTQVTVSS | 418 |
| 166-D7 | 466 | EVQLVESGGGLVQAGGSLRLSCAASGFTFS | 137 | DTTIG | 184 | WFRQAPGKEREGIS | 231 | CISTGDGSTYYAESVKG | 278 | RFTISSDNAKNTVYLQMNSLNPEDTAVYYCAL | 325 | DQAPLWSTWSAPYEYDY | 372 | WGQGTQVTVSS | 419 |
| 166-F8 | 467 | EVQLVESGGGLVQAGGSLRLSCAASGFTFG | 138 | TTTIG | 185 | WFRQAPGKEREVVS | 232 | CISTGGGTYYTESVKG | 279 | RFTISSDNAKNTVYLQMNSLKPEDTAVYYCAL | 326 | DQAPMWSNWSAPYEYDY | 373 | WGQGTQVTVSS | 420 |
| 166-G4 | 468 | EVQLVESGGGLVQAGGALRLSCAASGFTFS | 139 | DTTIG | 186 | WFRQAPGKEREGIS | 233 | CISTGDGSTYYAESVKG | 280 | RFTISSDNAKNTVYLQMNSLNPEDTAVYYCAL | 327 | DQAPLWSTWSAPYEYDY | 374 | WGQGTQVTVSS | 421 |
| 166-H4 | 469 | EVQLVESGGDLVQAGGSLRLSCAASGFTFG | 140 | DFTIG | 187 | WFRQAPGKEREGVS | 234 | CINTGDGSTNYAESVKG | 281 | RFTISSDNAKNTVYLQMNSLKPEDTAVYYCAL | 328 | DQAPMWSSWSAPYEYDY | 375 | WGQGTQVTVSS | 422 |
| 166-E12 | 470 | KVQLVESGGGLVQAGGSLRLSCAASGFTFG | 141 | STTIG | 188 | WFRQAPGKEREGVS | 235 | CISTGDGSTYYAESVKG | 282 | RFTISSDNAKNTVYLQMNSLKPEDTAVYYCAL | 329 | DQAPMWSSWSAPYEYDY | 376 | WGQGTQVTVSS | 423 |
| 166-D4 | 471 | EVQLVESGGGLVQAGGSLRLSCVASGRIFT | 142 | NTAMG | 189 | WYRQAPGKWRELVA | 236 | TIYSGGSTKYIDSVKG | 283 | RFIISRDNTRNTVHLQMNSLKPEDTAVYYCNT | 330 | VGAGSY | 377 | WGQGAQVTVSS | 424 |
| 173-H9 | 472 | EVQLVESGGGLVQPGGSLRLSCAASGFTLS | 143 | GNWMY | 190 | WLRQAPGKGLEWIS | 237 | TITPRGLTAYADSVKG | 284 | RFTISRDIAENTLYLQMNSLKSGDTAVYYCAR | 331 | DKTGER | 378 | RGQGTQVTVSS | 425 |
| 184-B6 | 476 | EVQLVESGGGLVQPGGSLRLSCAASGFTFS | 144 | NYAMT | 191 | WVRQAPGKGLEWVS | 238 | DISWDGDITTYAASVKG | 285 | RFTISRDNAKKTLYLQMNSLKPEDSAVYYCNT | 332 | YGYDSGRYYSY | 379 | WGQGTQVTVSS | 426 |
| 185-H5 | 474 | EVQLVESGGGLVQPGGSLRLSCAASGFTLD | 145 | YYAIG | 192 | WFRQAPGKEREGVS | 239 | YISSSDGRTYYADSVKG | 286 | RFTISRDNAKNTVYLQMNSLKPEDTAVYYCAT | 333 | DLSGRGDVSEYEYDY | 380 | WGQGTQVTVSS | 427 |
| 168-A3 | 475 | EVQLVESGGGLVQPGGSLRLSCAASGFTLS | 146 | GNWMY | 193 | WLRQAPGKGLEWIS | 240 | TITPRGLTAYADSVKG | 287 | RFTISRDIAENTLYLQMNSLKSGDTAVYYCAR | 334 | DKTGER | 381 | RGQGTQVTVSS | 428 |
| 168-E5 | 476 | EVQLVESGGGLVQPGGSLRLSCAASGFTLS | 147 | SNWMY | 194 | WLRQAPGKGLEWIS | 241 | TITPRDLTAYADSVKG | 288 | RFTISRDNAENTLYLQMNSLKSEDTAVYYCAK | 335 | DKAGER | 382 | RGQGTQVTVSS | 429 |
| 168-G3 | 477 | EVQLVESGGGLVQPGGSLRLSCAASGSTLD | 148 | YYAIG | 195 | WYRQAPGKEREWVS | 242 | CISSSNYGITTYADSVKG | 289 | RFTISRDNAKNTVYLQMNSLKPEDTAIYYCAT | 336 | NTRRKYGRLCDLNADY | 383 | WGQGTQVTVSS | 430 |
| 169-A10 | 478 | EVQLVESGGGLVQPGGSLRLSCATSGFTFS | 149 | PSWMY | 196 | WLRQAPGKGLEWVS | 243 | TITPRGLTEYANSVKG | 290 | RFTISKDNAKNTLYLQMNSLKSEDTAVYYCTR | 337 | DKNGPP | 384 | MGQGTQVTVSS | 431 |
| 169-A12 | 479 | EVQLVESGGGLVQPGGSLRLSCVASGSIRS | 150 | IIHMG | 197 | WYRQAPGNERDLVA | 244 | VIIDSRTTKYSESVKG | 291 | RFTISRDNAKNTVYLQMNSLKPEDTAVYYCNA | 338 | LALGTDQSSTFDS | 385 | WGQGTQVTVSS | 432 |
| 169-B12 | 480 | EVQLVESGGGLVQAGGSLRLSCAASGSIFS | 151 | INAMG | 198 | WYRQAPGNQRDLVA | 245 | AITSGDSTKYADFVKG | 292 | RFTISRDNAKNTVYLQMNSLKPEDTAVYYCAA | 339 | ELLGKWY | 386 | WGQGTQVTVSS | 433 |

TABLE A-1-continued

Preferred combinations of CDR sequences, preferred combinations of framework sequences, and preferred combinations of framework and CDR sequences.

| Clone | ID | FR1 | ID | CDR1 | ID | FR2 | ID | CDR2 | ID | FR3 | ID | CDR3 | ID | FR4 | ID |
|---|---|---|---|---|---|---|---|---|---|---|---|---|---|---|---|
| 169-C12 | 481 | EVQLVESGGGLVQPGGSLRLSCAASGSIRS | 152 | IIHMG | 199 | WYRQTPGNERDMVA | 246 | VIISRTTKYAESVKG | 293 | RFTISRDNAKNTVYLQMNSLKPEDTAVYYCNA | 340 | LALGTDQSSTFDS | 387 | WGQGTQVTVSS | 434 |
| 169-C8 | 482 | WVQLVESGGGLVQPGGSLRLSCATSGFTFS | 153 | TSWMY | 200 | WLRQAPGKGLEWVS | 247 | TITPRGLTDYTDSVKG | 294 | RFTISRDSAKNTLYLQMNSLKSEDTADYYCTR | 341 | DKNGPP | 388 | MGQGTQVTVSS | 435 |
| 169-E12 | 483 | EVQLVESGGGLVQAGGSLRLSCAASGSIFS | 154 | INTMG | 201 | WYRQAPGNQRDLVA | 248 | AITNGGSTKYVDSVKG | 295 | RFTISRDNAKNTVYLQMNSLKPEDTAVYYCAA | 342 | ESLGRWG | 389 | WGQGTQVTVSS | 436 |
| 169-F11 | 484 | EVQLVESGGGLVQPGGSLRLSCATSGFTFS | 155 | TSWMY | 202 | WLRQAPGKGLEWVS | 249 | TITPRGLTDYTNSVKG | 296 | RFTVSRDNAKNTLYLQMNSLKSEDTAVYYCTK | 343 | DKNGPP | 390 | MGQGTQVTVSS | 437 |
| 170-B1 | 485 | EVQLVESGGGLVQAGGSLRLSCAASESIFS | 156 | LYVTG | 203 | WYRQAPGKQRELVA | 250 | SITSGGSLTYADSVKG | 297 | RFTISRDNAKNTVHLQMHSLKPEDTAVYFCNG | 344 | RSIGVDDMPYVY | 391 | WGQGTQVTVSS | 438 |
| 170-C2 | 486 | EVQLVESGGGLVQPGGSLRLSCAASGFTFS | 157 | LNAMT | 204 | WVRQAPGKGLEWVS | 251 | TISSGGWTTSYADSVKG | 298 | RFTISRDNAKNTLYLQMNSLKPEDMAVYYCAK | 345 | GSEFNGYEV | 392 | RGQGTQVTVSS | 439 |
| 170-E2 | 487 | EVQLVESGGGLVQAGGSLRLSCAASGSISS | 158 | INVMG | 205 | WYRQAPGKQRDLVA | 252 | TITRALNTAYATSVKG | 299 | RFTISRDNFTNTVYLQMNSLEPEDTAVYYCNA | 346 | GGYYTNLRTGGNY | 393 | WGQGTQVTVSS | 440 |
| 170-F2 | 488 | EVQLVESGGGLVQAGGSLRLSCAASGIFII | 159 | DTMG | 206 | WYRQAPGKQRELVA | 253 | SITPTGNTNYVDSVKG | 300 | RFAISRDNNKNTMHLQMNSLKPEDTAVYYCNA | 347 | VYPRYYGDDDRPPVDS | 394 | WGQGTRVTVSS | 441 |
| 170-H1 | 489 | EVQLVESGGGLAQAGGSLRLSCAASGSISS | 160 | INVMG | 207 | WYRQAPGKQRDLVA | 254 | VITRALNTNYATSVKG | 301 | RFTISRDDFKDTVYLQMNSLEPEDTAVYYCNA | 348 | GGYYTNLRTGGNY | 395 | WGQGTQVTVSS | 442 |
| 171-A2 | 490 | EVQLVESGGGQVQAGDSLRLSCKASRRTIS | 161 | TYGMG | 208 | WFRQAPGDKRDLVS | 255 | SISASGASTYYVDSVKG | 302 | RFTISRDNIKNTVYLQMNSLKPEDAAVYYCA | 349 | APNGRFITMSAHVDS | 396 | WGQGTQVTVSS | 443 |
| 171-A3 | 491 | EVQLVESGGGQVQAGDSLRLSCKASRRTIS | 162 | TYGMG | 209 | WFRQAPGDKRDLVS | 256 | SISASGASTYYVDSVKG | 303 | RFTISRDNIKNTVYLQMNSLKPEDAAVYYCA | 350 | APNGRFITMSTHVDY | 397 | WGQGTQVTVSS | 444 |
| 171-C4 | 492 | EVQLVESGGGLVQPGGSLRLSCAASGRTFS | 163 | TFNTYSMG | 210 | WFRQAPGEREFVA | 257 | AISRGGNVTPYADSVKG | 304 | RFAISRDNAKNTVALQMNSLKPEDAVYYCAA | 351 | SKIGIASTIRYYDY | 398 | WGQGTQVTVSS | 445 |
| 171-D2 | 493 | EVQLVESGGGLVQAGGSLRLSCAASVLTFS | 164 | TYTVG | 211 | WFRQAPGEREFVS | 258 | IITGSGTYNDYADSVKG | 305 | RFTVSRDNAKNTVYLQMNSLKSEDAAVYYCAA | 352 | RHWGMFSRSENDYNY | 399 | WGQGTQVTVSS | 446 |
| 171-E2 | 494 | EVQLVESGGGLVQAGASL-RLSCVDSGDTFS | 165 | WYAMG | 212 | WFRQQAPGKEREFV | 259 | SSISGGGSNTVYADSVKG | 306 | RFTVSRDRAKNTVYLQMNSLKPEDSGVYYCAA | 353 | DKRWGSPATSRSTHDY | 400 | WGQGTQVTVSS | 447 |
| 171-E4 | 495 | EVQLVESGGGLVQPGGSLRLSCAASGRTFS | 166 | TFNTYSMG | 213 | WFRQAPGEREFVA | 260 | AISRGGNVTPYADSVKG | 307 | RFAISRDNAKNTLTLQMNSLKPEDTAVYYCA | 354 | SKIGIASTIRYYDY | 401 | WGQGTQVTVSS | 448 |
| 171-F3 | 496 | EVQLVESGGGLVQTGGSLRLSCAASGRSFN | 167 | LYYMG | 214 | WRQAPGREREFVA | 261 | GISGSGGSTFYGDSVKG | 308 | RFTISRDNLKNTMYLQMNSLKPEDTAVYYCQS | 355 | SRRIITNPREYGY | 402 | WGQGTQVTVSS | 449 |
| 171-G2 | 497 | EVQLVESGGGLVQAGGSLRLSCTASGLTFS | 168 | MYAMA | 215 | WIRLAPGKEREVIA | 262 | AIDWSGGSTFYGDSVKG | 309 | RFTISRDNAKNTVYLEMNSLKPEDTAVYYCA | 356 | NRRIYSGGSSLSDNSLYNF | 403 | WGQGTQVTVSS | 450 |
| 171-G4 | 498 | EVQLVESGGGLVQAGGSLRLSCVASGDTFN | 169 | WYAMG | 216 | WFRQQAPGKEREFV | 263 | SAISGGGSNIVYYDSVKG | 310 | RFAISRDNADSTYLRMNNLKPEDTAVYYCNA | 357 | DKRWGSPATSRSTHDYDF | 404 | WGQGTQVTVSS | 451 |

TABLE A-1-continued

Preferred combinations of CDR sequences, preferred combinations of framework sequences, and preferred combinations of framework and CDR sequences.

| Clone | ID | FR1 | ID | CDR1 | ID | FR2 | ID | CDR2 | ID | FR3 | ID | CDR3 | ID | FR4 | ID |
|---|---|---|---|---|---|---|---|---|---|---|---|---|---|---|---|
| 170-G3 | 499 | EVQLVESGGGL VQAGGSLRLSC AASETIFA | 170 | SAMG | 217 | WYRQPPG RELVA | 264 | RITRGGS TNYAESV KG | 311 | RFTISKDIAKNTVYLQ MNSLKPDDMAVYYC AA | 358 | DTIGHSSSY ITY | 405 | WGQGTQVTV SS | 452 |
| 171-G2 | 500 | EVQLVESGGGL VQAGGSLRLSC AASGRPFS | 171 | MYMAG | 218 | WFRQAPGKE REFVT | 265 | VITWSGG STYYADS VKG | 312 | RFTISKDIAKNTVYLQ MNSLKPDDMAVYYC AA | 259 | ARRYGNLY NTNNYDY | 406 | WGQGTQVTV SS | 453 |
| 171-H4 | 501 | EVQLVESGGGQ VQAGDSLRLSC KASRRTIS | 172 | TYGMG | 219 | WFRQAPGDK RDLVS | 266 | SISASGA STYYVDS VKG | 313 | RFTISKDNIKNTVYLQ MNSLKPDDAAVYYCA | 360 | APNGRFIT MSTHVDS | 407 | WGQGTVTV SS | 454 |

("ID" refers to the SEQ ID NO in the attached sequence listing)

Thus, in the Nanobodies of the invention, at least one of the CDR1. CDR2 and CDR3 sequences present is suitably chosen from the group consisting of the CDR1, CDR2 and CDR3 sequences, respectively, listed in Table A-1; or from the group of CDR1, CDR2 and CDR3 sequences, respectively, that have at least 80%, preferably at least 90%, more preferably at least 95%, even more preferably at least 99% "sequence identity" (as defined herein) with at least one of the CDR1, CDR2 and CDR3 sequences, respectively, listed in Table A-1; and/or from the group consisting of the CDR1, CDR2 and CDR3 sequences, respectively, that have 3, 2 or only 1 "amino acid difference(s)" (as defined herein) with at least one of the CDR1, CDR2 and CDR3 sequences, respectively, listed in Table A-1.

In this context, by "suitably chosen" is meant that, as applicable, a CDR1 sequence is chosen from suitable CDR1 sequences (i.e. as defined herein), a CDR2 sequence is chosen from suitable CDR2 sequences (i.e. as defined herein), and a CDR3 sequence is chosen from suitable CDR3 sequence (i.e. as defined herein), respectively. More in particular, the CDR sequences are preferably chosen such that the Nanobodies of the invention bind to Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein.

In particular, in the Nanobodies of the invention, at least the CDR3 sequence present is suitably chosen from the group consisting of the CDR3 sequences listed in Table A-1 or from the group of CDR3 sequences that have at least 80%, preferably at least 90%, more preferably at least 95%, even more preferably at least 99% sequence identity with at least one of the CDR3 sequences listed in Table A-1; and/or from the group consisting of the CDR3 sequences that have 3, 2 or only 1 amino acid difference(s) with at least one of the CDR3 sequences listed in Table A-1.

Preferably, in the Nanobodies of the invention, at least two of the CDR1, CDR2 and CDR3 sequences present are suitably chosen from the group consisting of the CDR1, CDR2 and CDR3 sequences, respectively, listed in Table A-1 or from the group consisting of CDR1, CDR2 and CDR3 sequences, respectively, that have at least 80%, preferably at least 90%, more preferably at least 95%, even more preferably at least 99% sequence identity with at least one of the CDR1, CDR2 and CDR3 sequences, respectively, listed in Table A-1; and/or from the group consisting of the CDR1, CDR2 and CDR3 sequences, respectively, that have 3, 2 or only 1 "amino acid difference(s)" with at least one of the CDR1, CDR2 and CDR3 sequences, respectively, listed in Table A-1.

In particular, in the Nanobodies of the invention, at least the CDR3 sequence present is suitably chosen from the group consisting of the CDR3 sequences listed in Table A-1 or from the group of CDR3 sequences that have at least 80%, preferably at least 90%, more preferably at least 95%, even more preferably at least 99% sequence identity with at least one of the CDR3 sequences listed in Table A-1, respectively; and at least one of the CDR1 and CDR2 sequences present is suitably chosen from the group consisting of the CDR1 and CDR2 sequences, respectively, listed in Table A-1 or from the group of CDR1 and CDR2 sequences, respectively, that have at least 80%, preferably at least 90%, more preferably at least 95%, even more preferably at least 99% sequence identity with at least one of the CDR1 and CDR2 sequences, respectively, listed in Table A-1; and/or from the group consisting of the CDR1 and CDR2 sequences, respectively, that have 3, 2 or only 1 amino acid difference(s) with at least one of the CDR1 and CDR2 sequences, respectively, listed in Table A-1.

Most preferably, in the Nanobodies of the invention, all three CDR1, CDR2 and CDR3 sequences present are suitably chosen from the group consisting of the CDR1. CDR2 and CDR3 sequences, respectively, listed in Table A-1 or from the group of CDR1, CDR2 and CDR3 sequences, respectively, that have at least 80%, preferably at least 90%, more preferably at least 95%, even more preferably at least 99% sequence identity with at least one of the CDR1, CDR2 and CDR3 sequences, respectively, listed in Table A-1; and/or from the group consisting of the CDR1, CDR2 and CDR3 sequences, respectively, that have 3, 2 or only 1 amino acid difference(s) with at least one of the CDR1. CDR2 and CDR3 sequences, respectively, listed in Table A-1.

Even more preferably, in the Nanobodies of the invention, at least one of the CDR1, CDR2 and CDR3 sequences present is suitably chosen from the group consisting of the CDR1, CDR2 and CDR3 sequences, respectively, listed in Table A-1. Preferably, in this aspect, at least one or preferably both of the other two CDR sequences present are suitably chosen from CDR sequences that have at least 80%, preferably at least 90%, more preferably at least 95%, even more preferably at least 99% sequence identity with at least one of the corresponding CDR sequences, respectively, listed in Table A-1; and/or from the group consisting of the CDR sequences that have 3, 2 or only 1 amino acid difference(s) with at least one of the corresponding sequences, respectively, listed in Table A-1.

In particular, in the Nanobodies of the invention, at least the CDR3 sequence present is suitably chosen from the group consisting of the CDR3 listed in Table A-1. Preferably, in this aspect, at least one and preferably both of the CDR1 and CDR2 sequences present are suitably chosen from the groups of CDR1 and CDR2 sequences, respectively, that have at least 80%, preferably at least 90%, more preferably at least 95%, even more preferably at least 99% sequence identity with the CDR1 and CDR2 sequences, respectively, listed in Table A-1; and/or from the group consisting of the CDR1 and CDR2 sequences, respectively, that have 3, 2 or only 1 amino acid difference(s) with at least one of the CDR1 and CDR2 sequences, respectively, listed in Table A-1.

Even more preferably, in the Nanobodies of the invention, at least two of the CDR1, CDR2 and CDR3 sequences present are suitably chosen from the group consisting of the CDR1, CDR2 and CDR3 sequences, respectively, listed in Table A-1. Preferably, in this aspect, the remaining CDR sequence present is suitably chosen from the group of CDR sequences that have at least 80%, preferably at least 90%, more preferably at least 95%, even more preferably at least 99% sequence identity with at least one of the corresponding CDR sequences listed in Table A-1; and/or from the group consisting of CDR sequences that have 3, 2 or only 1 amino acid difference(s) with at least one of the corresponding sequences listed in Table A-1.

In particular, in the Nanobodies of the invention, at least the CDR3 sequence is suitably chosen from the group consisting of the CDR3 sequences listed in Table A-1, and either the CDR1 sequence or the CDR2 sequence is suitably chosen from the group consisting of the CDR1 and CDR2 sequences, respectively, listed in Table A-1. Preferably, in this aspect, the remaining CDR sequence present is suitably chosen from the group of CDR sequences that have at least 80%, preferably at least 90%, more preferably at least 95%, even more preferably at least 99% sequence identity with at least one of the corresponding CDR sequences listed in Table A-1; and/or from the group consisting of CDR sequences that have 3, 2 or only 1 amino acid difference(s) with the corresponding CDR sequences listed in Table A-1.

Even more preferably, in the Nanobodies of the invention, all three CDR1, CDR2 and CDR3 sequences present are suitably chosen from the group consisting of the CDR1, CDR2 and CDR3 sequences, respectively, listed in Table A-1.

Also, generally, the combinations of CDR's listed in Table A-1 (i.e. those mentioned on the same line in Table A-1) are preferred. Thus, it is generally preferred that, when a CDR in a Nanobody of the invention is a CDR sequence mentioned in Table A-1 or is suitably chosen from the group of CDR sequences that have at least 80%, preferably at least 90%, more preferably at least 95%, even more preferably at least 99% sequence identity with a CDR sequence listed in Table A-1; and/or from the group consisting of CDR sequences that have 3, 2 or only 1 amino acid difference(s) with a CDR sequence listed in Table A-1, that at least one and preferably both of the other CDR's are suitably chosen from the CDR sequences that belong to the same combination in Table A-1 (i.e. mentioned on the same line in Table A-1) or are suitably chosen from the group of CDR sequences that have at least 80%, preferably at least 90%, more preferably at least 95%, even more preferably at least 99% sequence identity with the CDR sequence(s) belonging to the same combination and/or from the group consisting of CDR sequences that have 3, 2 or only 1 amino acid difference(s) with the CDR sequence(s) belonging to the same combination. The other preferences indicated in the above paragraphs also apply to the combinations of CDR's mentioned in Table A-1.

Thus, by means of non-limiting examples, a Nanobody of the invention can for example comprise a CDR1 sequence that has more than 80% sequence identity with one of the CDR1 sequences mentioned in Table A-1, a CDR2 sequence that has 3, 2 or 1 amino acid difference with one of the CDR2 sequences mentioned in Table A-1 (but belonging to a different combination), and a CDR3 sequence.

Some preferred Nanobodies of the invention may for example comprise: (1) a CDR1 sequence that has more than 80% sequence identity with one of the CDR1 sequences mentioned in Table A-1; a CDR2 sequence that has 3, 2 or 1 amino acid difference with one of the CDR2 sequences mentioned in Table A-1 (but belonging to a different combination); and a CDR3 sequence that has more than 80% sequence identity with one of the CDR3 sequences mentioned in Table A-1 (but belonging to a different combination); or (2) a CDR1 sequence that has more than 80% sequence identity with one of the CDR1 sequences mentioned in Table A-1; a CDR2 sequence, and one of the CDR3 sequences listed in Table A-1; or (3) a CDR1 sequence; a CDR2 sequence that has more than 80% sequence identity with one of the CDR2 sequence listed in Table A-1; and a CDR3 sequence that has 3, 2 or 1 amino acid differences with the CDR3 sequence mentioned in Table A-1 that belongs to the same combination as the CDR2 sequence.

Some particularly preferred Nanobodies of the invention may for example comprise: (1) a CDR1 sequence that has more than 80% sequence identity with one of the CDR1 sequences mentioned in Table A-1; a CDR2 sequence that has 3, 2 or 1 amino acid difference with the CDR2 sequence mentioned in Table A-1 that belongs to the same combination; and a CDR3 sequence that has more than 80% sequence identity with the CDR3 sequence mentioned in Table A-1 that belongs to the same combination; (2) a CDR1 sequence; a CDR 2 listed in Table A-1 and a CDR3 sequence listed in Table A-1 (in which the CDR2 sequence and CDR3 sequence may belong to different combinations).

Some even more preferred Nanobodies of the invention may for example comprise: (1) a CDR1 sequence that has more than 80% sequence identity with one of the CDR1 sequences mentioned in Table A-1; the CDR2 sequence listed in Table A-1 that belongs to the same combination; and a CDR3 sequence mentioned in Table A-1 that belongs to a different combination; or (2) a CDR1 sequence mentioned in Table A-1; a CDR2 sequence that has 3, 2 or 1 amino acid differences with the CDR2 sequence mentioned in Table A-1 that belongs to the same combination; and a CDR3 sequence that has more than 80% sequence identity with the CDR3 sequence listed in Table A-1 that belongs to the same or a different combination.

Particularly preferred Nanobodies of the invention may for example comprise a CDR1 sequence mentioned in Table A-1, a CDR2 sequence that has more than 80% sequence identity with the CDR2 sequence mentioned in Table A-1 that belongs to the same combination; and the CDR3 sequence mentioned in Table A-1 that belongs to the same combination.

In the most preferred Nanobodies of the invention, the CDR1, CDR2 and CDR3 sequences present are suitably chosen from one of the combinations of CDR1, CDR2 and CDR3 sequences, respectively, listed in Table A-1.

According to another preferred, but non-limiting aspect of the invention (a) CDR1 has a length of between 1 and 12 amino acid residues, and usually between 2 and 9 amino acid residues, such as 5, 6 or 7 amino acid residues; and/or (b) CDR2 has a length of between 13 and 24 amino acid residues, and usually between 15 and 21 amino acid residues, such as 16 and 17 amino acid residues; and/or (c) CDR3 has a length of between 2 and 35 amino acid residues, and usually between 3 and 30 amino acid residues, such as between 6 and 23 amino acid residues.

In another preferred, but non-limiting aspect, the invention relates to a Nanobody in which the CDR sequences (as defined herein) have more than 80%, preferably more than 90%, more preferably more than 95%, such as 99% or more sequence identity (as defined herein) with the CDR sequences of at least one of the amino acid sequences of SEQ ID NO's: 455 to 501, more preferably 455 to 457, 459, 460, 464 to 469.

Generally, Nanobodies with the above CDR sequences may be as further described herein, and preferably have framework sequences that are also as further described herein. Thus, for example and as mentioned herein, such Nanobodies may be naturally occurring Nanobodies (from any suitable species), naturally occurring $V_{HH}$ sequences (i.e. from a suitable species of *Camelid*) or synthetic or semi-synthetic amino acid sequences or Nanobodies, including but not limited to partially humanized Nanobodies or $V_{HH}$ sequences, fully humanized Nanobodies or $V_{HH}$-sequences, camelized heavy chain variable domain sequences, as well as Nanobodies that have been obtained by the techniques mentioned herein.

Thus, in one specific, but non-limiting aspect, the invention relates to a humanized Nanobody, which consists of 4 framework regions (FR1 to FR4 respectively) and 3 complementarity determining regions (CDR1 to CDR3 respectively), in which CDR1 to CDR3 are as defined herein and in which said humanized Nanobody comprises at least one humanizing substitution (as defined herein), and in particular at least one humanizing substitution in at least one of its framework sequences (as defined herein).

In another preferred, but non-limiting aspect, the invention relates to a Nanobody in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 455 to 501, more preferably 455 to 457, 459, 460, 464 to 469. This degree of amino acid identity can for example be determined by determining the degree of amino acid identity (in a manner described herein) between said Nanobody and one or more of the sequences of SEQ ID NO's: 455 to 501, more preferably 455 to 457, 459, 460, 464 to 469, in which the amino acid residues that form the framework regions are disregarded. Such Nanobodies can be as further described herein.

In another preferred, but non-limiting aspect, the invention relates to a Nanobody with an amino acid sequence that is chosen from the group consisting of SEQ ID NO's: 455 to 501, more preferably 455 to 457, 459, 460, 464 to 469 or from the group consisting of from amino acid sequences that have more than 80%, preferably more than 90%, more preferably more than 95%, such as 99% or more sequence identity (as defined herein) with at least one of the amino acid sequences of SEQ ID NO's: 455 to 501, more preferably 455 to 457, 459, 460, 464 to 469.

Another preferred, but non-limiting aspect of the invention relates to humanized variants of the Nanobodies of SEQ ID NO's: 455 to 501, more preferably 455 to 457, 459, 460, 464 to 469, that comprise, compared to the corresponding native $V_{HH}$-sequence, at least one humanizing substitution (as defined herein), and in particular at least one humanizing substitution in at least one of its framework sequences (as defined herein).

It will be clear to the skilled person that the Nanobodies that are mentioned herein as "preferred" (or "more preferred", "even more preferred", etc.) are also preferred (or more preferred, or even more preferred, etc.) for use in the polypeptides described herein. Thus, polypeptides that comprise or essentially consist of one or more "preferred" Nanobodies of the invention will generally be preferred, and polypeptides that comprise or essentially consist of one or more "more preferred" Nanobodies of the invention will generally be more preferred, etc.

Generally, proteins or polypeptides that comprise or essentially consist of a single Nanobody (such as a single Nanobody of the invention) will be referred to herein as "monovalent" proteins or polypeptides or as "monovalent constructs", Proteins and polypeptides that comprise or essentially consist of two or more Nanobodies (such as at least two Nanobodies of the invention or at least one Nanobody of the invention and at least one other Nanobody) will be referred to herein as "multivalent" proteins or polypeptides or as "multivalent constructs", and these may provide certain advantages compared to the corresponding monovalent Nanobodies of the invention. Some non-limiting examples of such multivalent constructs will become clear from the further description herein.

According to one specific, but non-limiting aspect, a polypeptide of the invention comprises or essentially consists of at least two Nanobodies of the invention, such as two or three Nanobodies of the invention. As further described herein, such multivalent constructs can provide certain advantages compared to a protein or polypeptide comprising or essentially consisting of a single Nanobody of the invention, such as a much improved avidity for Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2. Such multivalent constructs will be clear to the skilled person based on the disclosure herein.

According to another specific, but non-limiting aspect, a polypeptide of the invention comprises or essentially consists of at least one Nanobody of the invention and at least one other binding unit (i.e. directed against another epitope, antigen, target, protein or polypeptide), which is preferably also a Nanobody. Such proteins or polypeptides are also referred to herein as "multispecific" proteins or polypeptides or as 'multispecific constructs", and these may provide certain advantages compared to the corresponding monovalent Nanobodies of the invention (as will become clear from the further discussion herein of some preferred, but-nonlimiting multispecific constructs). Such multispecific constructs will be clear to the skilled person based on the disclosure herein.

According to yet another specific, but non-limiting aspect, a polypeptide of the invention comprises or essentially consists of at least one Nanobody of the invention, optionally one or more further Nanobodies, and at least one other amino acid sequence (such as a protein or polypeptide) that confers at least one desired property to the Nanobody of the invention and/or to the resulting fusion protein. Again, such fusion proteins may provide certain advantages compared to the corresponding monovalent Nanobodies of the invention. Some non-limiting examples of such amino acid sequences and of such fusion constructs will become clear from the further description herein.

It is also possible to combine two or more of the above aspects, for example to provide a trivalent bispecific construct comprising two Nanobodies of the invention and one other Nanobody, and optionally one or more other amino acid sequences. Further non-limiting examples of such constructs, as well as some constructs that are particularly preferred within the context of the present invention, will become clear from the further description herein.

In the above constructs, the one or more Nanobodies and/or other amino acid sequences may be directly linked to each other and/or suitably linked to each other via one or more linker sequences. Some suitable but non-limiting examples of such linkers will become clear from the further description herein.

In one specific aspect of the invention, a Nanobody of the invention or a compound, construct or polypeptide of the invention comprising at least one Nanobody of the invention may have an increased half-life, compared to the corresponding amino acid sequence of the invention. Some preferred, but non-limiting examples of such Nanobodies, compounds and polypeptides will become clear to the skilled person based on the further disclosure herein, and for example comprise Nanobodies sequences or polypeptides of the invention that have been chemically modified to increase the half-life thereof (for example, by means of pegylation); amino acid sequences of the invention that comprise at least one additional binding site for binding to a serum protein (such as serum albumin. Reference is for example made to the US provisional application by Ablynx N.V. entitled "Immunoglobulin domains with multiple binding sites" filed on Nov. 27, 2006); or polypeptides of the invention that comprise at least one Nanobody of the invention that is linked to at least one moiety (and in particular at least one amino acid sequence) that increases the half-life of the Nanobody of the invention. Examples of polypeptides of the invention that comprise such half-life extending moieties or amino acid sequences will become clear to the skilled person based on the further disclosure herein; and for example include, without limitation, polypeptides in which the one or more Nanobodies of the invention are suitable linked to one or more serum proteins or fragments thereof (such as serum albumin or suitable fragments thereof) or to one or more binding units that can bind to serum proteins (such as, for example, Nanobodies or (single) domain antibodies that can bind to serum proteins such as serum albumin, serum immunoglobulins such as IgG, or transferrine); polypeptides in which a Nanobody of the invention is linked to an Fc portion (such as a human Fe) or a suitable part or fragment thereof; or polypeptides in which the one or more Nanobodies of the invention are suitable linked to one or more small proteins or peptides that can bind to serum proteins (such as, without limitation, the proteins and peptides described in WO 91/01743, WO 01/45746, WO 02/076489 and to the US provisional application of Ablynx N.V. entitled "Peptides capable of binding to serum proteins" of Ablynx. N.V. filed on Dec. 5, 2006.

Again, as will be clear to the skilled person, such Nanobodies, compounds, constructs or polypeptides may contain one or more additional groups, residues, moieties or binding units, such as one or more further amino acid sequences and in particular one or more additional Nanobodies (i.e. not directed against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2), so as to provide a tri- of multispecific Nanobody construct.

Generally, the Nanobodies of the invention (or compounds, constructs or polypeptides comprising the same) with increased half-life preferably have a half-life that is at least 1.5 times, preferably at least 2 times, such as at least 5 times, for example at least 10 times or more than 20 times, greater than the half-life of the corresponding amino acid sequence of the invention per se. For example, the Nanobodies, compounds, constructs or polypeptides of the invention with increased half-life may have a half-life that is increased with more than 1 hours, preferably more than 2 hours, more preferably more than 6 hours, such as more than 12 hours, or even more than 24, 48 or 72 hours, compared to the corresponding amino acid sequence of the invention per se.

In a preferred, but non-limiting aspect of the invention, such Nanobodies, compound, constructs or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In another one aspect of the invention, a polypeptide of the invention comprises one or more (such as two or preferably one) Nanobodies of the invention linked (optionally via one or more suitable linker sequences) to one or more (such as two and preferably one) amino acid sequences that allow the resulting polypeptide of the invention to cross the blood brain barrier. In particular, said one or more amino acid sequences that allow the resulting polypeptides of the invention to cross the blood brain barrier may be one or more (such as two and preferably one) Nanobodies, such as the Nanobodies described in WO 02/057445, of which FC44 (SEQ ID NO: 189 of WO 06/040153) and FC5 (SEQ ID NO: 190 of WO 06/040154) are preferred examples.

In particular, polypeptides comprising one or more Nanobodies of the invention are preferably such that they:

bind to Tie1, Tie2, Ang1 Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that they:

bind to Tie1, Tie2, Ang1, Ang2, Ang3, Ang4, Angptl1, Angptl2, Angptl3, Angptl4, Angptl5, or Angptl6, more preferably Tie2, Ang2, Ang 1, Ang4, or Angptl4, more preferably Tie2 or Ang2 with a $k_{on}$-rate of between $10^2 M^{-1}s^{-1}$ to about $10^7 M^{-1}s^{-1}$, preferably between $10^3 M^{-1}s^{-1}$ and $10^7 M^{-1}s^{-1}$, more preferably between $10^4 M^{-1}s^{-1}$ and $10^7 M^{-1}s^{-1}$, such as between $10^5 M^{-1}s^{-1}$ and $10^7 M^{-1}s^{-1}$;

and/or such that they:

bind to Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 with a $k_{off}$ rate between $1\ s^{-1}$ ($t_{1/2}$=0.69 s) and $10^{-6}\ s^{-1}$ (providing a near irreversible complex with a $t_{1/2}$ of multiple days), preferably between $10^{-2}\ s^{-1}$ and $10^{-6}\ s^{-1}$, more preferably between $10^{-3}\ s^{-1}$ and $10^{-6}\ s^{-1}$, such as between $10^{-4}s^{-1}$ and $10^{-6}\ s^{-1}$.

Preferably, a polypeptide that contains only one amino acid sequence of the invention is preferably such that it will bind to Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 with an affinity less than 500 nM, preferably less than 200 nM, more preferably less than 10 nM, such as less than 500 μM. In this respect, it will be clear to the skilled person that a polypeptide that contains two or more Nanobodies of the invention may bind to Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 with an increased avidity, compared to a polypeptide that contains only one amino acid sequence of the invention.

Some preferred $IC_{50}$ values for binding of the amino acid sequences or polypeptides of the invention to Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 will become clear from the further description and examples herein.

Other polypeptides according to this preferred aspect of the invention may for example be chosen from the group consisting of amino acid sequences that have more than 80%, preferably more than 90%, more preferably more than 95%, such as 99% or more "sequence identity" (as defined herein) with one or more of the amino acid sequences of SEQ ID NO's: 455 to 501, more preferably, 455 to 457, 459, 460, 464 to 469, in which the Nanobodies comprised within said amino acid sequences are preferably as further defined herein.

Another aspect of this invention relates to a nucleic acid that encodes a Nanobody of the invention or a polypeptide of the invention comprising the same. Again, as generally described herein for the nucleic acids of the invention, such a nucleic acid may be in the form of a genetic construct, as defined herein.

In another aspect, the invention relates to host or host cell that expresses or that is capable of expressing a Nanobody of the invention and/or a polypeptide of the invention comprising the same; and/or that contains a nucleic acid of the invention. Some preferred but non-limiting examples of such hosts or host cells will become clear from the further description herein.

Another aspect of the invention relates to a product or composition containing or comprising at least one Nanobody of the invention, at least one polypeptide of the invention and/or at least one nucleic acid of the invention, and optionally one or more further components of such compositions known per se, i.e. depending on the intended use of the composition. Such a product or composition may for example be a pharmaceutical composition (as described herein), a veterinary composition or a product or composition for diagnostic use (as also described herein). Some preferred but non-limiting examples of such products or compositions will become clear from the further description herein.

The invention further relates to methods for preparing or generating the Nanobodies, polypeptides, nucleic acids, host cells, products and compositions described herein. Some preferred but non-limiting examples of such methods will become clear from the further description herein.

The invention further relates to applications and uses of the Nanobodies, polypeptides, nucleic acids, host cells, products and compositions described herein, as well as to methods for the prevention and/or treatment for diseases and disorders associated with Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2. Some preferred but non-limiting applications and uses will become clear from the further description herein.

Other aspects, embodiments, advantages and applications of the invention will also become clear from the further description herein below.

Generally, it should be noted that the term Nanobody as used herein in its broadest sense is not limited to a specific biological source or to a specific method of preparation. For example, as will be discussed in more detail below, the Nanobodies of the invention can generally be obtained: (1) by isolating the $V_{HH}$ domain of a naturally occurring heavy chain antibody; (2) by expression of a nucleotide sequence encoding a naturally occurring $V_{HH}$ domain; (3) by "humanization" (as described herein) of a naturally occurring $V_{HH}$ domain or by expression of a nucleic acid encoding a such humanized $V_{HH}$ domain; (4) by "camelization" (as described herein) of a naturally occurring $V_H$ domain from any animal species, and in particular a from species of mammal, such as from a human being, or by expression of a nucleic acid encoding such a camelized $V_H$ domain; (5) by "camelization" of a "domain antibody" or "Dab" as described by Ward et al (supra), or by expression of a nucleic acid encoding such a camelized $V_H$ domain; (6) by using synthetic or semi-synthetic techniques for preparing proteins, polypeptides or other amino acid sequences known per se; (7) by preparing a nucleic acid encoding a Nanobody using techniques for nucleic acid synthesis known per se, followed by expression of the nucleic acid thus obtained; and/or (8) by any combination of one or more of the foregoing. Suitable methods and techniques for performing the foregoing will be clear to the skilled person based on the disclosure herein and for example include the methods and techniques described in more detail herein.

One preferred class of Nanobodies corresponds to the $V_{HH}$ domains of naturally occurring heavy chain antibodies directed against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2. As further described herein, such $V_{HH}$ sequences can generally be generated or obtained by suitably immunizing a species of Camelid with Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 (i.e. so as to raise an immune response and/or heavy chain antibodies directed against Tie1, Tie2, Ang1, Ang2, Ang3, Ang4, Angptl1, Angptl2, Angptl3, Angptl4, Angptl5, or Angptl6, more preferably Tie2, Ang2, Ang 1, Ang4, or Angptl4, more preferably Tie2 or Ang2), by obtaining a suitable biological sample from said Camelid (such as a blood sample, serum sample or sample of B-cells), and by generating $V_{HH}$ sequences directed against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, starting from said sample, using any suitable technique known per se. Such techniques will be clear to the skilled person and/or are further described herein.

Alternatively, such naturally occurring $V_{HH}$ domains against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, can be obtained from naïve libraries of Camelid $V_{HH}$ sequences, for example by screening such a library using Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, or at least one part, fragment, antigenic determinant or epitope thereof using one or more screening techniques known per se. Such libraries and techniques are for example described in WO 99/37681, WO 01/90190, WO 03/025020 and WO 03/035694. Alternatively, improved synthetic or semi-synthetic libraries derived from naïve $V_{HH}$ libraries may be used, such as libraries obtained from naïve $V_{HH}$ libraries by techniques such as random mutagenesis and/or CDR shuffling, as for example described in WO 00/43507.

Thus, in another aspect, the invention relates to a method for generating Nanobodies, that are directed against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2. In one aspect, said method at least comprises the steps of:
a) providing a set, collection or library of Nanobody sequences; and
b) screening said set, collection or library of Nanobody sequences for Nanobody sequences that can bind to and/or have affinity for Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2;
and
c) isolating the amino acid sequence(s) that can bind to and/or have affinity for Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2.

In such a method, the set, collection or library of Nanobody sequences may be a naïve set, collection or library of Nanobody sequences; a synthetic or semi-synthetic set, collection or library of Nanobody sequences; and/or a set, collection or library of Nanobody sequences that have been subjected to affinity maturation.

In a preferred aspect of this method, the set, collection or library of Nanobody sequences may be an immune set, collection or library of Nanobody sequences, and in particular an immune set, collection or library of $V_{HH}$ sequences, that have been derived from a species of Camelid that has been suitably immunized with Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 or with a suitable antigenic determinant based thereon or derived there from, such as an antigenic part, fragment, region, domain, loop or other epitope thereof. In one particular aspect, said antigenic determinant may be an extracellular part, region, domain, loop or other extracellular epitope(s).

In the above methods, the set, collection or library of Nanobody or $V_{HH}$ sequences may be displayed on a phage, phagemid, ribosome or suitable micro-organism (such as yeast), such as to facilitate screening. Suitable methods, techniques and host organisms for displaying and screening (a set, collection or library of) Nanobody sequences will be clear to the person skilled in the art, for example on the basis of the further disclosure herein. Reference is also made to WO 03/054016 and to the review by Hoogenboom in Nature Biotechnology, 23, 9, 1105-1116 (2005).

In another aspect, the method for generating Nanobody sequences comprises at least the steps of:
a) providing a collection or sample of cells derived from a species of Camelid that express immunoglobulin sequences;
b) screening said collection or sample of cells for (i) cells that express an immunoglobulin sequence that can bind to and/or have affinity for Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2; and (ii) cells that express heavy chain antibodies, in which sub steps (i) and (ii) can be performed essentially as a single screening step or in any suitable order as two separate screening steps, so as to provide at least one cell that expresses a heavy chain antibody that can bind to and/or has affinity for Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2;
and
c) either (i) isolating from said cell the $V_{HH}$ sequence present in said heavy chain antibody; or (ii) isolating from said cell a nucleic acid sequence that encodes the $V_{HH}$ sequence present in said heavy chain antibody, followed by expressing said $V_{HH}$ domain.

In the method according to this aspect, the collection or sample of cells may for example be a collection or sample of B-cells. Also, in this method, the sample of cells may be derived from a Camelid that has been suitably immunized with Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 or a suitable antigenic determinant based thereon or derived there from, such as an antigenic part, fragment, region, domain, loop or other epitope thereof. In one particular aspect, said antigenic determinant may be an extracellular part, region, domain, loop or other extracellular epitope(s).

The above method may be performed in any suitable manner, as will be clear to the skilled person. Reference is for example made to EP 0 542 810, WO 05/19824, WO 04/051268 and WO 04/106377. The screening of step b) is preferably performed using a flow cytometry technique such as FACS. For this, reference is for example made to Lieby et al., Blood, Vol. 97, No. 12, 3820. Particular reference is made to the so-called "Nanoclone™" technique described in International application WO 06/079372 by Ablynx N.V.

In another aspect, the method for generating an amino acid sequence directed against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 may comprise at least the steps of:
a) providing a set, collection or library of nucleic acid sequences encoding heavy chain antibodies or Nanobody sequences;
b) screening said set, collection or library of nucleic acid sequences for nucleic acid sequences that encode a heavy chain antibody or a Nanobody sequence that can bind to and/or has affinity for Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2;
and
c) isolating said nucleic acid sequence, followed by expressing the $V_{HH}$ sequence present in said heavy chain antibody or by expressing said Nanobody sequence, respectively.

In such a method, the set, collection or library of nucleic acid sequences encoding heavy chain antibodies or Nanobody sequences may for example be a set, collection or library of nucleic acid sequences encoding a naïve set, collection or library of heavy chain antibodies or $V_{HH}$ sequences; a set, collection or library of nucleic acid sequences encoding a synthetic or semi-synthetic set, collection or library of Nanobody sequences; and/or a set, collection or library of nucleic acid sequences encoding a set, collection or library of Nanobody sequences that have been subjected to affinity maturation.

In a preferred aspect of this method, the set, collection or library of amino acid sequences may be an immune set, collection or library of nucleic acid sequences encoding heavy chain antibodies or $V_{HH}$ sequences derived from a Camelid that has been suitably immunized with Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 or with a suitable antigenic determinant based thereon or derived there from, such as an antigenic part, fragment, region, domain, loop or other epitope thereof. In one particular aspect, said antigenic determinant may be an extracellular part, region, domain, loop or other extracellular epitope(s).

In the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding amino acid sequences will be clear to the person skilled in the art, for example on the basis of the further disclosure herein. Reference is also made to WO 03/054016 and to the review by Hoogenboom in Nature Biotechnology, 23, 9, 1105-1116 (2005).

As will be clear to the skilled person, the screening step of the methods described herein can also be performed as a selection step. Accordingly the term "screening" as used in the present description can comprise selection, screening or any suitable combination of selection and/or screening techniques. Also, when a set, collection or library of sequences is used, it may contain any suitable number of sequences, such as 1, 2, 3 or about 5, 10, 50, 100, 500, 1000, 5000, $10^4$, $10^5$, $10^6$, $10^7$, $10^8$ or more sequences.

Also, one or more or all of the sequences in the above set, collection or library of amino acid sequences may be obtained or defined by rational, or semi-empirical approaches such as computer modelling techniques or biostatics or data mining techniques.

Furthermore, such a set, collection or library can comprise one, two or more sequences that are variants from one another (e.g. with designed point mutations or with randomized positions), compromise multiple sequences derived from a diverse set of naturally diversified sequences (e.g. an immune library)), or any other source of diverse sequences (as described for example in Hoogenboom et al, Nat Biotechnol 23:1105, 2005 and Binz et al, Nat Biotechnol 2005, 23:1247). Such set, collection or library of sequences can be displayed on the surface of a phage particle, a ribosome, a bacterium, a yeast cell, a mammalian cell, and linked to the nucleotide sequence encoding the amino acid sequence within these carriers. This makes such set, collection or library amenable to selection procedures to isolate the desired amino acid sequences of the invention. More generally, when a sequence is displayed on a suitable host or host cell, it is also possible (and customary) to first isolate from said host or host cell a nucleotide sequence that encodes the desired sequence, and then to obtain the desired sequence by suitably expressing said nucleotide sequence in a suitable host organism. Again, this can be performed in any suitable manner known per se, as will be clear to the skilled person.

Yet another technique for obtaining $V_{HH}$ sequences or Nanobody sequences directed against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 involves suitably immunizing a transgenic mammal that is capable of expressing heavy chain antibodies (i.e. so as to raise an immune response and/or heavy chain antibodies directed against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2), obtaining a suitable biological sample from said transgenic mammal that contains (nucleic acid sequences encoding) said $V_{HH}$ sequences or Nanobody sequences (such as a blood sample, serum sample or sample of B-cells), and then generating $V_{HH}$ sequences directed against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, starting from said sample, using any suitable technique known per se (such as any of the methods described herein or a hybridoma technique). For example, for this purpose, the heavy chain antibody-expressing mice and the further methods and techniques described in WO 02/085945, WO 04/049794 and WO 06/008548 and Janssens et al., Proc. Natl. Acad. Sci. USA. 2006 Oct. 10; 103(41):15130-5 can be used. For example, such heavy chain antibody expressing mice can express heavy chain antibodies with any suitable (single) variable domain, such as (single) variable domains from natural sources (e.g. human (single) variable domains, Camelid (single) variable domains or shark (single) variable domains), as well as for example synthetic or semi-synthetic (single) variable domains.

The invention also relates to the $V_{HH}$ sequences or Nanobody sequences that are obtained by the above methods, or alternatively by a method that comprises the one of the above methods and in addition at least the steps of determining the nucleotide sequence or amino acid sequence of said $V_{HH}$ sequence or Nanobody sequence; and of expressing or synthesizing said $V_{HH}$ sequence or Nanobody sequence in a manner known per se, such as by expression in a suitable host cell or host organism or by chemical synthesis.

As mentioned herein, a particularly preferred class of Nanobodies of the invention comprises Nanobodies with an amino acid sequence that corresponds to the amino acid sequence of a naturally occurring $V_{HH}$ domain, but that has been "humanized", i.e. by replacing one or more amino acid residues in the amino acid sequence of said naturally occurring $V_{HH}$ sequence (and in particular in the framework sequences) by one or more of the amino acid residues that occur at the corresponding position(s) in a $V_H$ domain from a conventional 4-chain antibody from a human being (e.g. indicated above). This can be performed in a manner known per se, which will be clear to the skilled person, for example on the basis of the further description herein and the prior art on humanization referred to herein. Again, it should be noted that such humanized Nanobodies of the invention can be obtained in any suitable manner known per se (i.e. as indicated under points (1)-(8) above) and thus are not strictly limited to polypeptides that have been obtained using a polypeptide that comprises a naturally occurring $V_{HH}$ domain as a starting material.

Another particularly preferred class of Nanobodies of the invention comprises Nanobodies with an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the further description herein. Such "camelizing" substitutions are preferably inserted at amino acid positions that form and/or are present at the $V_H$-$V_L$ interface, and/or at the so-called Camelidae hallmark residues, as defined herein (see for example WO 94/04678 and Davies and Riechmann (1994 and 1996), supra). Preferably, the $V_H$ sequence that is used as a starting material or starting point for generating or designing the camelized Nanobody is preferably a $V_H$ sequence from a mammal, more preferably the $V_H$ sequence of a human being, such as a $V_H3$ sequence. However, it should be noted that such camelized Nanobodies of the invention can be obtained in any suitable manner known per se (i.e. as indicated under points (1)-(8) above) and thus are not strictly limited to polypeptides that have been obtained using a polypeptide that comprises a naturally occurring $V_H$ domain as a starting material.

For example, again as further described herein, both "humanization" and "camelization" can be performed by providing a nucleotide sequence that encodes a naturally occurring $V_{HH}$ domain or $V_H$ domain, respectively, and then changing, in a manner known per se, one or more codons in said nucleotide sequence in such a way that the new nucleotide sequence encodes a "humanized" or "camelized" Nanobody of the invention, respectively. This nucleic acid can then be expressed in a manner known per se, so as to provide the desired Nanobody of the invention. Alternatively, based on the amino acid sequence of a naturally occurring $V_{HH}$ domain or $V_H$ domain, respectively, the amino acid sequence of the desired humanized or camelized Nanobody of the invention, respectively, can be designed and then synthesized de novo using techniques for peptide synthesis known per se. Also, based on the amino acid sequence or nucleotide sequence of a naturally occurring $V_{HH}$ domain or $V_H$ domain, respectively, a nucleotide sequence encoding the desired humanized or camelized Nanobody of the invention, respectively, can be designed and then synthesized de novo using techniques for nucleic acid synthesis known per se, after which the nucleic acid thus obtained can be expressed in a manner known per se, so as to provide the desired Nanobody of the invention.

Other suitable methods and techniques for obtaining the Nanobodies of the invention and/or nucleic acids encoding the same, starting from naturally occurring $V_H$ sequences or preferably $V_{HH}$ sequences, will be clear from the skilled person, and may for example comprise combining one or more parts of one or more naturally occurring $V_H$ sequences (such as one or more FR sequences and/or CDR sequences), one or more parts of one or more naturally occurring $V_{HH}$ sequences (such as one or more FR sequences or CDR sequences), and/or one or more synthetic or semi-synthetic sequences, in a suitable manner, so as to provide a Nanobody of the invention or a nucleotide sequence or nucleic acid encoding the same (which may then be suitably expressed). Nucleotide sequences encoding framework sequences of $V_{HH}$ sequences or Nanobodies will be clear to the skilled person based on the disclosure herein and/or the further prior art cited herein (and/or may alternatively be obtained by PCR starting from the nucleotide sequences obtained using the methods described herein) and may be suitably combined with nucleotide sequences that encode the desired CDR's (for example, by PCR assembly using overlapping primers), so as to provide a nucleic acid encoding a Nanobody of the invention.

As mentioned herein, Nanobodies may in particular be characterized by the presence of one or more "Hallmark residues" (as described herein) in one or more of the framework sequences.

Thus, according to one preferred, but non-limiting aspect of the invention, a Nanobody in its broadest sense can be generally defined as a polypeptide comprising:
a) an amino acid sequence that is comprised of four framework regions/sequences interrupted by three complementarity determining regions/sequences, in which the amino acid residue at position 108 according to the Kabat numbering is Q;
and/or:
b) an amino acid sequence that is comprised of four framework regions/sequences interrupted by three complementarity determining regions/sequences, in which the amino acid residue at position 45 according to the Kabat numbering is a charged amino acid (as defined herein) or a cysteine residue, and position 44 is preferably an E;
and/or:
c) an amino acid sequence that is comprised of four framework regions/sequences interrupted by three complementarity determining regions/sequences, in which the amino acid residue at position 103 according to the Kabat numbering is chosen from the group consisting of P, R and S, and is in particular chosen from the group consisting of R and S.

Thus, in a first preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which
a) the amino acid residue at position 108 according to the Kabat numbering is Q; and/or in which:
b) the amino acid residue at position 45 according to the Kabat numbering is a charged amino acid or a cysteine and the amino acid residue at position 44 according to the Kabat numbering is preferably E;
and/or in which:
c) the amino acid residue at position 103 according to the Kabat numbering is chosen from the group consisting of P, R and S, and is in particular chosen from the group consisting of R and S;
and in which:
d) CDR1, CDR2 and CDR3 are as defined herein, and are preferably as defined according to one of the preferred aspects herein, and are more preferably as defined according to one of the more preferred aspects herein.

In particular, a Nanobody in its broadest sense can be generally defined as a polypeptide comprising:
a) an amino acid sequence that is comprised of four framework regions/sequences interrupted by three complementarity determining regions/sequences, in which the amino acid residue at position 108 according to the Kabat numbering is Q;
and/or:
b) an amino acid sequence that is comprised of four framework regions/sequences interrupted by three complementarity determining regions/sequences, in which the amino acid residue at position 44 according to the Kabat numbering is E and in which the amino acid residue at position 45 according to the Kabat numbering is an R;
and/or:
c) an amino acid sequence that is comprised of four framework regions/sequences interrupted by three complementarily determining regions/sequences, in which the amino acid residue at position 103 according to the Kabat numbering is chosen from the group consisting of P, R and S, and is in particular chosen from the group consisting of R and S.

Thus, according to a preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which
a) the amino acid residue at position 108 according to the Kabat numbering is Q; and/or in which:
b) the amino acid residue at position 44 according to the Kabat numbering is E and in which the amino acid residue at position 45 according to the Kabat numbering is an R; and/or in which:
c) the amino acid residue at position 103 according to the Kabat numbering is chosen from the group consisting of P, R and S, and is in particular chosen from the group consisting of R and S;
and in which:
d) CDR1, CDR2 and CDR3 are as defined herein, and are preferably as defined according to one of the preferred aspects herein, and are more preferably as defined according to one of the more preferred aspects herein.

In particular, a Nanobody against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 according to the invention may have the structure:

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which
a) the amino acid residue at position 108 according to the Kabat numbering is Q;
and/or in which:
b) the amino acid residue at position 44 according to the Kabat numbering is E and in which the amino acid residue at position 45 according to the Kabat numbering is an R; and/or in which:
c) the amino acid residue at position 103 according to the Kabat numbering is chosen from the group consisting of P, R and S, and is in particular chosen from the group consisting of R and S;
and in which:
d) CDR1, CDR2 and CDR3 are as defined herein, and are preferably as defined according to one of the preferred aspects herein, and are more preferably as defined according to one of the more preferred aspects herein.

In particular, according to one preferred, but non-limiting aspect of the invention, a Nanobody can generally be defined as a polypeptide comprising an amino acid sequence that is comprised of four framework regions/sequences interrupted by three complementarity determining regions/sequences, in which;
a-1) the amino acid residue at position 44 according to the Kabat numbering is chosen from the group consisting of A, G, E, D, G, Q, R, S, L; and is preferably chosen from the group consisting of G, E or Q; and a-2) the amino acid residue at position 45 according to the Kabat numbering is chosen from the group consisting of L, R or C; and is preferably chosen from the group consisting of L or R; and
a-3) the amino acid residue at position 103 according to the Kabat numbering is chosen from the group consisting of W, R or S; and is preferably W or R, and is most preferably W;
a-4) the amino acid residue at position 108 according to the Kabat numbering is Q;
or in which:
b-1) the amino acid residue at position 44 according to the Kabat numbering is chosen from the group consisting of E and Q; and
b-2) the amino acid residue at position 45 according to the Kabat numbering is R; and
b-3) the amino acid residue at position 103 according to the Kabat numbering is chosen from the group consisting of W, R and S; and is preferably W;
b-4) the amino acid residue at position 108 according to the Kabat numbering is chosen from the group consisting of Q and L; and is preferably Q;
or in which:
c-1) the amino acid residue at position 44 according to the Kabat numbering is chosen from the group consisting of A, G, E, D, Q, R, S and L; and is preferably chosen from the group consisting of G, E and Q; and
c-2) the amino acid residue at position 45 according to the Kabat numbering is chosen from the group consisting of L, R and C; and is preferably chosen from the group consisting of L and R; and
c-3) the amino acid residue at position 103 according to the Kabat numbering is chosen from the group consisting of P, R and S; and is in particular chosen from the group consisting of R and S; and
c-4) the amino acid residue at position 108 according to the Kabat numbering is chosen from the group consisting of Q and L; is preferably Q;
and in which
d) CDR1, CDR2 and CDR3 are as defined herein, and are preferably as defined according to one of the preferred aspects herein, and are more preferably as defined according to one of the more preferred aspects herein.

Thus, in another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
a-1) the amino acid residue at position 44 according to the Kabat numbering is chosen from the group consisting of A, G, E, D, G, Q, R, S, L; and is preferably chosen from the group consisting of G, E or Q;
and in which:
a-2) the amino acid residue at position 45 according to the Kabat numbering is chosen from the group consisting of L, R or C; and is preferably chosen from the group consisting of L or R;
and in which:
a-3) the amino acid residue at position 103 according to the Kabat numbering is chosen from the group consisting of W, R or S; and is preferably W or R, and is most preferably W;
and in which a-4) the amino acid residue at position 108 according to the Kabat numbering is Q;
and in which:
d) CDR1, CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
b-1) the amino acid residue at position 44 according to the Kabat numbering is chosen from the group consisting of E and Q;
and in which:
b-2) the amino acid residue at position 45 according to the Kabat numbering is R;
and in which:
b-3) the amino acid residue at position 103 according to the Kabat numbering is chosen from the group consisting of W, R and S; and is preferably W;
and in which:
b-4) the amino acid residue at position 108 according to the Kabat numbering is chosen from the group consisting of Q and L; and is preferably Q;
and in which:
d) CDR1, CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
c-1) the amino acid residue at position 44 according to the Kabat numbering is chosen from the group consisting of A, G, E, D, Q, R, S and L; and is preferably chosen from the group consisting of G, E and Q;
and in which:
c-2) the amino acid residue at position 45 according to the Kabat numbering is chosen from the group consisting of L, R and C; and is preferably chosen from the group consisting of L and R;
and in which:
c-3) the amino acid residue at position 103 according to the Kabat numbering is chosen from the group consisting of P, R and S; and is in particular chosen from the group consisting of R and S;
and in which:
c-4) the amino acid residue at position 108 according to the Kabat numbering is chosen from the group consisting of Q and L; is preferably Q;
and in which:
d) CDR1, CDR2 and CDR3 are as defined herein, and are preferably as defined according to one of the preferred aspects herein, and are more preferably as defined according to one of the more preferred aspects herein.

Two particularly preferred, but non-limiting groups of the Nanobodies of the invention are those according to a) above; according to (a-1) to (a-4) above; according to b) above; according to (b-1) to (b-4) above; according to (c) above; and/or according to (c-1) to (c-4) above, in which either:
i) the amino acid residues at positions 44-47 according to the Kabat numbering form the sequence GLEW (or a GLEW-like sequence as described herein) and the amino acid residue at position 108 is Q;
or in which:
ii) the amino acid residues at positions 43-46 according to the Kabat numbering form the sequence KERE or KQRE (or a KERE-like sequence as described) and the amino acid residue at position 108 is Q or L, and is preferably Q.

Thus, in another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
i) the amino acid residues at positions 44-47 according to the Kabat numbering form the sequence GLEW (or a GLEW-like sequence as defined herein) and the amino acid residue at position 108 is Q;
and in which:
ii) CDR1, CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
i) the amino acid residues at positions 43-46 according to the Kabat numbering form the sequence KERE or KQRE (or a KERE-like sequence) and the amino acid residue at position 108 is Q or L, and is preferably Q;
and in which:
ii) CDR1, CDR2 and CDR3 are as defined herein, and are preferably as defined according to one of the preferred aspects herein, and are more preferably as defined according to one of the more preferred aspects herein.

In the Nanobodies of the invention in which the amino acid residues at positions 43-46 according to the Kabat numbering form the sequence KERE or KQRE, the amino acid residue at position 37 is most preferably F. In the Nanobodies of the invention in which the amino acid residues at positions 44-47 according to the Kabat numbering form the sequence GLEW, the amino acid residue at position 37 is chosen from the group consisting of Y, H, L, V or F, and is most preferably V.

Thus, without being limited hereto in any way, on the basis of the amino acid residues present on the positions mentioned above, the Nanobodies of the invention can generally be classified on the basis of the following three groups:
i) The "GLEW-group": Nanobodies with the amino acid sequence GLEW at positions 44-47 according to the Kabat numbering and Q at position 108 according to the Kabat numbering. As further described herein, Nanobodies within this group usually have a V at position 37, and can have a W, P, R or S at position 103, and preferably have a W at position 103. The GLEW group also comprises some GLEW-like sequences such as those mentioned in Table A-3 below. More generally, and without limitation, Nanobodies belonging to the GLEW-group can be defined as Nanobodies with a G at position 44 and/or with a W at position 47, in which position 46 is usually E and in which preferably position 45 is not a charged amino acid residue and not cysteine;

ii) The "KERE-group": Nanobodies with the amino acid sequence KERB or KQRE (or another KERE-like sequence) at positions 43-46 according to the Kabat numbering and Q or L at position 108 according to the Kabat numbering. As further described herein, Nanobodies within this group usually have a F at position 37, an L or F at position 47; and can have a W, P, R or S at position 103, and preferably have a W at position 103. More generally, and without limitation, Nanobodies belonging to the KERE-group can be defined as Nanobodies with a K, Q or R at position 44 (usually K) in which position 45 is a charged amino acid residue or cysteine, and position 47 is as further defined herein;

iii) The "103 P, R, S-group": Nanobodies with a P, R or S at position 103. These Nanobodies can have either the amino acid sequence GLEW at positions 44-47 according to the Kabat numbering or the amino acid sequence KERE or KQRE at positions 43-46 according to the Kabat numbering, the latter most preferably in combination with an F at position 37 and an L or an F at position 47 (as defined for the KERE-group); and can have Q or L at position 108 according to the Kabat numbering, and preferably have Q.

Also, where appropriate, Nanobodies may belong to (i.e. have characteristics of) two or more of these classes. For example, one specifically preferred group of Nanobodies has GLEW or a GLEW-like sequence at positions 44-47; P, R or S (and in particular R) at position 103; and Q at position 108 (which may be humanized to L).

More generally, it should be noted that the definitions referred to above describe and apply to Nanobodies in the form of a native (i.e. non-humanized) $V_{HH}$ sequence, and that humanized variants of these Nanobodies may contain other amino acid residues than those indicated above (i.e. one or more humanizing substitutions as defined herein). For example, and without limitation, in some humanized Nanobodies of the GLEW-group or the 103 P, R, S-group, Q at position 108 may be humanized to 108L. As already mentioned herein, other humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) a Nanobody may be partially humanized or fully humanized.

Thus, in another preferred, but non-limiting aspect, a Nanobody of the invention may be a Nanobody belonging to the GLEW-group (as defined herein), and in which CDR1, CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may be a Nanobody belonging to the KERE-group (as defined herein), and CDR1, CDR2 and CDR3 are as defined herein, and are preferably as defined according to one of the preferred aspects herein, and are more preferably as defined according to one of the more preferred aspects herein.

Thus, in another preferred, but non-limiting aspect, a Nanobody of the invention may be a Nanobody belonging to the 103 P, R, S-group (as defined herein), and in which CDR1, CDR2 and CDR3 are as defined herein, and are preferably as defined according to one of the preferred aspects herein, and are more preferably as defined according to one of the more preferred aspects herein.

Also, more generally and in addition to the 108Q, 43E/44R and 103 P,R,S residues mentioned above, the Nanobodies of the invention can contain, at one or more positions that in a conventional $V_H$ domain would form (part of) the $V_H/V_L$ interface, one or more amino acid residues that are more highly charged than the amino acid residues that naturally occur at the same position(s) in the corresponding naturally occurring $V_H$ sequence, and in particular one or more charged amino acid residues (as mentioned in Table A-2). Such substitutions include, but are not limited to, the GLEW-like sequences mentioned in Table A-3 below; as well as the substitutions that are described in the International Application WO 00/29004 for so-called "microbodies", e.g. so as to obtain a Nanobody with Q at position 108 in combination with KLEW at positions 44-47. Other possible substitutions at these positions will be clear to the skilled person based upon the disclosure herein.

In one aspect of the Nanobodies of the invention, the amino acid residue at position 83 is chosen from the group consisting of L, M, S, V and W; and is preferably L. Also, in one aspect of the Nanobodies of the invention, the amino acid residue at position 83 is chosen from the group consisting of R, K, N, E, G, I, T and Q; and is most preferably either K or E (for Nanobodies corresponding to naturally occurring $V_{HH}$ domains) or R (for "humanized" Nanobodies, as described herein). The amino acid residue at position 84 is chosen from the group consisting of P, A, R, S, D T, and V in one aspect, and is most preferably P (for Nanobodies corresponding to naturally occurring $V_{HH}$ domains) or R (for "humanized" Nanobodies, as described herein).

Furthermore, in one aspect of the Nanobodies of the invention, the amino acid residue at position 104 is chosen from the group consisting of G and D; and is most preferably G.

Collectively, the amino acid residues at positions 11, 37, 44, 45, 47, 83, 84, 103, 104 and 108, which in the Nanobodies are as mentioned above, will also be referred to herein as the "Hallmark Residues". The Hallmark Residues and the amino acid residues at the corresponding positions of the most closely related human $V_H$ domain, $V_H3$, are summarized in Table A-3.

Some especially preferred but non-limiting combinations of these Hallmark Residues as occur in naturally occurring $V_{HH}$ domains are mentioned in Table A-4. For comparison, the corresponding amino acid residues of the human $V_H3$ called DP-47 have been indicated in italics.

TABLE A-3

Hallmark Residues in Nanobodies

| Position | Human $V_H3$ | Hallmark Residues |
|---|---|---|
| 11 | L, V; predominantly L | L, M, S, V, W; preferably L |
| 37 | V, I, F; usually V | $F^{(1)}$, Y, H, I, L or V, preferably $F^{(1)}$ or Y |
| 44[8] | G | $G^{(2)}$, $E^{(3)}$, A, D, Q, R, S, L; preferably $G^{(2)}$, $E^{(3)}$ or Q; most preferably $G^{(2)}$ or $E^{(3)}$ |
| 45[8] | L | $L^{(2)}$, $R^{(3)}$, C, I, L, P, Q, V; preferably $L^{(2)}$ or $R^{(3)}$ |
| 47[8] | W, Y | $W^{(2)}$, $L^{(1)}$ or $F^{(1)}$, A, G, I, M, R, S, V or Y; preferably $W^{(2)}$, $L^{(1)}$, $F^{(1)}$ or R |
| 83 | R or K; usually R | R, $K^{(5)}$, N, $E^{(5)}$, G, I, M, Q or T; preferably K or R; most preferably K |
| 84 | A, T, D; predominantly A | $P^{(5)}$, A, L, R, S, T, D, V; preferably P |
| 103 | W | $W^{(4)}$, $P^{(6)}$, $R^{(6)}$, S; preferably W |
| 104 | G | G or D; preferably G |
| 108 | L, M or T; predominantly L | Q, $L^{(7)}$ or R; preferably Q or $L^{(7)}$ |

Notes:
[1] In particular, but not exclusively, in combination with KERE or KQRE at positions 43-46.
[2] Usually as GLEW at positions 44-47.
[3] Usually as KERE or KQRE at positions 43-46, e.g. as KEREL, KEREF, KQREL, KQREF or KEREG at positions 43-47. Alternatively, also sequences such as TERE (for example TEREL), KECE (for example KECEL or KECER), RERE (for example REREG), QERE (for example QEREG), KGRE (for example KGREG), KDRE (for example KDREV) are possible. Some other possible, but less preferred sequences include for example DECKL and NVCEL.
[4] With both GLEW at positions 44-47 and KERE or KQRE at positions 43-46.
[5] Often as KP or EP at positions 83-84 of naturally occurring $V_{HH}$ domains.
[6] In particular, but not exclusively, in combination with GLEW at positions 44-47.
[7] With the proviso that when positions 44-47 are GLEW, position 108 is always Q in (non-humanized) $V_{HH}$ sequences that also contain a W at 103.
[8] The GLEW group also contains GLEW-like sequences at positions 44-47, such as for example GVEW, EPEW, GLER, DQEW, DLEW, GIEW, ELEW, GPEW, EWLP, GPER, GLER and ELEW.

TABLE A-4

Some preferred but non-limiting combinations of Hallmark Residues in naturally occurring Nanobodies.

|  | 11 | 37 | 44 | 45 | 47 | 83 | 84 | 103 | 104 | 108 |
|---|---|---|---|---|---|---|---|---|---|---|
| DP-47 (human) | M | V | G | L | W | R | A | W | G | L |
| "KERE" group | L | F | E | R | L | K | P | W | G | Q |
|  | L | F | E | R | F | E | P | W | G | Q |
|  | L | F | E | R | F | K | P | W | G | Q |
|  | L | Y | Q | R | L | K | P | W | G | Q |
|  | L | F | L | R | V | K | P | Q | G | Q |
|  | L | F | Q | R | L | K | P | W | G | Q |
|  | L | F | E | R | F | K | P | W | G | Q |
| "GLEW" group | L | V | G | L | W | K | S | W | G | Q |
|  | M | V | G | L | W | K | P | R | G | Q |

For humanization of these combinations, reference is made to the specification.

In the Nanobodies, each amino acid residue at any other position than the Hallmark Residues can be any amino acid residue that naturally occurs at the corresponding position (according to the Kabat numbering) of a naturally occurring $V_{HH}$ domain.

Such amino acid residues will be clear to the skilled person. Tables A-5 to A-8 mention some non-limiting residues that can be present at each position (according to the Kabat numbering) of the FR1, FR2, FR3 and FR4 of naturally occurring $V_{HH}$ domains. For each position, the amino acid residue that most frequently occurs at each position of a naturally occurring $V_{HH}$ domain (and which is the most preferred amino acid residue for said position in a Nanobody) is indicated in bold; and other preferred amino acid residues for each position have been underlined (note: the number of amino acid residues that are found at positions 26-30 of naturally occurring $V_{HH}$ domains supports the hypothesis underlying the numbering by Chothia (supra) that the residues at these positions already form part of CDR1.)

In Tables A-5-A-8, some of the non-limiting residues that can be present at each position of a human $V_H3$ domain have also been mentioned. Again, for each position, the amino acid residue that most frequently occurs at each position of a naturally occurring human $V_H3$ domain is indicated in bold; and other preferred amino acid residues have been underlined.

For reference only, Tables A-5-A-8 also contain data on the $V_{HH}$ entropy ("$V_{HH}$ Ent") and $V_{HH}$ variability ("$V_{HH}$ Var.") at each amino acid position for a representative sample of 1118 $V_{HH}$ sequences (data kindly provided by David Lutje Hulsing and Prof. Theo Verrips of Utrecht University). The values for the $V_{HH}$ entropy and the $V_{HH}$ variability provide a measure for the variability and degree of conservation of amino acid residues between the 1118 $V_{HH}$ sequences analyzed: low values (i.e. <1, such as <0.5) indicate that an amino acid residue is highly conserved between the $V_{HH}$ sequences (i.e. little variability). For example, the G at position 8 and the G at position 9 have values for the $V_{HH}$ entropy of 0.1 and 0 respectively, indicating that these residues are highly conserved and have little variability (and in case of position 9 is G in all 1118 sequences analysed), whereas for residues that form part of the CDR's generally values of 1.5 or more are found (data not shown). Note that (1) the amino acid residues listed in the second column of Tables A-5-A-8 are based on a bigger sample than the 1118 $V_{HH}$ sequences that were analysed for determining the $V_{HH}$ entropy and $V_{HH}$ variability referred to in the last two columns; and (2) the data represented below support the hypothesis that the amino acid residues at positions 27-30 and maybe even also at positions 93 and 94 already form part of the CDR's (although the invention is not limited to any specific hypothesis or explanation, and as mentioned above, herein the numbering according to Kabat is used). For a general explanation of sequence entropy, sequence variability and the methodology for determining the same, see Oliveira et al, PROTEINS: Structure, Function and Genetics, 52: 544-552 (2003).

TABLE A-5

Non-limiting examples of amino acid residues in FR1 (for the footnotes, see the footnotes to Table A-3)

| | Amino acid residue(s): | | $V_{HH}$ Ent. | $V_{HH}$ Var. |
|---|---|---|---|---|
| Pos. | Human $V_H3$ | Camelid $V_{HH}$'s | | |
| 1 | E, Q | Q, A, E | — | — |
| 2 | V | V | 0.2 | 1 |
| 3 | Q | Q, K | 0.3 | 2 |

TABLE A-5-continued

Non-limiting examples of amino acid residues in FR1
(for the footnotes, see the footnotes to Table A-3)

| Pos. | Amino acid residue(s): Human $V_H3$ | Camelid $V_{HH}$'s | $V_{HH}$ Ent. | $V_{HH}$ Var. |
|---|---|---|---|---|
| 4  | L       | L                                           | 0.1 | 1 |
| 5  | V L     | Q, E, L, V                                  | 0.8 | 3 |
| 6  | E       | E, D, Q, A                                  | 0.8 | 4 |
| 7  | S, T    | S, F                                        | 0.3 | 2 |
| 8  | G, R    | G                                           | 0.1 | 1 |
| 9  | G       | G                                           | 0   | 1 |
| 10 | G, V    | G, D, R                                     | 0.3 | 2 |
| 11 |         | Hallmark residue: L, M, S, V, W; preferably L | 0.8 | 2 |
| 12 | V, I    | V, A                                        | 0.2 | 2 |
| 13 | Q, K, R | Q, E, K, P, R                               | 0.4 | 4 |
| 14 | P       | A, Q, A, G, P, S, T, V                      | 1   | 5 |
| 15 | G       | G                                           | 0   | 1 |
| 16 | G, R    | G, A, E, D                                  | 0.4 | 3 |
| 17 | S       | S, F                                        | 0.5 | 2 |
| 18 | L       | L, V                                        | 0.1 | 1 |
| 19 | R, K    | R, K, L, N, S, T                            | 0.6 | 4 |
| 20 | L       | L, F, I, V                                  | 0.5 | 4 |
| 21 | S       | S, A, F, T                                  | 0.2 | 3 |
| 22 | C       | C                                           | 0   | 1 |
| 23 | A, T    | A, D, E, P, S, T, V                         | 1.3 | 5 |
| 24 | A       | A, I, L, S, T, V                            | 1   | 6 |
| 25 | S       | S, A, F, P, T                               | 0.5 | 5 |
| 26 | G       | G, A, D, E, R, S, T, V                      | 0.7 | 7 |
| 27 | F       | S, F, R, L, P, G, N,                        | 2.3 | 13 |
| 28 | T       | N, T, E, D, S, I, R, A, G, R, F, Y          | 1.7 | 11 |
| 29 | F, V    | F, L, D, S, I, G, V, A                      | 1.9 | 11 |
| 30 | S, D, G | N, S, E, G, A, D, M, T                      | 1.8 | 11 |

TABLE A-6

Non-limiting examples of amino acid residues in FR2
(for the footnotes, see the footnotes to TABLE A-3)

| Pos. | Amino acid residue(s): Human $V_H3$ | Camelid $V_{HH}$'s | $V_{HH}$ Ent. | $V_{HH}$ Var. |
|---|---|---|---|---|
| 36 | W | W | 0.1 | 1 |
| 37 | Hallmark residue: $F^{(1)}$, H, I, L, Y or V, preferably $F^{(1)}$ or Y | | 1.1 | 6 |
| 38 | R | R | 0.2 | 1 |

TABLE A-6-continued

Non-limiting examples of amino acid residues in FR2
(for the footnotes, see the footnotes to TABLE A-3)

| Pos. | Human $V_H3$ | Camelid $V_{HH}$'s | $V_{HH}$ Ent. | $V_{HH}$ Var. |
|---|---|---|---|---|
| 39 | Q | Q, H, P, R | 0.3 | 2 |
| 40 | A | A, F, G, L, P, T, V | 0.9 | 7 |
| 41 | P, S, T | P, A, L, S | 0.4 | 3 |
| 42 | G | G, E | 0.2 | 2 |
| 43 | K | K, D, E, N, Q, R, T, V | 0.7 | 6 |
| 44 | Hallmark residue: $G^{(2)}$, $E^{(3)}$, A, D, Q, R, S, L; preferably $G^{(2)}$, $E^{(3)}$ or Q; most preferably $G^{(2)}$ or $E^{(3)}$ | | 1.3 | 5 |
| 45 | Hallmark residue: $L^{(2)}$, $R^{3)}$, C, I, L, P, Q, V; preferably $L^{(2)}$ or $R^{(3)}$ | | 0.6 | 4 |
| 46 | E, V | E, D, K, Q, V | 0.4 | 2 |
| 47 | Hallmark residue: $W^{(2)}$, $L^{(1)}$ or $F^{(1)}$, A, G, I, M, R, S, V or Y; preferably $W^{(2)}$, $L^{(1)}$, $F^{(1)}$ or R | | 1.9 | 9 |
| 48 | V | V, I, L | 0.4 | 3 |
| 49 | S, A, G | A, S, G, T, V | 0.8 | 3 |

TABLE A-7

Non-limiting examples of amino acid residues in FR3
(for the footnotes, see the footnotes to TABLE A-3)

| Pos. | Human $V_H3$ | Camelid $V_{HH}$'s | $V_{HH}$ Ent. | $V_{HH}$ Var. |
|---|---|---|---|---|
| 66 | R | R | 0.1 | 1 |
| 67 | F | F, L, V | 0.1 | 1 |
| 68 | T | T, A, N, S | 0.5 | 4 |
| 69 | I | I, L, M, V | 0.4 | 4 |
| 70 | S | S, A, F, T | 0.3 | 4 |
| 71 | R | R, G, H, I, L, K, Q, S, T, W | 1.2 | 8 |
| 72 | D, E | D, E, G, N, V | 0.5 | 4 |
| 73 | N, D, G | N, A, D, F, I, K, L, R, S, T, V, Y | 1.2 | 9 |
| 74 | A, S | A, D, G, N, P, S, T, V | 1 | 7 |
| 75 | K | K, A, E, K, L, N, Q, R | 0.9 | 6 |
| 76 | N, S | N, D, K, R, S, T, Y | 0.9 | 6 |
| 77 | S, T, I | T, A, E, I, M, P, S | 0.8 | 5 |
| 78 | L, A | V, L, A, F, G, I, M | 1.2 | 5 |
| 79 | Y, H | Y, A, D, F, H, N, S, T | 1 | 7 |
| 80 | L | L, F, V | 0.1 | 1 |
| 81 | Q | Q, E, I, L, R, T | 0.6 | 5 |
| 82 | M | M, I, L, V | 0.2 | 2 |
| 82a | N, G | N, D, G, H, S, T | 0.8 | 4 |
| 82b | S | S, N, D, G, R, T | 1 | 6 |

TABLE A-7-continued

Non-limiting examples of amino acid residues in FR3
(for the footnotes, see the footnotes to TABLE A-3)

| Pos. | Human V$_H$3 | Camelid V$_{HH}$'s | V$_{HH}$ Ent. | V$_{HH}$ Var. |
|---|---|---|---|---|
| 82c | L | L, P, V | 0.1 | 2 |
| 83 | Hallmark residue: R, K$^{(5)}$, N, E$^{(5)}$, G, I, M, Q or T; preferably K or R; most preferably K | | 0.9 | 7 |
| 84 | Hallmark residue: P$^{(5)}$, A, D, L, R, S, T, V; preferably P | | 0.7 | 6 |
| 85 | E, G | E, D, G, Q | 0.5 | 3 |
| 86 | D | D | 0 | 1 |
| 87 | T, M | T, A, S | 0.2 | 3 |
| 88 | A | A, G̲, S | 0.3 | 2 |
| 89 | V, L | V, A, D, I, L, M, N, R, T | 1.4 | 6 |
| 90 | Y | Y, F | 0 | 1 |
| 91 | Y, H | Y, D, F, H, L, S, T, V | 0.6 | 4 |
| 92 | C | C | 0 | 1 |
| 93 | A, K, T | A, N̲, G, H, K, N, R, S, T, V, Y | 1.4 | 10 |
| 94 | K, R, T | A, V̲, C, F, G, I, K, L, R, S or T | 1.6 | 9 |

TABLE A-8

Non-limiting examples of amino acid residues in FR4
(for the footnotes, see the footnotes to TABLE A-3)

| Pos. | Human V$_H$3 | Camelid V$_{HH}$'s | V$_{HH}$ Ent. | V$_{HH}$ Var. |
|---|---|---|---|---|
| 103 | Hallmark residue: W$^{(4)}$, P$^{(6)}$, R$^{(6)}$, S; preferably W | | 0.4 | 2 |
| 104 | Hallmark residue: G or D; preferably G | | 0.1 | 1 |
| 105 | Q, R̲ | Q, E, K, P, R | 0.6 | 4 |
| 106 | G | G | 0.1 | 1 |
| 107 | T | T, A, I | 0.3 | 2 |
| 108 | Hallmark residue: Q, L$^{(7)}$, or R; preferably Q or L$^{(7)}$ | | 0.4 | 3 |
| 109 | V | V | 0.1 | 1 |
| 110 | T | T, I, A | 0.2 | 1 |
| 111 | V | V, A, I | 0.3 | 2 |
| 112 | S | S, F | 0.3 | 1 |
| 113 | S | S, A, P, L, T | 0.4 | 3 |

Thus, in another preferred, but not limiting aspect, a Nanobody of the invention can be defined as an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
i) one or more of the amino acid residues at positions 11, 37, 44, 45, 47, 83, 84, 103, 104 and 108 according to the Kabat numbering are chosen from the Hallmark residues mentioned in Table A-3;
and in which:
ii) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

In particular, a Nanobody of the invention can be an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
i) (preferably) one or more of the amino acid residues at positions 11, 37, 44, 45, 47, 83, 84, 103, 104 and 108 according to the Kabat numbering are chosen from the Hallmark residues mentioned in Table A-3 (it being understood that $V_{HH}$ sequences will contain one or more Hallmark residues; and that partially humanized Nanobodies will usually, and preferably, [still] contain one or more Hallmark residues [although it is also within the scope of the invention to provide—where suitable in accordance with the invention—partially humanized Nanobodies in which all Hallmark residues, but not one or more of the other amino acid residues, have been humanized]; and that in fully humanized Nanobodies, where suitable in accordance with the invention, all amino acid residues at the positions of the Hallmark residues will be amino acid residues that occur in a human $V_H3$ sequence. As will be clear to the skilled person based on the disclosure herein that such $V_{HH}$ sequences, such partially humanized Nanobodies with at least one Hallmark residue, such partially humanized Nanobodies without Hallmark residues and such fully humanized Nanobodies all form aspects of this invention);
and in which:
ii) said amino acid sequence has at least 80% amino acid identity with at least one of the amino acid sequences of SEQ ID NO's: 1 to 22, in which for the purposes of determining the degree of amino acid identity, the amino acid residues that form the CDR sequences (indicated with X in the sequences of SEQ ID NO's: 1 to 22) are disregarded;
and in which:
iii) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

TABLE A-9

Representative amino acid sequences for Nanobodies of the KERE, GLEW and P, R, S 103 group.
The CDR's are indicated with XXXX

| | | |
|---|---|---|
| KERE sequence no. 1 | SEQ ID NO: 1 | EVQLVESGGGLVQPGGSLRLSCAASGIPFSXXXXXWFRQAPGKQRDSVAXXXXXRFTISRDNAKNTVYLQMNSLKPEDTAVRYCYFXXXXXWGQGTQVTVSS |
| KERE sequence no. 2 | SEQ ID NO: 2 | QVKLEESGGGLVQAGGSLRLSCVGSGRTFSXXXXXWFRLAPGKEREFVAXXXXXRFTISRDTASNRGYLHMNNLTPEDTAVYYCAAXXXXXWGQGTQVTVSS |
| KERE sequence no. 3 | SEQ ID NO: 3 | AVQLVDSGGGLVQAGDSLKLSCALTGGAFTXXXXXWFRQTPGREREFVAXXXXXRFTISRDNAKNMVYLRMNSLIPEDAAVYSCAAXXXXXWGQGTLVTVSS |
| KERE sequence no. 4 | SEQ ID NO: 4 | QVQLVESGGGLVEAGGSLRLSCTASESPFRXXXXXWFRQTSGQEREFVAXXXXXRFTISRDDAKNTVWLHGSTLKPEDTAVYYCAAXXXXXWGQGTQVTVSS |
| KERE sequence no. 5 | SEQ ID NO: 5 | AVQLVESGGGLVQGGGSLRLACAASERIFDXXXXXWYRQGPGNERELVAXXXXXRFTISMDYTKQTVYLHMNSLRPEDTGLYYCKIXXXXXWGQGTQVTVSS |
| KERE sequence no. 6 | SEQ ID NO: 6 | DVKFVESGGGLVQAGGSLRLSCVASGFNFDXXXXXWFRQAPGKEREEVAXXXXXRFTISSEKDKNSVYLQMNSLKPEDTALYICAGXXXXXWGRGTQVTVSS |
| KERE sequence no. 7 | SEQ ID NO: 7 | QVRLAESGGGLVQSGGSLRLSCVASGSTYTXXXXXWYRQYPGKQRALVAXXXXXRFTIARDSTKDTFCLQMNNLKPEDTAVYYCYAXXXXXWGQGTQVTVSS |
| KERE sequence no. 8 | SEQ ID NO: 8 | EVQLVESGGGLVQAGGSLRLSCAASGFTSDXXXXXWFRQAPGKPREGVSXXXXXRFTISTDNAKNTVHLLMNRVNAEDTALYYCAVXXXXXWGRGTRVTVSS |
| KERE sequence no. 9 | SEQ ID NO: 9 | QVQLVESGGGLVQPGGSLRLSCQASGDISTXXXXXWYRQVPGKLREFVAXXXXXRFTISGDNAKRAIYLQMNNLKPDOTAVYYCNRXXXXXWGQGTQVTVSP |
| KERE sequence no. 10 | SEQ ID NO: 10 | QVPVVESGGGLVQAGDSLRLFCAVPSFTSTXXXXXWFRQAPGKEREFVAXXXXXRFTISRNATKNTLTLRMDSLKPEDTAVYYCAAXXXXXWGDGTQVTVSS |

TABLE A-9-continued

Representative amino acid sequences for Nanobodies of the KERE, GLEW and P, R, S 103 group. The CDR's are indicated with XXXX

| | | |
|---|---|---|
| KERE sequence no. 11 | SEQ ID NO: 11 | EVQLVESGGGLVQAGDSLRLFCTVSGGTASXXXXXWFRQAPGEKREFVAXXXXXRFTI ARENAGNMVYLQMNNLKPDDTALYTCAAXXXXXXWGRGTQVTVSS |
| KERE sequence no. 12 | SEQ ID NO: 12 | AVQLVESGGDSVQPGDSQTLSCAASGRTNSXXXXXWFRQAPGKERVFLAXXXXXRFT ISRDSAKNMMYLQMNNLKPQDTAVYYCAAXXXXXXWGQGTQVTVSS |
| KERE sequence no. 13 | SEQ ID NO: 13 | AVQLVESGGGLVQAGGSLRLSCVVSGLTSSXXXXXWFRQTPWQERDFVAXXXXXRFT ISRDNYKDTVLLEMNFLKPEDTAIYYCAAXXXXXXWGQGTQVTVSS |
| KERE sequence no. 14 | SEQ ID NO: 14 | AVQLVESGGGLVQAGASLRLSCATSTRTLDXXXXXWFRQAPGRDREFVAXXXXXRFT VSRDSAENTVALQMNSLKPEDTAVYYCAAXXXXXXWGQGTRVTVSS |
| KERE sequence no. 15 | SEQ ID NO: 15 | QVQLVESGGGLVQPGGSLRLSCTVSRLTAHXXXXXWFRQAPGKEREAVSXXXXXRFTI SRDYAGNTAFLQMDSLKPEDTGVYYCATXXXXXWGQGTQVTVSS |
| KERE sequence no. 16 | SEQ ID NO: 16 | EVQLVESGGELVQAGGSLKLSCTASGRNFVXXXXXWFRRAPGKEREFVAXXXXXRFT VSRDNGKNTAYLRMNSLKPEDTADYYCAVXXXXXLGSGTQVTVSS |
| GLEW sequence no. 1 | SEQ ID NO: 17 | AVQLVESGGGLVQPGGSLRLSCAASGFTFSXXXXXWVRQAPGKVLEWVSXXXXXRFT ISRDNAKNTLYLQMNSLKPEDTAVYYCVKXXXXXXGSQGTQVTVSS |
| GLEW sequence no. 2 | SEQ ID NO: 18 | EVQLVESGGGLVQPGGSLRLSCVCVSSGCTXXXXXWVRQAPGKAEEWVSXXXXXRF KISRDNAKKTLYLQMNSLGPEDTAMYYCQRXXXXXRGQGTQVTVSS |
| GLEW sequence no. 3 | SEQ ID NO: 19 | EVQLVESGGGLALPGGSLTLSCVFSGSTFSXXXXXWVRHTPGKAEEWVSXXXXXRFTI SRDNAKNTLYLEMNSLSPEDTAMYYCGRXXXXXRSKGIQVTVSS |
| P, R, S 103 sequence no. 1 | SEQ ID NO: 20 | AVQLVESGGGLVQAGGSLRLSCAASGRTFSXXXXXWFRQAPGKEREFVAXXXXXRFTI SRDNAKNTVYLQMNSLKPEDTAVYYCAAXXXXXXRGQGTQVTVSS |
| P, R, S 103 sequence no. 2 | SEQ ID NO: 21 | DVQLVESGGDLVQPGGSLRLSCAASGFSFDXXXXXWLRQTPGKGLEWVGXXXXXRFT ISRDNAKNMLYLHLNNLKSEDTAVYYCRRXXXXXLGQGTQVTVSS |
| P, R, S 103 sequence no. 3 | SEQ ID NO: 22 | EVQLVESGGGLVQPGGSLRLSCVCVSSGCTXXXXXWVRQAPGKAEEWVSXXXXXRF KISRDNAKKTLYLQMNSLGPEDTAMYYCQRXXXXXRGQGTQVTVSS |

In particular, a Nanobody of the invention of the KERE group can be an amino acid sequence with the (general) structure

FR1-CDR1-FR2-CDR2-FR3-CDR3-FR4 in which:

i) the amino acid residue at position 45 according to the Kabat numbering is a charged amino acid (as defined herein) or a cysteine residue, and position 44 is preferably an E;

and in which:

ii) FR1 is an amino acid sequence that has at least 80% amino acid identity with at least one of the following amino acid sequences:

TABLE A-10

Representative FW1 sequences for Nanobodies of the KERE-group.

| | | |
|---|---|---|
| KERE FW1 sequence no. 1 | SEQ ID NO: 23 | QVQRVESGGGLVQAGGSLRLSCAASGRTSS |
| KERE FW1 sequence no. 2 | SEQ ID NO: 24 | QVQLVESGGGLVQTGDSLSLSCSASGRTFS |
| KERE FW1 sequence no. 3 | SEQ ID NO: 25 | QVKLEESGGGLVQAGDSLRLSCAATGRAFG |
| KERE FW1 sequence no. 4 | SEQ ID NO: 26 | AVQLVESGGGLVQPGESLGLSCVASGRDFV |
| KERE FW1 sequence no. 5 | SEQ ID NO: 27 | EVQLVESGGGLVQAGGSLRLSCEVLGRTAG |
| KERE FW1 sequence no. 6 | SEQ ID NO: 28 | QVQLVESGGGWVQPGGSLRLSCAASETILS |
| KERE FW1 sequence no. 7 | SEQ ID NO: 29 | QVQLVESGGGTVQPGGSLNLSCVASGNTFN |
| KERE FW1 sequence no. 8 | SEQ ID NO: 30 | EVQLVESGGGLAQPGGSLQLSCSAPGFTLD |
| KERE FW1 sequence no. 9 | SEQ ID NO: 31 | AQELEESGGGLVQAGGSLRLSCAASGRTFN | and in which:
iii) FR2 is an amino acid sequence that has at least 80% amino acid identity with at least one of the following amino acid sequences:

TABLE A-11

Representative FW2 sequences for Nanobodies of the KERE-group.

| | | |
|---|---|---|
| KERE FW2 sequence no. 1 | SEQ ID NO: 41 | WFRQAPGKEREFVA |
| KERE FW2 sequence no. 2 | SEQ ID NO: 42 | WFRQTPGREREFVA |
| KERE FW2 sequence no. 3 | SEQ ID NO: 43 | WYRQAPGKQREMVA |
| KERE FW2 sequence no. 4 | SEQ ID NO: 44 | WYRQGPGKQRELVA |
| KERE FW2 sequence no. 5 | SEQ ID NO: 45 | WIRQAPGKEREGVS |
| KERE FW2 sequence no. 6 | SEQ ID NO: 46 | WFREAPGKEREGIS |
| KERE FW2 sequence no. 7 | SEQ ID NO: 47 | WYRQAPGKERDLVA |
| KERE FW2 sequence no. 8 | SEQ ID NO: 48 | WFRQAPGKQREEVS |
| KERE FW2 sequence no. 9 | SEQ ID NO: 49 | WFRQPPGKVREFVG | and in which:
iv) FR3 is an amino acid sequence that has at least 80% amino acid identity with at least one of the following amino acid sequences:

TABLE A-12

Representative FW3 sequences for Nanobodies of the KERE-group.

| | | |
|---|---|---|
| KERE FW3 sequence no. 1 | SEQ ID NO: 50 | RFTISRDNAKNTVYLQMNSLKPEDTAVYRCYF |
| KERE FW3 sequence no. 2 | SEQ ID NO: 51 | RFAISRDNNKNTGYLQMNSLEPEDTAVYYCAA |
| KERE FW3 sequence no. 3 | SEQ ID NO: 52 | RFTVARNNAKNTVNLEMNSLKPEDTAVYYCAA |
| KERE FW3 sequence no. 4 | SEQ ID NO: 53 | RFTISRDIAKNTVDLLMNNLEPEDTAVYYCAA |
| KERE FW3 sequence no. 5 | SEQ ID NO: 54 | RLTISRDNAVDTMYLQMNSLKPEDTAVYYCAA |
| KERE FW3 sequence no. 6 | SEQ ID NO: 55 | RFTISRDNAKNTVYLQMDNVKPEDTAIYYCAA |
| KERE FW3 sequence no. 7 | SEQ ID NO: 56 | RFTISKDSGKNTVYLQMTSLKPEDTAVYYCAT |
| KERE FW3 sequence no. 8 | SEQ ID NO: 57 | RFTISRDSAKNMMYLQMNNLKPQDTAVYYCAA |
| KERE FW3 sequence no. 9 | SEQ ID NO: 58 | RFTISRENDKSTVYLQLNSLKPEDTAVYYCAA |
| KERE FW3 sequence no. 10 | SEQ ID NO: 59 | RFTISRDYAGNTAYLQMNSLKPEDTGVYYCAT | and in which:

v) FR4 is an amino acid sequence that has at least 80% amino acid identity with at least one of the following amino acid sequences:

TABLE A-13

Representative FW4 sequences for Nanobodies of the KERE-group.

| | | |
|---|---|---|
| KERE FW4 sequence no. 1 | SEQ ID NO: 60 | WGQGTQVTVSS |
| KERE FW4 sequence no. 2 | SEQ ID NO: 61 | WGKGTLVTVSS |
| KERE FW4 sequence no. 3 | SEQ ID NO: 62 | RGQGTRVTVSS |
| KERE FW4 sequence no. 4 | SEQ ID NO: 63 | WGLGTQVTISS | and in which:
vi) CDR1, CDR2 and CDR3 are as defined herein, and are preferably as defined according to one of the preferred aspects herein, and are more preferably as defined according to one of the more preferred aspects herein.

In the above Nanobodies, one or more of the further Hallmark residues are preferably as described herein (for example, when they are $V_{HH}$ sequences or partially humanized Nanobodies).

Also, the above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

With regard to framework 1, it will be clear to the skilled person that, when an amino acid sequence as outlined above is generated by expression of a nucleotide sequence, the first four amino acid sequences (i.e. amino acid residues 1-4 according to the Kabat numbering) may often be determined by the primer(s) that have been used to generate said nucleic acid. Thus, for determining the degree of amino acid identity, the first four amino acid residues are preferably disregarded.

Also, with regard to framework 1, and although amino acid positions 27 to 30 are according to the Kabat numbering considered to be part of the framework regions (and not the CDR's), it has been found by analysis of a database of more than 1000 $V_{HH}$ sequences that the positions 27 to 30 have a variability (expressed in terms of $V_{HH}$ entropy and $V_{HH}$ variability—see Tables A-5 to A-8) that is much greater than the variability on positions 1 to 26. Because of this, for determining the degree of amino acid identity, the amino acid residues at positions 27 to 30 are preferably also disregarded.

In view of this, a Nanobody of the KERE class may be an amino acid sequence that is comprised of four framework regions/sequences interrupted by three complementarity determining regions/sequences, in which:

i) the amino acid residue at position 45 according to the Kabat numbering is a charged amino acid (as defined herein) or a cysteine residue, and position 44 is preferably an E;

and in which:

ii) FR1 is an amino acid sequence that, on positions 5 to 26 of the Kabat numbering, has at least 80% amino acid identity with at least one of the following amino acid sequences:

TABLE A-14

Representative FW1 sequences (amino acid residues 5 to 26) for Nanobodies of the KERE-group.

| | | |
|---|---|---|
| KERE FW1 sequence no. 10 | SEQ ID NO: 32 | VESGGGLVQPGGSLRLSCAASG |
| KERE FW1 sequence no. 11 | SEQ ID NO: 33 | VDSGGGLVQAGDSLKLSCALTG |
| KERE FW1 sequence no. 12 | SEQ ID NO: 34 | VDSGGGLVQAGDSLRLSCAASG |
| KERE FW1 sequence no. 13 | SEQ ID NO: 35 | VDSGGGLVEAGGSLRLSCQVSE |
| KERE FW1 sequence no. 14 | SEQ ID NO: 36 | QDSGGGSVQAGGSLKLSCAASG |
| KERE FW1 sequence no. 15 | SEQ ID NO: 37 | VQSGGRLVQAGDSLRLSCAASE |
| KERE FW1 sequence no. 16 | SEQ ID NO. 38 | VESGGTLVQSGDSLKLSCASST |
| KERE FW1 sequence no. 17 | SEQ ID NO: 39 | MESGGDSVQSGGSLTLSCVASG |
| KERE FW1 sequence no. 18 | SEQ ID NO: 40 | QASGGGLVQAGGSLRLSCSASV | and in which:

iii) FR2, FR3 and FR4 are as mentioned herein for FR2, FR3 and FR4 of Nanobodies of the KERE-class;

and in which:

iv) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

A Nanobody of the GLEW class may be an amino acid sequence that is comprised of four framework regions/sequences interrupted by three complementarity determining regions/sequences, in which i) preferably, when the Nanobody of the GLEW-class is a non-humanized Nanobody, the amino acid residue in position 108 is Q;

ii) FR1 is an amino acid sequence that has at least 80% amino acid identity with at least one of the following amino acid sequences:

TABLE A-15

Representative FW1 sequences for Nanobodies of the GLEW-group.

| | | |
|---|---|---|
| GLEW FW1 sequence no. 1 | SEQ ID NO: 64 | QVQLVESGGGLVQPGGSLRLSCAASGFTFS |
| GLEW FW1 sequence no. 2 | SEQ ID NO: 65 | EVHLVESGGGLVRPGGSLRLSCAAFGFIFK |
| GLEW FW1 sequence no. 3 | SEQ ID NO: 66 | QVKLEESGGGLAQPGGSLRLSCVASGFTFS |

TABLE A-15-continued

Representative FW1 sequences for Nanobodies of the GLEW-group.

| | | |
|---|---|---|
| GLEW FW1 sequence no. 4 | SEQ ID NO: 67 | EVOLVESGGGLVQPGGSLRLSCVCVSSGCT |
| GLEW FW1 sequence no. 5 | SEQ ID NO: 68 | EVQLVESGGGLALPGGSLTLSCVFSGSTFS | and in which:

iii) FR2 is an amino acid sequence that has at least 80% amino acid identity with at least one of the following amino acid sequences:

TABLE A-16

Representative FW2 sequences for Nanobodies of the GLEW-group.

| | | |
|---|---|---|
| GLEW FW2 sequence no. 1 | SEQ ID NO: 72 | WVRQAPGKAEEWVS |
| GLEW FW2 sequence no. 2 | SEQ ID NO: 73 | WVRRPPGKGLEWVS |
| GLEW FW2 sequence no. 3 | SEQ ID NO: 74 | WVRQAPGMGLEWVS |

TABLE A-16-continued

Representative FW2 sequences for Nanobodies of the GLEW-group.

| | | |
|---|---|---|
| GLEW FW2 sequence no. 4 | SEQ ID NO: 75 | WVRQAPGKEPEWVS |
| GLEW FW2 sequence no. 5 | SEQ ID NO: 76 | WVRQAPGKDQEWVS |
| GLEW FW2 sequence no. 6 | SEQ ID NO: 77 | WVRQAPGKAEEWVS |
| GLEW FW2 sequence no. 7 | SEQ ID NO: 78 | WVRQAPGKGLEWVA |
| GLEW FW2 sequence no. 8 | SEQ ID NO: 79 | WVRQAPGRATEWVS | and in which:

iv) FR3 is an amino acid sequence that has at least 80% amino acid identity with at least one of the following amino acid sequences:

TABLE A-17

Representative FW3 sequences for Nanobodies of the GLEW-group.

| | | |
|---|---|---|
| GLEW FW3 sequence no. 1 | SEQ ID NO: 80 | RFTISRDNAKNTLYLQMNSLKPEDTAVYYCVK |
| GLEW FW3 sequence no. 2 | SEQ ID NO: 81 | RFTISRDNARNTLYLQMDSLIPEDTALYYCAR |
| GLEW FW3 sequence no. 3 | SEQ ID NO: 82 | RFTSSRDNAKSTLYLQMNDLKPEDTALYYCAR |
| GLEW FW3 sequence no. 4 | SEQ ID NO: 83 | RFIISRDNAKNTLYLQMNSLGPEDTAMYYCQR |
| GLEW FW3 sequence no. 5 | SEQ ID NO: 84 | RFTASRDNAKNTLYLQMNSLKSEDTARYYCAR |
| GLEW FW3 sequence no. 6 | SEQ ID NO: 85 | RFTISRDNAKNTLYLQMDDLQSEDTAMYYCGR | and in which:
v) FR4 is an amino acid sequence that has at least 80% amino acid identity with at least one of the following amino acid sequences:

TABLE A-18

Representative FW4 sequences for Nanobodies of the GLEW-group.

| | | |
|---|---|---|
| GLEW FW4 sequence no. 1 | SEQ ID NO: 86 | GSQGTQVTVSS |
| GLEW FW4 sequence no. 2 | SEQ ID NO: 87 | LRGGTQVTVSS |
| GLEW FW4 sequence no. 3 | SEQ ID NO: 88 | RGQGTLVTVSS |
| GLEW FW4 sequence no. 4 | SEQ ID NO: 89 | RSRGIQVTVSS |
| GLEW FW4 sequence no. 5 | SEQ ID NO: 90 | WGKGTQVTVSS |
| GLEW FW4 sequence no. 6 | SEQ ID NO: 91 | WGQGTQVTVSS | and in which:
vi) CDR1, CDR2 and CDR3 are as defined herein, and are preferably as defined according to one of the preferred aspects herein, and are more preferably as defined according to one of the more preferred aspects herein.

In the above Nanobodies, one or more of the further Hallmark residues are preferably as described herein (for example, when they are $V_{HH}$ sequences or partially humanized Nanobodies).

With regard to framework 1, it will again be clear to the skilled person that, for determining the degree of amino acid identity, the amino acid residues on positions 1 to 4 and 27 to 30 are preferably disregarded.

In view of this, a Nanobody of the GLEW class may be an amino acid sequence that is comprised of four framework regions/sequences interrupted by three complementarity determining regions/sequences, in which:
i) preferably, when the Nanobody of the GLEW-class is a non-humanized Nanobody, the amino acid residue in position. 108 is Q;
and in which:
ii) FR1 is an amino acid sequence that, on positions 5 to 26 of the Kabat numbering, has at least 80% amino acid identity with at least one of the following amino acid sequences:

and in which:

iii) FR2, FR3 and FR4 are as mentioned herein for FR2, FR3 and FR4 of Nanobodies of the GLEW-class;
and in which:

iv) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein. In the above Nanobodies, one or more of the further Hallmark residues are preferably as described herein (for example, when they are $V_{HH}$ sequences or partially humanized Nanobodies).

A Nanobody of the P, R, S 103 class may be an amino acid sequence that is comprised of four framework regions/sequences interrupted by three complementarity determining regions/sequences, in which i) the amino acid residue at position 103 according to the Kabat numbering is different from W;
and in which:

ii) preferably the amino acid residue at position 103 according to the Kabat numbering is P, R or S, and more preferably R;

and in which:

iii) FR1 is an amino acid sequence that has at least 80% amino acid identity with at least one of the following amino acid sequences:

TABLE A-19

Representative FW1 sequences (amino acid residues 5 to 26) for Nanobodies of the KERE-group.

| | | |
|---|---|---|
| GLEW FW1 sequence no. 6 | SEQ ID NO: 69 | VESGGGLVQPGGSLRLSCAASG |
| GLEW FW1 sequence no. 7 | SEQ ID NO: 70 | EESGGGLAQPGGSLRLSCVASG |
| GLEW FW1 sequence no. 8 | SEQ ID NO: 71 | VESGGGLALPGGSLTLSCVFSG |

TABLE A-20

Representative FW1 sequences for Nanobodies of the P, R, S 103-group.

| | | |
|---|---|---|
| P, R, S 103 FW1 sequence no. 1 | SEQ ID NO: 92 | AVQLVESGGGLVQAGGSLRLSCAASGRTFS |
| P, R, S 103 FW1 sequence no. 2 | SEQ ID NO: 93 | QVQLQESGGGMVQPGGSLRLSCAASGFDFG |
| P, R, S 103 FW1 sequence no. 3 | SEQ ID NO: 94 | EVHLVESGGGLVRPGGSLRLSCAAFGFIFK |
| P, R, S 103 FW1 sequence no. 4 | SEQ ID NO: 95 | QVQLAESGGGLVQPGGSLKLSCAASRTIVS |
| P, R, S 103 FW1 sequence no. 5 | SEQ ID NO: 96 | QEHLVESGGGLVDIGGSLRLSCAASERIFS |
| P, R, S 103 FW1 sequence no. 6 | SEQ ID NO: 97 | QVKLEESGGGLAQPGGSLRLSCVASGFTFS |
| P, R, S 103 FW1 sequence no. 7 | SEQ ID NO: 98 | EVQLVESGGGLVQPGGSLRLSCVCVSSGCT |
| P, R, S 103 FW1 sequence no. 8 | SEQ ID NO: 99 | EVQLVESGGGLALPGGSLTLSCVFSGSTFS | and in which iv) FR2 is an amino acid sequence that has at least 80% amino acid identity with at least one of the following amino acid sequences:

TABLE A-21

Representative FW2 sequences for Nanobodies of the P, R, S 103-group.

| | | |
|---|---|---|
| P, R, S 103 FW2 sequence no. 1 | SEQ ID NO: 102 | WFRQAPGKEREFVA |
| P, R, S 103 FW2 sequence no. 2 | SEQ ID NO: 103 | WVRQAPGKVLEWVS |
| P, R, S 103 FW2 sequence no. 3 | SEQ ID NO: 104 | WVRRPPGKGLEWVS |
| P, R, S 103 FW2 sequence no. 4 | SEQ ID NO: 105 | WIRQAPGKEREGVS |
| P, R, S 103 FW2 sequence no. 5 | SEQ ID NO: 106 | WVRQYPGKEPEWVS |
| P, R, S 103 FW2 sequence no. 6 | SEQ ID NO: 107 | WFRQPPGKEHEFVA |
| P, R, S 103 FW2 sequence no. 7 | SEQ ID NO: 108 | WYRQAPGKRTELVA |
| P, R, S 103 FW2 sequence no. 8 | SEQ ID NO: 109 | WLRQAPGQGLEWVS |
| P, R, S 103 FW2 sequence no. 9 | SEQ ID NO: 110 | WLRQTPGKGLEWVG |
| P, R, S 103 FW2 sequence no. 10 | SEQ ID NO: 111 | WVRQAPGKAEEFVS | and in which:

v) FR3 is an amino acid sequence that has at least 80% amino acid identity with at least one of the following amino acid sequences:

TABLE A-22

Representative FW3 sequences for Nanobodies of the P, R, S 103-group.

| | | |
|---|---|---|
| P, R, S 103 FW3 sequence no. 1 | SEQ ID NO: 112 | RFTISRDNAKNTVYLQMNSLKPEDTAVYYCAA |
| P, R, S 103 FW3 sequence no. 2 | SEQ ID NO: 113 | RFTISRDNARNTLYLQMDSLIPEDTALYYCAR |
| P, R, S 103 FW3 sequence no. 3 | SEQ ID NO: 114 | RFTISRDNAKNEMYLQMNNLKTEDTGVYWCGA |
| P, R, S 103 FW3 sequence no. 4 | SEQ ID NO: 115 | RFTISSDSNRNMIYLQMNNLKPEDTAVYYCAA |
| P, R, S 103 FW3 sequence no. 5 | SEQ ID NO: 116 | RFTISRDNAKNMLYLHLNNLKSEDTAVYYCRR |

TABLE A-22-continued

Representative FW3 sequences for Nanobodies of the P, R, S 103-group.

P, R, S 103 FW3 sequence no. 6    SEQ ID NO: 117    RFTISRDNAKKTVYLRLNSLNPEDTAVYSCNL P, R, S 103 FW3 sequence no. 7    SEQ ID NO: 118    RFKISRDNAKKTLYLQMNSLGPEDTAMYYCQR P, R, S 103 FW3 sequence no. 8    SEQ ID NO: 119    RFTVSRDNGKNTAYLRMNSLKPEDTADYYCAV and in which:
vi) FR4 is an amino acid sequence that has at least 80% amino acid identity with at least one of the following amino acid sequences:

TABLE A-23

Representative FW4 sequences for Nanobodies of the P, R, S 103-group.

| | | |
|---|---|---|
| P, R, S 103 FW4 sequence no. 1 | SEQ ID NO: 120 | RGQGTQVTVSS |
| P, R, S 103 FW4 sequence no. 2 | SEQ ID NO: 121 | LRGGTQVTVSS |
| P, R, S 103 FW4 sequence no. 3 | SEQ ID NO: 122 | GNKGTLVTVSS |
| P, R, S 103 FW4 sequence no. 4 | SEQ ID NO: 123 | SSPGTQVTVSS |
| P, R, S 103 FW4 sequence no. 5 | SEQ ID NO: 124 | SSQGTLVTVSS |
| P, R, S 103 FW4 sequence no. 6 | SEQ ID NO: 125 | RSRGIQVTVSS | and in which:
vii) CDR1, CDR2 and CDR3 are as defined herein, and are preferably as defined according to one of the preferred aspects herein, and are more preferably as defined according to one of the more preferred aspects herein.

In the above Nanobodies, one or more of the further Hallmark residues are preferably as described herein (for example, when they are $V_{HH}$ sequences or partially humanized Nanobodies).

With regard to framework 1, it will again be clear to the skilled person that, for determining the degree of amino acid identity, the amino acid residues on positions 1 to 4 and 27 to 30 are preferably disregarded.

In view of this, a Nanobody of the P,R,S 103 class may be an amino acid sequence that is comprised of four framework regions/sequences interrupted by three complementarity determining regions/sequences, in which:
i) the amino acid residue at position 103 according to the Kabat numbering is different from W;
and in which:
ii) preferably the amino acid residue at position 103 according to the Kabat numbering is P, R or S, and more preferably R;
and in which:
iii) FR1 is an amino acid sequence that, on positions 5 to 26 of the Kabat numbering, has at least 80% amino acid identity with at least one of the following amino acid sequences:

TABLE A-24

Representative FW1 sequences (amino acid residues 5 to 26) for Nanobodies of the P, R, S 103-group.

| | | |
|---|---|---|
| P, R, S 103 FW1 sequence no. 9 | SEQ ID NO: 100 | VESGGGLVQAGGSLRLSCAASG |
| P, R, S 103 FW1 sequence no. 10 | SEQ ID NO: 101 | AESGGGLVQPGGSLKLSCAASR | and in which:
iv) FR2, FR3 and FR4 are as mentioned herein for FR2, FR3 and FR4 of Nanobodies of the P,R,S 103 class;
and in which:
v) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

In the above Nanobodies, one or more of the further Hallmark residues are preferably as described herein (for example, when they are $V_{HH}$ sequences or partially humanized Nanobodies).

In another preferred, but non-limiting aspect, the invention relates to a Nanobody as described above, in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 455 to 501, more preferably 455 to 457, 459, 460, 464 to 469. This degree of amino acid identity can for example be determined by determining the degree of amino acid identity (in a manner described herein) between said Nanobody and one or more of the sequences of SEQ ID NO's: 455 to 501, more preferably 455 to 457, 459, 460, 464 to 469, in which the amino acid residues that form the framework regions are disregarded. Such Nanobodies can be as further described herein.

As already mentioned herein, another preferred but non-limiting aspect of the invention relates to a Nanobody with an amino acid sequence that is chosen from the group consisting of SEQ ID NO's: 455 to 501, more preferably 455 to 457, 459, 460, 464 to 469 or from the group consisting of from amino acid sequences that have more than 80%, preferably more than 90%, more preferably more than 95%, such as 99% or more sequence identity (as defined herein) with at least one of the amino acid sequences of SEQ ID NO's: 455 to 501, more preferably 455 to 457, 459, 460, 464 to 469.

Also, in the above Nanobodies:
i) any amino acid substitution (when it is not a humanizing substitution as defined herein) is preferably, and compared to the corresponding amino acid sequence of SEQ ID NO's: 455 to 501, more preferably 455 to 457, 459, 460, 464 to 469, a conservative amino acid substitution, (as defined herein);
and/or:
ii) its amino acid sequence preferably contains either only amino acid substitutions, or otherwise preferably no more than 5, preferably no more than 3, and more preferably only 1 or 2 amino acid deletions or insertions, compared to the corresponding amino acid sequence of SEQ ID NO's: 455 to 501, more preferably 455 to 457, 459, 460, 464 to 469;
and/or
iii) the CDR's may be CDR's that are derived by means of affinity maturation, for example starting from the CDR's of to the corresponding amino acid sequence of SEQ ID NO's: 455 to 501, more preferably 455 to 457, 459, 460, 464 to 469.

Preferably, the CDR sequences and FR sequences in the Nanobodies of the invention are such that the Nanobodies of the invention (and polypeptides of the invention comprising the same):
bind to Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);
and/or such that they:
bind to Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 with a $k_{on}$-rate of between $10^2$ $M^{-1}s^{-1}$ to about $10^7 M^{-1}s^{-1}$, preferably between $10^3$ $M^{-1}s^{-1}$ and $10^7 M^{-1}s^{-1}$, more preferably between $10^4$ $M^{-1}s^{-1}$ and $10^7 M^{-1}s^{-1}$, such as between $10^5 M^{-1}s^{-1}$ and $10^7 M^{-1}s^{-1}$;
and/or such that they:
bind to Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 with a $k_{off}$ rate between $1s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Preferably, CDR sequences and FR sequences present in the Nanobodies of the invention are such that the Nanobodies of the invention will bind to Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 with an affinity less than 500 nM, preferably less than 200 nM, more preferably less than 10 nM, such as less than 500 pM.

According to one non-limiting aspect of the invention, a Nanobody may be as defined herein, but with the proviso that it has at least "one amino acid difference" (as defined herein) in at least one of the framework regions compared to the corresponding framework region of a naturally occurring human $V_H$ domain, and in particular compared to the corresponding framework region of DP-47. More specifically, according to one non-limiting aspect of the invention, a Nanobody may be as defined herein, but with the proviso that it has at least "one amino acid difference" (as defined herein) at least one of the Hallmark residues (including those at positions 108, 103 and/or 45) compared to the corresponding framework region of a naturally occurring human $V_H$ domain, and in particular compared to the corresponding framework region of DP-47. Usually, a Nanobody will have at least one such amino acid difference with a naturally occurring $V_H$ domain in at least one of FR2 and/or FR4, and in particular at least one of the Hallmark residues in FR2 and/or FR4 (again, including those at positions 108, 103 and/or 45).

Also, a humanized Nanobody of the invention may be as defined herein, but with the proviso that it has at least "one amino acid difference" (as defined herein) in at least one of the framework regions compared to the corresponding framework region of a naturally occurring $V_{HH}$ domain. More specifically, according to one non-limiting aspect of the invention, a humanized Nanobody may be as defined herein, but with the proviso that it has at least "one amino acid difference" (as defined herein) at least one of the Hallmark residues (including those at positions 108, 103 and/or 45) compared to the corresponding framework region of a naturally occurring $V_{HH}$ domain. Usually, a humanized Nanobody will have at least one such amino acid difference with a naturally occurring $V_{HH}$ domain in at least one of FR2 and/or FR4, and in particular at least one of the Hallmark residues in FR2 and/or FR4 (again, including those at positions 108, 103 and/or 45).

As will be clear from the disclosure herein, it is also within the scope of the invention to use natural or synthetic analogs, mutants, variants, alleles, homologs and orthologs (herein collectively referred to as "analogs") of the Nanobodies of the invention as defined herein, and in particular analogs of the Nanobodies of SEQ ID NO's 455 to 501, more preferably 455 to 457, 459, 460, 464 to 469. Thus, according to one aspect of the invention, the term "Nanobody of the invention" in its broadest sense also covers such analogs.

Generally, in such analogs, one or more amino acid residues may have been replaced, deleted and/or added, compared to the Nanobodies of the invention as defined herein. Such substitutions, insertions or deletions may be made in one or more of the framework regions and/or in one or more of the CDR's. When such substitutions, insertions or deletions are made in one or more of the framework regions, they may be made at one or more of the Hallmark residues and/or at one or more of the other positions in the framework residues, although substitutions, insertions or deletions at the Hallmark residues are generally less preferred (unless these are suitable humanizing substitutions as described herein).

By means of non-limiting examples, a substitution may for example be a conservative substitution (as described herein) and/or an amino acid residue may be replaced by another amino acid residue that naturally occurs at the same position in another $V_{HH}$ domain (see Tables A-5 to A-8 for some non-limiting examples of such substitutions), although the invention is generally not limited thereto. Thus, any one or more substitutions, deletions or insertions, or any combination thereof, that either improve the properties of the Nanobody of the invention or that at least do not detract too much from the desired properties or from the balance or combination of desired properties of the Nanobody of the invention (i.e. to the extent that the Nanobody is no longer suited for its intended use) are included within the scope of the invention.

A skilled person will generally be able to determine and select suitable substitutions, deletions or insertions, or suitable combinations of thereof, based on the disclosure herein and optionally after a limited degree of routine experimentation, which may for example involve introducing a limited number of possible substitutions and determining their influence on the properties of the Nanobodies thus obtained.

For example, and depending on the host organism used to express the Nanobody or polypeptide of the invention, such deletions and/or substitutions may be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example to allow site-specific pegylation (again as described herein).

As can be seen from the data on the $V_{HH}$ entropy and $V_{HH}$ variability given in Tables A-5 to A-8 above, some amino acid residues in the framework regions are more conserved than others. Generally, although, the invention in its broadest sense is not limited thereto, any substitutions, deletions or insertions are preferably made at positions that are less conserved. Also, generally, amino acid substitutions are preferred over amino acid deletions or insertions.

The analogs are preferably such that they can bind to Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the Nanobodies of the invention.

The analogs are preferably also such that they retain the favourable properties the Nanobodies, as described herein.

Also, according to one preferred aspect, the analogs have a degree of sequence identity of at least 70%, preferably at least 80%, more preferably at least 90%, such as at least 95% or 99% or more; and/or preferably have at most 20, preferably at most 10, even more preferably at most 5, such as 4, 3, 2 or only 1 amino acid difference (as defined herein), with one of the Nanobodies of SEQ ID NOs: 455 to 501, more preferably 455 to 457, 459, 460, 464 to 469.

Also, the framework sequences and CDR's of the analogs are preferably such that they are in accordance with the preferred aspects defined herein. More generally, as described herein, the analogs will have (a) a Q at position 108; and/or (b) a charged amino acid or a cysteine residue at position 45 and preferably an E at position 44, and more preferably E at position 44 and R at position 45; and/or (c) P, R or S at position 103.

One preferred class of analogs of the Nanobodies of the invention comprise Nanobodies that have been humanized (i.e. compared to the sequence of a naturally occurring Nanobody of the invention). As mentioned in the background art cited herein, such humanization generally involves replacing one or more amino acid residues in the sequence of a naturally occurring $V_{HH}$ with the amino acid residues that occur at the same position in a human $V_H$ domain, such as a human $V_H3$ domain. Examples of possible humanizing substitutions or combinations of humanizing substitutions will be clear to the skilled person, for example from the Tables herein, from the possible humanizing substitutions mentioned in the background art cited herein, and/or from a comparison between the sequence of a Nanobody and the sequence of a naturally occurring human $V_H$ domain.

The humanizing substitutions should be chosen such that the resulting humanized Nanobodies still retain the favourable properties of Nanobodies as defined herein, and more preferably such that they are as described for analogs in the preceding paragraphs. A skilled person will generally be able to determine and select suitable humanizing substitutions or suitable combinations of humanizing substitutions, based on the disclosure herein and optionally after a limited degree of routine experimentation, which may for example involve introducing a limited number of possible humanizing substitutions and determining their influence on the properties of the Nanobodies thus obtained.

Generally, as a result of humanization, the Nanobodies of the invention may become more "human-like", while still retaining the favourable properties of the Nanobodies of the invention as described herein. As a result, such humanized Nanobodies may have several advantages, such as a reduced immunogenicity, compared to the corresponding naturally occurring $V_{HH}$ domains. Again, based on the disclosure herein and optionally after a limited degree of routine experimentation, the skilled person will be able to select humanizing substitutions or suitable combinations of humanizing substitutions which optimize or achieve a desired or suitable balance between the favourable properties provided by the humanizing substitutions on the one hand and the favourable properties of naturally occurring $V_{HH}$ domains on the other hand.

The Nanobodies of the invention may be suitably humanized at any framework residue(s), such as at one or more Hallmark residues (as defined herein) or at one or more other framework residues (i.e. non-Hallmark residues) or any suitable combination thereof. One preferred humanizing substitution for Nanobodies of the "P,R,S-103 group" or the "KERE group" is Q108 into L108. Nanobodies of the "GLEW class" may also be humanized by a Q108 into L108 substitution, provided at least one of the other Hallmark residues contains a *Camelid* (camelizing) substitution (as defined herein). For example, as mentioned above, one particularly preferred class of humanized Nanobodies has GLEW or a GLEW-like sequence at positions 44-47; P, R or S (and in particular R) at position 103, and an L at position 108.

The humanized and other analogs, and nucleic acid sequences encoding the same, can be provided in any manner known per se. For example, the analogs can be obtained by providing a nucleic acid that encodes a naturally occurring $V_{HH}$ domain, changing the codons for the one or more amino acid residues that are to be substituted into the codons for the corresponding desired amino acid residues (e.g. by site-directed mutagenesis or by PCR using suitable mismatch primers), expressing the nucleic acid/nucleotide sequence thus obtained in a suitable host or expression system; and optionally isolating and/or purifying the analog thus obtained to provide said analog in essentially isolated form (e.g. as further described herein). This can generally be performed using methods and techniques known per se, which will be clear to the skilled person, for example from the handbooks and references cited herein, the background art cited herein and/or from the further description herein. Alternatively, a nucleic acid encoding the desired analog can be synthesized in a manner known per se (for example using an automated apparatus for synthesizing nucleic acid sequences with a predefined amino acid sequence) and can then be expressed as described herein. Yet another technique may involve combining one or more naturally occurring and/or synthetic nucleic acid sequences each encoding a part of the desired analog, and then expressing the combined nucleic acid sequence as described herein. Also, the analogs can be provided using chemical synthesis of the pertinent amino acid sequence using techniques for peptide synthesis known per se, such as those mentioned herein.

In this respect, it will be also be clear to the skilled person that the Nanobodies of the invention (including their analogs) can be designed and/or prepared starting from human $V_H$ sequences (i.e. amino acid sequences or the corresponding nucleotide sequences), such as for example from human $V_H3$ sequences such as DP-47, DP-51 or DP-29, i.e. by introducing one or more camelizing substitutions (i.e. changing one or more amino acid residues in the amino acid sequence of said human $V_H$ domain into the amino acid residues that occur at the corresponding position in a $V_{HH}$ domain), so as to provide the sequence of a Nanobody of the invention and/or so as to confer the favourable properties of a Nanobody to the sequence thus obtained. Again, this can generally be performed using the various methods and techniques referred to in the previous paragraph, using an amino acid sequence and/or nucleotide sequence for a human $V_H$ domain as a starting point.

Some preferred, but non-limiting camelizing substitutions can be derived from Tables A-5-A-8. It will also be clear that camelizing substitutions at one or more of the Hallmark residues will generally have a greater influence on the desired properties than substitutions at one or more of the other amino acid positions, although both and any suitable combination thereof are included within the scope of the invention. For example, it is possible to introduce one or more camelizing substitutions that already confer at least some the desired properties, and then to introduce further camelizing substitutions that either further improve said properties and/or confer additional favourable properties. Again, the skilled person will generally be able to determine and select suitable camelizing substitutions or suitable combinations of camelizing substitutions, based on the disclosure herein and optionally after a limited degree of routine experimentation, which may for example involve introducing a limited number of possible camelizing substitutions and determining whether the favourable properties of Nanobodies are obtained or improved (i.e. compared to the original Y domain). Generally, however, such camelizing substitutions are preferably such that the resulting an amino acid sequence at least contains (a) a Q at position 108; and/or (b) a charged amino acid or a cysteine residue at position 45 and preferably also an E at position 44, and more preferably E at position 44 and R at position 45; and/or (c) P, R or S at position 103; and optionally one or more further camelizing substitutions. More preferably, the camelizing substitutions are such that they result in a Nanobody of the invention and/or in an analog thereof (as defined herein), such as in a humanized analog and/or preferably in an analog that is as defined in the preceding paragraphs.

As will also be clear from the disclosure herein, it is also within the scope of the invention to use parts or fragments, or combinations of two or more parts or fragments, of the Nanobodies of the invention as defined herein, and in particular parts or fragments of the Nanobodies of SEQ ID NQ's: 455 to 501, more preferably 455 to 457, 459, 460, 464 to 469. Thus, according to one aspect of the invention, the term "Nanobody of the invention" in its broadest sense also covers such parts or fragments.

Generally, such parts or fragments of the Nanobodies of the invention (including analogs thereof) have amino acid sequences in which, compared to the amino acid sequence of the corresponding full length Nanobody of the invention (or analog thereof), one or more of the amino acid residues at the N-terminal end, one or more amino acid residues at the C-terminal end, one or more contiguous internal amino acid residues, or any combination thereof, have been deleted and/or removed.

The parts or fragments are preferably such that they can bind to Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the Nanobodies of the invention.

Any part or fragment is preferably such that it comprises at least 10 contiguous amino acid residues, preferably at least 20 contiguous amino acid residues, more preferably at least 30 contiguous amino acid residues, such as at least 40 contiguous amino acid residues, of the amino acid sequence of the corresponding full length Nanobody of the invention.

Also, any part or fragment is such preferably that it comprises at least one of CDR1, CDR2 and/or CDR3 or at least part thereof (and in particular at least CDR3 or at least part thereof). More preferably, any part or fragment is such that it comprises at least one of the CDR's (and preferably at least CDR3 or part thereof) and at least one other CDR (i.e. CDR1 or CDR2) or at least part thereof, preferably connected by suitable framework sequence(s) or at least part thereof. More preferably, any part or fragment is such that it comprises at least one of the CDR's (and preferably at least CDR3 or part thereof) and at least part of the two remaining CDR's, again preferably connected by suitable framework sequence(s) or at least part thereof.

According to another particularly preferred, but non-limiting aspect, such a part or fragment comprises at least CDR3, such as FR3, CDR3 and FR4 of the corresponding full length Nanobody of the invention, i.e. as for example described in the International application WO 03/050531 (tasters et al.).

As already mentioned above, it is also possible to combine two or more of such parts or fragments (i.e. from the same or different Nanobodies of the invention), i.e. to provide an analog (as defined herein) and/or to provide further parts or fragments (as defined herein) of a Nanobody of the invention. It is for example also possible to combine one or more parts or fragments of a Nanobody of the invention with one or more parts or fragments of a human $V_H$ domain.

According to one preferred aspect, the parts or fragments have a degree of sequence identity of at least 50%, preferably at least 60%, more preferably at least 70%, even more preferably at least 80%, such as at least 90%, 95% or 99% or more with one of the Nanobodies of SEQ ID NOs 455 to 501, more preferably 455 to 457, 459, 460, 464 to 469.

The parts and fragments, and nucleic acid sequences encoding the same, can be provided and optionally combined in any manner known per se. For example, such parts or fragments can be obtained by inserting a stop codon in a nucleic acid that encodes a full-sized Nanobody of the invention, and then expressing the nucleic acid thus obtained in a manner known per se (e.g. as described herein). Alternatively, nucleic acids encoding such parts or fragments can be obtained by suitably restricting a nucleic acid that encodes a full-sized Nanobody of the invention or by synthesizing such a nucleic acid in a manner known per se. Parts or fragments may also be provided using techniques for peptide synthesis known per se.

The invention in its broadest sense also comprises derivatives of the Nanobodies of the invention. Such derivatives can generally be obtained by modification, and in particular by chemical and/or biological (e.g. enzymatic) modification, of the Nanobodies of the invention and/or of one or more of the amino acid residues that form the Nanobodies of the invention.

Examples of such modifications, as well as examples of amino acid residues within the Nanobody sequence that can be modified in such a manner (i.e. either on the protein backbone but preferably on a side chain), methods and techniques that can be used to introduce such modifications and the potential uses and advantages of such modifications will be clear to the skilled person.

For example, such a modification may involve the introduction (e.g. by covalent linking or in an other suitable manner) of one or more functional groups, residues or moieties into or onto the Nanobody of the invention, and in particular of one or more functional groups, residues or moieties that confer one or more desired properties or functionalities to the Nanobody of the invention. Example of such functional groups will be clear to the skilled person.

For example, such modification may comprise the introduction (e.g. by covalent binding or in any other suitable manner) of one or more functional groups that increase the half-life, the solubility and/or the absorption of the Nanobody of the invention, that reduce the immunogenicity and/or the toxicity of the Nanobody of the invention, that eliminate or attenuate any undesirable side effects of the Nanobody of the invention, and/or that confer other advantageous properties to and/or reduce the undesired properties of the Nanobodies and/or polypeptides of the invention; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and single domain antibodies), for which reference is for example made to Remington's Pharmaceutical Sciences, 16th ed., Mack Publishing Co., Easton, Pa. (1980). Such functional groups may for example be linked directly (for example covalently) to a Nanobody of the invention, or optionally via a suitable linker or spacer, as will again be clear to the skilled person.

One of the most widely used techniques for increasing the half-life and/or reducing the immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to for example Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO 04/060965. Various reagents for pegylation of proteins are also commercially available, for example from Nektar Therapeutics, USA.

Preferably, site-directed pegylation is used, in particular via a cysteine-residue (see for example Yang et al., Protein Engineering, 16, 10, 761-770 (2003). For example, for this purpose, PEG may be attached to a cysteine residue that naturally occurs in a Nanobody of the invention, a Nanobody of the invention may be modified so as to suitably introduce one or more cysteine residues for attachment of PEG, or an amino acid sequence comprising one or more cysteine residues for attachment of PEG may be fused to the N- and/or C-terminus of a Nanobody of the invention, all using techniques of protein engineering known per se to the skilled person.

Preferably, for the Nanobodies and proteins of the invention, a PEG is used with a molecular weight of more than 5000, such as more than 10,000 and less than 200,000, such as less than 100,000; for example in the range of 20,000-80,000.

Another, usually less preferred modification comprises N-linked or O-linked glycosylation, usually as part of co-translational and/or post-translational modification, depending on the host cell used for expressing the Nanobody or polypeptide of the invention.

Yet another modification may comprise the introduction of one or more detectable labels or other signal-generating groups or moieties, depending on the intended use of the labelled Nanobody. Suitable labels and techniques for attaching, using and detecting them will be clear to the skilled person, and for example include, but are not limited to, fluorescent labels (such as fluorescein, isothiocyanate, rhodamine, phycoerythrin, phycocyanin, allophycocyanin, o-phthaldehyde, and fluorescamine and fluorescent metals such as $^{152}$Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes (such as $^{3}$H, $^{125}$I, $^{32}$P, $^{35}$S, $^{14}$C, $^{51}$Cr, $^{36}$Cl, $^{57}$Co, $^{58}$Co, $^{59}$Fe, and $^{75}$Se), metals, metal chelates or metallic cations (for example metallic cations such as $^{99m}$Tc $^{123}$I, $^{111}$In, $^{131}$I, $^{97}$Ru, $^{67}$Cu, $^{67}$Ga, and $^{68}$Ga or other metals or metallic cations that are particularly suited for use in in vivo, in vitro or in situ diagnosis and imaging, such as ($^{157}$Gd, $^{55}$Mn, $^{162}$Dy, $^{52}$Cr, and $^{56}$Fe), as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels will be clear to the skilled person, and for example include moieties that can be detected using NMR or ESR spectroscopy.

Such labelled Nanobodies and polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylenediaminetetraacetic acid. (EDTA).

Yet another modification may comprise the introduction of a functional group that is one part of a specific binding pair, such as the biotin-(strept)avidin binding pair. Such a functional group may be used to link the Nanobody of the invention to another protein, polypeptide or chemical compound that is bound to the other half of the binding pair, i.e. through formation of the binding pair. For example, a Nanobody of the invention may be conjugated to biotin, and linked to another protein, polypeptide, compound or carrier conjugated to avidin or streptavidin. For example, such a conjugated Nanobody may be used as a reporter, for example in a diagnostic system where a detectable signal-producing agent is conjugated to avidin or streptavidin. Such binding pairs may for example also be used to bind the Nanobody of the invention to a carrier, including carriers suitable for pharmaceutical purposes. One non-limiting example are the liposomal formulations described by Cao and Suresh, Journal of Drug Targetting, 8, 4, 257 (2000). Such binding pairs may also be used to link a therapeutically active agent to the Nanobody of the invention.

For some applications, in particular for those applications in which it is intended to kill a cell that expresses the target against which the Nanobodies of the invention are directed (e.g. in the treatment of cancer), or to reduce or slow the growth and/or proliferation such a cell, the Nanobodies of the invention may also be linked to a toxin or to a toxic residue or moiety. Examples of toxic moieties, compounds or residues which can be linked to a Nanobody of the invention to provide—for example—a cytotoxic compound will be clear to the skilled person and can for example be found in the prior art cited above and/or in the further description herein. One example is the so-called ADEPT™ technology described in WO 03/055527.

Other potential chemical and enzymatic modifications will be clear to the skilled person. Such modifications may also be introduced for research purposes (e.g. to study function-activity relationships). Reference is for example made to Lundblad and Bradshaw, Biotechnol. Appl. Biochem., 26, 143-151 (1997).

Preferably, the derivatives are such that they bind to Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the Nanobodies of the invention.

As mentioned above, the invention also relates to proteins or polypeptides that essentially consist of or comprise at least one Nanobody of the invention. By "essentially consist of" is meant that the amino acid sequence of the polypeptide of the invention either is exactly the same as the amino acid sequence of a Nanobody of the invention or corresponds to the amino acid sequence of a Nanobody of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the amino acid sequence of the Nanobody.

Said amino acid residues may or may not change, alter or otherwise influence the (biological) properties of the Nanobody and may or may not add further functionality to the Nanobody. For example, such amino acid residues:

can comprise an N-terminal Met residue, for example as result of expression in a heterologous host cell or host organism.

may form a signal sequence or leader sequence that directs secretion of the Nanobody from a host cell upon synthesis. Suitable secretory leader peptides will be clear to the skilled person, and may be as further described herein. Usually, such a leader sequence will be linked to the N-terminus of the Nanobody, although the invention in its broadest sense is not limited thereto;

may form a sequence or signal that allows the Nanobody to be directed towards and/or to penetrate or enter into specific organs, tissues, cells, or parts or compartments of cells, and/or that allows the Nanobody to penetrate or cross a biological barrier such as a cell membrane, a cell layer such as a layer of epithelial cells, a tumour including solid tumours, or the blood-brain-barrier. Examples of such amino acid sequences will be clear to the skilled person. Some non-limiting examples are the small peptide vectors ("Pep-trans vectors") described in WO 03/026700 and in Temsamani et al., Expert Opin. Biol. Ther., 1, 773 (2001); Temsamani and Vidal, Drug Discov. Today, 9, 1012 (004) and Rousselle, J. Pharmacol. Exp. Ther., 296, 124-131 (2001), and the membrane translocator sequence described by Zhao et al., Apoptosis, 8, 631-637 (2003). C-terminal and N-terminal amino acid sequences for intracellular targeting of antibody fragments are for example described by Cardinale et al., Methods, 34, 171 (2004). Other suitable techniques for intracellular targeting involve the expression and/or use of so-called "intrabodies" comprising a Nanobody of the invention, as mentioned below;

may form a "tag", for example an amino acid sequence or residue that allows or facilitates the purification of the Nanobody, for example using affinity techniques directed against said sequence or residue. Thereafter, said sequence or residue may be removed (e.g. by chemical or enzymatical cleavage) to provide the Nanobody sequence (for this purpose, the tag may optionally be linked to the Nanobody sequence via a cleavable linker sequence or contain a cleavable motif). Some preferred, but non-limiting examples of such residues are multiple histidine residues, glutatione residues and a myc-tag (see for example SEQ ID NO:31 of WO 06/12282).

may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the Nanobodies of the invention.

According to another aspect, a polypeptide of the invention comprises a Nanobody of the invention, which is fused at its amino terminal end, at its carboxy terminal end, or both at its amino terminal end and at its carboxy terminal end to at least one further amino acid sequence, i.e. so as to provide a fusion protein comprising said Nanobody of the invention and the one or more further amino acid sequences. Such a fusion will also be referred to herein as a "Nanobody fusion".

The one or more further amino acid sequence may be any suitable and/or desired amino acid sequences. The further amino acid sequences may or may not change, alter or otherwise influence the (biological) properties of the Nanobody, and may or may not add further functionality to the Nanobody or the polypeptide of the invention. Preferably, the further amino acid sequence is such that it confers one or more desired properties or functionalities to the Nanobody or the polypeptide of the invention.

For example, the further amino acid sequence may also provide a second binding site, which binding site may be directed against any desired protein, polypeptide, antigen, antigenic determinant or epitope (including but not limited to the same protein, polypeptide, antigen, antigenic determinant or epitope against which the Nanobody of the invention is directed, or a different protein, polypeptide, antigen, antigenic determinant or epitope).

Example of such amino acid sequences will be clear to the skilled person, and may generally comprise all amino acid sequences that are used in peptide fusions based on conventional antibodies and fragments thereof (including but not limited to ScFv's and single domain antibodies). Reference is for example made to the review by Holliger and Hudson, Nature Biotechnology, 23, 9, 1126-1136 (2005).

For example, such an amino acid sequence may be an amino acid sequence that increases the half-life, the solubility, or the absorption, reduces the immunogenicity or the toxicity, eliminates or attenuates undesirable side effects, and/or confers other advantageous properties to and/or reduces the undesired properties of the polypeptides of the invention, compared to the Nanobody of the invention per se. Some non-limiting examples of such amino acid sequences are serum proteins, such as human serum albumin (see for example WO 00/27435) or haptenic molecules (for example haptens that are recognized by circulating antibodies, see for example WO 98/22141).

In particular, it has been described in the art that linking fragments of immunoglobulins (such as $V_H$ domains) to serum albumin or to fragments thereof can be used to increase the half-life. Reference is for made to WO 00/27435 and WO 01/077137). According to the invention, the Nanobody of the invention is preferably either directly linked to serum albumin (or to a suitable fragment thereof) or via a suitable linker, and in particular via a suitable peptide linked so that the polypeptide of the invention can be expressed as a genetic fusion (protein). According to one specific aspect, the Nanobody of the invention may be linked to a fragment of serum albumin that at least comprises the domain III of serum albumin or part thereof. Reference is for example made to the U.S. provisional application 60/788,256 of Ablynx N.V. entitled "Albumin derived amino acid sequence, use thereof for increasing the half-life of therapeutic proteins and of other therapeutic proteins and entities, and constructs comprising the same" filed on Mar. 31, 2006.

Alternatively, the further amino acid sequence may provide a second binding site or binding unit that is directed against a serum protein (such as, for example, human serum albumin or another serum protein such as IgG), so as to provide increased half-life in serum. Such amino acid sequences for example include the Nanobodies described below, as well as the small peptides and binding proteins described in WO 91/01743, WO 01/45746 and WO 02/076489 and the dAb's described in WO 03/002609 and WO 04/003019. Reference is also made to Harmsen et al., Vaccine, 23 (41); 4926-42, 2005, as well as to EP 0 368 684, as well as to the following the U.S. provisional applications 60/843,349, 60/850,774, 60/850,775 by Ablynx N.V. mentioned herein and US provisional application of Ablynx N.V. entitled "Peptides capable of binding to serum proteins" filed on Dec. 5, 2006 (also mentioned herein).

Such amino acid sequences may in particular be directed against serum albumin (and more in particular human serum albumin) and/or against IgG (and more in particular human IgG). For example, such amino acid sequences may be amino acid sequences that are directed against (human) serum albumin and amino acid sequences that can bind to amino acid residues on (human) serum albumin that are not involved in binding of serum albumin to FcRn (see for example WO 06/0122787) and/or amino acid sequences that are capable of binding to amino acid residues on serum albumin that do not form part of domain III of serum albumin (see again for example WO 06/0122787); amino acid sequences that have or can provide an increased half-life (see for example the U.S. provisional application 60/843,349 by Ablynx N.V. entitled "Serum albumin binding proteins with long half-lives" filed on Sep. 8, 2006); amino acid sequences against human serum albumin that are cross-reactive with serum albumin from at least one species of mammal, and in particular with at least one species of primate (such as, without limitation, monkeys from the genus *Macaca* (such as, and in particular, cynomologus monkeys (*Macaca fascicularis*) and/or rhesus monkeys (*Macaca mulatta*)) and baboon (*Papio ursinus*), reference is again made to the U.S. provisional application 60/843,349); amino acid sequences that can bind to serum albumin in a pH independent manner (see for example the U.S. provisional application 60/850,774 by Ablynx N.V. entitled "Amino acid sequences that bind to serum proteins in a manner that is essentially independent of the pH, compounds comprising the same, and uses thereof", filed on Oct. 11, 2006) and/or amino acid sequences that are conditional binders (see for example the U.S. provisional application 60/850,775 by Ablynx N.V. entitled "Amino acid sequences that bind to a desired molecule in a conditional manner", filed on Oct. 11, 2006).

According to another aspect, the one or more further amino acid sequences may comprise one or more parts, fragments or domains of conventional 4-chain antibodies (and in particular human antibodies) and/or of heavy chain antibodies. For example, although usually less preferred, a Nanobody of the invention may be linked to a conventional (preferably human) $V_H$ or $V_L$ domain or to a natural or synthetic analog of a $V_H$ or $V_L$ domain, again optionally via a linker sequence (including but not limited to other (single) domain antibodies, such as the dAb's described by Ward et al.).

The at least one Nanobody may also be linked to one or more (preferably human) $C_H1$ $C_H2$ and/or $C_H3$ domains, optionally via a linker sequence. For instance, a Nanobody linked to a suitable $C_H1$ domain could for example be used—together with suitable light chains—to generate antibody fragments/structures analogous to conventional Fab fragments or $F(ab')_2$ fragments, but in which one or (in case of an $F(ab')_2$ fragment) one or both of the conventional $V_H$ domains have been replaced by a Nanobody of the invention. Also, two Nanobodies could be linked to a $C_H3$ domain (optionally via a linker) to provide a construct with increased half-life in vivo.

According to one specific aspect of a polypeptide of the invention, one or more Nanobodies of the invention may be linked to one or more antibody parts, fragments or domains that confer one or more effector functions to the polypeptide of the invention and/or may confer the ability to bind to one or more Fc receptors. For example, for this purpose, and without being limited thereto, the one or more further amino acid sequences may comprise one or more $C_H2$ and/or $C_H3$ domains of an antibody, such as from a heavy chain antibody (as described herein) and more preferably from a conventional human 4-chain antibody; and/or may form (part of) and Fc region, for example from IgG, from IgE or from another human Ig. For example, WO 94/04678 describes heavy chain antibodies comprising a Camelid $V_{HH}$ domain or a humanized derivative thereof (i.e. a Nanobody), in which the Camelidae $C_H2$ and/or $C_H3$ domain have been replaced by human $C_H2$ and $C_H3$ domains, so as to provide an immunoglobulin that consists of 2 heavy chains each comprising a Nanobody and human $C_H2$ and $C_H3$ domains (but no $C_H1$ domain), which immunoglobulin has the effector function provided by the $C_H2$ and $C_H3$ domains and which immunoglobulin can function without the presence of any light chains. Other amino acid sequences that can be suitably linked to the Nanobodies of the invention so as to provide an effector function will be clear to the skilled person, and may be chosen on the basis of the desired effector function(s). Reference is for example made to WO 04/058820, WO 99/42077 and WO 05/017148, as well as the review by Holliger and Hudson, supra. Coupling of a Nanobody of the invention to an Fc portion may also lead to an increased half-life, compared to the corresponding Nanobody of the invention. For some applications, the use of an Fc portion and/or of constant domains (i.e. $C_H2$ and/or $C_H3$ domains) that confer increased half-life without any biologically significant effector function may also be suitable or even preferred. Other suitable constructs comprising one or more Nanobodies and one or more constant domains with increased half-life in vivo will be clear to the skilled person, and may for example comprise two Nanobodies linked to a $C_H3$ domain, optionally via a linker sequence. Generally, any fusion protein or derivatives with increased half-life will preferably have a molecular weight of more than 50 kD, the cut-off value for renal absorption.

The further amino acid sequences may also folio a signal sequence or leader sequence that directs secretion of the Nanobody or the polypeptide of the invention from a host cell upon synthesis (for example to provide a pre-, pro- or prepro-form of the polypeptide of the invention, depending on the host cell used to express the polypeptide of the invention).

The further amino acid sequence may also form a sequence or signal that allows the Nanobody or polypeptide of the invention to be directed towards and/or to penetrate or enter into specific organs, tissues, cells, or parts or compartments of cells, and/or that allows the Nanobody or polypeptide of the invention to penetrate or cross a biological barrier such as a cell membrane, a cell layer such as a layer of epithelial cells, a tumor including solid tumours, or the blood-brain-barrier. Suitable examples of such amino acid sequences will be clear to the skilled person, and for example include, but are not limited to, the "Peptrans" vectors mentioned above, the sequences described by Cardinale et al. and the amino acid sequences and antibody fragments known per se that can be used to express or produce the Nanobodies and polypeptides of the invention as so-called "intrabodies", for example as described in WO 94/02610, WO 95/22618, U.S. Pat. No. 7,004,940, WO 03/014960, WO 99/07414; WO 05/01690; EP 1 512 696; and in Cattaneo, A. & Biocca, S. (1997) Intracellular Antibodies: Development and Applications. Landes and Springer-Verlag; and in Kontermann, Methods 34, (2004), 163-170, and the further references described therein.

For some applications, in particular for those applications in which it is intended to kill a cell that expresses the target against which the Nanobodies of the invention are directed (e.g. in the treatment of cancer), or to reduce or slow the growth and/or proliferation of such a cell, the Nanobodies of the invention may also be linked to a (cyto)toxic protein or polypeptide. Examples of such toxic proteins and polypeptides which can be linked to a Nanobody of the invention to provide—for example—a cytotoxic polypeptide of the invention will be clear to the skilled person and can for example be found in the prior art cited above and/or in the further description herein. One example is the so-called ADEPT™ technology described in WO 03/055527.

According to one preferred, but non-limiting aspect, said one or more further amino acid sequences comprise at least one further Nanobody, so as to provide a polypeptide of the invention that comprises at least two, such as three, four, five or more Nanobodies, in which said Nanobodies may optionally be linked via one or more linker sequences (as defined herein). Polypeptides of the invention that comprise two or more Nanobodies, of which at least one is a Nanobody of the invention, will also be referred to herein as "multivalent" polypeptides of the invention, and the Nanobodies present in such polypeptides will also be referred to herein as being in a "multivalent format". For example a "bivalent" polypeptide of the invention comprises two Nanobodies, optionally linked via a linker sequence, whereas a "trivalent" polypeptide of the invention comprises three Nanobodies, optionally linked via two linker sequences; etc.; in which at least one of the Nanobodies present in the polypeptide, and up to all of the Nanobodies present in the polypeptide, is/are a Nanobody of the invention.

In a multivalent polypeptide of the invention, the two or more Nanobodies may be the same or different, and may be directed against the same antigen or antigenic determinant (for example against the same part(s) or epitope(s) or against different parts or epitopes) or may alternatively be directed against different antigens or antigenic determinants; or any suitable combination thereof. For example, a bivalent polypeptide of the invention may comprise (a) two identical Nanobodies; (b) a first Nanobody directed against a first antigenic determinant of a protein or antigen and a second Nanobody directed against the same antigenic determinant of said protein or antigen which is different from the first Nanobody; (c) a first Nanobody directed against a first antigenic determinant of a protein or antigen and a second Nanobody directed against another antigenic determinant of said protein or antigen; or (d) a first Nanobody directed against a first protein or antigen and a second Nanobody directed against a second protein or antigen (i.e. different from said first antigen). Similarly, a trivalent polypeptide of the invention may, for example and without being limited thereto. comprise (a) three identical Nanobodies; (b) two identical Nanobody against a first antigenic determinant of an antigen and a third Nanobody directed against a different antigenic determinant of the same antigen; (c) two identical Nanobody against a first antigenic determinant of an antigen and a third Nanobody directed against a second antigen different from said first antigen; (d) a first Nanobody directed against a first antigenic determinant of a first antigen, a second Nanobody directed against a second antigenic determinant of said first antigen and a third Nanobody directed against a second antigen different from said first antigen; or (e) a first Nanobody directed against a first antigen, a second Nanobody directed against a second antigen different from said first antigen, and a third Nanobody directed against a third antigen different from said first and second antigen.

Polypeptides of the invention that contain at least two Nanobodies, in which at least one Nanobody is directed against a first antigen (i.e. against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2,) and at least one Nanobody is directed against a second antigen (i.e. different from Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2,), will also be referred to as "multispecific" polypeptides of the invention, and the Nanobodies present in such polypeptides will also be referred to herein as being in a "multispecific format". Thus, for example, a "bispecific" polypeptide of the invention is a polypeptide that comprises at least one Nanobody directed against a first antigen (i.e. Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2,) and at least one further Nanobody directed against a second antigen (i.e. different from Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2,), whereas a "trispecific" polypeptide of the invention is a polypeptide that comprises at least one Nanobody directed against a first antigen (i.e. Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2,), at least one further Nanobody directed against a second antigen (i.e. different from Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2,) and at least one further Nanobody directed against a third antigen (i.e. different from both Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, and the second antigen); etc.

Accordingly, in its simplest form, a bispecific polypeptide of the invention is a bivalent polypeptide of the invention (as defined herein), comprising a first Nanobody directed against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, and a second Nanobody directed against a second antigen, in which said first and second Nanobody may optionally be linked via a linker sequence (as defined herein); whereas a trispecific polypeptide of the invention in its simplest form is a trivalent polypeptide of the invention (as defined herein), comprising a first Nanobody directed against Tie1, Tie2, Ang1, Ang2, Ang3, Ang4, Angptl1, Angptl2, Angptl3, Angptl4, Angptl5, or Angptl6, more preferably Tie2, Ang2, Ang3, Ang4, or Angptl4, more preferably Tie2 or Ang2, a second Nanobody directed against a second antigen and a third Nanobody directed against a third antigen, in which said first, second and third Nanobody may optionally be linked via one or more, and in particular one and more, in particular two, linker sequences.

However, as will be clear from the description hereinabove, the invention is not limited thereto, in the sense that a multispecific polypeptide of the invention may comprise at least one Nanobody against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, and any number of Nanobodies directed against one or more antigens different from Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2.

Furthermore, although it is encompassed within the scope of the invention that the specific order or arrangement of the various Nanobodies in the polypeptides of the invention may have some influence on the properties of the final polypeptide of the invention (including but not limited to the affinity, specificity or avidity for Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, or against the one or more other antigens), said order or arrangement is usually not critical and may be suitably chosen by the skilled person, optionally after some limited routine experiments based on the disclosure herein. Thus, when reference is made to a specific multivalent or multispecific polypeptide of the invention, it should be noted that this encompasses any order or arrangements of the relevant Nanobodies, unless explicitly indicated otherwise.

Finally, it is also within the scope of the invention that the polypeptides of the invention contain two or more Nanobodies and one or more further amino acid sequences (as mentioned herein).

For multivalent and multispecific polypeptides containing one or more $V_{HH}$ domains and their preparation, reference is also made to Conrath et al., J. Biol. Chem., Vol. 276, 10. 7346-7350, 2001; Muyldermans, Reviews in Molecular Biotechnology 74 (2001), 277-302; as well as to for example WO 96/34103 and WO 99/23221. Some other examples of some specific multispecific and/or multivalent polypeptide of the invention can be found in the applications by Ablynx N.V. referred to herein.

One preferred, but non-limiting example of a multispecific polypeptide of the invention comprises at least one Nanobody of the invention and at least one Nanobody that provides for an increased half-life. Such Nanobodies may for example be Nanobodies that are directed against a serum protein, and in particular a human serum protein, such as human serum albumin, thyroxine-binding protein, (human) transferrin, fibrinogen, an immunoglobulin such as IgG, IgE or IgM, or against one of the serum proteins listed in WO 04/003019. Of these, Nanobodies that can bind to serum albumin (and in particular human serum albumin) or to IgG (and in particular human IgG, see for example Nanobody VH-1 described in the review by Muyldermans, supra) are particularly preferred (although for example, for experiments in mice or primates, Nanobodies against or cross-reactive with mouse serum albumin (MSA) or serum albumin from said primate, respectively, can be used. However, for pharmaceutical use, Nanobodies against human serum albumin or human IgG will usually be preferred). Nanobodies that provide for increased half-life and that can be used in the polypeptides of the invention include the Nanobodies directed against serum albumin that are described in WO 04/041865, in WO 06/122787 and in the further patent applications by Ablynx N.V., such as those mentioned above.

For example, the some preferred Nanobodies that provide for increased half-life for use in the present invention include Nanobodies that can bind to amino acid residues on (human) serum albumin that are not involved in binding of serum albumin to FcRn (see for example WO 06/0122787); Nanobodies that are capable of binding to amino acid residues on serum albumin that do not form part of domain III of serum albumin (see for example WO 06/0122787); Nanobodies that have or can provide an increased half-life (see for example the U.S. provisional application 60/843,349 by Ablynx N.V mentioned herein); Nanobodies against human serum albumin that are cross-reactive with serum albumin from at least one species of mammal, and in particular with at least one species of primate (such as, without limitation, monkeys from the genus *Macaca* (such as, and in particular, cynomologus monkeys (*Macaca fascicularis*) and/or rhesus monkeys (*Macaca mulatta*)) and baboon (*Papio ursinus*)) (see for example the U.S. provisional application 60/843,349 by Ablynx N.V); Nanobodies that can bind to serum albumin in a pH independent manner (see for example the U.S. provisional application 60/850,774 by Ablynx. N.V. mentioned herein) and/or Nanobodies that are conditional binders (see for example the U.S. provisional application 60/850,775 by Ablynx N.V.).

Some particularly preferred Nanobodies that provide for increased half-life and that can be used in the polypeptides of the invention include the Nanobodies ALB-1 to ALB-10 disclosed in WO 06/122787 (see Tables II and III) of which ALB-8 (SEQ ID NO: 62 in WO 06/122787) is particularly preferred.

Some preferred, but non-limiting examples of polypeptides of the invention that comprise at least one Nanobody of the invention and at least one Nanobody that provides for increased half-life.

According to a specific, but non-limiting aspect of the invention, the polypeptides of the invention contain, besides the one or more Nanobodies of the invention, at least one Nanobody against human serum albumin.

Generally, any polypeptides of the invention with increased half-life that contain one or more Nanobodies of the invention, and any derivatives of Nanobodies of the invention or of such polypeptides that have an increased half-life, preferably have a half-life that is at least 1.5 times, preferably at least 2 times, such as at least 5 times, for example at least 10 times or more than 20 times, greater than the half-life of the corresponding Nanobody of the invention per se. For example, such a derivative or polypeptides with increased half-life may have a half-life that is increased with more than 1 hours, preferably more than 2 hours, more preferably more than 6 hours, such as more than 12 hours, or even more than 24, 48 or 72 hours, compared to the corresponding Nanobody of the invention per se.

In a preferred, but non-limiting aspect of the invention, such derivatives or polypeptides may exhibit a serum half-life in human of at least about 12 hours, preferably at least 24 hours, more preferably at least 48 hours, even more preferably at least 72 hours or more. For example, such derivatives or polypeptides may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

According to one aspect of the invention the polypeptides are capable of binding to one or more molecules which can increase the half-life of the polypeptide in vivo.

The polypeptides of the invention are stabilised in vivo and their half-life increased by binding to molecules which resist degradation and/or clearance or sequestration. Typically, such molecules are naturally occurring proteins which themselves have a long half-life in vivo.

Another preferred, but non-limiting example of a multispecific polypeptide of the invention comprises at least one Nanobody of the invention and at least one Nanobody that directs the polypeptide of the invention towards, and/or that allows the polypeptide of the invention to penetrate or to enter into specific organs, tissues, cells, or parts or compartments of cells, and/or that allows the Nanobody to penetrate or cross a biological barrier such as a cell membrane, a cell layer such as a layer of epithelial cells, a tumor including solid tumours, or the blood-brain-barrier. Examples of such Nanobodies include Nanobodies that are directed towards specific cell-surface proteins, markers or epitopes of the desired organ, tissue or cell (for example cell-surface markers associated with tumor cells), and the single-domain brain targeting antibody fragments described in WO 02/057445 and WO 06/040153, of which FC44 (SEQ ID NO: 189 of WO 06/040153) and FC5 (SEQ ID NO: 190 of WO 06/040154) are preferred examples.

In the polypeptides of the invention, the one or more Nanobodies and the one or more polypeptides may be directly linked to each other (as for example described in WO 99/23221) and/or may be linked to each other via one or more suitable spacers or linkers, or any combination thereof.

Suitable spacers or linkers for use in multivalent and multispecific polypeptides will be clear to the skilled person, and may generally be any linker or spacer used in the art to link amino acid sequences. Preferably, said linker or spacer is suitable for use in constructing proteins or polypeptides that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, its should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each Nanobody by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_x ser_y)_z$, such as (for example $(gly_4 ser)_3$ or $(gly_3 ser_2)_3$, as described in WO 99/42077 and the GS30, GS15, GS9 and GS7 linkers described in the applications by Ablynx mentioned herein (see for example WO 06/040153 and WO 06/122825), as well as hinge-like regions, such as the hinge regions of naturally occurring heavy chain antibodies or similar sequences (such as described in WO 94/04678).

Some other particularly preferred linkers are poly-alanine (such as AAA), as well as the linkers GS30 (SEQ ID NO: 85 in WO 06/122825) and GS9 (SEQ ID NO: 84 in WO 06/122825).

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final polypeptide of the invention, including but not limited to the affinity, specificity or avidity for Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, or for one or more of the other antigens. Based on the disclosure herein, the skilled person will be able to determine the optimal linker(s) for use in a specific polypeptide of the invention, optionally after some limited routine experiments.

For example, in multivalent polypeptides of the invention that comprise Nanobodies directed against a multimeric antigen (such as a multimeric receptor or other protein), the length and flexibility of the linker are preferably such that it allows each Nanobody of the invention present in the polypeptide to bind to the antigenic determinant on each of the subunits of the multimer. Similarly, in a multispecific polypeptide of the invention that comprises Nanobodies directed against two or more different antigenic determinants on the same antigen (for example against different epitopes of an antigen and/or against different subunits of a multimeric receptor, channel or protein), the length and flexibility of the linker are preferably such that it allows each Nanobody to bind to its intended antigenic determinant. Again, based on the disclosure herein, the skilled person will be able to determine the optimal linker(s) for use in a specific polypeptide of the invention, optionally after some limited routine experiments.

It is also within the scope of the invention that the linker(s) used confer one or more other favourable properties or functionality to the polypeptides of the invention, and/or provide one or more sites for the formation of derivatives and/or for the attachment of functional groups (e.g. as described herein for the derivatives of the Nanobodies of the invention). For example, linkers containing one or more charged amino acid residues (see Table A-2 above) can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the polypeptides of the invention, these linkers may be the same or different. Again, based on the disclosure herein, the skilled person will be able to determine the optimal linkers for use in a specific polypeptide of the invention, optionally after some limited routine experiments.

Usually, for easy of expression and production, a polypeptide of the invention will be a linear polypeptide. However, the invention in its broadest sense is not limited thereto. For example, when a polypeptide of the invention comprises three of more Nanobodies, it is possible to link them by use of a linker with three or more "arms", which each "arm" being linked to a Nanobody, so as to provide a "star-shaped" construct. It is also possible, although usually less preferred, to use circular constructs.

The invention also comprises derivatives of the polypeptides of the invention, which may be essentially analogous to the derivatives of the Nanobodies of the invention, i.e. as described herein.

The invention also comprises proteins or polypeptides that "essentially consist" of a polypeptide of the invention (in which the wording "essentially consist of" has essentially the same meaning as indicated hereinabove).

According to one aspect of the invention, the polypeptide of the invention is in essentially isolated from, as defined herein.

The amino acid sequences, Nanobodies, polypeptides and nucleic acids of the invention can be prepared in a manner known per se, as will be clear to the skilled person from the further description herein. For example, the Nanobodies and polypeptides of the invention can be prepared in any manner known per se for the preparation of antibodies and in particular for the preparation of antibody fragments (including but not limited to (single) domain antibodies and ScFv fragments). Some preferred, but non-limiting methods for preparing the amino acid sequences, Nanobodies, polypeptides and nucleic acids include the methods and techniques described herein.

As will be clear to the skilled person, one particularly useful method for preparing an amino acid sequence, Nanobody and/or a polypeptide of the invention generally comprises the steps of:

i) the expression, in a suitable host cell or host organism (also referred to herein as a "host of the invention") or in another suitable expression system of a nucleic acid that encodes said amino acid sequence, Nanobody or polypeptide of the invention (also referred to herein as a "nucleic acid of the invention"), optionally followed by:

ii) isolating and/or purifying the amino acid sequence, Nanobody or polypeptide of the invention thus obtained.

In particular, such a method may comprise the steps of:

i) cultivating and/or maintaining a host of the invention under conditions that are such that said host of the invention expresses and/or produces at least one amino acid sequence, Nanobody and/or polypeptide of the invention; optionally followed by:

ii) isolating and/or purifying the amino acid sequence, Nanobody or polypeptide of the invention thus obtained.

A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one aspect of the invention, the nucleic acid of the invention is in essentially isolated from, as defined herein.

The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the amino acid sequences for the polypeptides of the invention given herein, and/or can be isolated from a suitable natural source. To provide analogs, nucleotide sequences encoding naturally occurring $V_{HH}$ domains can for example be subjected to site-directed mutagenesis, so at to provide a nucleic acid of the invention encoding said analog. Also, as will be clear to the skilled person, to prepare a nucleic acid of the invention, also several nucleotide sequences, such as at least one nucleotide sequence encoding a Nanobody and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences for two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers, using for example a sequence of a naturally occurring form of Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 as a template. These and other techniques will be clear to the skilled person, and reference is again made to the standard handbooks, such as Sambrook et al. and Ausubel et al., mentioned above, as well as the Examples below.

The nucleic acid of the invention may also be in the form of, be present in and/or be part of a genetic construct, as will be clear to the person skilled in the art. Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting aspect, a genetic construct of the invention comprises
i) at least one nucleic acid of the invention; operably connected to
ii) one or more regulatory elements, such as a promoter and optionally a suitable terminator;
and optionally also
iii) one or more further elements of genetic constructs known per se;
in which the terms "regulatory element", "promoter", "terminator" and "operably connected" have their usual meaning in the art (as further described herein); and in which said "further elements" present in the genetic constructs may for example be 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used, the intended host cell or host organism; the manner in which the nucleotide sequences of the invention of interest are to be expressed (e.g. via constitutive, transient or inducible expression); and/or the transformation technique to be used. For example, regulatory sequences, promoters and terminators known per se for the expression and production of antibodies and antibody fragments (including but not limited to (single) domain antibodies and ScFv fragments) may be used in an essentially analogous manner.

Preferably, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promotor). Generally, when two nucleotide sequences are operably linked, they will be in the same orientation and usually also in the same reading frame. They will usually also be essentially contiguous, although this may also not be required.

Preferably, the regulatory and further elements of the genetic constructs of the invention are such that they are capable of providing their intended biological function in the intended host cell or host organism.

For instance, a promoter, enhancer or terminator should be "operable" in the intended host cell or host organism, by which is meant that (for example) said promoter should be capable of initiating or otherwise controlling/regulating the transcription and/or the expression of a nucleotide sequence—e.g. a coding sequence—to which it is operably linked (as defined herein).

Some particularly preferred promoters include, but are not limited to, promoters known per se for the expression in the host cells mentioned herein; and in particular promoters for the expression in the bacterial cells, such as those mentioned herein and/or those used in the Examples.

A selection marker should be such that it allows—i.e. under appropriate selection conditions—host cells and/or host organisms that have been (successfully) transformed with the nucleotide sequence of the invention to be distinguished from host cells/organisms that have not been (successfully) transformed. Some preferred, but non-limiting examples of such markers are genes that provide resistance against antibiotics (such as kanamycin or ampicillin), genes that provide for temperature resistance, or genes that allow the host cell or host organism to be maintained in the absence of certain factors, compounds and/or (food) components in the medium that are essential, for survival of the non-transformed cells or organisms.

A leader sequence should be such that—in the intended host cell or host organism—it allows for the desired post-translational modifications and/or such that it directs the transcribed mRNA to a desired part or organelle of a cell. A leader sequence may also allow for secretion of the expression product from said cell. As such, the leader sequence may be any pro-, pre-, or prepro-sequence operable in the host cell or host organism. Leader sequences may not be required for expression in a bacterial cell. For example, leader sequences known per se for the expression and production of antibodies and antibody fragments (including but not limited to single domain antibodies and ScFv fragments) may be used in an essentially analogous manner.

An expression marker or reporter gene should be such that—in the host cell or host organism—it allows for detection of the expression of (a gene or nucleotide sequence present on) the genetic construct. An expression marker may optionally also allow for the localisation of the expressed product, e.g. in a specific part or organelle of a cell and/or in (a) specific cell(s), tissue(s), organ(s) or part(s) of a multicellular organism. Such reporter genes may also be expressed as a protein fusion with the amino acid sequence of the invention. Some preferred, but non-limiting examples include fluorescent proteins such as GFP.

Some preferred, but non-limiting examples of suitable promoters, terminator and further elements include those that can be used for the expression in the host cells mentioned herein; and in particular those that are suitable for expression in bacterial cells, such as those mentioned herein and/or those used in the Examples below. For some (further) non-limiting examples of the promoters, selection markers, leader sequences, expression markers and further elements that may be present/used in the genetic constructs of the invention—such as terminators, transcriptional and/or translational enhancers and/or integration factors—reference is made to the general handbooks such as Sambrook et al. and Ausubel et al. mentioned above, as well as to the examples that are given in WO 95/07463, WO 96/23810, WO 95/07463, WO 95/21191, WO 97/11094, WO 97/42320, WO 98/06737, WO 98/21355, U.S. Pat. No. 7,207,410, U.S. Pat. No. 5,693,492 and EP 1 085 089. Other examples will be clear to the skilled person. Reference is also made to the general background art cited above and the further references cited herein.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

Often, the genetic constructs of the invention will be obtained by inserting a nucleotide sequence of the invention in a suitable (expression) vector known per se. Some preferred, but non-limiting examples of suitable expression vectors are those used in the Examples below, as well as those mentioned herein.

The nucleic acids of the invention and/or the genetic constructs of the invention may be used to transform a host cell or host organism, i.e. for expression and/or production of the amino acid sequence, Nanobody or polypeptide of the invention. Suitable hosts or host cells will be clear to the skilled person, and may for example be any suitable fungal, prokaryotic or eukaryotic cell or cell line or any suitable fungal, prokaryotic or eukaryotic organism, for example:

- a bacterial strain, including but not limited to gram-negative strains such as strains of *Escherichia coli*; of *Proteus*, for example of *Proteus mirabilis*; of *Pseudomonas*, for example of *Pseudomonas fluorescens*; and gram-positive strains such as strains of *Bacillus*, for example of *Bacillus subtilis* or of *Bacillus brevis*; of *Streptomyces*, for example of *Streptomyces lividans*; of *Staphylococcus*, for example of *Staphylococcus carnosus*; and of *Lactococcus*, for example of *Lactococcus lactis*;
- a fungal cell, including but not limited to cells from species of *Trichoderma*, for example from *Trichoderma reesei*; of *Neurospora*, for example from *Neurospora crassa*; of Sordaria, for example from *Sordaria macrospora*; of *Aspergillus*, for example from *Aspergillus niger* or from *Aspergillus sojae*; or from other filamentous fungi;
- a yeast cell, including but not limited to cells from species of *Saccharomyces*, for example of *Saccharomyces cerevisiae*; of *Schizosaccharomyces*, for example of *Schizosaccharomyces pombe*; of *Pichia*, for example of *Pichia pastoris* or of *Pichia methanolica*; of *Hansenula*, for example of *Hansenula polymorpha*; of *Kluyveromyces*, for example of *Kluyveromyces lactis*; of *Arxula*, for example of *Arxula adeninivorans*; of *Yarrowia*, for example of *Yarrowia lipolytica*;
- an amphibian cell or cell line, such as *Xenopus* oocytes;
- an insect-derived cell or cell line, such as cells/cell lines derived from lepidoptera, including but not limited to *Spodoptera* SF9 and Sf21 cells or cells/cell lines derived from *Drosophila*, such as Schneider and Kc cells;
- a plant or plant cell, for example in tobacco plants; and/or
- a mammalian cell or cell line, for example a cell or cell line derived from a human, a cell or a cell line from mammals including but not limited to CHO-cells, BHK-cells (for example BHK-21 cells) and human cells or cell lines such as HeLa, COS (for example COS-7) and PER.C6 cells;

as well as all other hosts or host cells known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al., (1998), supra; Riechmann and Muyldermans, (1999), supra; van der Linden, (2000), supra; Thomassen et al., (2002), supra; Joosten et al. (2003), supra; Joosten et al., (2005), supra; and the further references cited herein.

The amino acid sequences, Nanobodies and polypeptides of the invention can also be introduced and expressed in one or more cells, tissues or organs of a multicellular organism, for example for prophylactic and/or therapeutic purposes (e.g. as a gene therapy). For this purpose, the nucleotide sequences of the invention may be introduced into the cells or tissues in any suitable way, for example as such (e.g. using liposomes) or after they have been inserted into a suitable gene therapy vector (for example derived from retroviruses such as adenovirus, or parvoviruses such as adeno-associated virus). As will also be clear to the skilled person, such gene therapy may be performed in vivo and/or in situ in the body of a patient by administering a nucleic acid of the invention or a suitable gene therapy vector encoding the same to the patient or to specific cells or a specific tissue or organ of the patient; or suitable cells (often taken from the body of the patient to be treated, such as explanted lymphocytes, bone marrow aspirates or tissue biopsies) may be treated in vitro with a nucleotide sequence of the invention and then be suitably (re-) introduced into the body of the patient. All this can be performed using gene therapy vectors, techniques and delivery systems which are well known to the skilled person, and for example described in Culver, K. W., "Gene Therapy", 1994, p. xii, Mary Ann Liebert, Inc., Publishers, New York, N.Y.); Giordano, Nature F Medicine 2 (1996), 534-539; Schaper, Circ. Res. 79 (1996), 911-919; Anderson, Science 256 (1992), 808-813; Verma, Nature 389 (1994), 239; Isner, Lancet 348 (1996), 370-374; Muhlhauser, Circ. Res. 77 (1995) 0077-1086; Onodera, Blood 91; (1998), 30-36; Verma, Gene Ther. 5 (1998), 692-699; Nabel, Ann. N.Y. Acad. Sci.: 811 (1997), 289-292; Verzeletti, Hum. Gene Ther. 9 (1998), 2243-51; Wang, Nature Medicine 2 (1996), 714-716; WO 94/29469; WO 97/00957, U.S. Pat. No. 5,580,859; U.S. Pat. No. 5,589,5466; or Schaper, Current Opinion in Biotechnology 7 (1996), 635-640. For example, in situ expression of ScFv fragments (Afanasieva et al., Gene Ther., 10, 1850-1859 (2003)) and of diabodies (Blanco et al., J. Immunol, 171, 1070-1077 (2003)) has been described in the art.

For expression of the Nanobodies in a cell, they may also be expressed as so-called "intrabodies", as for example described in WO 94/02610, WO 95/22618 and U.S. Pat. No. 7,004,940; WO 03/014960; in Cattaneo, A. & Biocca, S. (1997) Intracellular Antibodies: Development and Applications. Landes and Springer-Verlag; and in Kontermann, Methods 34, (2004), 163-170.

The amino acid sequences, Nanobodies and polypeptides of the invention can for example also be produced in the milk of transgenic mammals, for example in the milk of rabbits, cows, goats or sheep (see for example U.S. Pat. No. 6,741,957, U.S. Pat. No. 6,304,489 and U.S. Pat. No. 6,849,992 for general techniques for introducing transgenes into mammals), in plants or parts of plants including but not limited to their leaves, flowers, fruits, seed, roots or turbers (for example in tobacco, maize, soybean or alfalfa) or in for example pupae of the silkworm *Bombix mori*.

Furthermore, the amino acid sequences, Nanobodies and polypeptides of the invention can also be expressed and/or produced in cell-free expression systems, and suitable examples of such systems will be clear to the skilled person. Some preferred, but non-limiting examples include expression in the wheat germ system; in rabbit reticulocyte lysates; or in the *E. coli* Zubay system.

As mentioned above, one of the advantages of the use of Nanobodies is that the polypeptides based thereon can be prepared through expression in a suitable bacterial system, and suitable bacterial expression systems, vectors, host cells, regulatory elements, etc., will be clear to the skilled person, for example from the references cited above. It should however be noted that the invention in its broadest sense is not limited to expression in bacterial systems.

Preferably, in the invention, an (in vivo or in vitro) expression system, such as a bacterial expression system, is used that provides the polypeptides of the invention in a form that is suitable for pharmaceutical use, and such expression systems will again be clear to the skilled person. As also will be clear to the skilled person, polypeptides of the invention suitable for pharmaceutical use can be prepared using techniques for peptide synthesis.

For production on industrial scale, preferred heterologous hosts for the (industrial) production of Nanobodies or Nanobody-containing protein therapeutics include strains of *E. coli, Pichia pastoris, S. cerevisiae* that are suitable for large scale expression/production/fermentation, and in particular for large scale pharmaceutical (i.e. GMP grade) expression/production/fermentation. Suitable examples of such strains will be clear to the skilled person. Such strains and production/expression systems are also made available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

The choice of the specific expression system would depend in part on the requirement for certain post-translational modifications, more specifically glycosylation. The production of a Nanobody-containing recombinant protein for which glycosylation is desired or required would necessitate the use of mammalian expression hosts that have the ability to glycosylate the expressed protein. In this respect, it will be clear to the skilled person that the glycosylation pattern obtained (i.e. the kind, number and position of residues attached) will depend on the cell or cell line that is used for the expression. Preferably, either a human cell or cell line is used (i.e. leading to a protein that essentially has a human glycosylation pattern) or another mammalian cell line is used that can provide a glycosylation pattern that is essentially and/or functionally the same as human glycosylation or at least mimics human glycosylation. Generally, prokaryotic hosts such as *E. coli* do not have the ability to glycosylate proteins, and the use of lower eukaryotes such as yeast usually leads to a glycosylation pattern that differs from human glycosylation. Nevertheless, it should be understood that all the foregoing host cells and expression systems can be used in the invention, depending on the desired amino acid sequence, Nanobody or polypeptide to be obtained.

Thus, according to one non-limiting aspect of the invention, the amino acid sequence, Nanobody or polypeptide of the invention is glycosylated. According to another non-limiting aspect of the invention, the amino acid sequence, Nanobody or polypeptide of the invention is non-glycosylated.

According to one preferred, but non-limiting aspect of the invention, the amino acid sequence, Nanobody or polypeptide of the invention is produced in a bacterial cell, in particular a bacterial cell suitable for large scale pharmaceutical production, such as cells of the strains mentioned above.

According to another preferred, but non-limiting aspect of the invention, the amino acid sequence, Nanobody or polypeptide of the invention is produced in a yeast cell, in particular a yeast cell suitable for large scale pharmaceutical production, such as cells of the species mentioned above.

According to yet another preferred, but non-limiting aspect of the invention, the amino acid sequence, Nanobody or polypeptide of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

When expression in a host cell is used to produce the amino acid sequences, Nanobodies and the polypeptides of the invention, the amino acid sequences, Nanobodies and polypeptides of the invention can be produced either intracellular (e.g. in the cytosol, in the periplasma or in inclusion bodies) and then isolated from the host cells and optionally further purified; or can be produced extracellular (e.g. in the medium in which the host cells are cultured) and then isolated from the culture medium and optionally further purified.

When eukaryotic host cells are used, extracellular production is usually preferred since this considerably facilitates the further isolation and downstream processing of the Nanobodies and proteins obtained. Bacterial cells such as the strains of *E. coli* mentioned above normally do not secrete proteins extracellular, except for a few classes of proteins such as toxins and haemolysin, and secretory production in *E. coli* refers to the translocation of proteins across the inner membrane to the periplasma space. Periplasma production provides several advantages over cytosolic production. For example, the N-terminal amino acid sequence of the secreted product can be identical to the natural gene product after cleavage of the secretion signal sequence by a specific signal peptidase. Also, there appears to be much less protease activity in the periplasma than in the cytoplasm. In addition, protein purification is simpler due to fewer contaminating proteins in the periplasma. Another advantage is that correct disulfide bonds may form because the periplasma provides a more oxidative environment than the cytoplasm. Proteins over expressed in *E. coli* are often found in insoluble aggregates, so-called inclusion bodies. These inclusion bodies may be located in the cytosol or in the periplasm; the recovery of biologically active proteins from these inclusion bodies requires a denaturation/refolding process. Many recombinant proteins, including therapeutic proteins, are recovered from inclusion bodies. Alternatively, as will be clear to the skilled person, recombinant strains of bacteria that have been genetically modified so as to secrete a desired protein, and in particular an amino acid sequence, Nanobody or a polypeptide of the invention, can be used.

Thus, according to one non-limiting aspect of the invention, the amino acid sequence, Nanobody or polypeptide of the invention is an amino acid sequence, Nanobody or polypeptide that has been produced intracellularly and that has been isolated from the host cell, and in particular from a bacterial cell or from an inclusion body in a bacterial cell. According to another non-limiting aspect of the invention, the amino acid sequence, Nanobody or polypeptide of the invention is an amino acid sequence, Nanobody or polypeptide that has been produced extracellularly, and that has been isolated from the medium in which the host cell is cultivated.

Some preferred, but non-limiting promoters for use with these host cells include,

- for expression in *E. coli*: lac promoter (and derivatives thereof such as the lacUV5 promoter); arabinose promoter; left- (PL) and rightward (PR) promoter of phage lambda; promoter of the trp operon; hybrid lac/trp promoters (tac and trc); T7-promoter (more specifically that of T7-phage gene 10) and other T-phage promoters; promoter of the Tn10 tetracycline resistance gene; engineered variants of the above promoters that include one or more copies of an extraneous regulatory operator sequence;
- for expression in *S. cerevisiae*: constitutive: ADH1 (alcohol dehydrogenase 1), ENO (enolase), CYC1 (cytochrome c iso-1), GAPDH (glyceraldehydes-3-phosphate dehydrogenase), PGK1 (phosphoglycerate kinase), PYK1 (pyruvate kinase); regulated: GAL1,10,7 (galactose metabolic enzymes), ADH2 (alcohol dehydrogenase 2), PHOS (acid phosphatase), CUP1 (copper metallothionein); heterologous: CaMV (cauliflower mosaic virus $^{35}$S promoter);
- for expression in *Pichia pastoris*: the AOX1 promoter (alcohol oxidase I);
- for expression in mammalian cells: human cytomegalovirus (hCMV) immediate early enhancer/promoter;

human cytomegalovirus (hCMV) immediate early promoter variant that contains two tetracycline operator sequences such that the promoter can be regulated by the Tet repressor; Herpes Simplex Virus thymidine kinase (TK) promoter; Rous Sarcoma Virus long terminal repeat (RSV LTR) enhancer/promoter; elongation factor 1α (hEF-1α) promoter from human, chimpanzee, mouse or rat; the SV40 early promoter; HIV-1 long terminal repeat promoter; β-actin promoter;

Some preferred, but non-limiting vectors for use with these host cells include:

vectors for expression in mammalian cells: pMAMneo (Clontech), pcDNA3 (Invitrogen), pMC1neo (Stratagem), pSG5 (Stratagene), EBO-pSV2-neo (ATCC 37593), pBPV-1 (8-2) (ATCC 37110), pdBPV-MMTneo (342-12) (ATCC 37224), pRSVgpt (ATCC37199), pRSVneo (ATCC37198), pSV2-dhfr (ATCC 37146), pUC-Tag (ATCC 37460) and 1ZD35 (ATCC 37565), as well as viral-based expression systems, such as those based on adenovirus;

vectors for expression in bacterial cells: pET vectors (Novagen) and pQE vectors (Qiagen);

vectors for expression in yeast or other fungal cells: pYES2 (Invitrogen) and *Pichia* expression vectors (Invitrogen);

vectors for expression in insect cells: pBlueBacII (Invitrogen) and other baculovirus vectors vectors for expression in plants or plant cells: for example vectors based on cauliflower mosaic virus or tobacco mosaic virus, suitable strains of *Agrobacterium*, or Ti-plasmid based vectors.

Some preferred, but non-limiting secretory sequences for use with these host cells include:

for use in bacterial cells such as *E. coli*; PelB, Bla, OmpA, OmpC, OmpF, OmpT, PhoA, PhoE, MalE, Lpp, LamB, and the like; TAT signal peptide, hemolysin C-terminal secretion signal;

for use in yeast: α-mating factor prepro-sequence, phosphatase (pho1), invertase (Sue), etc.;

for use in mammalian cells: indigenous signal in case the target protein is of eukaryotic origin; murine Ig κ-chain V-J2-C signal peptide; etc.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the amino acid sequence of the invention, e.g. using specific antibodies.

The transformed host cell (which may be in the form or a stable cell line) or host organisms (which may be in the form of a stable mutant line or strain) form further aspects of the present invention.

Preferably, these host cells or host organisms are such that they express, or are (at least) capable of expressing (e.g. under suitable conditions), an amino acid sequence, Nanobody or polypeptide of the invention (and in case of a host organism: in at least one cell, part, tissue or organ thereof). The invention also includes further generations, progeny and/or offspring of the host cell or host organism of the invention, that may for instance be obtained by cell division or by sexual or asexual reproduction.

To produce/obtain expression of the amino acid sequences of the invention, the transformed host cell or transformed host organism may generally be kept, maintained and/or cultured under conditions such that the (desired) amino acid sequence, Nanobody or polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the amino acid sequences of the invention may be expressed in a constitutive manner, in a transient manner, or only when suitably induced.

It will also be clear to the skilled person that the amino acid sequence, Nanobody or polypeptide of the invention may (first) be generated in an immature form (as mentioned above), which may then be subjected to post-translational modification, depending on the host cell/host organism used. Also, the amino acid sequence, Nanobody or polypeptide of the invention may be glycosylated, again depending on the host cell/host organism used.

The amino acid sequence, Nanobody or polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the amino acid sequence, Nanobody or polypeptide of the invention) and/or preparative immunological techniques (i.e. using antibodies against the amino acid sequence to be isolated).

Generally, for pharmaceutical use, the polypeptides of the invention may be formulated as a pharmaceutical preparation or compositions comprising at least one polypeptide of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. Such suitable administration forms—which may be solid, semi-solid or liquid, depending on the manner of administration—as well as methods and carriers for use in the preparation thereof, will be clear to the skilled person, and are further described herein.

Thus, in a further aspect, the invention relates to a pharmaceutical composition that contains at least one amino acid of the invention, at least one Nanobody of the invention or at least one polypeptide of the invention and at least one suitable carrier, diluent or excipient (i.e. suitable for pharmaceutical use), and optionally one or more further active substances.

Generally, the amino acid sequences, Nanobodies and polypeptides of the invention can be formulated and administered in any suitable manner known per se, for which reference is for example made to the general background art cited above (and in particular to WO 04/041862, WO 04/041863, WO 04/041865 and WO 04/041867) as well as to the standard handbooks, such as Remington's Pharmaceutical Sciences, 18th Ed., Mack Publishing Company, USA (1990) or Remington, the Science and Practice of Pharmacy, 21st Edition, Lippincott Williams and Wilkins (2005).

For example, the amino acid sequences, Nanobodies and polypeptides of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (for example intravenous, intraperitoneal, subcutaneous, intramuscular, intraluminal, intra-arterial or intrathecal administration) or for topical (i.e. transdermal or intradermal) administration.

Preparations for parenteral administration may for example be sterile solutions, suspensions, dispersions or emulsions that are suitable for infusion or injection. Suitable carriers or diluents for such preparations for example include, without limitation, sterile water and aqueous buffers and solutions such as physiological phosphate-buffered saline, Ringer's solutions, dextrose solution, and Hank's solution; water oils; glycerol; ethanol; glycols such as propylene glycol or as well as mineral oils, animal oils and vegetable oils, for example peanut oil, soybean oil, as well as suitable mixtures thereof. Usually, aqueous solutions or suspensions will be preferred.

The amino acid sequences, Nanobodies and polypeptides of the invention can also be administered using gene therapy methods of delivery. See, e.g., U.S. Pat. No. 5,399,346, which is incorporated by reference in its entirety. Using a gene therapy method of delivery, primary cells transfected with the gene encoding an amino acid sequence, Nanobody or polypeptide of the invention can additionally be transfected with tissue specific promoters to target specific organs, tissue, grafts, tumors, or cells and can additionally be transfected with signal and stabilization sequences for subcellularly localized expression.

Thus, the amino acid sequences, Nanobodies and polypeptides of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the amino acid sequences, Nanobodies and polypeptides of the invention may be combined with one or more excipients and used in the form of ingestible tablets, buccal tablets, troches, capsules, elixirs, suspensions, syrups, wafers, and the like. Such compositions and preparations should contain at least 0.1% of the amino acid sequence, Nanobody or polypeptide of the invention. Their percentage in the compositions and preparations may, of course, be varied and may conveniently be between about 2 to about 60% of the weight of a given unit dosage form. The amount of the amino acid sequence, Nanobody or polypeptide of the invention in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the amino acid sequences, Nanobodies and polypeptides of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the amino acid sequences, Nanobodies and polypeptides of the invention may be incorporated into sustained-release preparations and devices.

Preparations and formulations for oral administration may also be provided with an enteric coating that will allow the constructs of the invention to resist the gastric environment and pass into the intestines. More generally, preparations and formulations for oral administration may be suitably formulated for delivery into any desired part of the gastrointestinal tract. In addition, suitable suppositories may be used for delivery into the gastrointestinal tract.

The amino acid sequences, Nanobodies and polypeptides of the invention may also be administered intravenously or intraperitoneally by infusion or injection. Solutions of the amino acid sequences. Nanobodies and polypeptides of the invention or their salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of micro organisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the amino acid sequences, Nanobodies and polypeptides of the invention in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the amino acid sequences, Nanobodies and polypeptides of the invention may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, hydroxyalkyls or glycols or water-alcohol/glycol blends, in which the amino acid sequences, Nanobodies and polypeptides of the invention can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the amino acid sequences, Nanobodies and polypeptides of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the amino acid sequences, Nanobodies and polypeptides of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the amino acid sequences, Nanobodies and polypeptides of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the amino acid sequences, Nanobodies and polypeptides of the invention required for use in treatment will vary not only with the particular amino acid sequence, Nanobody or polypeptide selected but also with the route of administration, the nature of the condition being treated and the age and condition of the patient and will be ultimately at the discretion of the attendant physician or clinician. Also the dosage of the amino acid sequences, Nanobodies and polypeptides of the invention varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

In another aspect, the invention relates to a method for the prevention and/or treatment of at least one disease from the group of diseases consisting of diseases related to i) excessive angiogenesis such as angiogenesis such as cancer, diabetic blindness, age-related macular degeneration, rheumatoid arthritis, psoriasis, and more than 70 other conditions and related to ii) insufficient angiogenesis such as coronary artery disease, stroke, and delayed wound healing, said method comprising administering, to a subject in need thereof, a pharmaceutically active amount of an amino acid sequence of the invention, of a Nanobody of the invention, of a polypeptide of the invention, and/or of a pharmaceutical composition comprising the same.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

The invention relates to a method for the prevention and/or treatment of at least one disease or disorder that is associated with Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, with its biological or pharmacological activity, and/or with the biological pathways or signalling in which Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 is involved, said method comprising administering, to a subject in need thereof, a pharmaceutically active amount of an amino acid sequence of the invention, of a Nanobody of the invention, of a polypeptide of the invention, and/or of a pharmaceutical composition comprising the same. In particular, the invention relates to a method for the prevention and/or treatment of at least one disease or disorder that can be treated by modulating Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, its biological or pharmacological activity, and/or the biological pathways or signalling in which Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 is involved, said method comprising administering, to a subject in need thereof, a pharmaceutically active amount of an amino acid sequence of the invention, of a Nanobody of the invention, of a polypeptide of the invention, and/or of a pharmaceutical composition comprising the same. In particular, said pharmaceutically effective amount may be an amount that is sufficient to modulate Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, its biological or pharmacological activity, and/or the biological pathways or signalling in which Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 is involved; and/or an amount that provides a level of the amino acid sequence of the invention, of a Nanobody of the invention, of a polypeptide of the invention in the circulation that is sufficient to modulate Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, its biological or pharmacological activity, and/or the biological pathways or signalling in which Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 is involved.

The invention furthermore relates to a method for the prevention and/or treatment of at least one disease or disorder that can be prevented and/or treated by administering an amino acid sequence of the invention, a Nanobody of the invention or a polypeptide of the invention to a patient, said method comprising administering, to a subject in need thereof, a pharmaceutically active amount of an amino acid sequence of the invention, of a Nanobody of the invention, of a polypeptide of the invention, and/or of a pharmaceutical composition comprising the same.

More in particular, the invention relates to a method for the prevention and/or treatment of at least one disease or disorder chosen from the group consisting of the diseases and disorders listed herein, said method comprising administering, to a subject in need thereof, a pharmaceutically active amount of an amino acid sequence of the invention, of a Nanobody of the invention, of a polypeptide of the invention, and/or of a pharmaceutical composition comprising the same.

In another aspect, the invention relates to a method for immunotherapy, and in particular for passive immunotherapy, which method comprises administering, to a subject suffering from or at risk of the diseases and disorders mentioned herein, a pharmaceutically active amount of an amino acid sequence of the invention, of a Nanobody of the invention, of a polypeptide of the invention, and/or of a pharmaceutical composition comprising the same.

In the above methods, the amino acid sequences, Nanobodies and/or polypeptides of the invention and/or the compositions comprising the same can be administered in any suitable manner, depending on the specific pharmaceutical formulation or composition to be used. Thus, the amino acid sequences, Nanobodies and/or polypeptides of the invention and/or the compositions comprising the same can for example be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease or disorder to be prevented or treated and other factors well known to the clinician.

The amino acid sequences. Nanobodies and/or polypeptides of the invention and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific amino acid sequence, Nanobody or polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more amino acid sequences, Nanobodies and/or polypeptides of the invention, or of one or more compositions comprising the same, in one or more pharmaceutically effective amounts or doses. The specific amount(s) or doses to administered can be determined by the clinician, again based on the factors cited above.

Generally, for the prevention and/or treatment of the diseases and disorders mentioned herein and depending on the specific disease or disorder to be treated, the potency of the specific amino acid sequence, Nanobody and polypeptide of the invention to be used, the specific route of administration and the specific pharmaceutical formulation or composition used, the amino acid sequences, Nanobodies and polypeptides of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Usually, in the above method, a single amino acid sequence, Nanobody or polypeptide of the invention will be used. It is however within the scope of the invention to use two or more amino acid sequences, Nanobodies and/or polypeptides of the invention in combination.

The Nanobodies, amino acid sequences and polypeptides of the invention may also be used in combination with one or more further pharmaceutically active compounds or principles, i.e. as a combined treatment regimen, which may or may not lead to a synergistic effect. Again, the clinician will be able to select such further compounds or principles, as well as a suitable combined treatment regimen, based on the factors cited above and his expert judgement.

In particular, the amino acid sequences, Nanobodies and polypeptides of the invention may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In another aspect, the invention relates to the use of an amino acid sequence, Nanobody or polypeptide of the invention in the preparation of a pharmaceutical composition for prevention and/or treatment of at least one i) excessive angiogenesis such as cancer, diabetic blindness, age-related macular degeneration, rheumatoid arthritis, psoriasis, and others, ii) insufficient angiogenesis such as coronary artery disease, stroke, and delayed wound healing; and/or for use in one or more of the methods of treatment mentioned herein.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

The invention also relates to the use of an amino acid sequence, Nanobody or polypeptide of the invention in the preparation of a pharmaceutical composition for the prevention and/or treatment of at least one disease or disorder that can be prevented and/or treated by administering an amino acid sequence, Nanobody or polypeptide of the invention to a patient.

More in particular, the invention relates to the use of an amino acid sequence, Nanobody or polypeptide of the invention in the preparation of a pharmaceutical composition for the prevention and/or treatment of i) excessive angiogenesis such as cancer, diabetic blindness, age-related macular degeneration, rheumatoid arthritis, psoriasis, and others, and of ii) insufficient angiogenesis such as coronary artery disease, stroke, and delayed wound healing, and in particular for the prevention and treatment of one or more of the diseases and disorders listed herein.

Again, in such a pharmaceutical composition, the one or more amino acid sequences, Nanobodies or polypeptides of the invention may also be suitably combined with one or more other active principles, such as those mentioned herein.

Finally, although the use of the Nanobodies of the invention (as defined herein) and of the polypeptides of the invention is much preferred, it will be clear that on the basis of the description herein, the skilled person will also be able to design and/or generate, in an analogous manner, other amino acid sequences and in particular (single) domain antibodies against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, as well as polypeptides comprising such (single) domain antibodies.

For example, it will also be clear to the skilled person that it may be possible to "graft" one or more of the CDR's mentioned above for the Nanobodies of the invention onto such (single) domain antibodies or other protein scaffolds, including but not limited to human scaffolds or non-immunoglobulin scaffolds. Suitable scaffolds and techniques for such CDR grafting will be clear to the skilled person and are well known in the art, see for example U.S. Pat. No. 7,180,370, WO 01/27160, EP 0 605 522, EP 0 460 167, U.S. Pat. No. 7,054,297, Nicaise et al., Protein Science (2004), 13:1882-1891; Ewert et al., Methods, 2004 October; 34(2):184-199; Kettleborough et al., Protein Eng. 1991 October; 4(7): 773-783; O'Brien and Jones, Methods Mol. Biol. 2003: 207: 81-100; Skerra, J. Mol. Recognit. 2000: 13: 167-187, and Saerens et al., J. Mol. Biol. 2005 Sep. 23; 352(3):597-607, and the further references cited therein. For example, techniques known per se for grafting mouse or rat CDR's onto human frameworks and scaffolds can be used in an analogous manner to provide chimeric proteins comprising one or more of the CDR's of the Nanobodies of the invention and one or more human framework regions or sequences.

It should also be noted that, when the Nanobodies of the inventions contain one or more other CDR sequences than the preferred CDR sequences mentioned above, these CDR sequences can be obtained in any manner known per se, for example from Nanobodies (preferred), $V_H$; domains from conventional antibodies (and in particular from human antibodies), heavy chain antibodies, conventional 4-chain antibodies (such as conventional human 4-chain antibodies) or other immunoglobulin sequences directed against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2. Such immunoglobulin sequences directed against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 can be generated in any manner known per se, as will be clear to the skilled person, i.e. by immunization with Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 or by screening a suitable library of immunoglobulin sequences with Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, or any suitable combination thereof. Optionally, this may be followed by techniques such as random or site-directed mutagenesis and/or other techniques for affinity maturation known per se. Suitable techniques for generating such immunoglobulin sequences will be clear to the skilled person, and for example include the screening techniques reviewed by Hoogenboom, Nature Biotechnology, 23, 9, 1105-1116 (2005) Other techniques for generating immunoglobulins against a specified target include for example the Nanoclone technology (as for example described in the published US patent application 2006-0211088), so-called SLAM technology (as for example described in the European patent application 0 542 810), the use of transgenic mice expressing human immunoglobulins or the well-known hybridoma techniques (see for example Larrick et al, Biotechnology, Vol. 7, 1989, p. 934). All these techniques can be used to generate immunoglobulins against Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2, and the CDR's of such immunoglobulins can be used in the Nanobodies of the invention, i.e. as outlined above. For example, the sequence of such a CDR can be determined, synthesized and/or isolated, and inserted into the sequence of a Nanobody of the invention (e.g. so as to replace the corresponding native CDR), all using techniques known per se such as those described herein, or Nanobodies of the invention containing such CDR's (or nucleic acids encoding the same) can be synthesized de novo, again using the techniques mentioned herein.

Further uses of the amino acid sequences, Nanobodies, polypeptides, nucleic acids, genetic constructs and hosts and host cells of the invention will be clear to the skilled person based on the disclosure herein. For example, and without limitation, the amino acid sequences of the invention can be linked to a suitable carrier or solid support so as to provide a medium than can be used in a manner known per se to purify Tie1, Tie2, Ang1 Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 from compositions and preparations comprising the same. Derivatives of the amino acid sequences of the invention that comprise a suitable detectable label can also be used as markers to determine (qualitatively or quantitatively) the presence of Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 in a composition or preparation or as a marker to selectively detect the presence of Tie1, Tie2, Ang1, Ang2, Ang3, Ang4, Angptl1, Angptl2, Angptl3, Angptl4, Angptl5, or Angptl6, more preferably Tie2, Ang2, Ang1, Ang4, or Angptl4, more preferably Tie2 or Ang2 on the surface of a cell or tissue (for example, in combination with suitable cell sorting techniques).

The invention will now be further described by means of the following non-limiting figures:

FIG. 1. Tie2 binding assay for a selection of clones. Negative controls are addition of irrelevant phage selected against a viral antigen and no phage addition.

Figure 2:
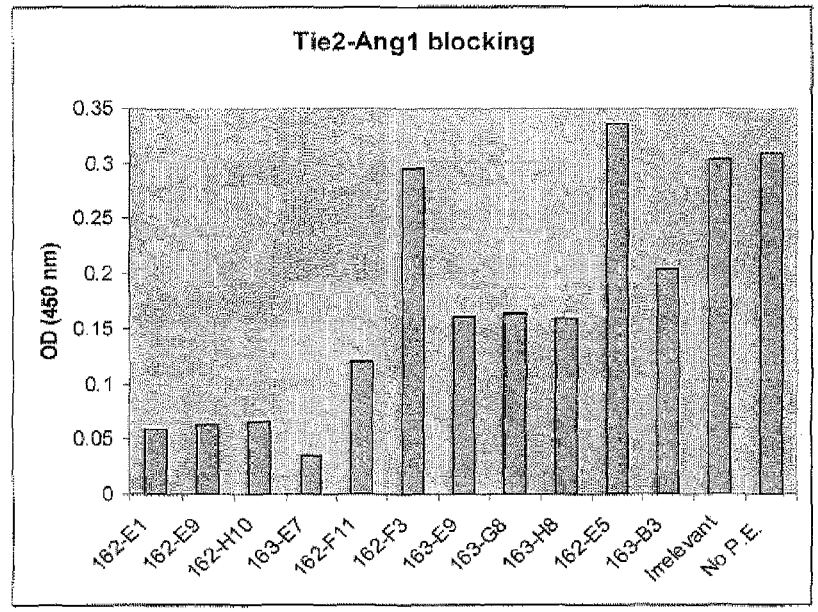

FIG. 2. Tie2-Ang1 blocking assay of selected P.E. Negative controls are addition of irrelevant P.E. selected against a viral antigen and no P.E. addition. 5 clones (family I, II, III and IV) show significant blocking of Ang-1 binding.

Figure 3:
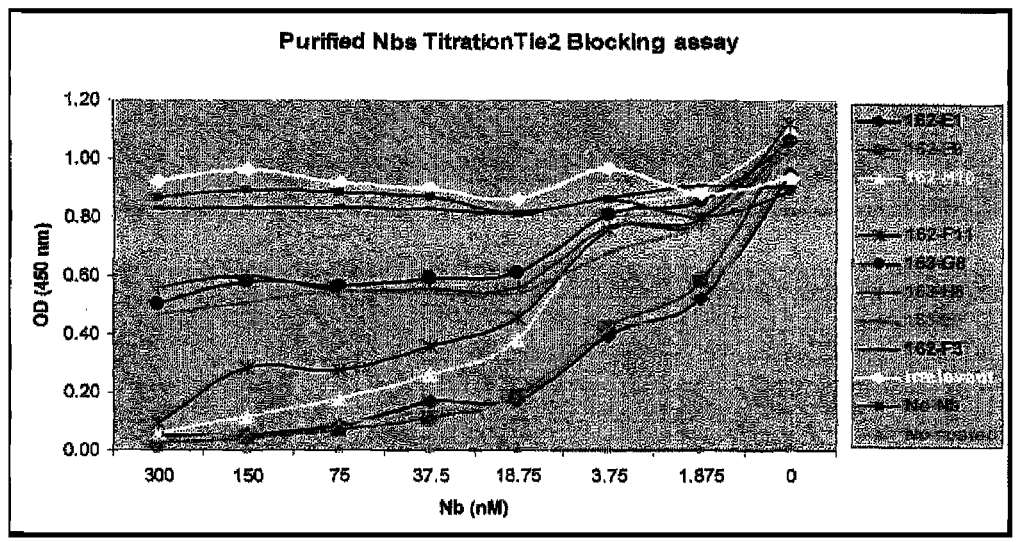

FIG. 3. Tie2-Ang1 blocking assay of purified nanobodies in a dilution series. Negative controls are addition of irrelevant nanobody selected against a viral antigen and no nanobody addition.

Figure 4:
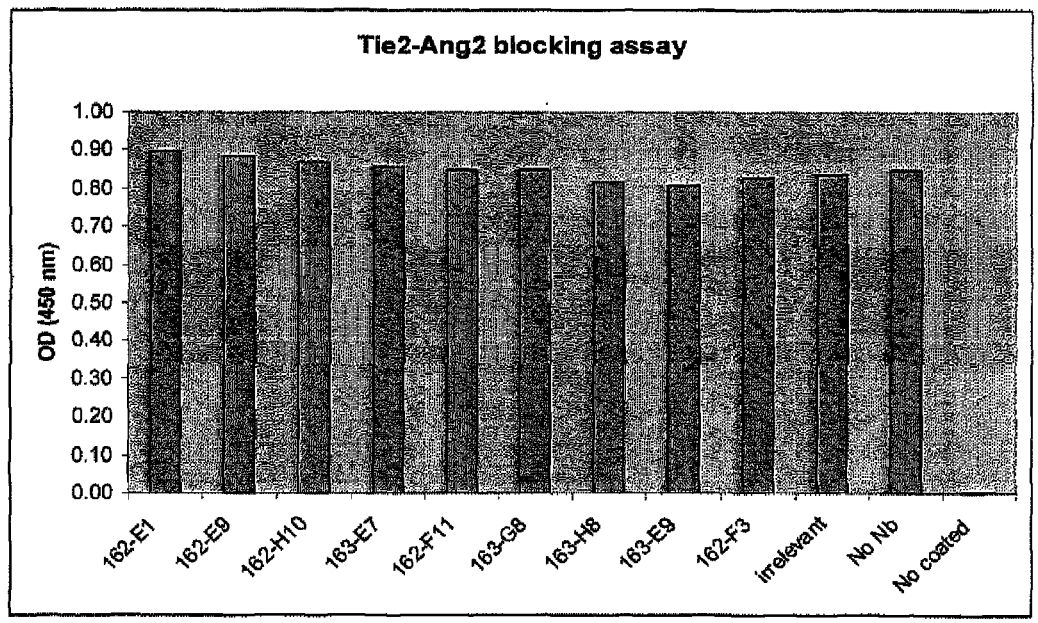

FIG. 4. Tie2-Ang2 blocking assay of purified nanobodies in a dilution series. Negative controls are addition of irrelevant nanobody selected against a viral antigen and no nanobody addition. None of the Tie2-Ang1 blocking nanobodies is able to block binding of Ang2 to Tie2.

Figure 5:
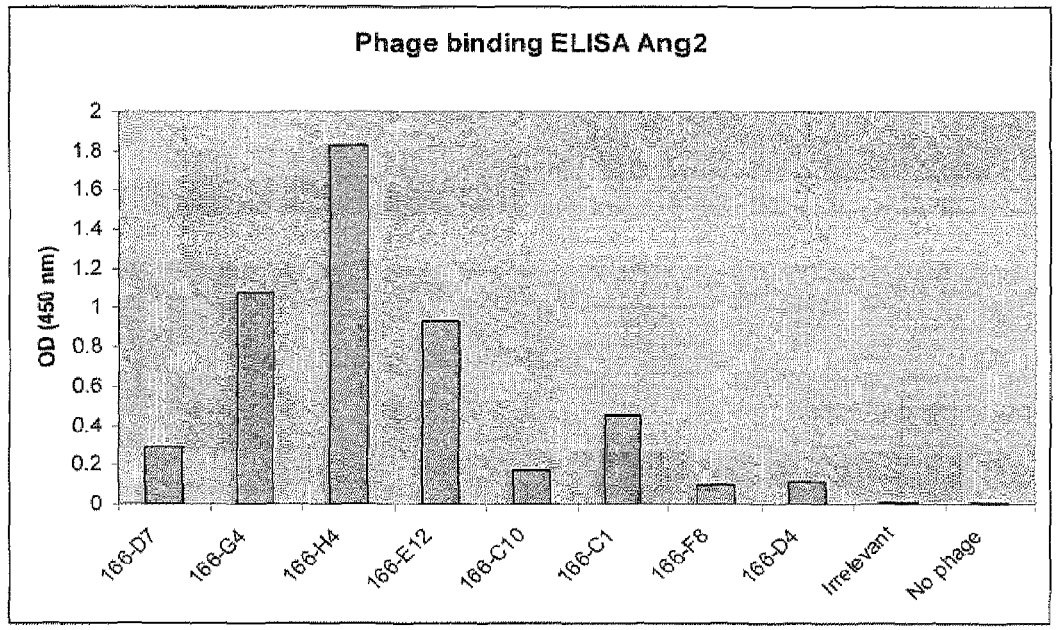

FIG. 5. Ang2 binding assay for a selection of clones. Negative controls are addition of irrelevant phage selected against a viral antigen and no phage addition.

Figure 6:
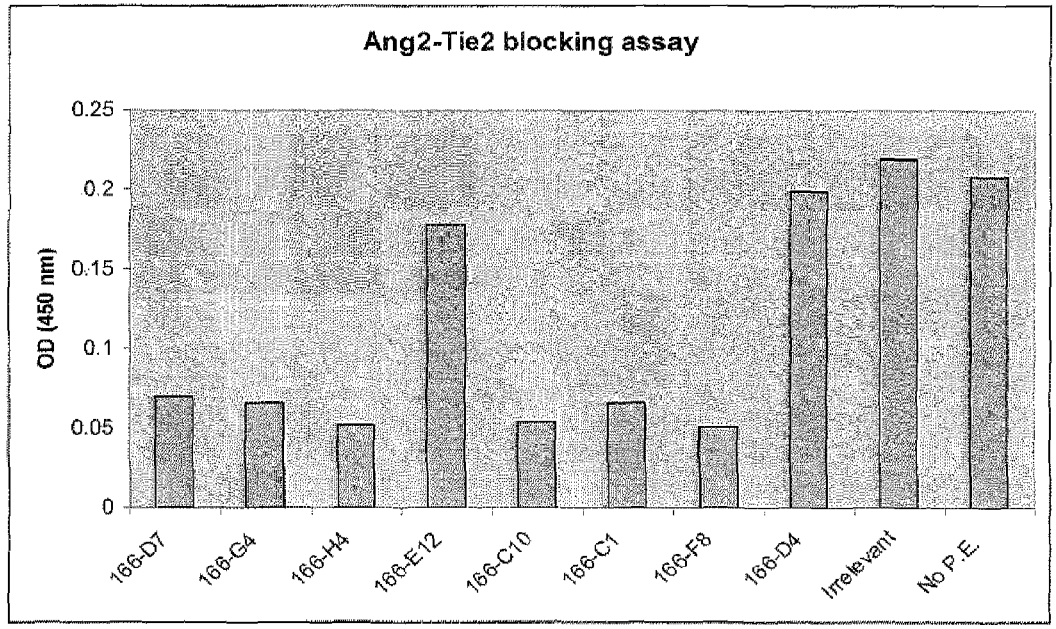

FIG. 6. Ang2-Tie2 blocking assay for a selection of clones. Negative controls are addition of irrelevant P.E. selected against a viral antigen and no P.E. addition. 6 clones (family 1) show significant blocking of Ang-2 binding to Tie2.

Figure 7:
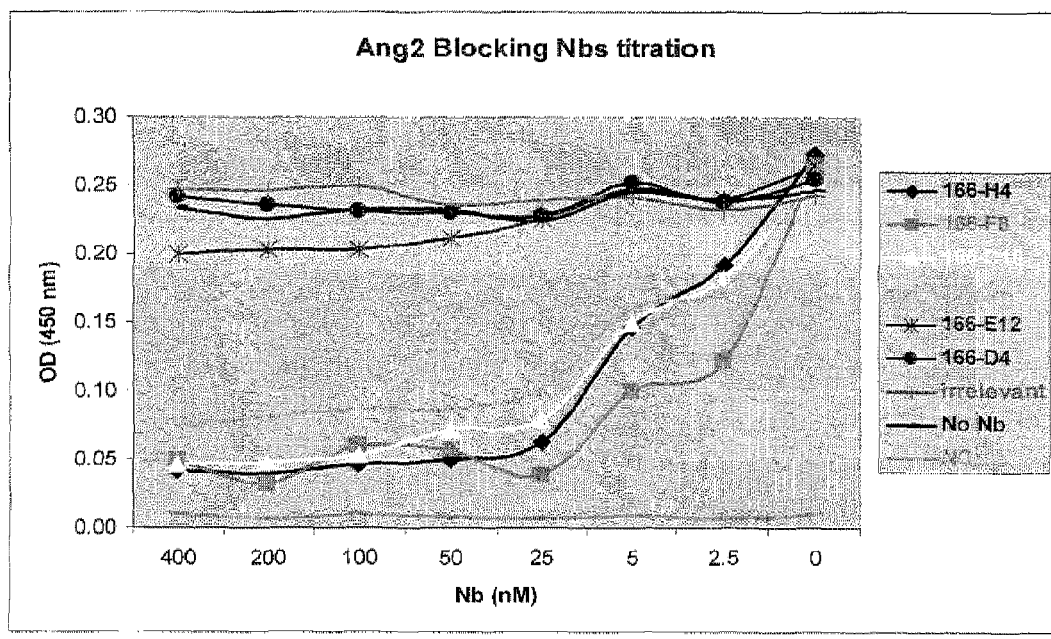

FIG. 7. Ang2-Tie2 blocking assay of purified nanobodies in a dilution series. Negative controls are addition of irrelevant nanobody selected against a viral antigen and no nanobody addition.

Figure 8:
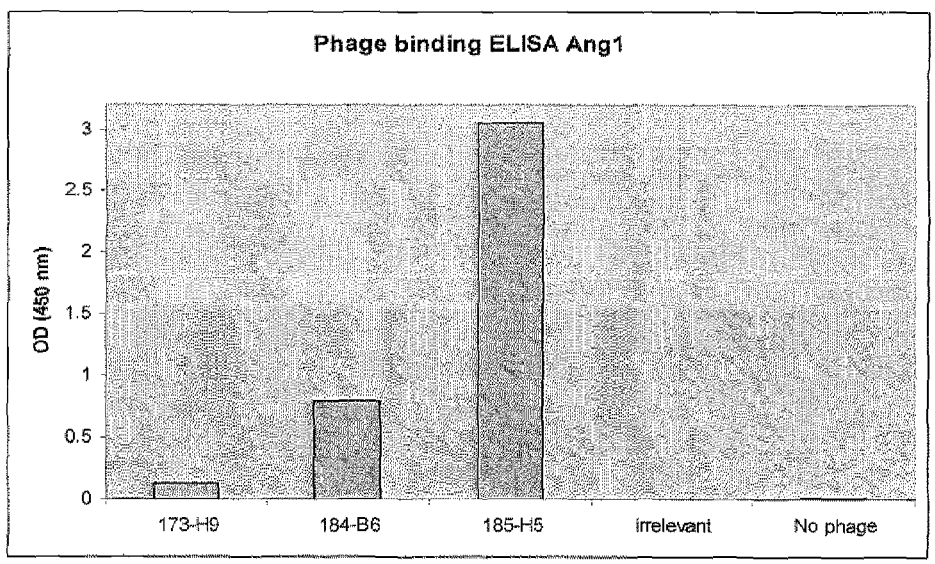

FIG. 8. Ang1 binding assay for a selection of clones. Negative controls are addition of irrelevant phage selected against a viral antigen and no phage addition.

Figure 9:
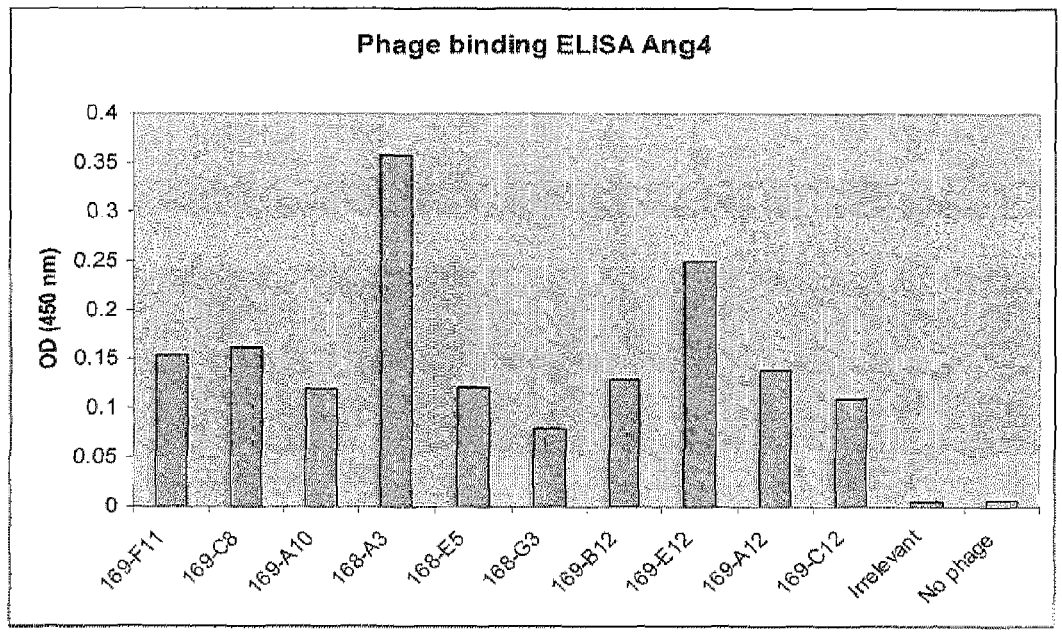

FIG. 9. Ang4 binding assay for a selection of clones. Negative controls are addition of irrelevant phage selected against a viral antigen and no phage addition.

Figure 10:
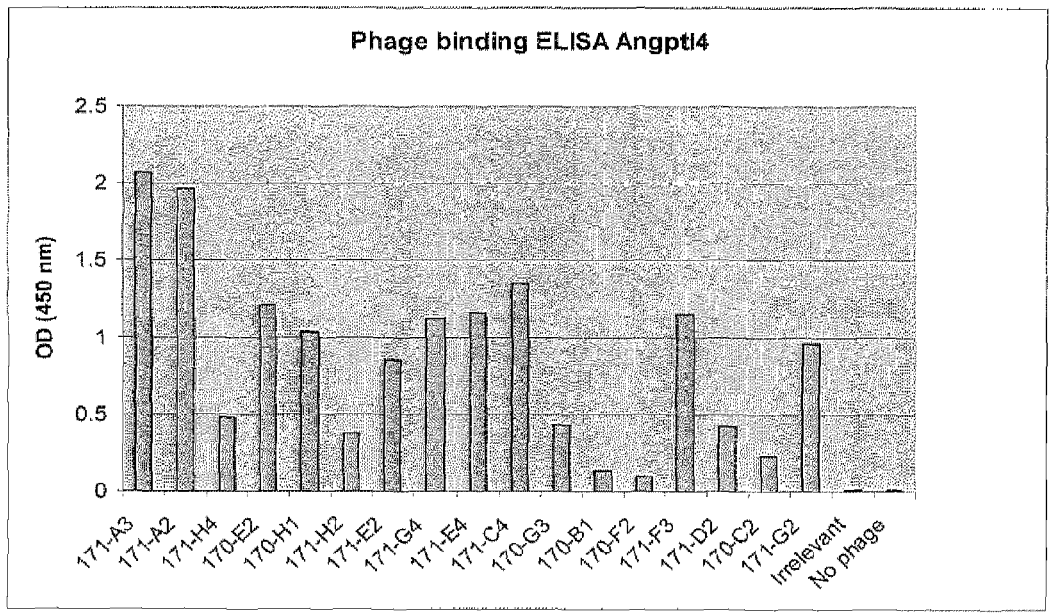

FIG. 10. Angptl4 binding assay for a selection of clones. Negative controls are addition of irrelevant phage selected against a viral antigen and no phage addition.

Figure 11:
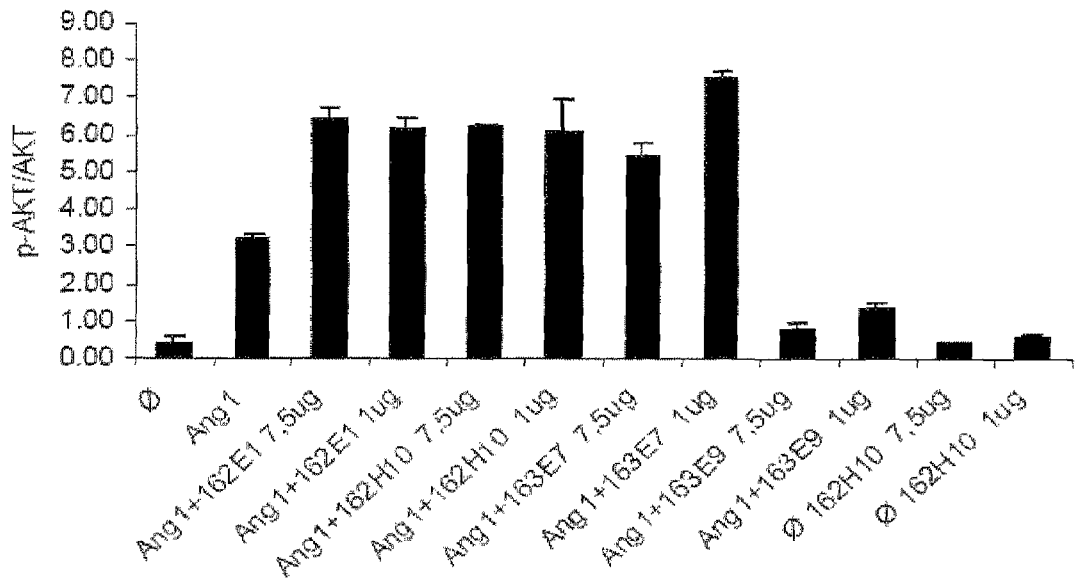
Figure 12:
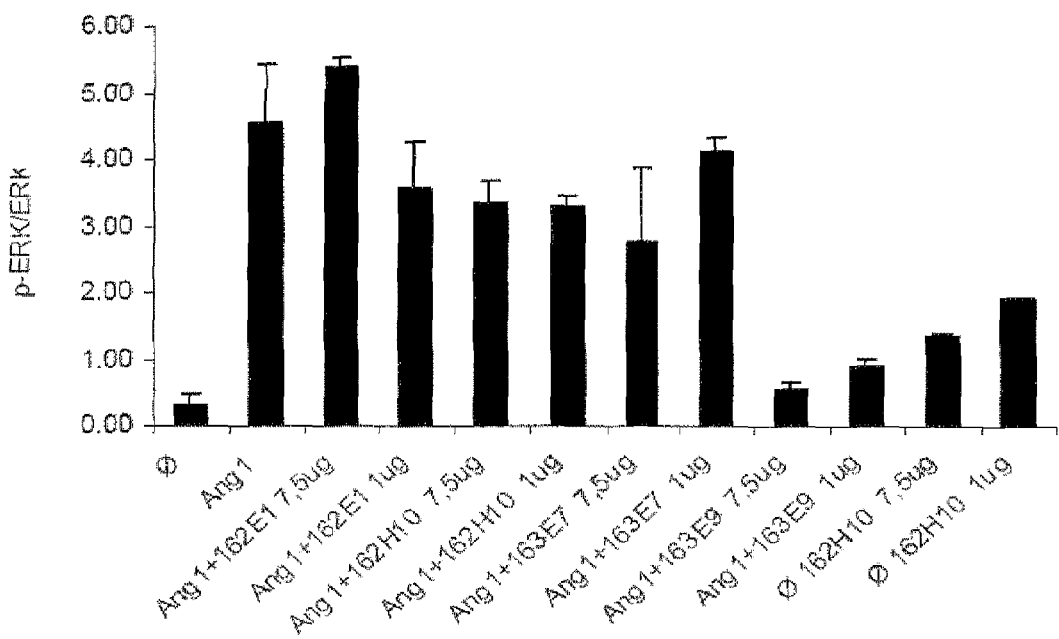

FIGS. 11&12. Ratio of phospho-Akt to Akt (FIG. 11) and phospho-ERK to ERK (FIG. 12) is reported. Ø indicate non Ang-1 stimulated samples. Among anti-Tie2 NBs tested, only Nanobody 163E9 was able to block the Ang1-induced Akt and Erk phosphorylation both at 7.5 ug/ml (~500 nM) and 1 ug/ml (~67 nM). None of the others Tie-2 Nanobodies inhibited phosphorylation of AKt and Erk.

Figure 13:
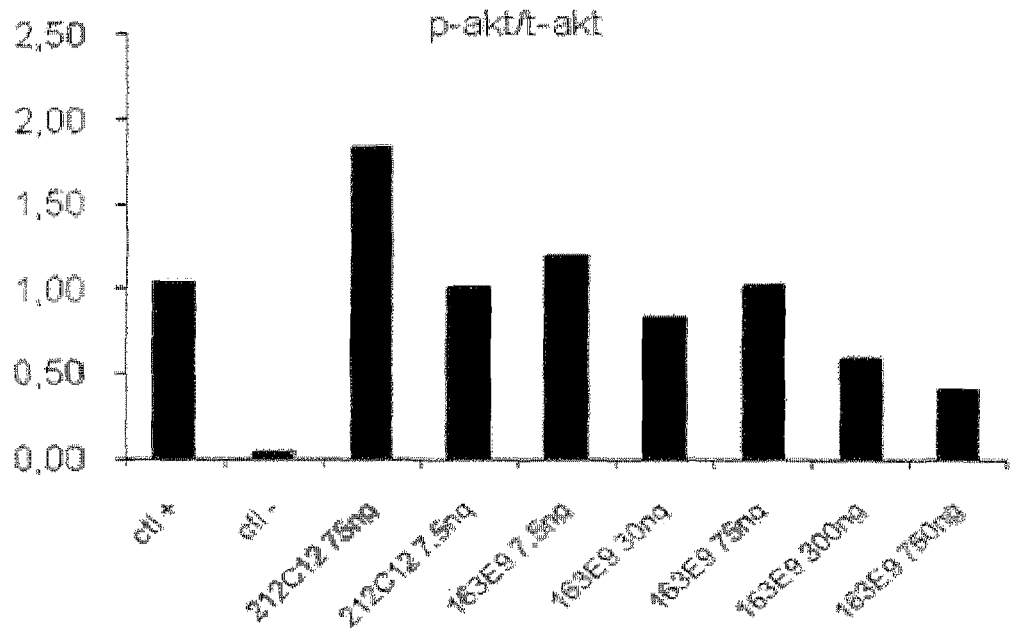
Figure 14:
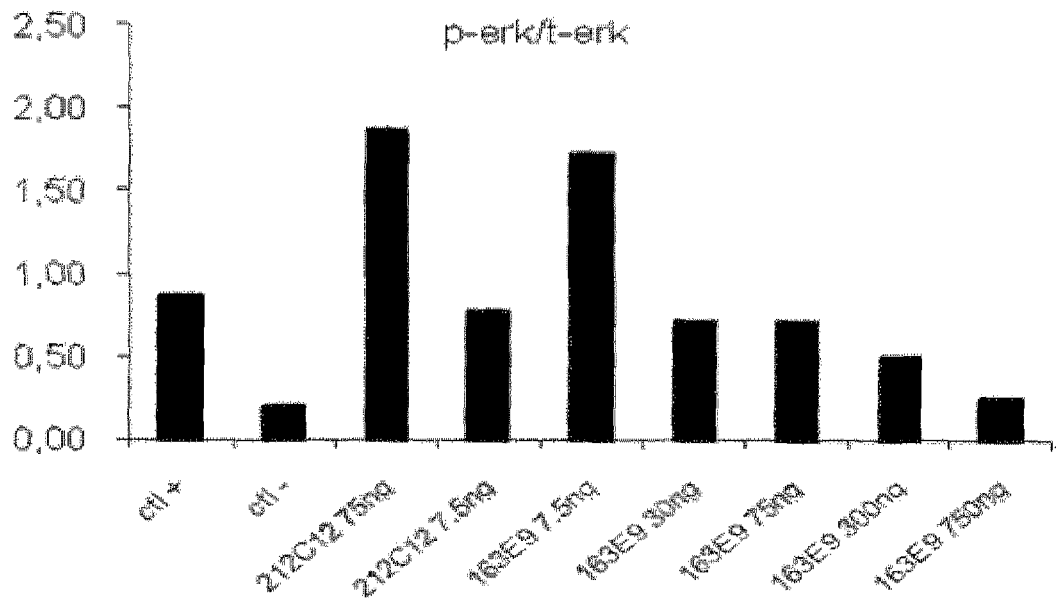

FIGS. 13&14. Ratio of phospho-Akt to Akt (FIG. 13) and phospho-ERK to ERK (FIG. 14) is reported. Nanobody 163E9 dose-dependently inhibited Ang-1 induced phosphorylation of Akt and Erk.

Figure 15:
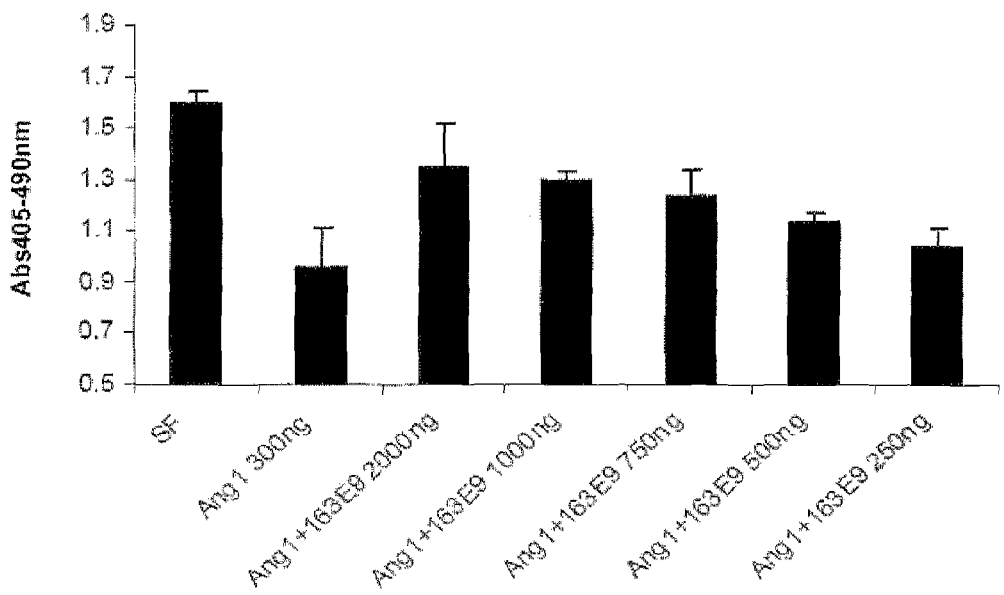

FIG. 15. The Tie-2 Nanobody 163E9 reverses the anti-apoptotic effect of Ang-1

Figure 16:
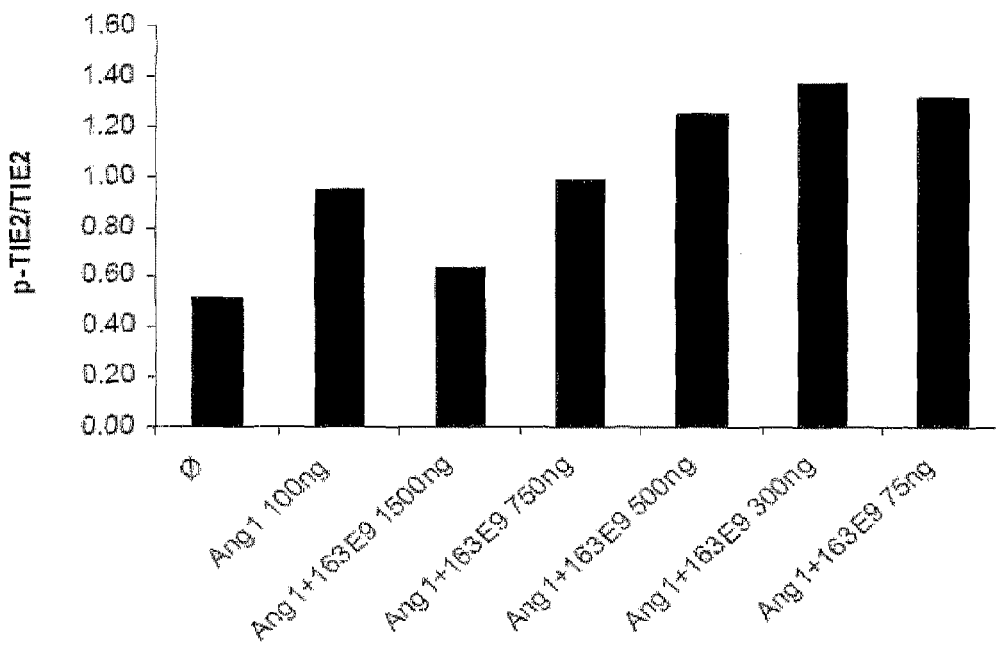

FIG. 16. Nanobody 163E9 dose-dependently inhibits Ang-1 induced phosphorylation of Tie-2

Figure 17:
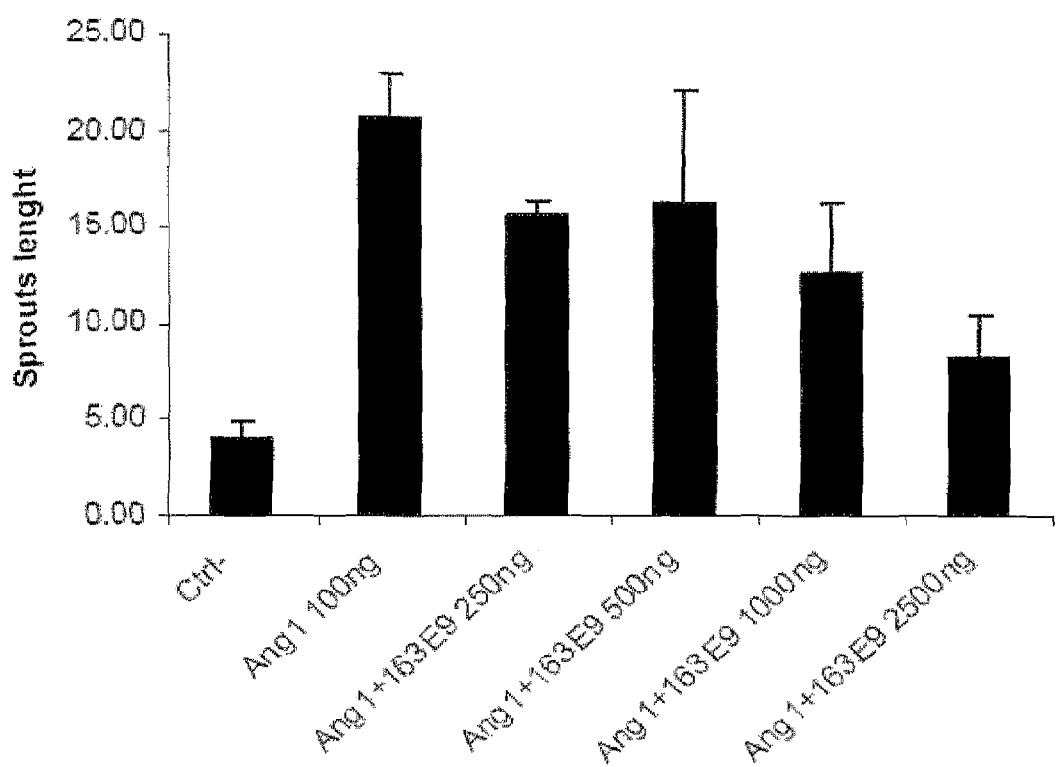

FIG. 17. Nanobody 163E9 dose-dependently inhibits Ang-1 induced sprouting of endothelial cells.

The invention will now be further described by means of the following non-limiting experimental part.

Experimental Part:

Example 1

Animal Immunizations

Two llamas (161 and 166) are immunized, according to standard protocols, with 6 boosts of a cocktail 121 containing recombinant human Tie2/Fc Chimera (R&D Systems Cat No 313-TI, Lot No BKC06). Blood is collected from these animals 5 and 8 days after boost 6. In addition, approximately 1 g of lymph node is collected from each animal 5 days after boost 6.

Example 2

Library Construction

Peripheral blood mononuclear cells are prepared from blood samples using Ficoll-Hypaque according to the manufacturer's instructions. Next, total RNA is extracted from these cells and lymph node tissue and used as starting material for RT-PCR to amplify Nanobody encoding gene fragments.

These fragments are cloned into phagemid vector pAX50 (see below). Phage is prepared according to standard methods (see for example the prior art and applications filed by applicant cited herein).

pAX50—An expression vector is used derived from pLTC119 which contains the LacZ promoter, a coliphage pIII protein coding sequence, a resistance gene for ampicillin or carbenicillin, a multicloning site and the gen3 leader sequence. In frame with the Nanobody® coding sequence, the vector codes for a C-terminal c-myc tag and a (His)6 tag.

Example 3

Selections Of Phage Displaying Tie2 Binding Nanobodies

Phage libraries 161 and 166 are used for selections on recombinant human Tie2/Fc Chimera (R&D Systems Cat No 313-TI, Lot No BKC06). Tie2/Fc is immobilized directly on Maxisorp 96 well microtiter plates (Nunc) at 5 ug/ml, 0.5 ug/ml and 0 ug/ml (control). To minimize the number of phage binding to the Fc-portion of Tie2/Fc the phage is pre-incubated with 250 ug/ml human IgG. Following incubation with the phage libraries and extensive washing, bound phage was eluted with trypsin. The eluted phage are amplified and applied in a second round of selection on 2 ug/ml, 0.2 ug/ml, 0.02 ug/ml and 0 ug/ml (control) immobilized Tie2/Fc. To minimize the number of phage binding to the Fc-portion of Tie2/Fc the phage is pre-incubated with 100 ug/ml human IgG plus 100 ug/ml rh B7.2/Fc (R&D Systems Cat No 141-B2, Lot No BOT 075031). Individual colonies obtained from the eluted phage pools are grown and i) induced for new phage production and ii) induced with IPTG for Nanobody expression and extraction (periplasmic extracts) according to standard methods (see for example the prior art and applications filed by applicant cited herein).

Example 4

Screening for Tie2 Binding Nanobodies

In order to determine binding specificity to Tie2, the clones are tested in an ELISA binding assay setup, using the monoclonal phage pools. Phage binding to Tie2/Fc Chimera (R&D Systems Cat No 313-TI, Lot No BKC06) is tested. Shortly, 0.2 ug/ml receptor is immobilized on Maxisorp ELISA plates (Nunc) and free binding sites are blocked using 4% Marvel skimmed milk in PBS. Next, 10 ul of supernatant from the monoclonal phage inductions of the different clones in 100 ul 2% Marvel PBS are allowed to bind to the immobilized antigen. After incubation and a wash step, phage binding is revealed using a HRP-conjugated monoclonal-anti-M13 antibody (Gentaur Cat#27942101). Binding specificity is determined based on OD values compared to controls having received no phage and to controls where in a similar ELISA binding assay the same monoclonal phage are tested for binding to 0.2 ug/ml of immobilized human IgG and 0.2 ug/ml of rh B7.2/Fc.

FIG. 1 and Table B-1 show a selection of clones binding to Tie2 (see Table B-1 for definition of clones).

TABLE B-1

Nanobodies against Tie2.

| Name | SEQ ID NO: | Sequence |
|---|---|---|
| 162-E1 | 455 | EVQLVESGGGLVQAGGSLRLSCAASGSIFSINAMGWYQQAPGKQR ELVAFITSVGTTNYADSVKGRFIISRDNAKNTVYLQMNSLKPEDTA VYYCAADLHYSGPNYWGQGTQVTVSS |
| 162-E9 | 456 | EVQLVESGGGLVQPGGSLRLSCAASGFTLDDYAIGWFRQAPGKER EAVSCISSVDGSTHYADSVKGRFTISRDNAKDTVYLQMNSLKPED TAAYYCAVQGYSGGYYYTCEDSADFGFWGQGTQVTVSS |
| 162-F11 | 457 | EVQLVESGGGLVQAGGSLRLSCAASGFTFDDYAIGWFRQAPGKER EGVACISSSDGSTYYADSVKGRFTISSDNAKNTVYLQMNSLKPEDT AVYSCSAGSVAGCIPYYWGQGTQVTVSS |
| 162-F3 | 458 | EVQLVESGGGLVQAGDSLRLSCTTSGRTFSDDTMGWFRQAPRKER EFVAAILWDSIKTYYADSVKGRFTISRDNAKNTVYLQMDSLKPED TAVYYCAATPTAYGTDWYRNNYHYWGQGTQVTVSS |
| 162-H10 | 459 | EVQLVESGGGLVQPGGSLRLSCAASGFTLDDYAVGWFRQAPGKE REGVSCIGSSYGSTYYADSVKGRFTISRDNAKNTVYLQMNSLKPE DTAVYYCAVQGYSGGYYYTCEDSADFGFWGQGTQVTVSS |
| 163-E7 | 460 | EVQLVESGGGLVQPGGSLRLSCAASGFTFSDYSMSWVRQAPGKGL EWVSAISGGGEVTTYADSVKGRFTISRDNAKNTLYLQMSSLKPED TALYYCAEHLNFYSVSVRSSPTSQGTQVTVSS |
| 163-E9 | 461 | EVQLVESGGGLVQPGDSLRLSCAASGFTFGSNGMRWVRQAPGKG PEWVSSINSDGTSTYYADSVKGRFTISRDNAKNTLCLQMNSLKPED TAVYYCTTTEDPYPRGQGTQVTVSS |
| 163-G8 | 462 | EVQLVESGGGLVQPGGSLRLSCAASGFTFGSNGMRWVRQAPGKG PEWVSSINSDGTSAFYAESVKGRFTISRDNAKNTLYLQMNSLKPED TAVYYCTTTMNPNPRGQGTQVTVSS |
| 163-H8 | 463 | EVQLVESGGGLVQPGGSLRLSCAASGFTFGSNGMRWVRQAPGKG PEWVSSINSDGTSTYYAESVKGRFTISRDNAKNTLYLQMHSLKPED TAVYYCTTTENPNPRGPGTQVTVSS |

Example 5

Screening for Nanobodies Blocking Tie2-Ang1 Interaction

Clones tested positive in the Tie2 binding assay are screened for their ability to block Ang1 binding to Tie2/Fc. For this, Nanobody-containing periplasmic extracts (P.E.) are used in an ELISA-based ligand competition setup. In short, 0.75 ug/ml human Ang1 (R&D Systems Cat No 923-AN/CF Lot No FHWO73091) is coated in 96 well Maxisorp microtiter plates (Nunc) and blocked with 4% Marvel skimmed milk in PBS. In parallel, 0.2 ug/ml Tie2/Fc is incubated with 10 ul of periplasmic extract P.E. containing nanobody of the different clones in 100 ul 2% Marvel/PBS. After 1 hour, the receptor-Nanobody pre-mixes are incubated 1 hour with the coated ligand. Bound Tie2/Fc is detected using HRP-conjugated goat anti-human IgG (Jackson Immunoresearch, Cat #109-035-098). Blocking activity is determined as loss of OD signal, as compared to wells where no P.E., or irrelevant P.E., has been added.

FIG. 2 shows results of this blocking assay using a selection of clones binding to Tie2.

162-E1, 162-E9, 162-F11, 162-H10, 163-E7 (see Table B-2 below) show significant blocking of Ang1 binding to Tie2.

TABLE B-2

Nanobodies against Tie2 and able to block Ang1 binding to Tie2.

| Name | SEQ ID NO: | Sequence |
|---|---|---|
| 162-E1 | 455 | EVQLVESGGGLVQAGGSLRLSCAASGSIFSINAMGWYQQAPGKQRELVAFITSVGTTNYADSVKGRIISRDNAKNTVYLQMNSLKPEDTAVYYCAADLHYSGPNYWGQGTQVTVSS |
| 162-E9 | 456 | EVQLVESGGGLVQPGGSLRLSCAASGFTLDDYAIGWFRQAPGKEREAVSCISSVDGSTHYADSVKGRFTISRDNAKDTVYLQMNSLKPEDTAAYYCAVQGYSGGYYYTCEDSADFGFWGQGTQVTVSS |
| 162-F11 | 457 | EVQLVESGGGLVQAGGSLRLSCAASGFTFDDYAIGWFRQAPGKEREGVACISSSDGSTYYADSVKGRFTISSDNAKNTVYLQMNSLKPEDTAVYSCSAGSVAGCIPYYWGQGTQVTVSS |
| 162-H10 | 459 | EVQLVESGGGLVQPGGSLRLSCAASGFTLDDYAVGWFRQAPGKEREGVSCIGSSYGSTYYADSVKGRFTISRDNAKNTVYLQMNSLKPEDTAVYYCAVQGYSGGYYYTCEDSADFGFWGQGTQVTVSS |
| 163-E7 | 460 | EVQLVESGGGLVQPGGSLRLSCAASGFTFSDYSMSWVRQAPGKGLEWVSAISGGGEVTTYADSVKGRFTISRDNAKNTLYLQMSSLKPEDTALYYCAEHLNFYSVSVRSSPTSQGTQVTVSS |

Example 6

Determining Tie2-Ang1 Interaction Blocking Efficiency by Titration of Purified Nanobody In order to determine the receptor blocking efficiency of clones tested positive for Ang1 competition, a dilution series of purified Nanobodies are tested in the ELISA-based ligand competition setup. In short, 0.75 ug/ml human. Ang1 (R&D Systems Cat No 923-AN/CF Lot No FHWO73091) is coated in 96 well Maxisorp microliter plates (Nunc) and blocked with 4% Marvel skimmed milk in PBS. In parallel, 0.2 ug/ml Tie2/Fc is incubated with a dilution series of purified Nanobodies. After 1 hour, the receptor-Nanobody pre-mixes are incubated 1 hour with the coated ligand. Bound Tie2/Fc is detected using HRP-conjugated goat anti-human IgG (Jackson Immunoresearch, Cat #109-035-098). Blocking activity is determined as loss of OD signal, as compared to wells where no P.E., or irrelevant P.E., has been added. FIG. 3 shows the results of this assay.

Example 7

Screening for Tie2-Ang2 Blocking Among the Purified Tie2-Ang1 Blocking Nanobodies In order to investigate whether the clones tested positive for Ang1 competition can also block binding of Ang2 to the receptor the pervious purified Nanobodies are tested in a new ELISA-based ligand competition setup. In short, 0.75 ug/ml human Ang2 (R&D Systems Cat No 923-AN/CF) is coated in 96 well Maxisorp microtiter plates (Nunc) and blocked with 4% Marvel skimmed milk in PBS. In parallel, 0.2 ug/ml Tie2/Fc is incubated with 150 nM of purified Nanobodies. After 1 hour, the receptor-Nanobody pre-mixes are incubated 1 hour with the coated ligand. Bound Tie2/Fc was detected using HRP-conjugated goat anti-human IgG (Jackson Immunoresearch. Cat #109-035-098). Blocking activity is determined as loss of OD signal, as compared to wells where no P.E., or irrelevant P.E., has been added. FIG. 4 shows the result of this example. None of the Tie2-Ang1 blocking nanobodies is able to block binding of Ang2 to Tie2.

```
Sequences alignments of Tie2 binding Nanobodies (FRs in small
                   letters, CDRs in capital letters):

163-G8    evqlvesggglvqpggslrlscaasgftfgSNGMRwvrqapgkgpewvsSINSDGTSAFY

163-H8    evqlvesggglvqpggslrlscaasgftfgSNGMRwvrqapgkgpewvsSINSDGTSTYY

163-E9    evqlvesggglvqpgdslrlscaasgftfgSNGMRwvrqapgkgpewvsSINSDGTSTYY

163-E7    evqlvesggglvqpggslrlscaasgftfsDYSMSwvrqapgkglewvsAISGGGEVTTY

162-E1*   evqlvesggglvqaggslrlscaasgsifsINAMGwyqqapgkqrelvaFITSVG-TTNY

162-F3    evqlvesggglvqagdslrlscttsgrtfsDDTMGwfrqaprkerefvaAILWDSIKTYY

162-E9    evqlvesggglvqpggslrlscaasgftldDYAIGwfrqapgkereavsCISSVDGSTHY

162-H10   evqlvesggglvqpggslrlscaasgftldDYAVGwfrqapgkeregvsCIGSSYGSTYY

162-F11   evqlvesggglvqaggslrlscaaagftfdDYAIGwfrqapgkeregvaCISSSDGSTYY

163-G8    AESVKGrftisrdnakntlylqmnslkpedtavyycttTM-----NPN----------Pr

163-H8    AESVKGrftisrdnakntlylqmhslkpedtavyycttTE-----NPN----------Pr

163-E9    ADSVKGrftisrdnakntlclqmnslkpedtavyycttTE-----DPY----------Pr

163-E7    ADSVKGrftisrdnakntlylqmsslkpedtalyycaeHL-----NFYSV---SVRSSPt

162-E1    ADSVKGrfiisrdnakntvylqmnslkpedtavyycaa-------DLHYS-----GPNYw

162-F3    ADSVKGrftisrdnakntvylqmdslkpedtavyycaaTPTAYGTDWYRN-----NYHYw

162-E9    ADSVKGrftisrdnakdtvylqmnslkpedtaayycavQG--YSGGYYYTCEDSADFGFw

162-H10   ADSVKGrftisrdnakntvylqmnslkpedtavvycavQG--YSGGYYYTCEDSADEGFw

162-F11   ADSVKGrftissdnakntvylqmnslkpedtavyscsaGS--VAGCIPY---------Yw

163-G8    gqgtqvtvss

163-H8    gpgtqvtvss

163-E9    gqgtqvtvss

163-E7    sqgtqvtvss

162-E1    gqgtqvtvss

162-F3    gqgtqvtvss
```

-continued

```
162-E9   gqgtqvtvss

162-H10  gqgtqvtvss

162-F11  gqgtqvtvss
```

Members:
Families of binders (one family of Nanobodies has same CDR3):

| | members: |
|---|---|
| I | 162-E1 |
| II | 162-E9, 162-H10 |
| III | 163-E7 |
| IV | 162-F11 |
| V | 162-F3 |
| VI | 163-E9, 163-G8, 163-H8 |

*q in FR2 of 162-E1 from an Amber stop codon

Example 8

Animal Immunizations

Two llamas (171 and 172) are immunized, according to standard protocols, with 6 boosts of a cocktail 121 containing:

Recombinant human Angiopoietin-1 (R&D Systems Cat No 923-AN/CF),

Recombinant human Angiopoietin-2 (R&D Systems Cat No 623-AN/CF),

Recombinant human. Angiopoietin-4 (R&D Systems Cat No 964-AN/CF),

Recombinant human Angiopoietin-like-4 (R&D Systems Cat No 3485-AN)

Blood is collected from these animals 8 days after boost 6.

Example 9

Library Construction

Peripheral blood mononuclear cells are prepared from blood samples using Ficoll-Hypaque according to the manufacturer's instructions. Next, total RNA is extracted from these cells and used as starting material for RT-PCR to amplify Nanobody encoding gene fragments. These fragments are cloned into phagemid vector pAX50. Phage is prepared according to standard methods (see for example the prior art and applications filed by applicant cited herein). Example results in phage libraries 171 (from Llama 171) and 172 (from Llama 172).

Example 10

Selections of Phage Displaying Ang2 Binding Nanobodies

Phage libraries 171 and 172 are used for selections on recombinant human Ang2 (R&D Systems Cat No 623-AN/CF). Ang2 is immobilized directly on Maxisorp 96 well microliter plates (Nunc) at 5 ug/ml, 0.5 ug/ml and 0 ug/ml (control). Following incubation with the phage libraries and extensive washing, bound phage is eluted with trypsin. The eluted phage are amplified and applied in a second round of selection on 2 ug/ml, 0.2 ug/ml, 0.02 ug/ml and 0 ug/ml (control) immobilized Ang2. Individual colonies obtained from the eluted phage pools are grown and i) induced for new phage production and ii) induced with IPTG for Nanobody expression and extraction (periplasmic extracts) according to standard methods (see for example the prior art and applications filed by applicant cited herein).

Example 11

Screening for Ang2 Binding Nanobodies

In order to determine binding specificity to Ang2, the clones are tested in an ELISA binding assay setup, using the monoclonal phage pools. Phage binding to Ang2 (R&D Systems Cat No 623-AN/CF) is tested. Shortly, 0.2 ug/ml Ang2 is immobilized on Maxisorp ELISA plates (Nuns) and free binding sites are blocked using 4% Marvel skimmed milk in PBS. Next, 10 ul of supernatant from the monoclonal phage inductions of the different clones in 100 ul 2% Marvel. PBS are allowed to bind to the immobilized antigen. After incubation and a wash step, phage binding is revealed using a HRP-conjugated monoclonal-anti-M13 antibody (Gentaur Cat#27942101). Binding specificity is determined based on OD values compared to controls having received an irrelevant phage or no phage.

FIG. 5 and Table B-3 shows a selection of clones binding to Ang2.

TABLE B-3

Nanobodies against Ang2

| Name | SEQ ID NO: | Sequence |
|------|------------|----------|
| 166-C1 | 464 | EVQLVESGGGLVQAGGSLRLSCAASGPTFGSTTIGWFRQAPGKEREGVSCISTGDGSTYYAESVKGRFTISSDNAKNTVYLQMNSLKPEDTAVYYCALDQAPMWSSWSAPYEYDYWGQGTQVTVSS |
| 166-C10 | 465 | EVQLVESGGGLVQAGGSLRLSCAASGFTFGTTTIGWFRQAPGKEREGVSCISTGDGSTNYAESVKGRFTISSDNAKNTVYLQMNSLKPEDTAVYYCALDQAPMWSSWSAPYEYDYWGQGTQVTVSS |
| 166-D7 | 466 | EVQLVESGGGLVQAGGSLRLSCAASGFTFSDTTIGWFRQAPGKEREGISCISTGDGSTYYAESVKGRFTISSDNAKNTVYLQMNSLNPEDTAVYYCALDQAPLWSTWSAPYEYDYWGQGTQVTVSS |
| 166-F8 | 467 | EVQLVESGGGLVQAGGSLRLSCAASGFTFGTTTIGWFRQAPGKEREVVSCISTGGGSTYYTESVKGRFTISSDNAKNTVYLQMNSLKPEDTAVYYCALDQAPMWSNWSAPYEYDYWGQGTQVTVSS |
| 166-G4 | 468 | EVQLVESGGGLVQAGGSLRLSCAASGFTFSDTTIGWFRQAPGKEREGISCISTGDGSTYYAESVKGRFTISSDNAKNTVYLQMNSLNPEDTAVYYCALDQAPLWSTWSAPYEYDYWGQGT QVTVSS |
| 166-H4 | 469 | EVQLVESGGDLVQAGGSLRLSCAASGFTFGDFTIGWFRQAPGKEREGVSCINTGDGSTNYAESVKGRFTISSDNAKNTVYLQMNSLKPEDTAVYYCALDQAPMWSSWSAPYEYDYWGQGTQVTVSS |
| 166-E12 | 470 | KVQLVESGGGLVQAGGSLRLSCAASGFTFGSTTIGWFRQAPGKEREGVSCISTGDGSTYYAESVKGRFTISSDNAKNTVYLQMNSLKPEDTAVYYCALDQAPMWSSWSAPYEYDYWGQGTQVTVSS |
| 166-D4 | 471 | EVQLVESGGGLVQAGGSLRLSCVASGRIFTNTAMGWYRQAPGKWRELVATIYSGGSTKYIDSVKGRFIISRDNTRNTVHLQMNSLKPEDTAVYYCNTVGAGSYWGQGAQVTVSS |

Example 12

Screening for Nanobodies Blocking Ang2-Tie2 Interaction

Clones tested positive in the Ang2 binding assay are screened for their ability to block Ang2 binding to Tie2/Fc. For this, Nanobody-containing periplasmic extracts (P.E.) are used in an ELISA-based ligand competition setup. In short, 4 ug/ml human Tie2/Fc Chimera (R&D Systems Cat No 313-TI, Lot No BKC06)) is coated in 96 well Maxisorp microliter plates (Nunc) and blocked with 4% Marvel skimmed milk in PBS. In parallel, 0.05 ug/ml biotinylated rh Ang2 (R&D Systems Cat No BT623, Lot No BNR174091) is incubated with 10 ul of periplasmic extract containing nanobody of the different clones in 100 ul 2% Marvel/PBS. After 1 hour, the biotinylated Ang2-Nanobody pre-mixes are incubated 1 hour with the coated receptor. Bound biotinylated. Ang2 is detected using HRP-conjugated extravidin (SIGMA E2886-1ML, 126K4801). Blocking activity is determined as loss of OD signal, as compared to wells where no P.E., or irrelevant P.E., has been added. FIG. 6 shows results of this blocking assay using a selection of clones binding to Ang2.

166-D7, 166-G4, 166-114, 166-C10, 166-C1, 166-F8 (see Table B-4 below) show significant blocking of Ang2 binding to Tie2.

TABLE B-4

Nanobodies against Ang2 and able to block Ang2 binding to Tie2.

| Name | SEQ ID NO: | Sequence |
|------|------------|----------|
| 166-C1 | 464 | EVQLVESGGGLVQAGGSLRLSCAASGFTFGSTTIGWFRQAPGKEREGVSCISTGDGSTYYAESVKGRFTISSDNAKNTVYLQMNSLKPEDTAVYYCALDQAPMWSSWSAPIEYDYWGQGTQVTVSS |
| 166-C10 | 465 | EVQLVESGGGLVQAGGSLRLSCAASGFTFGTTTIGWFRQAPGKEREGVSCISTGDGSTNYAESVKGRFTISSDNAKNTVYLQMNSLKPEDTAVYYCALDQAPMWSSWSAPYEYDYWGQGTQVTVSS |
| 166-D7 | 466 | EVQLVESGGGLVQAGGSLRLSCAASGFTFSDTTIGWFRQAPGKEREGISCISTGDGSTYYAESVKGRFTISSDNAKNTVYLQMNSLNPEDTAVYYCALDQAPLWSTWSAPYEYDYWGQGTQVTVSS |
| 166-F8 | 467 | EVQLVESGGGLVQAGGSLRLSCAASGFTFGTTTIGWFRQAPGKEREVVSCISTGGGSTYYTESVKGRFTISSDNAKNTVYLQMNSLKPEDTAVYYCALDQAPMWSNWSAPYEYDYWGQGTQVTVSS |

TABLE B-4-continued

Nanobodies against Ang2 and able to block Ang2 binding to Tie2.

| Name | SEQ ID NO: | Sequence |
|---|---|---|
| 166-G4 | 468 | EVQLVESGGGLVQAGGSLRLSCAASGFTFSDTTIGWFRQAPGKE REGISCISTGDGSTYYAESVKGRFTISSDNAKNTVYLQMNSLNPE DTAVYYCALDQAPLWSTWSAPYEYDYWGQGT QVTVSS |
| 166-H4 | 469 | EVQLVESGGDLVQAGGSLRLSCAASGFTFGDFTIGWFRQAPGKE REGVSCINTGDGSTNYAESVKGRFTISSDNAKNTVYLQMNSLKPE DTAVYYCALDQAPMWSSWSAPYEYDYWGQGTQVTVSS |

Example 13

Determining Ang2-Tie2 Interaction Blocking Efficiency by Titration of Purified Nanobody In order to determine the receptor blocking efficiency of clones tested positive for Ang2 blocking, a dilution series of purified Nanobodies are tested in the ELISA-based ligand competition setup. In short, 4 ug/ml human Tie2/Fc Chimera (R&D Systems Cat No 313-TI, Lot No BKC06)) is coated in 96 well Maxisorp microtiter plates (Nunc) and blocked with 4% Marvel skimmed milk in PBS. In parallel, 0.05 ug/ml biotinylated rh Ang2 (R&D Systems Cat No BT623, Lot No BNR174091) is incubated with a dilution series of purified Nanobodies. After 1 hour, the biotinylated Ang2-Nanobody pre-mixes are incubated 1 hour with the coated receptor. Bound biotinylated Ang2 is detected using HRP-conjugated extravidin (SIGMA E2886-1ML, 126K4801). Blocking activity is determined as loss of OD signal, as compared to wells where no P.E., or irrelevant P.E. has been added. FIG. 7 shows the results of this assay.

```
Sequences alignments of Ang2 binding Nanobodies (FRs in small
                    letters, CDRs in capital letters):

166-D7    evqlvesggglvqaggslrlscaasgftfsDTTIGwfrqapgkeregisCISTGDGSTYY

166-G4    evqlvesggglvqaggslrlscaasgftfsDTTIGwfrqapgkeregisCISTGDGSTYY

166-H4    evqlvesggdlvqaggslrlscaasgftfgDFTIGwfrqapgkeregvsCINTGDGSTNY

166-E12   kvqlvesggglvqaggslrlscaasgftfgSTTIGwfrqapgkeregvsCISTGDGSTYY

166-C10   evqlvesggglvqaggslrlscaasgftfgTTTIGwfrqapgkeregvsCISTGDGSTNY

166-C1    evqlvesggglvqaggslrlscaasgftfgSTTIGwfrqapgkeregvsCISTGDGSTYY

166-F8    evqlvesggglvqaggslrlscaasgftfgTTTIGwfrqapgkerevvsCISTGGGSTYY

166-D4    evqlvesggglvqaggslrlscvasgriftNTANGwyrqapgkwrelva.TIYSGGSTKY

166-H5    evqlvesggglvqaggslslacvvsgrfsrINSMAwsrqvpgnarelva.SVTSGGYTNY

166-D7    AESVKGrftissdnakntvylqmnslnpedtavyycalDQAPLWSTWSAPYEYDYwgqgt

166-G4    AESVKGrftissdnakntvylqmnslnpedtavyycalDQAPLWSTWSAPYEYDYwgqgt

166-H4    AESVKGrftissdnakntvylqmnslkpedtavyycalDQAPMWSSWSAPYEYDYwgqgt

166-E12   AESVKGrftissdnakntvylqmnslkpedtavyycalDQAPMWSSWSAPYEYDYwgqgt

166-C10   AESVKGrftissdnaktnyylqmnslkpedtavyycalDQAPMWSSWSAPYEYDYwgqgt

166-C1    AESVKGrftissdnakntvylqmnslkpedtavyycalDQAPMWSSWSAPYEYDYwgqgt

166-F8    TESVKGrftissdnakntvylqmnslkpedtavyycalDQAPMWSNWSAPYEYDYwgqgt

166-D4    IDSVKGrfiisrdntrntvhlqmnslkpedtavyycnt.......VGAGSY....wgqga

166-H5    VDSVKGrftisrdnaknaiylqmnslksedtavyycna...RVVVRTAHGFEDNYwgqgt

166-D7    qvtvss

166-G4    qvtvss

166-H4    qvtvss

166-E12   qvtvss

166-C10   qvtvss
```

-continued

```
166-C1    qvtvss
166-F8    qvtvss
166-D4    qvtvss
166-H5    qvtvss
```

Members:
Families of binders (one family of Nanobodies has same CDR3):

```
       members:
I      166-D7, 166-G4, 166-H4, 166-E12, 166-C10, 166-C1, 166-F8
II     166-D4
```

Example 14

Selections of Phage Displaying Ang1 Binding Nanobodies

Phage libraries 171 and 172 (Example 9) are used for selections on recombinant human Ang1 (R&D Systems Cat No 923-AN/CF, Lot No FHWO73091). Ang1 is immobilized directly on Maxisorp 96 well microtiter plates (Nunc) at 5 ug/ml, 0.5 ug/ml and 0 ug/ml (control). Following incubation with the phage libraries and extensive washing, bound phage is eluted with trypsin. The eluted phage are amplified and applied in a second round of selection on 2 ug/ml, 0.2 ug/ml, 0.02 ug/ml and 0 ug/ml (control) immobilized Ang1. In this second round, and following incubation with the phage libraries and extensive washing, bound phage is eluted with trypsin and 100 fold excess (nM compared to coated Ang1) recombinant human Tie2/Fc Chimera (R&D Systems Cat No 313-T1, Lot No BKC06). Individual colonies obtained from the eluted phage pools are grown and i) induced for new phage production and ii) induced with IPTG for Nanobody expression and extraction (periplasmic extracts) according to standard methods (see for example the prior art and applications filed by applicant cited herein).

Example 15

Screening for Ang1 Binding Nanobodies

In order to determine binding specificity to Ang1, the clones are tested in an ELISA binding assay setup, using the monoclonal phage pools. Phage binding to Ang1 (R&D Systems Cat No 923-AN/CF, Lot No FHWO73091) is tested. Shortly, 0.2 ug/ml Ang1 is immobilized on Maxisorp ELISA plates (Nunc) and free binding sites are blocked using 4% Marvel skimmed milk in PBS. Next, 10 ul of supernatant from the monoclonal phage inductions of the different clones in 100 ul 2% Marvel PBS are allowed to bind to the immobilized antigen. After incubation and a wash step, phage binding is revealed using a HRP-conjugated monoclonal-anti-M13 antibody (Gentaur Cat#27942101). Binding specificity is determined based on OD values compared to controls having received an irrelevant phage or no phage.

FIG. 8 and Table B-5 show a selection of clones binding to Ang1.

TABLE B-5

Nanobodies against Ang1

| Name | SEQ ID NO: | Sequence |
|---|---|---|
| 173-H9 | 472 | EVQLVESGGGLVQPGGSLRLSCAASGFTLSGNWMYWLRQAPGKG LEWISTITPRGLTAYADSVKGRFTISRDIAENTLYLQMNSLKSGDTA VYYCARDKTGERRGQGTQVTVSS |
| 184-B6 | 473 | EVQLVESGGGLVQPGGSLRLSCAASGFTFSNYAMTWVRQAPGKG LEWVSDISWDGDITTYAASVKGRFTISRDNAKKTLYLQMNSLKPE DSAVYYCNTYGYDSGRYYSYWGQGTQVTVSS |
| 185-H5 | 474 | EVQLVESGGGLVQPGGSLRLSCAASGFTLDYYAIGWFRQAPGKER EGVSYISSSDGRTYYADSVKGRFTISRDNAKNTVYLQMNSLKPED TAVYYCATDLSGRGDVSEYEYDYWGQGTQVTVSS |

Sequences alignments of Ang1 binding Nanobodies (FRs in small
letters, CDRs in capital letters):

| | |
|---|---|
| 185-H5 | evqlvesggglvqpggslrlscaasgftld.YYAIGwfrqapgkeregvsYISSSDGRTY |
| 173-H9 | evqlvesggglvqpggslrlscaasgftlsGNWMY.wlrqapgkglewis.TITPRGLTA |
| 184-B6 | evqlvesggglvqpggslrlscaasgftfs.NYAMTwvrqapgkglewvsDISWDGDITT |
| 185-H5 | YADSVNGrftisrdnakntvylqmnslkpedtavyycatDLSGRGDVSEYEYDYwgqgtq |
| 173-H9 | YADSVKGrftisrdiaentlylqmnslksgdtavyycarDKTGER.........rgqgtq |
| 184-B6 | YAASVKGrftisrdnakktlylqmnslkpedsavyycnt..YGYDSGRYYSY..wgqgtq |
| 185-H5 | vtvss |
| 173-H9 | vtvss |
| 184-B6 | vtvss |

Members:
Families of binders (one family of Nanobodies has same CDR3):

| | Members: |
|---|---|
| I | 173-H9 |
| II | 184-B6 |
| III | 185-H5 |

Example 16

Selections of Phage Displaying Ang4 Binding Nanobodies

Phage libraries 171 and 172 (see example 9) are used for selections on recombinant human Angiopoietin-4 (R&D Systems Cat No 964-AN/CF). Ang4 is immobilized directly on Maxisorp 96 well microtiter plates (Nunc) at 5 ug/ml, 0.5 ug/ml and 0 ug/ml (control).
Following incubation with the phage libraries and extensive washing, bound phage is eluted with trypsin. The eluted phage are amplified and applied in a second round of selection on 2 ug/ml, 0.2 ug/ml, 0.02 ug/ml and 0 ug/ml (control) immobilized Ang4. In this second round, and following incubation with the phage libraries and extensive washing, bound phage is eluted with trypsin. Individual colonies obtained from the eluted phage pools are grown and i) induced for new phage production and ii) induced with IPTG for Nanobody expression and extraction (periplasmic extracts) according to standard methods (see for example the prior art and applications filed by applicant cited herein).

Example 17

Screening for Ang4 Binding Nanobodies

In order to determine binding specificity to Ang4, the clones are tested in an ELISA binding assay setup, using the monoclonal phage pools. Phage binding to Angiopoietin-4 (R&D Systems Cat No 964-AN/CF) was tested. Shortly, 0.2 ug/ml Ang1 is immobilized on Maxisorp ELISA plates (Nuns) and free binding sites are blocked using 4% Marvel skimmed milk in PBS. Next, 10 ul of supernatant from the monoclonal phage inductions of the different clones in 100 ul 2% Marvel PBS are allowed to bind to the immobilized antigen. After incubation and a wash step, phage binding is revealed using a HRP-conjugated monoclonal-anti-M13 antibody (Gentaur Cat#27942101). Binding specificity is determined based on OD values compared to controls having received an irrelevant phage or no phage.

FIG. 9 and Table B-6 show a selection of clones binding to Ang4.

TABLE B-6

Nanobodies against Ang4

| Name | SEQ ID NO: | Sequence |
|---|---|---|
| 168-A3 | 475 | EVQLVESGGGLVQPGGSLRLSCAASGFTLSGNWMYWLRQAPGK GLEWISTITPRGLTAYADSVKGRFTISRDIAENTLYLQMNSLKSGD TAVYYCARDKTGERRGQGTQVTVSS |
| 168-E5 | 476 | EVQLVESGGGLVQPGGSLRLSCAASGFTLSSNWMYWLRQAPGK GLEWISTITPRDLTAYADSVKGRFTISRDNAENTLYLQMNSLKSE DTAVYYCAKDKAGERRGQGTQVTVSS |

TABLE B-6-continued

Nanobodies against Ang4

| Name | SEQ ID NO: | Sequence |
|---|---|---|
| 168-G3 | 477 | EVQLVESGGGLVQPGGSLRLSCAASGSTLDYYAIGWYRQAPGKE REWVSCISSSNYGITTYADSVKGRFTISRDNAKNTVYLQMNSLKP EDTAIYYCATNTRRKYGRLCDLNADYWGQGTQVTVSS |
| 169-A10 | 478 | EVQLVESGGGLVQPGGSLRLSCATSGFTFSPSWMYWLRQAPGKG LEWVSTITPRGLTEYANSVKGRFTISKDNAKNTLYLQMNSLKSED TAVYYCTRDKNGPPMGQGTQVTVSS |
| 169-A12 | 479 | EVQLVESGGGLVQPGGSLRLSCVASGSIRSIIHMGWYRQAPGNER DLVAVIIDSRTTKYSESVKGRFTISRDNAKNTVYLQMNSLKPEDT AVYYCNALALGTDQSSTFDSWGQGTQVTVSS |
| 169-B12 | 480 | EVQLVESGGGLVQAGGSLRLSCAASGSIFSINAMGWYRQAPGNQ RDLVAAITSGDSTKYADFVKGRFTISRDNAKNTVYLQMNSLKPE DTAVYYCAAELLGKWYWGQGTQVTVSS |
| 169-C12 | 481 | EVQLVESGGGLVQPGGSLRLSCAASGSIRSIIHMGWYRQTPGNER DMVAVIIDSRTTKYAESVKGRFTISRDNAKNTVYLQMNSLKPED TAVYYCNALALGTDQSSTFDSWGQGTQVTVSS |
| 169-C8 | 482 | EVQLVESGGGLVQPGGSLRLSCATSGFTFSTSWMYWLRQAPGKG LEWVSTITPRGLTDYTDSVKGRFTISRDSAKNTLYLQMNSLKSED TADYYCTRDKNGPPMGQGTQVTVSS |
| 169-E12 | 483 | EVQLVESGGGLVQAGGSLRLSCAASGSIFSINTMGWYRQAPGNQ RDLVAAITNGGSTKYVDSVKGRFTISRDNAKNTVYLQMNSLKPE DTAVYYCAAESLGRWGWGQGTQVTVSS |
| 169-F11 | 484 | EVQLVESGGGLVQPGGSLRLSCATSGFTFSTSWMYWLRQAPGKG LEWVSTITPRGLTDYTNSVKGRFTVSRDNAKNTLYLQMNSLKSE DTAVYYCTKDKNGPPMGQGTQVTVSS |

Sequences alignments of Ang4 binding Nanobodies (FRs in small letters, CDRs in capital letters):

```
169-F11  evqlvesggglvqpggslrlscatsgftfsTSWMYwlrqapgkglewvs..TITPRGLTD

169-C8   evqlvesggglvqpggslrlscatsgftfsTSWMYwlrqapgkglewvs..TITPRGLTD

169-A10  evqlvesggglvqpggslrlscatsgftfsPSWMYwlrqapgkglewvs..TITPRGLTE

168-E5   evqlvesggglvqpggslrlscaasgftlsSNWMYwlrqapgkglewis..TITPRDLTA

168-A3   evqlvesggglvqpggslrlscaasgftlsGNWMYwlrqapgkglewis..TITPRGLTA

168-G3   evqlvesggglvqpggslrlscaasgstldYYAIGwyrqapgkerewvsCISSSNYGITT

169-B12  evqlvesggglvqaggslrlscaasgsifsINAMGwyrqapgnqrdlva..AITSGDSTK

169-E12  evqlvesggglvqaggslrlscaasgsifsINTMGwyrqapgnqrdlva..AITNGGSTK

169-A12  evqlvesggglvqpggslrlscvasgsirsIIHMGwyrqapgnerdlva..VIIDSRTTK

169-C12  evqlvesggglvqpggslrlscaasgsirsIIHMGwyrqtpgnerdmva..VIIDSRTTK

169-F11  YTNSVKGrftvsrdnakntlylqmnslksedtavyyctk..........DKNGPP.....

169-C8   YTDSVKGrftisrdsakntlylqmnslksedtadyyctr..........DKNGPP.....

169-A10  YANSVKGrftiskdnakntlylqmnslksedtavyyctr..........DKNGPP.....

168-E5   YADSVKGrftisrdnaentlylqmnslksedtavyycak..........DKAGER.....

168-A3   YADSVKGrftisrdiaentlylqmnslksgdtavyycar..........DKTGER.....

168-G3   YADSVKGrftisrdnakntvylqmnslkpedtaiyycatNTRRKYGRLQDLNADY.....

169-B12  YADFVKGrftisrdnakntvylqmnslkpedtavyycaa..........ELLGKWY....

169-E12  YVDSVKGrftisrdnakntvylqmnslkpedtavyycaa..........ESLGRWG....
```

```
169-A12  YSESVKGrftisrdnakntvylqmnslkpedtavyycna..........LALGTDQQSTF

169-C12  YAESVKGrftisrdnakntvylqmnslkpedtavyycna..........LALGTDQSSTF

169-F11  ..mgqgtqvtvss

169-C8   ..mgqgtqvtvss

169-A10  ..mgqgtqvtvss

168-E5   ..rgqgtqvtvss

168-A3   ..rgqgtqvtvss

168-G3   ..wgqgtqvtvss

169-B12  ..wgqgtqvtvss

169-E12  ..wgqgtqvtvss

169-A12  DSwgqgtqvtvss

169-C12  DSwgqgtqvtvss
```

Members:
Families of binders (one family of Nanobodies has same CDR3):

| | Members: |
|---|---|
| I | 169-F11, 169-C8, 169-A10 |
| II | 168-A3, 168-E5 |
| III | 168-G3 |
| IV | 169-B12, 169-E12 |
| V | 169-A12, 169-C12 |

Example 18

Selections of Phage Displaying Angptl4 Binding Nanobodies

Phage libraries 171 and 172 (see Example 9) are used for selections on recombinant human Angiopoietin-like-4 (R&D Systems Cat No 3485-AN).

Angptl4 is immobilized directly on Maxisorp 96 well microtiter plates (Nunc) at 5 ug/ml, 0.5 ug/ml and 0 ug/ml (control). Following incubation with the phage libraries and extensive washing, bound phage is eluted with trypsin. The eluted phage are amplified and applied in a second round of selection on 2 ug/ml, 0.2 ug/ml, 0.02 ug/ml and 0 ug/ml (control) immobilized Angptl4. In this second round, and following incubation with the phage libraries and extensive washing, bound phage is eluted with trypsin. Individual colonies obtained from the eluted phage pools are grown and i) induced for new phage production and ii) induced with IPTG for Nanobody expression and extraction (periplasmic extracts) according to standard methods (see for example the prior art and applications filed by applicant cited herein).

Example 19

Screening for Angptl4 Binding Nanobodies

In order to determine binding specificity to Angptl4, the clones are tested in an ELISA binding assay setup, using the monoclonal phage pools. Phage binding to recombinant human Angiopoietin-like-4 (R&D Systems Cat No 3485-AN) is tested. Shortly, 0.2 ug/ml Ang1 was immobilized on Maxisorp ELISA plates (Nunc) and free binding sites are blocked using 4% Marvel skimmed milk in PBS. Next, 10 ul of supernatant from the monoclonal phage inductions of the different clones in 100 ul 2% Marvel PBS are allowed to bind to the immobilized antigen. After incubation and a wash step, phage binding is revealed using a HRP-conjugated monoclonal-anti-M13 antibody (Gentaur Cat#27942101). Binding specificity is determined based on OD values compared to controls having received an irrelevant phage or no phage.

FIG. 10 and Table B-7 show a selection of clones binding to Angptl4.

TABLE B-7

Nanobodies against Angptl4

| Name | SEQ ID NO: | Sequence |
|---|---|---|
| 170-B1 | 485 | EVQLVESGGGLVQAGGSLRLSCAASESIFSLYVTGWYRQAPGKQREL VASITSGGSLTYADSVKGRFTISRDNAKNTVHLQMHSLKPEDTAVYF CNGRSIGVDDMPYVYWGQGTQVTVSS |

TABLE B-7-continued

Nanobodies against Angptl4

| Name | SEQ ID NO: | Sequence |
|---|---|---|
| 170-C2 | 486 | EVQLVESGGGLVQPGGSLRLSCAASGFTFSLNAMTWVRQAPGKGLE<br>WVSTISSGGWTTSYADSVKGRFTISRDNAKNTLYLQMNSLKPEDMA<br>VYYCAKGSEFNGYEVRGQGTQVTVSS |
| 170-E2 | 487 | EVQLVESGGGLVQAGGSLRLSCAASGSISSINVMGWYRQAPGKQRDL<br>VATITRALNTAYATSVKGRFTISRDNFTNTVYLQMNSLEPEDTAVYY<br>CNAGGYYTNLRTGGNYWGQGTQVTVSS |
| 170-F2 | 488 | EVQLVESGGGLVQAGGSLRLSCAASGIFIIDTMGWYRQAPGKQRELV<br>ASITPTGNTNYVDSVKGRFAISRDNNKNTMHLQMNSLKPEDTAVYY<br>CNAVYPRYYGDDDRPPVDSWGQGTRVTVSS |
| 170-H1 | 489 | EVQLVESGGGLAQAGGSLRLSCAASGSISSINVMGWYRQAPGKQRDL<br>VAVITRALNTNYATSVKGRFTISRDDFKDTVYLQMNSLEPEDTAVYY<br>CNAGGYYTNLRTGGNYWGQGTQVTVSS |
| 171-A2 | 490 | EVQLVESGGGQVQAGDSLRLSCKASRRTISTYGMGWFRQAPGDKRD<br>LVSSISASGASTYYVDSVKGRFTISRDNIKNTVYLQMNSLKPEDAAVY<br>YCAAAPNGRFITMSAHVDSWGQGTQVTVSS |
| 171-A3 | 491 | EVQLVESGGGQVQAGDSLRLSCKASRRTISTYGMGWERQAPGDKRD<br>LVSSISASGASTYYVDSVKGRFTISRDNIKNTVYLQMNSLKPEDAAVY<br>YCAAAPNGRFITMSTHVDYWGQGTQVTVSS |
| 171-C4 | 492 | EVQLVESGGGLVQPGGSLRLSCAASGRTFSTFNTYSMGWFRQAPGKE<br>REFVAAISRGGNVTPYADSVKGRFAISRDNAKNTVALQMNSLKPEDT<br>AVYYCAASKIGIASTIRYYDYWGQGTQVTVSS |
| 171-D2 | 493 | EVQLVESGGGLVQAGGSLRLSCAASVLTFGTYTVGWFRQAPGKERE<br>FVSIITGSGTYNDYADSVKGRFTVSRDNAKNTVYLQMNSLKSEDTAV<br>YYCAARHWGMFSRSENDYNYWGQGTQVTVSS |
| 171-E2 | 494 | EVQLVESGGGLVQAGASLRLSCVDSGDTFSWYAMGWFRQQAPGKE<br>REFVSSISGGGSNTVYADSVKGRFTVSRDRAKNTVYLQMNSLKPEDS<br>GVYYCAADKRWGSPATSRSTHDYDFWGQGTQVTVSS |
| 171-E4 | 495 | EVQLVESGGGLVQPGGSLRLSCAASGRTFSTFNTYSMGWFRQAPGKE<br>REFVAAISRSGNVTPYADSVKGRFAISRDNAKNTLTLQMNSLKPEDT<br>AVYYCAASKIGIASTIRYYDYWGQGTQVTVSS |
| 171-F3 | 496 | EVQLVESGGGLVQTGGSLRLSCAASGRSFNLYYMGWFRQAPGRERE<br>FVAGISGSGGSTFYGDSVKGRFTISRDNLKNTMYLQMNSLKPEDTAV<br>YYCQSSRRIITNPREYGYWGQGTQVTVSS |
| 171-G2 | 497 | EVQLVESGGGLVQAGGSLRLSCTASGLTFSMYAMAWIRLAPGKERE<br>VIAAIDWSGGSTFYGDSVKGRFTISRDNAKNTVYLEMNSLKPEDTAV<br>YYCAANRRIYSSGSSLSDNSLYNFWGQGTQVTVSS |
| 171-G4 | 498 | EVQLVESGGGLVQAGGSLRLSCVASGDTFNWYAMGWFRQQAPGKE<br>REFVSAISGGGSNIVYVDSVKGRFTVSRDRIKNTVYLQMNSLKPEDSG<br>VYYCAVDKRWGSPATSRSTHDYDFWGQGTQVTVSS |
| 170-G3 | 499 | EVQLVESGGGLVQAGGSLRLSCAASETIFASAMGWYRQPPGKQREL<br>VARITRGGSTNYAESVKGRFAISRDNADSTLYLRMNNLKPEDTAVYY<br>CNADTIGHSSSYITYWGQGTQVTVSS |
| 171-H2 | 500 | EVQLVESGGGLVQAGGSLRLSCAASGRPFSMYAMGWFRQAPGKERE<br>FVTVITWSGGSTYYADSVKGRFTISKDIAKNTVYLQMNSLKPDDMAV<br>YYCAAARRYGNLYNTNNYDYWGQGTQVTVSS |
| 171-H4 | 501 | EVQLVESGGGQVQAGDSLRLSCKASRRTISTYGMGWFRQAPGDKRD<br>LVSSISASGASTYYVDSVKGRFTISRDNIKNTVYLQMNSLKPEDAAVY<br>YCAAAPNGRFITMSTHVDSWGQGTQVTVSS |

| | Sequences alignments of Angptl4 Nanobodies (FRs in small letters, CDRs in capital letters): |
|---|---|
| 171-G4 | evqlvesggglvqaggslrlscvasgdtfn...WYAMGwfrqqapgkerefv.SAISGGG |
| 171-E2 | evqlvesggglvqagaslrlscvdsgdtfs...WYAMGwfrqqapgkerefv.SSISGGG |
| 170-H1 | evqlvesgggglaqaggslrlscaasgsiss...INVMGwyr.qapgkqrdlva..VITRA |
| 170-E2 | evqlvesggglvqaggslrlscaasgsiss...INVMGwyr.qapgkgrdlva..TITRA |
| 171-H2 | evqlvesggglvqaggslrlscaasgrpfs...MYAMGwfr.qapgkerefvt.VITWSG |
| 171-E4 | evqlvesggglvqpggslrlscaasgrtfsTFNTYSMGwfr.qapgkerefva.AISRSG |
| 171-C4 | evqlvesggglvqpggslrlscaasgrtfsTFNTYSMGwfr.qapgkerefva.AISRGG |
| 170-F2 | evqlvesggglvqaggslrlscaasgifii....DTMGwyr.qapgkqrelva..SITPT |
| 170-B1 | evqlvesggglvqaggslrlscaasesifs...LYVTGwyr.qapgkqrelva..SITSG |
| 171-F3 | evqlvesggglvqtggslrlscaasgrsfn...LYYMGwfr.qapgrerefva.GISGSG |
| 171-H4 | evqlvesgggqvqagdslrlsckasrrtis...TYGMGwfr.qapgdkrdlvs.SISASG |
| 171-A2 | evqlvesgggqvqagdslrlsckasrrtis...TYGMGwfr.qapgdkrdlvs.SISASG |
| 171-A3 | evqlvesgggqvqagdslrlsckasrrtis...TYGMGwfr.qapgdkrdlvs.SISASG |
| 171-D2 | evqlvesggglvqaggslrlscaasvltfg...TYTVGwfr.qapgkerefvs.IITGSG |
| 170-G3 | evqlvesggglvqaggslrlscaasetifa....SAMGwyr.qppgkqrelva..RITRG |
| 170-C2 | evqlvesggglvqpggslrlscaasgftfs...LNAMTwvr.qapgkglewvs.TISSGG |
| 171-G2 | evqlvesggglvqaggslrlsctasgltfs...MYAMAwir.lapgkerevia.AIDWSG |
| 171-G4 | SNIVYVDSVKGrftvsrdrikntvylqmnslkpedsgvyycav...DKRWGSPATSRSTH |
| 171-E2 | SNTVYADSVKGrftvsrdrakntvylqmnslkpedsgvyycaa...DKRWGSPATSRSTH |
| 170-H1 | LNTNYATSVKGrftisrddfkdtvylqmnslepedtavyycna......GGYYTNLRTGG |
| 170-E2 | LNTAYATSVKGrftisrdnftntvylqmnslepedtavyycna......GGYYTNLRTGG |
| 171-H2 | GSTYYADSVKGrftiskdiakntvylqmnslkpddmavyycaa......ARRYGNLYNTN |
| 171-E4 | NVTPYADSVKGrfaisrdnakntltlqmnslkpedtavyycaa....SKIGIASTIRYYD |
| 171-C4 | NVTPYADSVKGrfaisrdnakntvalqmnslkpedtavyycaa....SKIGIASTIRYYD |
| 170-F2 | GNTNYVDSVKGrfaisrdnnkntmhlqmnslkpedtavyycna...VYPRYYGDDDRPPV |
| 170-B1 | GSLTYADSVKGrftisrdnakntvhlqmhslkpedtavyfcng......RSIGVDDMPYV |
| 171-F3 | GSTFYGDSVKGrftisrdnlkntmylqmnslkpedtavyycqs.....SRRIITNPREYG |
| 171-H4 | ASTYYVDSVKGrftisrdnikntvylqmnslkpedaavyycaa....APNGRFITMSTHV |
| 171-A2 | ASTYVDSVKGrftisrdnikntvylqmnslkpedaavyycaa....APNGRFITMSAHV |
| 171-A3 | ASTYYVDSVKGrftisrdnikntvylqmnslkpedaavyycaa....APNGRFITMSTHV |
| 171-D2 | TYNDYADSVKGrftvsrdnakntvylqmnslksedtavyycaa....RHWGMFSRSENDY |
| 170-G3 | GSTNYAESVKGrfaisrdnadstlylrmnnlkpedtavyycna.......DTIGHSSSYI |
| 170-C2 | WTTSYADSVKGrftisrdnakntlylqmnslkpedmavyycak.......GSEFNGYEV. |
| 171-G2 | GSTFYGDSVKGrftisrdnakntvylemnslkpedtavyycaaNRRIYSGSSLSDNSLY |
| 171-G4 | DYDFwgqgtqvtvss |
| 171-E2 | DYDFwgqgtqvtvss |
| 170-H1 | NY..wgqgtqvtvss |
| 170-E2 | NY..wgqgtqvtvss |
| 171-H2 | NYDYwgqgtqvtvss |

| | | |
|---|---|---|
| 171-E4 | Y...wgqgtqvtvss | |
| 171-C4 | Y...wgqgtqvtvss | |
| 170-F2 | DS..wgqgtrvtvss | |
| 170-B1 | Y...wgqgtqvtvss | |
| 171-F3 | Y...wgqgtqvtvss | |
| 171-H4 | DS..wgqgtqvtvss | |
| 171-A2 | DS..wgqgtqvtvss | |
| 171-A3 | DY..wgqgtqvtvss | |
| 171-D2 | NY..wgqgtqvtvss | |
| 170-G3 | TY..wgqgtqvtvss | |
| 170-C2 | ....rgqgtqvtvss | |
| 171-G2 | NF..wgqgtqvtvss | |

Members:
Families of binders (one family of Nanobodies has same CDR3):

| | members: |
|---|---|
| I | 171-A3, 171-A2 |
| II | 170-E2, 170-H1 |
| III | 171-H2 |
| IV | 171-E2, 171-G4 |
| V | 171-E4, 171-C4 |
| VI | 170-G3 |
| VII | 170-B1 |
| VIII | 170-F2 |
| IX | 171-F3 |
| X | 171-D2 |
| XI | 170-C2 |
| XII | 171-G2 |

Example 20

List of General In Vitro, Cell-Based or In Vivo Assays

In vitro binding assays: ELISA, Biacore

In vivo binding assay: Flow cytometry

Solid-phase receptor binding and blocking assays (Onliner et al. 2004, supra): ELISA-based assays with either immobilized ligand or receptor, where inhibition of binding of receptor/ligand is determined. E.g. suitable cell-based assay for Tie2, Ang1 or/and Ang2 Nanobodies.

Receptor activation/inactivation assays (Fiedler et al., 2003, Harfouche and Hussain, 2006: both supra): Western blot detection of phosphorylated receptor (activated) or phosphorylation of components of the downstream signalling pathways. E.g. suitable cell-based assay for Tie2, Ang1 or/and Ang2 Nanobodies.

Cell proliferation assays (Onliner et al., 2004, supra): Inhibition of tumour endothelial cell (e.g. specific tumor cell lines or "general" endothelial cells such as human umbilical cord endothelial cells (HUVECs) proliferation is assayed on tumour cells stimulated with or without addition of the neutralizing nanobody. Cell proliferation is determined by counting the number of live cells by FACS analysis.

In vivo angiogenesis assay (Onliner et al. 2004, supra): Assay determining the effect on the tumour growth by addition of neutralizing nanobodies in xenografts studies. E.g. suitable in vivo assay for Tie2, Ang1 or/and Ang2 Nanobodies.

In vivo direct anti angiogenic effect (Onliner et al. 2004, supra): Assay determining a direct antineovascular effect in viva by rat corneal angiogenesis model. E.g. suitable in vivo assay for Tie2, Ang1 or/and Ang2 Nanobodies.

Lipoprotein lipase (LPL) assay: Measurement of LPL activity using $^3$H-oleic acid as substrate (Yoshida et al., 2002, supra). E.g. suitable in vitro assay for Angptl4.

In vivo .CAM (chick chorioallantoric membrane) assay: Assay determining inhibition or not of vascularisation by addition of Angptl4 binding nanobodies using a CHO-Angptl4 expressing cell line (Le Jan et al., 2003, supra). E.g. suitable in vivo assay for Angptl4.

In vivo animal model studies: Assay determine the effect of injecting Angptl4 nanobodies on the lipid metabolism of transgenic mice overexpressing h Angptl4 (Koster et al., 2005, supra). E.g. suitable in vivo assay for Angptl4.

Example 21

List of Particularly Preferred Embodiments of Amino Acid Sequences of the Invention Amino acid sequence comprising e.g. 2 Nanobodies with antagonistic effect for the same target, e.g. Tie2, either being directed against two different epitopes, or being against the same epitope.

Amino acid sequence comprising a Nanobody against the Tie2 receptor and a Nanobody against angiopoietin 1.

Amino acid sequence comprising a Nanobody against the Tie2 receptor and a Nanobody against angiopoietin 2.

Amino acid sequence comprising a cytotoxic compound (e.g. peptidic toxin, e.g. immunotoxin) and a Nanobody wherein the said Nanobody is able to disrupt at least one of the Tie/Ang or Angptl interactions, e.g. Ang1/Tie2 or Ang2/Tie2 interactions. The amino acid sequences of the invention such as those presented e.g. in SEQ ID NOs: 455 to 501 may be used for targeting specific types of cancers.

Example 22

List of Target Proteins of the Invention (Links to Nucleic and Amino Acid Sequence)

| Tie1, Tie2, Ang1, Ang2, Ang3, Ang4, Angptl1, Angptl2, Angptl3, Angptl4, Angptl5, and Angptl6 | Sequences from various species found e.g. on http://www.ncbi.nlm.nih.gov/sites/entrez |
|---|---|
| Human Tie1 | NM_005424 |
| Human Tie2 | NM_000459 |
| Human Ang1 | NM_001146 |
| Human Ang2 | NM_001147 |
| Human Ang3 | AF074332 |
| Human Ang4 | NM_015985 |
| Human Angptl1 | NM_004673 |
| Human Angptl2 | BC012368 |
| Human Angptl3 | NM_014495 |
| Human Angptl4 | NM_001039667 |
| Human Angptl5 | NM_178127 |
| Human Angptl6 | NM_031917 |

Example 23

Further Analysis of Tie-2 Nanobody 163E9

Reagents Used
Recombinant Human Angiopoietin-1 (R&D SYSTEM catolog number: 923-AN); Recombinant Human Angiopoietin-2 (R&D SYSTEM catolog number: 623-AN); Anti-total Erk p44/42 MAPK (Cell Signaling Technology catolog number 49102); Anti-Phospho Erk p44/42 MAPK (Thr 202/Tyr 204) (E10) (Cell Signaling Technology catolog number #9106S); Anti-total Akt (C67E7) (Cell Signaling Technology catolog number 44691); Anti-Phospho-Akt (Ser473) (D9E) (Cell Signaling Technology catalog number #4060); Anti Tie-2/TEK, clone Ab33 (UPSTATE catalog number #05-584); Anti-Phosphotyrosine, 4G10 (Platinum Millipore)

Example 23a

The Tie-2 Nanobody 163E9 Inhibits Ang-1 Induced Phosphorylation of Akt and Erk as Determined by Bioplex Analysis To identify Tie-2 Nanobodies that inhibits Ang-1-induced activation of Tie-2, signalling pathways, the Bio-Plex phosphoprotein and total target assays was used. With this assay the phosphorylation and expression of proteins in lysates derived from cell culture or tissue samples, respectively are determined. The Bio-Plex total target assay reports the abundance of the target protein in one well, while the Bio-Plex phosphoprotein assay reports the phosphorylation level of the same protein in a separate well.

Method:
The Bio-Plex assay used a selection of beads with different spectral addresses, each coupled to antibodies against a different target, (in total target assay Akt and ERK 1/2; in phosphoprotein assay Akt ($Ser^{473}$) and ERK 1/2 ($Thr^{202}/Tyr^{204}$, $Thr^{185}/Tyr^{187}$)) The coup beads were added to wells of a 96-well plate. Cell lysates, in a protein range concentration of 200-900 µg/ml derived from HUVECs appropriately treated, were added to the wells containing coupled beads. The incubation was left for 15-18 hr. Biotin-labeled detection antibodies specific for secondary epitopes on each target are added to wells. The incubation was left for 30 min. Fluorescently labeled streptavidin reporter, able to bind to biotin-labeled detection antibodies, was added to the wells. The incubation was left for 10 min. After rinse, the complex was resuspended in assay buffer. In The Bio-Flex array reader, a red classification laser and a green reporter laser illuminated individual beads to identify each bead's spectral address and associated reporter signal. Dyed beads were identified by their internal fluorescent signature, the level of target bound to beads was indicated by intensity of reporter signal. Multiplex data were reported simultaneously.

HUVECs (Human umbilical vein endothelial cells) were obtained by treating human umbilical cord vein with collagenase and cultured in M199 containing 20% FCS (2% Penicillin-Streptomycin, brain extract and 25 µg Heparin sodium sulfate). After starvation for 3-4 hr in M199 containing 0.5% BSA, the cells were treated with indicated concentration of Tie-2 Nanobodies for 10 min and then stimulated with 100 ng/ml h-Ang-1 for 10 min. Cells were rinsed in ice-cold cell wash buffer and lysed in buffer with protease and phosphatase inhibitors. Proteins concentration were measured through BCA (Bicinchoninic acid) assay and an equal amount of protein for each sample, ranging between 200-900 µg/ml, was used for Bio-plex analysis. Ratio of phospho-Akt to Akt and phospho-ERK to ERK is reported in FIGS. 11 and 12 respectively. Ø indicate non Ang-1 stimulated samples. Among anti-Tie2 NBs tested, only Nanobody 163E9 was able to block the Ang1-induced Akt and Erk phosphorylation both at 7.5 ug/ml (~500 nM) and 1 ug/ml (~67 nM). None of the others Tie-2 Nanobodies inhibited phosphorylation of AKt and Erk.

Example 23b

Nanobody 163E9 Dose-Dependently Inhibits Ang-1 Induced Phosphorylation of Akt and Erk as Determined by Western Blotting HUVEC (Human umbilical vein endothelial cells) were obtained by treating human umbilical cord vein with collagenase and cultured in M199 containing 20% FCS (2% Penicillin-Streptomycin, brain extract and 25 µg Heparin sodium sulfate).

HUVECs were plated in 6-well plates and used in subconfluent condition ($1.5 \pm 10^5/9.6$ mm dishes). After starvation in M199 containing 0.5% BSA for 3-4 hr, the cells were treated with indicated concentration (of Nanobodies for 10 min and then stimulated with 100 ng/ml h-Ang-1 for 10 mM. Cells were rinsed in ice-cold PBS and lysed in boiling buffer (500 mM Tris HCl, ph 6.8; 10% SDS, Glycerol). Lysates were clarified by centrifugation and proteins concentration was measured through BCA (Bicinchoninic acid) assay. 10 µg proteins were resolved by 10% SDS-PAGE, transferred to nitrocellulose membrane and subject to Western Blot analysis with anti-total Erk 1/2, anti-phospho-Erk 1/2, anti total Akt and anti-phospho-Akt. The corresponding chemiluminescent signal is acquired and quantified by a CCD camera. Ratio of phospho-Akt to Akt (FIG. 13) and phospho-ERK to ERK (FIG. 14) is reported. Nanobody 163E9 dose-dependently inhibited Ang-1 induced phosphorylation of Akt and Erk.

Example 23c

The Tie-2 Nanobody 163E9 Reverses the Anti-Apoptotic Effect of Ang-1

Serum starvation of HUVECS is known to result in apoptotic cell death, a process that can be inhibited by Ang-1. To further demonstrate that the Tie-2 Nanobody 163E9 interferes with Ang-1 induced activities through Tie-2, it was investigated if Nanobody 163E9 would be able to reverse the anti-apoptotic activity of Ang-1.

Apoptosis experiments were performed using the Cell Death Detection ELISA$^{PLUS}$ kit (Roche) evaluating the level of nucleosome associated DNA fragments. HUVECs cells were seeded in 24 wells ($2\ 10^4$ cells/well) or 6 wells ($9.8\ 10^4$ cells/well) and treated over-night with different growth factors indicated. Buffers and reagents used in the procedure are supplied with the kit. Cells were lysed with 200 µl or 980 µl of Lysis Buffer for 30 min at room temperature and lysates were centrifuged at 200 g for 10 min. ELISA assay was performed with 20 µl of the sample supernatant and 80 µl of the immunoreagent. The immunoreagent was prepared by mixing 1/20 volume of Anti-DNA-HRP and 1/20 Anti-histon-biotin with 18/20 volumes of incubation Buffer. The immunoassay binding reaction was allowed to proceed for 2 hours after which the excess of reagent was removed with two washes of Incubation Buffer (200 µl each). The quantitative determination of the amount of nucleosome was assessed by the evaluation of HRP (Horse Readish Peroxidase) retained by the immunocomplex which is photometrically measured with ABTS as substrate. Finally the colorimetric reaction is blocked after 10-15 min with ABST Stop Solution.

Nanobodies against Tie-2 were tested in HUVECs cells, stimulated over-night with Ang-1 (300 ng/ml) or growth factors-starved (SF) as a control. As shown in FIG. 15, Ang-1 strongly inhibited apoptosis following serum starvation. Importantly, Nanobody 163E9 dose-dependently inhibited the anti-apoptotic activity of Ang-1. Indeed lowering the Nanobody concentrations resulted in reduced cell apoptotsis.

Example 23d

Nanobody 163E9 Dose-Dependently Inhibits Ang-1 Induced Phosphorylation of Tie-2

Following binding of Ang-1 to Tie-2, the cytoplasmic tail of Tie-2 becomes phosphorylated. To further demonstrate that the Tie-2 Nanobody 163E9 interferes with Ang-1-induced activities through Tie-2, it was investigated if Nanobody 163E9 would be able to inhibit phosphorylation of Tie-2.

HUVEC (Human umbilical vein endothelial cells) were obtained by treating human umbilical cord vein with collagenase and cultured in M199 containing 20% FCS (2% Penicillin-Streptomycin, brain extract and 25 µg Heparin sodium sulfate).

After starvation in M199 containing 0.5% BSA for 3-4 hr, the cells were treated with indicated concentration (ng/ml) of Nanobodies for 10 min and then stimulated with h-Ang-1 for 10 min. Cells were rinsed in ice-cold PBS 1× and lysed at 4° C. in EB buffer (10 mM TrisHCl, ph 7.5, 150 mM NaCl, 5 mM EDTA, 1% Triton X100, 10% Glycerol) with protease and phosphatase inhibitors (50 µg/ml pepstatin, 50 µg/ml leupeptin, 10 µg/ml aprotinin, 1 mM phenylmethylsulfonyl fluoride, 100 µM $ZnCl_2$, 1 mM $Na_3VO_4$). Lysates (450-800 µg) were incubated with protein G-Sepharose and anti-Tie-2 antibody (1 µg) for 2 hr at 4° C. After washes, immunoprecipitates were resolved in 6% SDS-PAGE and immunoblotted for P-Tyr and Tie-2. As shown in FIG. 16, at the highest concentration of Nanobody 163E9 used, phosphorylation of Tie-2 was indeed reduced.

Example 23e

Nanobody 163E9 Dose-Dependently Inhibits Ang-1 Induced Sprouting of Endothelial Cells HUVECS were trypsinized, counted, and suspended at a density of 4 cells/µl in culture medium containing 20% Methocel (Sigma) (20 ml of Methocel stock with 80 ml of M-199 20% FCS, 0.1 mg/ml heparin, and 0.1 mg/ml brain extract). 800 cells were seeded into non-adherent round-bottom 96-well plates, and cultured overnight at 37° C. The following day the formed spheroids were harvested, centrifuged for 15' at 300 g at room temperature, and embedded into Collagen gels. A diluted collagen-I (Sigma, from rat tail) solution was prepared before use by mixing 7 vol collagen (equilibrated to 3 mg/ml in sterile 0.2% acetic acid pH 3, 4° C.), 1 vol 10×M-199, 1 vol 0.1 N NaOH, and 1 vol 0.2 M HEPES pH 7.3. The EC spheroids were suspended in 200 µl of M-199 medium containing 40% FCS with or without 100 ng/ml Ang1 and Nanobody 163E9 at concentrations indicated, and mixed with an equal volume of diluted collagen solution. The spheroids were rapidly transferred into 96-well plates (400 µl/well) to allow polymerizing.

Capillary-like sprouts were examined with inverted-phase contrast microscope (Leica Microsystem, Heerbrugg, Switzerland) and photographed. The lengths and projected areas of the capillary-like structures were quantified with the imaging software winRHIZO Pro (Regent Instruments Inc.).

As shown in FIG. 17, Nanobody 163E9 dose-dependently inhibited sprouting of HUVEC cells induced by Ang-1.

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety for the purpose and information indicated in the specification.

Preferred Embodiments

1. Amino acid sequence comprising at least one single variable domain that is directed against and/or that specifically binds to a protein selected from the group consisting of Tie1, Tie2, Ang1, Ang2, Ang3, Ang4, Angptl1, Angptl2, Angptl3, Angptl4, Angptl5, and Angptl 6.

2. Amino acid sequence comprising at least one single variable domain that is directed against and/or that specifically binds to a protein selected from the group consisting of Tie1 and Tie2.

3. Amino acid sequence comprising at least one single variable domain that is directed against and/or that specifically binds to a protein selected from the group consisting of Ang1, Ang2. Ang3, and Ang4.

4. Amino acid sequence comprising at least one single variable domain that is directed against and/or that specifically binds to a protein selected from the group consisting of Angptl1, Angptl2, Angptl3, Angptl4, Angptl5, and Angptl6.

5. Amino acid sequence according to any previous or following embodiments that is in essentially isolated form.

6. Amino acid sequence comprising at least one single variable domain that is directed against and/or that specifically binds to a protein selected from the group consisting of human Tie1, human Tie2, human Ang1, human Ang2, human Ang3, human Ang4, human Angptl1, human Angptl2, human Angptl3, human Angptl4, human Angptl5, and human Angptl6.

7. Amino acid sequence comprising at least one single variable domain that is directed against and/or that specifically binds to a protein selected from the group consisting of human Tie1 and human Tie2.

8. Amino acid sequence comprising at least one single variable domain that is directed against and/or that specifically binds to a protein selected from the group consisting of human Ang1, human Ang2, human Ang3, and human Ang4.

9. Amino acid sequence comprising at least one single variable domain that is directed against and/or that specifically binds to a protein selected from the group consisting of human Angptl1, human Angptl2, human Angptl3, human Angptl4, human Angptl5, and human Angptl6.

10. Amino acid sequence comprising at least one single variable domain that is directed against and/or that specifically binds to a protein selected from the group consisting of the human Tie2, human Ang1, human Ang2, human Ang4, and human Angptl4.

11. Amino acid sequence comprising at least one single variable domain that is directed against and/or that specifically binds to a protein selected from the group consisting of human Tie2 and human Ang2.

12. Amino acid sequence according to any previous or following embodiments, wherein the variable domain i) is directed against and/or specifically binds to human Tie2; and ii) blocks the interaction between human Tie2 and at least one Ang, e.g. a human Ang.

13. Amino acid sequence according to any previous or following embodiments, wherein the variable domain i) is directed against and/or specifically binds to human Tie2; and ii) blocks the interaction between human Tie2 and only one Ang, e.g. a human Ang.

14. Amino acid sequence according to any previous or following embodiments, wherein the variable domain i) is directed against and/or specifically binds to human Tie2; and ii) blocks the interaction between human Tie2 and human Ang1.

15. Amino acid sequence according to any previous or following embodiments, wherein the variable domain i) is directed against and/or specifically binds to human Tie2; and ii) blocks the interaction between human Ang1 and human Tie2; and iii) does not block the interaction between human Ang2 and human Tie2.

16. Amino acid sequence according to any previous or following embodiments, wherein the variable domain i) is directed against and/or specifically binds to human Ang2; and ii) blocks the interaction between human Tie2 and human Ang2.

17. Amino acid sequence according to any previous or following embodiments, wherein the variable domain has an antagonistic effect to at least one member of the group of proteins consisting of Tie1 and Tie2.

18. An amino acid sequence according to any previous or following embodiments, wherein the variable domain has an agonistic effect to at least one member of the group of proteins consisting of Tie1 and Tie2.

19. Amino acid sequence according to any previous or following embodiments, wherein the variable domain has an antagonistic effect to human Tie2.

20. An amino acid sequence according to any previous or following embodiments, wherein the variable domain has an agonistic effect to human Tie2.

21. Amino acid sequence according to any previous or following embodiments, wherein the variable domain is able to inhibit the assembly of human Tie2 homodimers.

22. An amino acid sequence according to any previous or following embodiments, wherein the variable domain is able to enhance the assembly of human Tie2 homodimers.

23. An amino acid sequence according to any previous or following embodiments, wherein the variable domain is able to inhibit angiogenesis as e.g. measured in any of the herein disclosed in vitro cell based—or animal models.

24. Amino acid sequence according to any previous or following embodiments that can specifically bind to at least one member of the group of proteins consisting of Tie1, Tie2, Ang1, Ang2, Ang3, Ang4, Angptl1, Angptl2, Angptl3, Angptl4, Angptl5, and Angptl6 with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter.

25. Amino acid sequence according to any previous or following embodiments, that can specifically bind to at least one member of the group of proteins consisting of Tie1, Tie2, Ang1, Ang2, Ang3, Ang4, Angptl1, Angptl2, Angptl3, Angptl4, Angptl5, and Angptl6 with a rate of association (L-rate) of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ and $10^7$ 26. Amino acid sequence according to any previous or following embodiments, that can specifically bind to at least one member of the group of proteins consisting of Tie1, Tie2, Ang1, Ang2, Ang3, Ang4, Angptl1, Angptl2, Angptl3, Angptl4, Angptl5, and Angptl6 with a rate of dissociation ($k_{off}$ rate) between $1s^{-1}$ and $10^{-6}$ $s^{-1}$, preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

27. Amino acid sequence according to any previous or following embodiments, that can specifically bind to at least one member of the group of proteins consisting of Tie1, Tie2, Ang1, Ang2, Ang3, Ang4, Angptl1, Angptl2, Angptl3, Angptl4, Angptl5, and Angptl6 with an affinity less than 500 nM, preferably less than 200 nM, more preferably less than 10 nM, such as less than 500 µM.

28. Amino acid sequence according to any previous or following embodiments, that is a naturally occurring amino acid sequence (from any suitable species) or a synthetic or semi-synthetic amino acid sequence.

29. Amino acid sequence according to any previous or following embodiments, that comprises an immunoglobulin fold or that under suitable conditions is capable of forming an immunoglobulin fold.

30. Amino acid sequence according to any previous or following embodiments, that essentially consists of 4 framework regions (FR1 to FR4 respectively) and 3 complementarity determining regions (CDR1 to CDR3 respectively).

31. Amino acid sequence according to any previous or following embodiments that is an immunoglobulin sequence.

32. Amino acid sequence according to any previous or following embodiments that is a naturally occurring immunoglobulin sequence (from any suitable species) or a synthetic or semi-synthetic immunoglobulin sequence.

33. Amino acid sequence according to any previous or following embodiments that is a humanized immunoglobulin sequence, a camelized immunoglobulin sequence or an immunoglobulin sequence that has been obtained by techniques such as affinity maturation.

34. Amino acid sequence according to any previous or following embodiments that essentially consists of a light chain variable domain sequence (e.g. a $V_L$-sequence); or of a heavy chain variable domain sequence (e.g. a $V_H$-sequence).

35. Amino acid sequence according to any previous or following embodiments that essentially consists of a heavy chain variable domain sequence that is derived from a conventional four-chain antibody or that essentially consist of a heavy chain variable domain sequence that is derived from heavy chain antibody.

36. Amino acid sequence according to any previous or following preceding embodiments that essentially consists of a domain antibody (or an amino acid sequence that is suitable for use as a domain antibody), of a single domain antibody (or an amino acid sequence that is suitable for use as a single domain antibody), of a "dAb" (or an amino acid sequence that is suitable for use as a dAb) or of a Nanobody™ (including but not limited to a $V_{HH}$ sequence).

37. Amino acid sequence according to any previous or following embodiments that essentially consists of a Nanobody™.

38. Amino acid sequence according to any previous or following embodiments that essentially consists of a Nanobody™ that
i) has 80% amino acid identity with at least one of the amino acid sequences of SEQ ID NO's: 1 to 22, in which for the purposes of determining the degree of amino acid identity, the amino acid residues that form the CDR sequences are disregarded;
and in which:
ii) preferably one or more of the amino acid residues at positions 11, 37, 44, 45, 47, 83, 84, 103, 104 and 108 according to the Kabat numbering are chosen from the Hallmark residues mentioned in Table A-3.

39. Amino acid sequence according to any previous or following embodiments that essentially consists of a Nanobody™ that
i) has 80% amino acid identity with at least one of the amino acid sequences of SEQ ID NO's: 455 to 501, in which for the purposes of determining the degree of amino acid identity, the amino acid residues that form the CDR sequences are disregarded;
and in which:
ii) preferably one or more of the amino acid residues at positions 11, 37, 44, 45, 47, 83, 84, 103, 104 and 108 according to the Kabat numbering are chosen from the Hallmark residues mentioned in Table A-3.

40a. An amino acid sequence according to any previous or following embodiments comprising at least one variable domain that cross-blocks the binding of at least one of the amino acid sequences with SEQ ID NOs 455 to 501 to a Tie, Ang and/or an Angptl.

40b. An amino acid sequence according to any previous or following embodiments comprising at least one variable domain that is cross-blocked by at least one of the amino acid sequences with SEQ ID NOs 455 to 501 to a Tie, Ang and/or an Angptl.

40c. An amino acid sequence according to embodiments 40a or 40b wherein the ability of said amino acid sequence to cross-block or to be cross-blocked is detected in a Biacore assay.

40d. An amino acid sequence according to embodiments 40a or 40b wherein the ability of said amino acid sequence to cross-block or to be cross-blocked is detected in an ELISA assay.

40. Amino acid sequence according to any previous or following embodiments that essentially consists of a humanized Nanobody™.

41. Construct to any following embodiments that comprises or essentially consists of one or more amino acid sequences according to any of embodiments 1 to 40, and optionally further comprises one or more other groups, residues, moieties or binding units, optionally linked via one or more linkers.

42. Construct according to any previous or following embodiments that comprises or essentially consists of one or more amino acid sequences according to any of embodiments 1 to 40, and wherein the construct is able to inhibit angiogenesis as e.g. measured in any of the herein disclosed in vitro cell based—or animal models.

43. Construct according to any previous or following embodiments, in which said one or more other groups, residues, moieties or binding units are amino acid sequences.

44. Construct according to any previous or following embodiments, in which said one or more linkers, if present, are one or more amino acid sequences.

45. Construct according to embodiments 42 to 44, in which said one or more other groups, residues, moieties or binding units are immunoglobulins.

46. Construct according to embodiments 42 to 45, in which said one or more other groups, residues, moieties or binding units are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

47. Construct according to embodiments 42 to 46, in which said one or more amino acid sequences of the invention are immunoglobulin sequences.

48. Construct according to embodiments 42 to 47, in which said one or more amino acid sequences of the invention are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

49. Construct, that comprises or essentially consists of one or more Nanobodies according to any of embodiments 42 to 48 and in which said one or more other groups, residues, moieties or binding units are Nanobodies.

50. Construct according to any of embodiments 41 following, which is a multivalent construct.

51. Construct according to any of embodiments 41 following, which is a multispecific construct.

52. Construct according to any of embodiments 29 to 38, which has an increased half-life, compared to the corresponding amino acid sequence according to any of embodiments 1 to 40 per se.

53. Construct according to embodiment 39, in which said one or more other groups, residues, moieties or binding units provide the compound or construct with increased half-life, compared to the corresponding amino acid sequence according to any of embodiments 1 to 40 per se.

54. Construct according to embodiment 53, in which said one or more other groups, residues, moieties or binding units that provide the compound or construct with increased half-life is chosen from the group consisting of serum proteins or fragments thereof, binding units that can bind to serum proteins, an Fc portion, and small proteins or peptides that can bind to serum proteins.

55. Construct according to embodiment 54, in which said one or more other groups, residues, moieties or binding units that provide the compound or construct with increased half-life is chosen from the group consisting of human serum albumin or fragments thereof.

56. Construct according to embodiment 55, in which said one or more other groups, residues, moieties or binding units that provides the compound or construct with increased half-life are chosen from the group consisting of binding units that can bind to scrum albumin (such as human serum albumin) or a serum immunoglobulin (such as IgG).

57. Construct according to embodiment 56, in which said one or more other groups, residues, moieties or binding units that provides the compound or construct with increased half-life are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies that can bind to serum albumin (such as human serum albumin) or a serum immunoglobulin (such as IgG).

58. Construct according to embodiment 57, in which said one or more other groups, residues, moieties or binding units that provides the compound or construct with increased half-life is a Nanobody that can bind to serum albumin (such as human serum albumin) or a serum immunoglobulin (such as IgG).

59. Construct according to any of embodiments 53 to 58, that has a serum half-life that is at least 1.5 times, preferably at least 2 times, such as at least 5 times, for example at least 10 times or more than 20 times, greater than the half-life of the corresponding amino acid sequence according to any of embodiments 1 to 21 per se.

60. Construct according to any of embodiments 53 to 59, that has a serum half-life that is increased with more than 1 hours, preferably more than 2 hours, more preferably more than 6 hours, such as more than 12 hours, or even more than 24, 48 or 72 hours, compared to the corresponding amino acid sequence according to any of embodiments 1 to 21 per se.

61. Construct according to any of embodiments 53 to 60, that has a serum half-life in human of at least about 12 hours, preferably at least 24 hours, more preferably at least 48 hours, even more preferably at least 72 hours or more; for example, of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

62. Construct according to any of embodiments 53 to 61 that comprises or essentially consists of two amino acid sequences according to any of embodiments 1 to 28.

63. Construct according to embodiment 62, wherein said two amino acid sequences are directed against and/or specifically bind to same target protein which is selected from the group consisting of Tie1, Tie2, Ang1, Ang2, Ang3, Ang4, Angptl1, Angptl2, Angptl3, Angptl4, Angptl5, and Angptl6, said binding either being directed against two different epitopes or being against the same epitope.

64. Construct according to embodiment 63, wherein said target protein is selected from the group consisting of human Tie1, human Tie2, human Ang1, human Ang2, human Ang3, human Ang4, human Angptl1, human Angptl2, human Angptl3, human Angptl4, human Angptl5, and human Angptl6.

65. Construct according to embodiment 64, wherein said first amino acid sequence is directed against and/or specifically binds to human Tie2 and wherein said second amino acid sequence is directed against and/or specifically binds to human Ang1.

66. Construct according to embodiment 64, wherein said first amino acid sequence is directed against and/or specifically binds to human Tie2 and wherein said second amino acid sequence is directed against and/or specifically binds to human Ang2.

67. Construct according to embodiment 64, wherein said first amino acid sequence is directed against and/or specifically binds to human Tie2 and wherein said second amino acid sequence is directed against and/or specifically binds to human Ang4.

68. Construct according to embodiments 53 to 67, that comprises or essentially consists of one or more amino acid sequences according to any of embodiments 1 to 40, and optionally further comprises one or more toxic groups, toxic residues, toxic moieties or toxic binding units, optionally linked via one or more linkers.

69. Construct according to embodiment 68, wherein the toxic group is selected from the group of immunotoxins.

70. Construct according to any previous and following embodiments that comprises at least 3 variable domains, e.g. Nanobodies.

71. Construct according to any previous and following embodiments that comprises at least 3 variable domains, e.g. Nanobodies, and that is able to inhibit excessive angiogenesis and/or tumourgenesis, wherein said biological effect may be tested in a suitable cell based and/or animal model such as described herein.

72. Construct according to any previous and following embodiments that comprises at least 3 variable domains, e.g. Nanobodies, and that is able to either inhibit cluster formation of Tie2 or able to cluster Tie2 but without inducing any or only partial biological effect or effects such as inhibiting excessive angiogenesis and/or tumourgenesis to normalized levels, wherein said biological effect may be tested in a suitable cell based and/or animal model such as described herein.

73. Monovalent construct, comprising or essentially consisting of one amino acid sequence according to any of embodiments 1 to 40.

74. Monovalent construct according to embodiment 57, in which said amino acid sequence of the invention is chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

75. Monovalent construct, comprising or essentially consisting of one Nanobody according to any of embodiments 1 to 40.

76. Nucleic acid or nucleotide sequence, that encodes an amino acid sequence according to any of embodiments 1 to 40, a compound or construct according to any of embodiments 41 to 72, or a monovalent construct according to any of embodiments 73 to 75.

77. Nucleic acid or nucleotide sequence according to embodiment 76, that is in the form of a genetic construct.

78. Host or host cell that expresses, or that under suitable circumstances is capable of expressing, an amino acid sequence according to any of embodiments 1 to 40, a compound or construct according to any of embodiments 41 to 72, or a monovalent construct according to any of embodiments 73 to 75; and/or that comprises a nucleic acid or nucleotide sequence according to embodiment 76 or 77.

79. Method for producing an amino acid sequence according to any of embodiments 1 to 40, a compound or construct according to any of embodiments 41 to 72, or a monovalent construct according to any of embodiments 73 to 75, said method at least comprising the steps of:
a) expressing, in a suitable host cell or host organism or in another suitable expression system, a nucleic acid or nucleotide sequence according to embodiment 76, or a genetic construct according to embodiment 77; optionally followed by:
b) isolating and/or purifying the amino acid sequence according to any of embodiments 1 to 40, a compound or construct according to any of embodiments 41 to 72, or a monovalent construct according to any of embodiments 73 to 75.

80. Method for an amino acid sequence according to any of embodiments 1 to 40, a compound or construct according to any of embodiments 41 to 72, or a monovalent construct according to any of embodiments 73 to 75, said method at least comprising the steps of:
a) cultivating and/or maintaining a host or host cell according to embodiment 78 under conditions that are such that said host or host cell expresses and/or produces at least one amino acid sequence according to any of embodiments 1 to 40, a compound or construct according to any of embodiments 41 to 72, or a monovalent construct according to any of embodiments 73 to 75; optionally followed by:
b) isolating and/or purifying the amino acid sequence according to any of embodiments 1 to 40, a compound or construct according to any of embodiments 41 to 72, or a monovalent construct according to any of embodiments 73 to 75.

81. Composition, comprising at least one an amino acid sequence according to any of embodiments 1 to 40, a compound or construct according to any of embodiments 41 to 72, or a monovalent construct according to any of embodiments 73 to 75, or nucleic acid or nucleotide sequence according to embodiments 76 or 77.

82. Composition according to embodiment 81, which is a pharmaceutical composition 83. Composition according to embodiment 82, which is a pharmaceutical composition, that further comprises at least one pharmaceutically acceptable carrier, diluent or excipient and/or adjuvant, and that optionally comprises one or more further pharmaceutically active polypeptides and/or compounds.

84. Method for the prevention and/or treatment of at least one disease or disorder related to excessive or insufficient angiogenesis, said method comprising administering, to a subject in need thereof, a pharmaceutically active amount of at least one amino acid sequence according to any of embodiments 1 to 40, a compound or construct according to any of embodiments 41 to 72, or a monovalent construct according to any of embodiments 73 to 75, or composition according to any of embodiments 81 to 83.

85. Method for the prevention and/or treatment of at least one disease or disorder that is associated with a protein selected from the group consisting of Tie1, Tie2, Ang1, Ang2, Ang3, Ang4, Angptl1, Angptl2, Angptl3, Angptl4, Angptl5, and Angptl6, with its biological or pharmacological activity, and/or with the biological pathways or signalling in which said protein is involved, said method comprising administering, to a subject in need thereof, a pharmaceutically active amount of at least one amino acid sequence according to any of embodiments 1 to 40, a compound or construct according to any of embodiments 41 to 72, or a monovalent construct according to any of embodiments 73 to 75, or composition according to any of embodiments 81 to 83.

86. Method for the prevention and/or treatment of at least one disease or disorder related to cancer that can be prevented and/or treated by administering, to a subject in need thereof, amino acid sequence according to any of embodiments 1 to 40, a compound or construct according to any of embodiments 41 to 72, or a monovalent construct according to any of embodiments 73 to 75, or composition according to any of embodiments 81 to 83, said method comprising administering, to a subject in need thereof, a pharmaceutically active amount of at least one amino acid sequence according to any of embodiments 1 to 40, a compound or construct according to any of embodiments 41 to 72, or a monovalent construct according to any of embodiments 73 to 75, or composition according to any of embodiments 81 to 83.

87. Use of an amino acid sequence according to any of embodiments 1 to 40, a compound or construct according to any of embodiments 41 to 72, or a monovalent construct according to any of embodiments 73 to 75, in the preparation of a pharmaceutical composition for prevention and/or treatment of at least one disease or disorder related to excessive or insufficient angiogenesis.

88. Use of an amino acid sequence according to any of embodiments 1 to 40, a compound or construct according to any of embodiments 41 to 72, or a monovalent construct according to any of embodiments 73 to 75, for the prevention and/or treatment of at least one disease or disorder related to excessive or insufficient angiogenesis.

89. Use of an amino acid sequence according to any of embodiments 1 to 40, a compound or construct according to any of embodiments 41 to 72, or a monovalent construct according to any of embodiments 73 to 75 for the treatment of disease wherein excessive angiogenesis is the underlying cause, and wherein the dosing regimen used is controlled in such a way that the ratio of functional Ang1 to functional Ang2 in the serum of a patient is between 0.5 and 2, preferably between 0.6 and 1.67, more preferably between 0.7 and 1.4, more preferably between 0.8 and 1.25, more preferably between 0.9 and 1.1.

90. Use according to embodiment 89, wherein the concentration of functional Ang2 is considered to be the total concentration of Ang2 in serum minus the total concentration of the amino acid sequence directed against Ang2 in serum.

91. Method for the prevention and/or treatment of at least one disease or disorder related to cancer that can be prevented and/or treated by administering, to a subject in need thereof, an amino acid sequence according to any of embodiments 1 to 40, a compound or construct according to any of embodiments 41 to 72, or a monovalent construct according to any of embodiments 73 to 75, or composition according to any of embodiments 81 to 83, said method comprising administering, to a subject in need thereof, a pharmaceutically active amount of at least one amino acid sequence according to any of embodiments 1 to 40, a compound or construct according to any of embodiments 41 to 72, or a monovalent construct according to any of embodiments 73 to 75, or composition according to any of embodiments 81 to 83; and wherein the dosing regimen used is controlled in such a way that the ratio of functional Ang1 to functional Ang2 in the serum of a patient is between 0.5 and 2, preferably between 0.6 and 1.67, more preferably between 0.7 and 1.4, more preferably between 0.8 and 1.25, more preferably between 0.9 and 1.1.

92. Method according to embodiment 91, wherein the concentration of functional Ang2 is considered to be the total concentration of Ang2 in serum minus the total concentration of the amino acid sequence directed against Ang2 in serum.

Even More Preferred Aspects:

1. Amino acid sequence comprising at least one single variable domain that is directed against a protein selected from the group consisting of Tie1, Tie2, Ang1, Ang2, Ang3, Ang4, Angptl1, Angptl2, Angptl3, Angptl4, Angptl5, and Angptl6.

2. Amino acid sequence according to any previous aspects, which is in essentially isolated form.

3. Amino acid sequence according to any previous aspects, wherein the variable domain is directed against a protein selected from the group consisting of the human Tie1, human Tie2, human Ang1, human Ang2, human Ang3, human Ang4, human Angptl1, human Angptl2, human Angptl3, human Angptl4, human Angptl5, and human Angptl6, preferably human Ang1, human Ang2, human Ang4, human Angptl4 and human Tie2.

4. Amino acid sequence according to any previous aspects, wherein the single variable domain has an antagonistic effect to at least one member of the group of proteins consisting of Tie1 and Tie2.

5. Amino acid sequence according to any previous aspects, wherein the single variable domain has an antagonistic effect to human Tie2.

6. Amino acid sequence according to any previous aspects, wherein the single variable domain has an antagonistic effect to human Tie2 and does not block interaction between human Ang2 and human Tie2.

7. Amino acid sequence according to any previous aspects, wherein the single variable domain has the CDRs of SEQ ID NO 461.

8. Amino acid sequence according to any previous aspects, wherein the single variable domain has 80%, preferably 90%, more preferably 95% sequence identity with SEQ ID NO: 461.

9. Polypeptide comprising at least 2 identical or different amino acid sequence of any of the aspects 1 to 8.

10. Single variable domain with a CDR combination of any of the single variable domain in any of aspects 1 to 8, e.g. of SEQ ID NO: 461.

11. Single variable domain with 80%, preferably 90%, more preferably 95% sequence identity with any of the single variable domains in any of aspects 1 to 8, e.g. SEQ ID NO: 461.

12. Pharmaceutical composition comprising an amino acid sequence, a polypeptide, or a single variable domain according to any previous aspects and at least one pharmaceutically acceptable carrier, diluent or excipient and/or adjuvant.

13. Method for the prevention and/or treatment of at least one disease or disorder related to excessive or insufficient angiogenesis, said method comprising administering, to a subject in need thereof, a pharmaceutically active amount of at least one amino acid sequence, a polypeptide, or a single variable domain according to any of aspects 1 to 11.

14. Use of an amino acid sequence, a polypeptide, or a single variable domain according to any of aspects 1 to 11 for prevention and/or treatment of at least one disease or disorder related to excessive or insufficient angiogenesis.

15. Method for producing an amino acid sequence, a polypeptide, or a single variable domain according to any of aspects 1 to 11, said method at least comprising the steps of:
  i. cultivating and/or maintaining a suitable host or host cell under conditions that are such that said host or host cell expresses and/or produces at least one amino acid sequence, a polypeptide, or a single variable domain according to any of aspects 1 to 11; optionally followed by:
  ii. isolating and/or purifying the amino acid sequence, a polypeptide, or a single variable domain according to any of aspects 1 to 11.

The invention claimed is:

1. An isolated polypeptide comprising at least one single variable domain that binds to Tie2, wherein said at least one single variable domain consists of the structure FR1 - CDR1 - FR2 - CDR2 - FR3 - CDR3 - FR4 in which FR1 to FR4 refer to framework regions 1 to 4, respectively, and in which CDR1 to CDR3 refer to complementarity determining regions 1 to 3, respectively, in which CDR1 is SEQ ID NO: 178; CDR2 is SEQ ID NO: 272; and CDR3 is SEQ ID NO: 366; and wherein the single variable domain is capable of forming a single antigen binding unit.

2. The isolated polypeptide according to claim 1, which is purified at least 2-fold.

3. The isolated polypeptide according to claim 1, wherein the single variable domain binds to human Tie2.

4. The isolated polypeptide according to claim 3, wherein the single variable domain does not block interaction between human Ang2 and human Tie2.

5. An isolated polypeptide comprising at least two identical or different polypeptides of claim 1.

6. A pharmaceutical composition comprising the isolated polypeptide according to claim 1 and at least one pharmaceutically acceptable carrier, diluent, excipient, and/or adjuvant.

7. The isolated polypeptide according to claim 1, wherein the single variable domain has at least 80% amino acid identity with SEQ ID NO: 460.

8. The isolated polypeptide according to claim 1, wherein the single variable domain has 100% amino acid identity with SEQ ID NO: 460.

9. A single variable domain that binds to Tie2, wherein said single variable domain consists of the structure FR1 - CDR1 - FR2 - CDR2 - FR3 - CDR3 - FR4 in which FR1 to FR4 refer to framework regions 1 to 4, respectively, and in which CDR1 to CDR3 refer to complementarity determining regions 1 to 3, respectively, in which CDR1 is SEQ ID NO: 178; CDR2 is SEQ ID NO: 272; and CDR3 is SEQ ID NO: 366.

10. The isolated polypeptide according to claim 9, wherein the single variable domain has at least 80% amino acid identity with SEQ ID NO: 460.

11. The isolated polypeptide according to claim 9, wherein the single variable domain has 100% amino acid identity with SEQ ID NO: 460.

* * * * *